(12) United States Patent
Johansson et al.

(10) Patent No.: US 11,970,463 B2
(45) Date of Patent: Apr. 30, 2024

(54) COMPOUNDS AND THEIR USE

(71) Applicants: ASTRAZENECA AB, Södertälje (SE); Mitsubishi Tanabe Pharma Corporation, Osaka (JP)

(72) Inventors: Lars Anders Mikael Johansson, Södertälje (SE); Giulia Bergonzini, Södertälje (SE); Henrik Gradén, Södertälje (SE); Hiroshi Sugama, Osaka (JP); Takehiko Matsumura, Osaka (JP)

(73) Assignees: AstraZeneca AB, Södertälje (SE); Mitsubishi Tanabe Pharma Corporation, Osaka (JP)

( * ) Notice: Subject to any disclaimer, the term of this patent is extended or adjusted under 35 U.S.C. 154(b) by 0 days.

(21) Appl. No.: 17/810,367

(22) Filed: Jul. 1, 2022

(65) Prior Publication Data
US 2023/0110122 A1   Apr. 13, 2023

Related U.S. Application Data

(60) Provisional application No. 63/217,970, filed on Jul. 2, 2021.

(51) Int. Cl.
 *C07D 237/28* (2006.01)
 *C07D 237/34* (2006.01)
 *C07D 471/04* (2006.01)

(52) U.S. Cl.
 CPC ......... *C07D 237/28* (2013.01); *C07D 471/04* (2013.01)

(58) Field of Classification Search
 CPC ... C07D 237/28; C07D 237/34; C07D 471/04
 See application file for complete search history.

(56) References Cited

U.S. PATENT DOCUMENTS 11,319,319 B1   5/2022   Dorich et al.

FOREIGN PATENT DOCUMENTS

| WO | 2006004589 A2 | 1/2006 |
|---|---|---|
| WO | 2019/092170 A1 | 5/2019 |
| WO | 2020/234715 A1 | 11/2020 |
| WO | 2021/193897 A1 | 9/2021 |
| WO | 2022/135567 A1 | 6/2022 |
| WO | 2022/166890 A1 | 8/2022 |
| WO | 2022216971 A1 | 10/2022 |
| WO | 2022230912 A1 | 11/2022 |
| WO | 2023278438 A1 | 1/2023 |

*Primary Examiner* — Sun Jae Yoo

(57) ABSTRACT

The specification generally relates to compounds of Formula (I), and pharmaceutically acceptable salts thereof, where $R^1$, $R^{2A}$, $R^{2B}$, $R^{2C}$, $R^{2D}$, W, X, Y, and Z have the meanings defined herein. Such compounds are useful in inhibiting NLRP3 inflammasome activity and may be useful as therapeutic agents. The specification also relates to the use of such compounds to treat or prevent diseases and conditions in which the NLRP3 inflammasome is implicated. The specification further relates to compositions comprising such compounds.

43 Claims, No Drawings

COMPOUNDS AND THEIR USE

FIELD

Described in this specification are compounds (including salts thereof) that are inhibitors of the NLRP3 inflammasome, uses of such compounds, and compositions containing such compounds.

BACKGROUND

The NLRP3 inflammasome is a multi-protein complex consisting of the NLR family pyrin domain containing 3 (NLRP3) protein, PYD and CARD domain containing (ASC, also known as PYCARD), and caspase 1 (CASP1), and is a stress sensing pathway leading to an inflammatory response (Swanson K V et al. Nat Rev Immunol. 2019 August; 19(8):477-489). When activated, these three proteins condense into a large multiprotein complex; a speck.

The NLRP3 protein consists of three domains, PYD, NACHT and LRR (Sharif H et al. Nature. 2019 June; 570(7761):338-343). The aminoterminal PYD domain is thought to be important in the binding of NLRP3 to the PYD domain of ASC, the NACHT domain has ATPase activity suggested to regulate the oligomerization, potentially through conformational change of the LRR domain, and the LRR domain is considered to induce autoinhibition by folding onto the NACHT domain. The activity of the NLRP3 protein is further regulated by a multitude of post-translational modifications including phosphorylations and ubiquitinylations.

A multitude of cellular stressors such as pathogen associated molecular patterns (PAMP's), endogenous danger signals (DAMP's) and environmental irritants have been shown to lead to the condensation of the inflammasome into a speck. It is considered that the activation of the inflammasome requires two steps (McKee C M et al. J Leukoc Biol. 2020 September; 108(3):937-952). The initial priming step serves to increase the levels of inflammasome components and can be initiated by for example lipopolysaccharide (LPS, a common PAMP). LPS is detected through toll-like receptors resulting in NF-kB driven transcription of NLRP3 and IL1B. A secondary insult initiates rapid oligomerization of the inflammasome components into a speck, producing activated caspase 1.

In addition to this two step process a very high induction of NLRP3 transcription has been demonstrated to drive the inflammasome activation in a single step, typically through prolonged LPS exposure.

Downstream effects of an activated NLRP3 inflammasome is further expanded through caspase-1 mediated cleavage and hence activation of gasdermin D. When activated, gasdermin D forms a large pore leading to a regulated form of lytic cell death called pyroptosis (Kovacs S B et al. Trends Cell Biol. 2017 September; 27(9):673-684). In effect, pyroptosis amplifies inflammation through release of cellular contents subsequently leading to the recruitment and influx of additional immune cells.

It is likely that a dysregulated inflammasome drive can, even at low levels over several years, lead to tissue damage and chronic disease. This is proven for cryopyrin-associated periodic syndromes 1, 2 and 3 where causative genetic lesions in NLRP3 have been identified (Kacar M et al. Rheumatology (Oxford). 2019 Nov. 1; 58(Suppl 6):vi31-vi43).

NLRP3 inflammasome activation has been linked to multiple indications (as discussed herein) often with demonstrated presence or activity in the affected tissue, and inhibition of the NLRP3 inflammasome will therefore resolve unfavorable inflammation.

The NLRP3 inflammasome can modulate both acute kidney injury (AKI) and chronic kidney disease (CKD); mice deficient in NLRP3 inflammasome components and its downstream mediators can be protected from renal injury in experimental models of both AKI and CKD (Hutton H L et al. Nephrology. 2016 21(9):736-744). Inflammation plays a key role in the pathogenesis of AKI; after an initial ischaemic, septic or nephrotoxic trigger, release of inflammatory cytokines and chemokines by renal endothelial cells and tubular epithelium can result in leukocyte recruitment and subsequent renal injury. The role of the inflammasome in this process is evident in both studies on biomarkers and experimental models of AKI (Andersen K et al. Kidney Int. 2014 November; 86(5):965-78). Increasing evidence from clinical and experimental studies indicates that both systemic and local renal inflammation have crucial roles in the development and progression of diabetic kidney disease (DKD) (Tang S C W et al. Nat Rev Nephrol. 2020 April; 16(4):206-222). Specifically, the NLRP3 inflammasome links sensing of metabolic stress in the diabetic kidney to activation of pro-inflammatory cascades via the induction of IL-1β and IL-18 leading to chronic injury and kidney functional decline in CKD/DKD (Shahzad K et al. J Am Soc Nephrol. 2016 August; 27(8):2270-5).

Studies have implicated the NLRP3 inflammasome in cardiovascular diseases (An N et al. Front Immunol. 2019 Jul. 10; 10:1592). The relationship between the NLRP3 inflammasome and coronary atherosclerotic heart disease through cholesterol crystals/monosodium glutamate and downstream factors and vascular injury is well described (Jin Y et al. J Am Heart Assoc. 2019 Jun. 18; 8(12): e012219). In addition, the NLRP3 inflammasome may also be involved in the pathological mechanism of cardiomyopathies, including myocardial infarction (MI), cardiac remodelling and cardiac hypertrophy (An N et al. Front Immunol. 2019 Jul. 10; 10:1592).

Nonalcoholic fatty liver disease (NAFLD) is defined as excess liver fat accumulation (fatty liver) greater than 5% induced by causes other than alcohol intake. Fatty liver progresses to nonalcoholic steatohepatitis (NASH) with or without fibrosis in a variable proportion of individuals, ultimately leading to liver cirrhosis, liver failure and hepatocellular carcinoma in susceptible individuals (Friedman et al Nat Med. 2018 July; 24(7):908-922). Inflammation including the NLRP3 inflammasome contributes to the pathogenesis of most acute and chronic liver diseases including NAFLD, NASH, alcoholic steatohepatitis, chronic hepatitis C virus (HCV) infection, ischaemia-reperfusion injury and paracetamol-induced liver injury (Szabo et al Nat Rev Gastroenterol Hepatol 2015; 12:387-400). Hepatic NLRP3 and down-stream target mRNA levels are increased in NASH and correlate with liver collagen expression levels in humans. In addition, NLRP3 inducible activation increases liver fibrosis in mice and NLRP3 knock-out mice are protected from experimentally induced NASH including liver inflammation and fibrosis (Wree et al J Mol Med, 2014, DOI: 10.1007/s00109-014-1170-1). NLRP3 inflammasome inhibition using a small molecule inhibitor (MCC950) reduces liver inflammation and fibrosis in experimental models of NASH where mice were fed a high fat diet or a methionine and choline deficient diet (Mridha et al Journal of Hepatology, 2017, DOI: 10.1016/j.jhep.2017.01.022). Thus, NLRP3 inflammasome inhibition can protect against liver diseases including NAFLD and NASH.

Several overactivating mutations in NLRP3 have been linked to autoinflammatory disorders leading to inappropriate release of inflammatory cytokines including IL-1β and inflammatory symptoms. Cryopyrin-associated periodic syndromes, CAPS, include familial cold autoinflammatory syndrome (FCAS), Muckle-Wells syndrome (MWS), chronic infantile neurologic cutaneous articular (CINCA) syndrome or neonatal onset multi-system inflammatory disease (NOMID) (Booshehri M L et al. J Clin Immunol. 2019 April; 39(3):277-286).

The NLRP3 inflammasome has also been indicated in gout and pseudo gout since monosodium urate (MSU) and calcium pyrophosphate dihydrate (CPPD), both crystals found in gout, are activators of the NLRP3 inflammasome (Martinon F et al. Nature 440: 237-241, 2006). In sarcoidosis, the NLRP3 inflammasome has been identified as one of the key cellular pathways (Riteau N et al. Eur Respir J. 2020; 55(3):2000149) and increased activity has been demonstrated in the lungs of sarcoid patients.

Evidence suggest that inflammasomes play a role in auto-immune diseases and inhibition of the NLRP3 inflammasome may have a positive effect in rheumatoid arthritis (RA), multiple sclerosis (MS), Addison's disease, celiac disease, systemic lupus erythematous (SLE) and vitiligo (Shaw P J et al. Trends Mol Med. 2011 February; 17(2):57-64).

In inflammatory skin diseases, NLRP3 inflammasome activation has been demonstrated in acne vulgaris (Li Z J et al. J Invest Dermatol. 2014 November; 134(11):2747-2756) and hidradenitis suppurativa (Kelly G et al. Br J Dermatol. 2015 December; 173(6):1431-9).

Emerging evidence suggest that persistent activation of NLRP3 may be involved in the progression of several chronic pulmonary diseases, including idiopathic pulmonary fibrosis (IPF), chronic obstructive pulmonary disease (COPD) and asthma (De Nardo D. et al. Am J Pathol. 2014 January; 184(1):42-54).

In inflammatory bowel disease (IBD) there is evidence showing that inflammasome-driven IL-1β and IL-18 play a role in IBD pathology and that NLRP3 inflammasome inhibitors may be efficacious in ulcerative colitis (UC) and Crohn's disease. (Zhen Y et al. Front Immunol. 2019 Feb. 28; 10:276).

Accordingly, inhibitors of the NLRP3 inflammasome may be useful in the treatment of the diseases and conditions described herein which are linked to NLRP3 inflammasome activation. However, to date, no small-molecule synthetic inhibitor of the NLRP3 inflammasome has been approved for medical use.

Small-molecule inhibitors of the NLRP3 inflammasome have been previously discussed, for example, in WO2020/234715 A1, but, despite the foregoing, a need continues to exist for further compounds that are inhibitors of the NLRP3 inflammasome which may make the compounds especially promising for development as therapeutic agents. The compounds disclosed herein may also exhibit improved inhibition (in vitro and in vivo) of the NLRP3 inflammasome in comparison with other known NLRP3 inflammasome inhibitors. The compounds disclosed herein may also exhibit favourable toxicological profiles (for example, reduced hERG inhibition), favourable pharmacokinetic profiles, and/or advantageous physical properties (for example, higher aqueous solubility) in comparison with other known NLRP3 inflammasome inhibitors. Therefore, such compound(s) may be especially useful in the treatment of disease states in which inhibition of the NLRP3 inflammasome is beneficial.

SUMMARY

Briefly, this specification describes, in part, a compound of Formula (I):

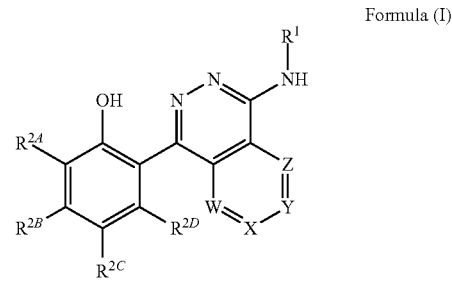

Formula (I)

or a pharmaceutically acceptable salt thereof, wherein $R^1$ is selected from

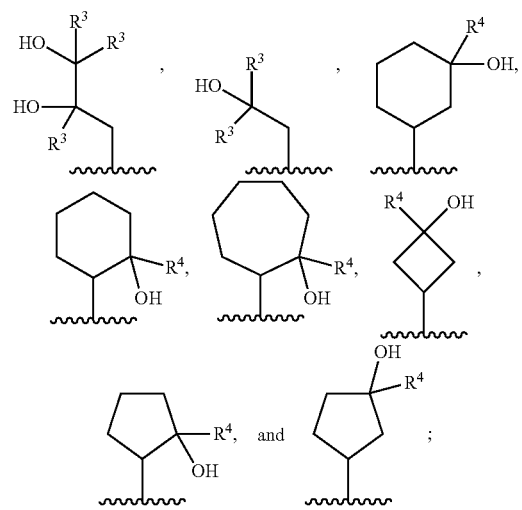

each $R^3$ is independently selected from —H and —$C_{1-3}$ alkyl;
$R^4$ is selected from —H and —$C_{1-3}$ alkyl;
$R^{2A}$, $R^{2B}$, $R^{2C}$, and $R^{2D}$ are each independently selected from —H, —F, —Cl, —$C_{1-3}$ alkyl substituted with 0-3 —F substituents, cyclopropyl, —$OCF_3$, and —$SO_2Me$;
W, X, Y and Z are each independently selected from $CR^5$ and N; zero or one of W, X, Y and Z are N, and the remainder of W, X, Y and Z are $CR^5$;
each $R^5$ is independently selected from —H, -Me and —F.

This specification also describes, in part, a pharmaceutical composition which comprises a compound of Formula (I), or a pharmaceutically acceptable salt thereof, and at least one pharmaceutically acceptable excipient.

This specification also describes, in part, a compound of Formula (I), or a pharmaceutically acceptable salt thereof, for use in therapy.

This specification also describes, in part, a compound of Formula (I), or a pharmaceutically acceptable salt thereof, for use in the treatment of a subject with a disease or condition in which NLRP3 inflammasome activity is implicated.

This specification also describes, in part, a compound of Formula (I), or a pharmaceutically acceptable salt thereof, for use in the treatment of a disease or condition selected from kidney diseases, cardiovascular diseases, liver diseases, inflammatory diseases, inflammatory skin diseases, inflammatory bowel diseases, autoimmune diseases, and respiratory diseases.

This specification also describes, in part, the use of a compound of Formula (I), or a pharmaceutically acceptable salt thereof, in the manufacture of a medicament for the treatment of a disease or condition in which NLRP3 inflammasome activity is implicated.

This specification also describes, in part, the use of a compound of Formula (I), or a pharmaceutically acceptable salt thereof, in the manufacture of a medicament for the treatment of a disease or condition selected from kidney diseases, cardiovascular diseases, liver diseases, inflammatory diseases, inflammatory skin diseases, inflammatory bowel diseases, autoimmune diseases, and respiratory diseases.

This specification also describes, in part, a method for treating a disease or condition in which NLRP3 inflammasome activity is implicated, in a subject in need of such treatment, which comprises administering to said subject a therapeutically effective amount of a compound of Formula (I), or a pharmaceutically acceptable salt thereof.

This specification also describes, in part, a method for treating a disease or condition selected from kidney diseases, cardiovascular diseases, liver diseases, inflammatory diseases, inflammatory skin diseases, inflammatory bowel diseases, autoimmune diseases, and respiratory diseases, in a subject in need of such treatment, which comprises administering to said subject a therapeutically effective amount of a compound of Formula (I), or a pharmaceutically acceptable salt thereof.

Further aspects of the disclosure will be apparent to one skilled in the art from reading this specification.

DESCRIPTION OF ILLUSTRATIVE EMBODIMENTS

Many embodiments are detailed throughout the specification and will be apparent to a reader skilled in the art. The specification is not to be interpreted as being limited to any particular embodiment(s) described herein.

In an embodiment there is provided a compound of Formula (I):

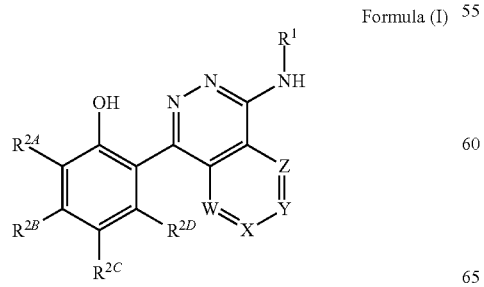

Formula (I)

or a pharmaceutically acceptable salt thereof, wherein $R^1$ is selected from

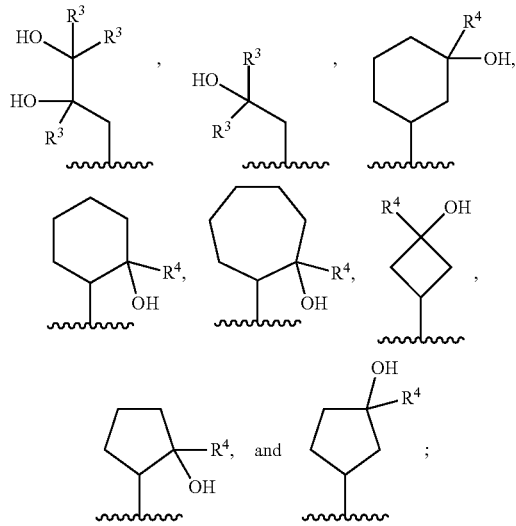

each $R^3$ is independently selected from —H and —$C_{1-3}$ alkyl;

$R^4$ is selected from —H and —$C_{1-3}$ alkyl;

$R^{2A}$, $R^{2B}$, $R^{2C}$, and $R^{2D}$ are each independently selected from —H, —F, —Cl, —$C_{1-3}$ alkyl substituted with 0-3 —F substituents, cyclopropyl, —$OCF_3$, and —$SO_2Me$;

W, X, Y and Z are each independently selected from $CR^5$ and N; zero or one of W, X, Y and Z are N, and the remainder of W, X, Y and Z are $CR^5$;

each $R^5$ is independently selected from —H, -Me and —F.

The following embodiments of moieties $R^1$, $R^{2A}$, $R^{2B}$, $R^{2C}$, $R^{2D}$, $R^3$, $R^4$, $R^5$, W, X, Y, Z may be applied, alone or in combination, to the descriptions of the compounds of Formula (I) provided herein.

In an embodiment, $R^1$ is selected from

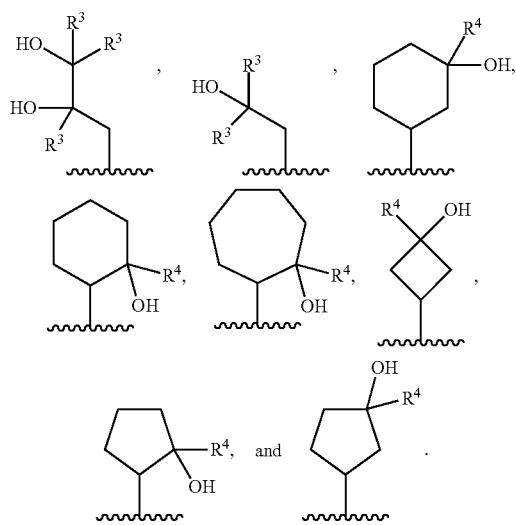

In an embodiment, R¹ is selected from
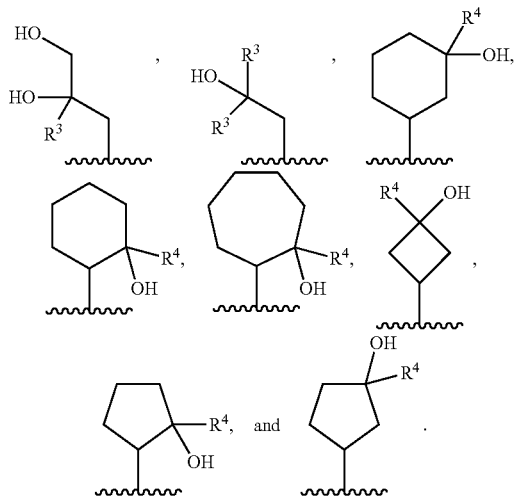
In an embodiment, R¹ is selected from
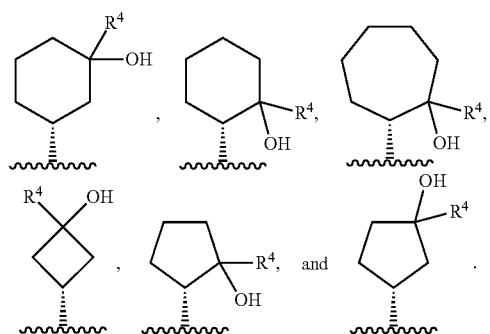
In an embodiment, R¹ is selected from
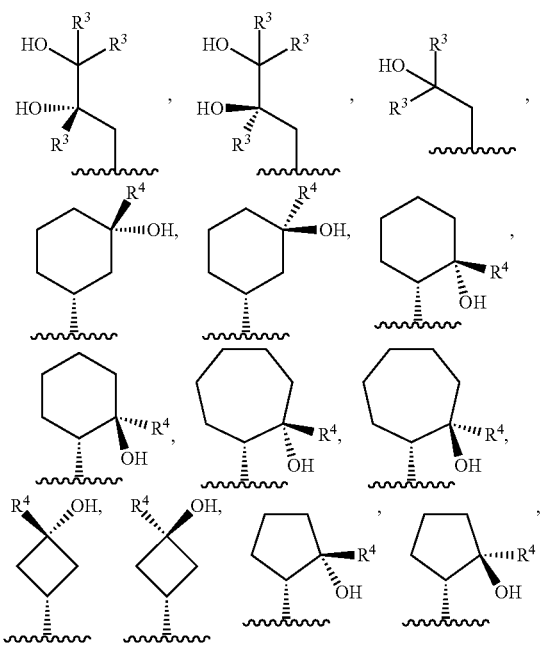
-continued
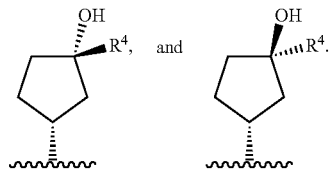
In an embodiment, R¹ is selected from
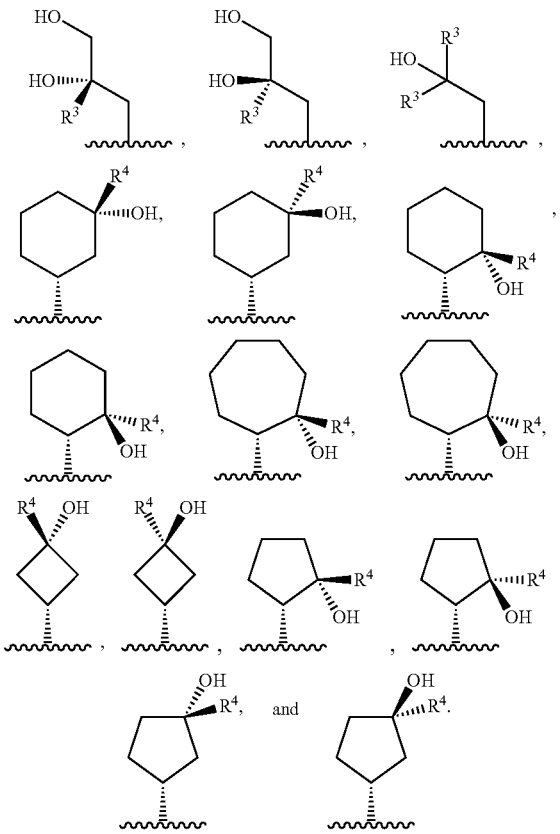
In an embodiment, R¹ is selected from
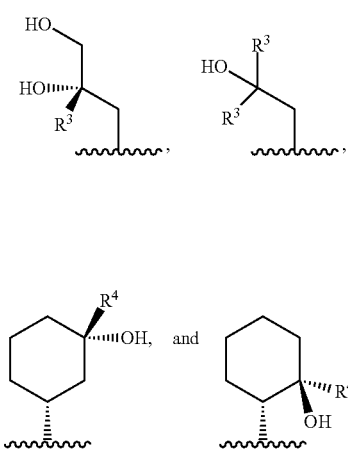

In an embodiment, $R^1$ is selected from

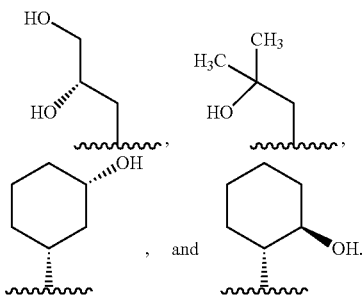

, and

In an embodiment, $R^1$ is

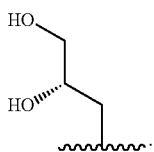

In an embodiment, $R^1$ is

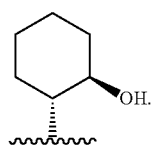 [SMILES: *[C@@H]1CCCC[C@H]1O]

In an embodiment, each $R^3$ is independently selected from —H and —$C_{1-3}$ alkyl.

In an embodiment, each $R^3$ is independently selected from —H and -Me.

In an embodiment, each $R^3$ is —H.

In an embodiment, each $R^3$ is -Me.

In an embodiment, $R^4$ is selected from —H and —$C_{1-3}$ alkyl.

In an embodiment, $R^4$ is selected from —H and -Me.

In an embodiment, $R^4$ is —H.

In an embodiment, $R^4$ is -Me.

In an embodiment, $R^{2A}$, $R^{2B}$, $R^{2C}$, and $R^{2D}$ are each independently selected from —H, —F, —Cl, —$C_{1-3}$ alkyl substituted with 0-3 —F substituents, cyclopropyl, —$OCF_3$, and —$SO_2Me$.

In an embodiment, $R^{2A}$, $R^{2B}$, $R^{2C}$, and $R^{2D}$ are each independently selected from —H, —F, —Cl, -Me, -Et, -n-Pr, -i-Pr, —$CH_2F$, —$CHF_2$, —$CF_3$, cyclopropyl, —$OCF_3$, and —$SO_2Me$.

In an embodiment, $R^{2A}$, $R^{2B}$, $R^{2C}$, and $R^{2D}$ are each independently selected from —H, —F, —Cl, -Me, -Et, cyclopropyl, —$CF_3$, —$OCF_3$, and —$SO_2Me$.

In an embodiment, two, three or four of $R^{2A}$, $R^{2B}$, $R^{2C}$, and $R^{2D}$ are —H, and the remainder of $R^{2A}$, $R^{2B}$, $R^{2C}$, and $R^{2D}$ are not —H.

In an embodiment, two or three of $R^{2A}$, $R^{2B}$, $R^{2C}$, and $R^{2D}$ are —H, and the remainder of $R^{2A}$, $R^{2B}$, $R^{2C}$, and $R^{2D}$ are not —H.

In an embodiment, two of $R^{2A}$, $R^{2B}$, $R^{2C}$, and $R^{2D}$ are —H, and two of $R^{2A}$, $R^{2B}$, $R^{2C}$, and $R^{2D}$ are not —H.

In an embodiment, three of $R^{2A}$, $R^{2B}$, $R^{2C}$, and $R^{2D}$ are —H, and one of $R^{2A}$, $R^{2B}$, $R^{2C}$, and $R^{2D}$ is not —H.

In an embodiment, $R^{2A}$ is selected from —H, —F, —Cl, —$C_{1-3}$ alkyl substituted with 0-3 —F substituents, cyclopropyl, —$OCF_3$, and —$SO_2Me$.

In an embodiment, $R^{2A}$ is selected from —H, —F, —Cl, -Me, -Et, cyclopropyl, —$CF_3$, —$OCF_3$, and —$SO_2Me$.

In an embodiment, $R^{2A}$ is selected from —H and —F.

In an embodiment, $R^{2A}$ is —H.

In an embodiment, $R^{2B}$ is selected from —H, —F, —Cl, —$C_{1-3}$ alkyl substituted with 0-3 —F substituents, cyclopropyl, —$OCF_3$, and —$SO_2Me$.

In an embodiment, $R^{2B}$ is selected from —H, —F, —Cl, -Me, -Et, cyclopropyl, —$CF_3$, —$OCF_3$, and —$SO_2Me$.

In an embodiment, $R^{2B}$ is selected from —H, —F, —$CF_3$, and —$SO_2Me$.

In an embodiment, $R^{2B}$ is selected from —F, —$CF_3$, and —$SO_2Me$.

In an embodiment, $R^{2B}$ is —H.

In an embodiment, $R^{2B}$ is not —H.

In an embodiment, $R^{2B}$ is —F.

In an embodiment, $R^{2B}$ is —$CF_3$.

In an embodiment, $R^{2B}$ is —$SO_2Me$.

In an embodiment, $R^{2C}$ is selected from —H, —F, —Cl, —$C_{1-3}$ alkyl substituted with 0-3 —F substituents, cyclopropyl, —$OCF_3$, and —$SO_2Me$.

In an embodiment, $R^{2C}$ is selected from —H, —F, —Cl, -Me, -Et, cyclopropyl, —$CF_3$, —$OCF_3$, and —$SO_2Me$.

In an embodiment, $R^{2C}$ is selected from —H and —F.

In an embodiment, $R^{2C}$ is —H.

In an embodiment, $R^{2D}$ is selected from —H, —F, —Cl, —$C_{1-3}$ alkyl substituted with 0-3 —F substituents, cyclopropyl, —$OCF_3$, and —$SO_2Me$.

In an embodiment, $R^{2D}$ is selected from —H, —F, —Cl, -Me, -Et, cyclopropyl, —$CF_3$, —$OCF_3$, and —$SO_2Me$.

In an embodiment, $R^{2D}$ is selected from —H and —F.

In an embodiment, $R^{2D}$ is —H.

In an embodiment, $R^{2D}$ is —F.

In an embodiment, $R^{2A}$ and $R^{2C}$ are —H.

In an embodiment, $R^{2A}$ is —H, $R^{2B}$ is selected from —H, —F, —$CF_3$, and —$SO_2Me$, $R^{2C}$ is —H, and $R^{2D}$ is —H.

In an embodiment, $R^{2A}$ is —H, $R^{2B}$ is selected from —F, —$CF_3$, and —$SO_2Me$, $R^{2C}$ is —H, and $R^{2D}$ is —H.

In an embodiment, $R^{2A}$ is —H, $R^{2B}$ is —F, $R^{2C}$ is —H, and $R^{2D}$ is —H.

In an embodiment, $R^{2A}$ is —H, $R^{2B}$ is —$CF_3$, $R^{2C}$ is —H, and $R^{2D}$ is —H.

In an embodiment, $R^{2A}$ is —H, $R^{2B}$ is —$SO_2Me$, $R^{2C}$ is —H, and $R^{2D}$ is —H.

In an embodiment, $R^{2A}$ is —H, $R^{2B}$ is selected from —H or —Cl, $R^{2C}$ is —H, and $R^{2D}$ is —F.

In an embodiment, W, X, Y and Z are each independently selected from $CR^5$ and N; zero or one of W, X, Y and Z are N, and the remainder of W, X, Y and Z are $CR^5$.

In an embodiment, W, X and Z are each $CR^5$; and Y is $CR^5$ or N.

In an embodiment, W, X, Y and Z are each $CR^5$.

In an embodiment, W, X, and Z are each $CR^5$ and Y is N.

In an embodiment, one of W, X, Y and Z is $CR^5$; zero or one of W, X, Y and Z is N; and the remainder of W, X, Y and Z are CH.

In an embodiment, each $R^5$ is independently selected from —H, -Me and —F.

In an embodiment, each $R^5$ is —H.

In an embodiment, W, X, Y and Z are each CH.

In an embodiment, W, X, and Z are each CH and Y is N.

In an embodiment, R¹ is selected from

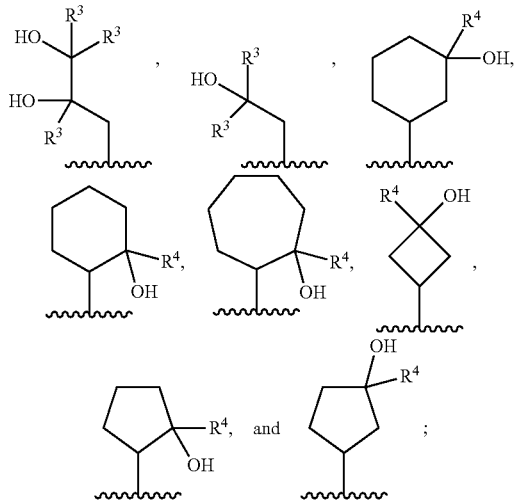

each R³ is independently selected from —H and -Me, optionally each R³ is —H;
R⁴ is selected from —H and -Me; optionally R⁴ is —H;
$R^{2A}$ and $R^{2C}$ are each —H;
$R^{2B}$ is selected from —H, —F, —CF₃, and —SO₂Me; optionally $R^{2B}$ is —CF₃;
$R^{2D}$ is selected from —H and —F; optionally $R^{2D}$ is —H;
one of W, X, Y and Z is CR⁵; zero or one of W, X, Y and Z is N; and the remainder of W, X, Y and Z are CH;
R⁵ is selected from —H, -Me and —F.

In an embodiment, R¹ is selected from

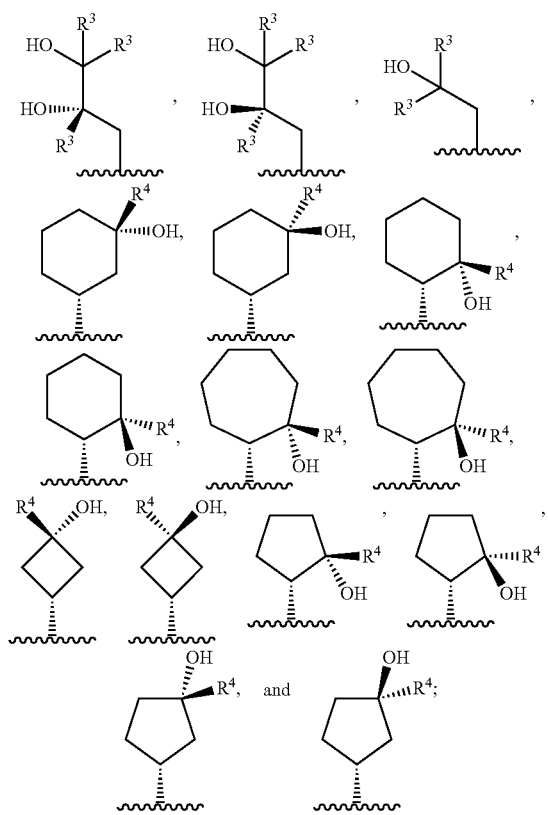

each R³ is independently selected from —H and -Me, optionally each R³ is —H;
R⁴ is selected from —H and -Me; optionally R⁴ is —H;
$R^{2A}$ and $R^{2C}$ are each —H;
$R^{2B}$ is selected from —H, —F, —CF₃, and —SO₂Me; optionally $R^{2B}$ is —CF₃;
$R^{2D}$ is selected from —H and —F; optionally $R^{2D}$ is —H;
one of W, X, Y and Z is CR⁵; zero or one of W, X, Y and Z is N; and the remainder of W, X, Y and Z are CH;
R⁵ is selected from —H, -Me and —F.

In an embodiment, R¹ is selected from

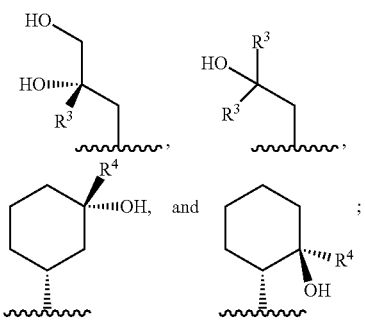

each R³ is independently selected from —H and -Me, optionally each R³ is —H;
R⁴ is selected from —H and -Me; optionally R⁴ is —H;
$R^{2A}$ and $R^{2C}$ are each —H;
$R^{2B}$ is selected from —H, —F, —CF₃, and —SO₂Me; optionally $R^{2B}$ is —CF₃;
$R^{2D}$ is selected from —H and —F; optionally $R^{2D}$ is —H;
W, X and Z are each CH; and Y is CH or N.

In an embodiment, there is provided a compound selected from:
3-[[4-[2-hydroxy-4-(trifluoromethyl)phenyl]phthalazin-1-yl]amino]propane-1,2-diol;
3-[[4-(4-chloro-3-fluoro-2-hydroxy-phenyl)phthalazin-1-yl]amino]propane-1,2-diol;
3-[[4-(4,5-difluoro-2-hydroxy-phenyl)phthalazin-1-yl]amino]propane-1,2-diol;
3-[[4-(2-fluoro-6-hydroxy-phenyl)phthalazin-1-yl]amino]propane-1,2-diol;
3-[[4-(4-chloro-2-hydroxy-phenyl)phthalazin-1-yl]amino]propane-1,2-diol;
3-[[4-[2-hydroxy-4-(trifluoromethoxy)phenyl]phthalazin-1-yl]amino]propane-1,2-diol;
3-[[4-[2-fluoro-6-hydroxy-4-(trifluoromethyl)phenyl]phthalazin-1-yl]amino]propane-1,2-diol;
3-[[4-(2,4-difluoro-6-hydroxy-phenyl)phthalazin-1-yl]amino]propane-1,2-diol;
3-[[4-(4-chloro-2-fluoro-6-hydroxy-phenyl)phthalazin-1-yl]amino]propane-1,2-diol;
3-[[4-(2-chloro-6-hydroxy-phenyl)phthalazin-1-yl]amino]propane-1,2-diol;
3-[[4-(2-hydroxy-4-methyl-phenyl)phthalazin-1-yl]amino]propane-1,2-diol;
3-[[4-(2-hydroxy-5-methyl-phenyl)phthalazin-1-yl]amino]propane-1,2-diol;
3-[[4-[2-hydroxy-4-(trifluoromethyl)phenyl]-7-methyl-phthalazin-1-yl]amino]propane-1,2-diol;
3-[[4-[2-hydroxy-4-(trifluoromethyl)phenyl]-6-methyl-phthalazin-1-yl]amino]propane-1,2-diol;
2-[4-[[3-hydroxycyclopentyl]amino]phthalazin-1-yl]-5-(trifluoromethyl)phenol;

2-[4-[[3-hydroxycyclopentyl]amino]phthalazin-1-yl]-5-methylsulfonyl-phenol;
2-[4-[[2-hydroxycyclopentyl]amino]phthalazin-1-yl]-5-(trifluoromethyl)phenol;
2-[4-[[2-hydroxycyclohexyl]amino]phthalazin-1-yl]-5-(trifluoromethyl)phenol;
2-[[4-[2-hydroxy-4-(trifluoromethyl)phenyl]phthalazin-1-yl]amino]cycloheptanol;
2-(4-((3-hydroxycyclohexyl)amino)phthalazin-1-yl)-5-(trifluoromethyl)phenol;
2-(4-((3-hydroxycyclobutyl)amino)phthalazin-1-yl)-5-(trifluoromethyl)phenol;
3-fluoro-2-(4-((3-hydroxy-3-methylcyclobutyl)amino)phthalazin-1-yl)phenol;
2-(4-((3-hydroxy-3-methylcyclobutyl)amino)phthalazin-1-yl)-5-(trifluoromethyl)phenol;
2-[4-[[3-hydroxy-3-methyl-cyclopentyl]amino]pyrido[3,4-d]pyridazin-1-yl]-5-(trifluoromethyl)phenol;
2-[4-[[3-hydroxycyclohexyl]amino]pyrido[3,4-d]pyridazin-1-yl]-5-(trifluoromethyl)phenol;
2-[1-[[3-hydroxycyclohexyl]amino]pyrido[3,4-d]pyridazin-4-yl]-5-(trifluoromethyl)phenol;
5-chloro-2-[4-[[3-hydroxycyclohexyl]amino]pyrido[3,4-d]pyridazin-1-yl]phenol;
3-fluoro-2-[4-[[3-hydroxycyclohexyl]amino]pyrido[3,4-d]pyridazin-1-yl]-5-(trifluoromethyl)phenol;
5-chloro-3-fluoro-2-[4-[[3-hydroxycyclohexyl]amino]pyrido[3,4-d]pyridazin-1-yl]phenol;
3-fluoro-2-[4-[[3-hydroxycyclohexyl]amino]pyrido[3,4-d]pyridazin-1-yl]phenol;
2-[4-[[3-hydroxycyclohexyl]amino]pyrido[3,4-d]pyridazin-1-yl]-5-(trifluoromethoxy)phenol;
2-[4-[[3-hydroxycyclohexyl]amino]pyrido[3,4-d]pyridazin-1-yl]-3-(trifluoromethyl)phenol;
5-ethyl-2-[4-[[3-hydroxycyclohexyl]amino]pyrido[3,4-d]pyridazin-1-yl]phenol;
5-cyclopropyl-2-[4-[[3-hydroxycyclohexyl]amino]pyrido[3,4-d]pyridazin-1-yl]phenol;
4-fluoro-2-[4-[[3-hydroxycyclohexyl]amino]pyrido[3,4-d]pyridazin-1-yl]-5-(trifluoromethyl)phenol;
4-fluoro-2-[4-[[2-hydroxycyclohexyl]amino]pyrido[3,4-d]pyridazin-1-yl]-5-(trifluoromethyl)phenol;
3-fluoro-2-[4-[[2-hydroxycyclohexyl]amino]pyrido[3,4-d]pyridazin-1-yl]-5-(trifluoromethyl)phenol;
2-[4-[[2-hydroxycyclohexyl]amino]pyrido[3,4-d]pyridazin-1-yl]-5-(trifluoromethoxy)phenol;
5-chloro-3-fluoro-2-[4-[[2-hydroxycyclohexyl]amino]pyrido[3,4-d]pyridazin-1-yl]phenol;
5-chloro-2-[4-[[2-hydroxycyclohexyl]amino]pyrido[3,4-d]pyridazin-1-yl]phenol;
2-[4-[[3-hydroxy-3-methyl-cyclohexyl]amino]pyrido[3,4-d]pyridazin-1-yl]-5-(trifluoromethyl)phenol;
2-(4-((3-hydroxy-3-methylcyclobutyl)amino)pyrido[3,4-d]pyridazin-1-yl)-5-(trifluoromethoxy)phenol;
3-fluoro-2-(4-((3-hydroxy-3-methylcyclobutyl)amino)pyrido[3,4-d]pyridazin-1-yl)phenol;
3-chloro-2-fluoro-6-(4-((3-hydroxy-3-methylcyclobutyl)amino)pyrido[3,4-d]pyridazin-1-yl)phenol;
4,5-difluoro-2-(4-((3-hydroxy-3-methylcyclobutyl)amino)pyrido[3,4-d]pyridazin-1-yl)phenol;
3-fluoro-2-(4-((3-hydroxy-3-methylcyclobutyl)amino)pyrido[3,4-d]pyridazin-1-yl)-5-(trifluoromethyl)phenol;
5-chloro-2-(4-((3-hydroxy-3-methylcyclobutyl)amino)pyrido[3,4-d]pyridazin-1-yl)phenol;
3,5-difluoro-2-(4-((3-hydroxy-3-methylcyclobutyl)amino)pyrido[3,4-d]pyridazin-1-yl)phenol;
2-[4-[(2-hydroxy-2-methyl-propyl)amino]pyrido[3,4-d]pyridazin-1-yl]-5-(trifluoromethyl)phenol;
5-chloro-2-[4-[(2-hydroxy-2-methyl-propyl)amino]pyrido[3,4-d]pyridazin-1-yl]phenol;
2-[4-[(2-hydroxy-2-methyl-propyl)amino]pyrido[3,4-d]pyridazin-1-yl]-5-(trifluoromethoxy)phenol;
5-chloro-3-fluoro-2-[4-[(2-hydroxy-2-methyl-propyl)amino]pyrido[3,4-d]pyridazin-1-yl]phenol;
3-fluoro-2-[4-[(2-hydroxy-2-methyl-propyl)amino]pyrido[3,4-d]pyridazin-1-yl]-5-(trifluoromethyl)phenol;
5-fluoro-2-(4-((2-hydroxycyclohexyl)amino)pyrido[3,4-d]pyridazin-1-yl)phenol;
3-fluoro-2-(4-((2-hydroxycyclohexyl)amino)pyrido[3,4-d]pyridazin-1-yl)phenol;
3-fluoro-2-(1-((2-hydroxycyclohexyl)amino)pyrido[3,4-d]pyridazin-4-yl)phenol;
5-fluoro-2-(1-((2-hydroxycyclohexyl)amino)pyrido[3,4-d]pyridazin-4-yl)phenol;
2-[4-[[2-hydroxycyclohexyl]amino]pyrido[3,4-d]pyridazin-1-yl]-5-(trifluoromethyl)phenol;
2-[4-[[3-hydroxycyclopentyl]amino]pyrido[3,4-d]pyridazin-1-yl]-5-(trifluoromethyl)phenol;
2-(4-((3-hydroxy-3-methylcyclobutyl)amino)pyrido[3,4-d]pyridazin-1-yl)-5-(trifluoromethyl)phenol;
5-fluoro-2-(4-((3-hydroxycyclopentyl)amino)pyrido[3,4-d]pyridazin-1-yl)phenol;
3-fluoro-2-(1-((3-hydroxycyclopentyl)amino)pyrido[3,4-d]pyridazin-4-yl)phenol;
3-[[1-[2-hydroxy-4-(trifluoromethyl)phenyl]pyrido[3,4-d]pyridazin-4-yl]amino]propane-1,2-diol;
2-[8-[[3-hydroxycyclohexyl]amino]pyrido[2,3-d]pyridazin-5-yl]-5-(trifluoromethyl)phenol;
3-fluoro-2-(8-((3-hydroxy-3-methylcyclobutyl)amino)pyrido[2,3-d]pyridazin-5-yl)phenol;
2-[8-[[3-hydroxycyclohexyl]amino]-2-methyl-pyrido[2,3-d]pyridazin-5-yl]-5-(trifluoromethyl)phenol; and
3-[[4-[2-hydroxy-4-(trifluoromethyl)phenyl]phthalazin-1-yl]amino]-2-methyl-propane-1,2-diol;
or a pharmaceutically acceptable salt thereof.

In an embodiment, there is provided a compound selected from:
(2S)-3-[[4-[2-hydroxy-4-(trifluoromethyl)phenyl]phthalazin-1-yl]amino]propane-1,2-diol;
(2R)-3-[[4-[2-hydroxy-4-(trifluoromethyl)phenyl]phthalazin-1-yl]amino]propane-1,2-diol;
(2S)-3-[[4-(4-chloro-3-fluoro-2-hydroxy-phenyl)phthalazin-1-yl]amino]propane-1,2-diol;
(2R)-3-[[4-(4-chloro-3-fluoro-2-hydroxy-phenyl)phthalazin-1-yl]amino]propane-1,2-diol;
(2S)-3-[[4-(4,5-difluoro-2-hydroxy-phenyl)phthalazin-1-yl]amino]propane-1,2-diol;
(2R)-3-[[4-(4,5-difluoro-2-hydroxy-phenyl)phthalazin-1-yl]amino]propane-1,2-diol;
(2S)-3-[[4-(2-fluoro-6-hydroxy-phenyl)phthalazin-1-yl]amino]propane-1,2-diol;
(2R)-3-[[4-(2-fluoro-6-hydroxy-phenyl)phthalazin-1-yl]amino]propane-1,2-diol;
(2S)-3-[[4-(4-chloro-2-hydroxy-phenyl)phthalazin-1-yl]amino]propane-1,2-diol;
(2R)-3-[[4-(4-chloro-2-hydroxy-phenyl)phthalazin-1-yl]amino]propane-1,2-diol;
(2S)-3-[[4-[2-hydroxy-4-(trifluoromethoxy)phenyl]phthalazin-1-yl]amino]propane-1,2-diol;
(2R)-3-[[4-[2-hydroxy-4-(trifluoromethoxy)phenyl]phthalazin-1-yl]amino]propane-1,2-diol;
(2S)-3-[[4-[2-fluoro-6-hydroxy-4-(trifluoromethyl)phenyl]phthalazin-1-yl]amino]propane-1,2-diol;

(2R)-3-[[4-[2-fluoro-6-hydroxy-4-(trifluoromethyl)phenyl] phthalazin-1-yl]amino]propane-1,2-diol;
(2S)-3-[[4-(2,4-difluoro-6-hydroxy-phenyl)phthalazin-1-yl] amino]propane-1,2-diol;
(2R)-3-[[4-(2,4-difluoro-6-hydroxy-phenyl)phthalazin-1-yl] amino]propane-1,2-diol;
(2S)-3-[[4-(4-chloro-2-fluoro-6-hydroxy-phenyl)phthalazin-1-yl]amino]propane-1,2-diol;
(2R)-3-[[4-(4-chloro-2-fluoro-6-hydroxy-phenyl)phthalazin-1-yl]amino]propane-1,2-diol;
(2S)-3-[[4-(2-chloro-6-hydroxy-phenyl)phthalazin-1-yl] amino]propane-1,2-diol;
(2R)-3-[[4-(2-chloro-6-hydroxy-phenyl)phthalazin-1-yl] amino]propane-1,2-diol;
(2S)-3-[[4-(2-hydroxy-4-methyl-phenyl)phthalazin-1-yl] amino]propane-1,2-diol;
(2R)-3-[[4-(2-hydroxy-4-methyl-phenyl)phthalazin-1-yl] amino]propane-1,2-diol;
(2S)-3-[[4-(2-hydroxy-5-methyl-phenyl)phthalazin-1-yl] amino]propane-1,2-diol;
(2R)-3-[[4-(2-hydroxy-5-methyl-phenyl)phthalazin-1-yl] amino]propane-1,2-diol;
(2S)-3-[[4-[2-hydroxy-4-(trifluoromethyl)phenyl]-7-methyl-phthalazin-1-yl]amino]propane-1,2-diol;
(2R)-3-[[4-[2-hydroxy-4-(trifluoromethyl)phenyl]-7-methyl-phthalazin-1-yl]amino]propane-1,2-diol;
(2S)-3-[[4-[2-hydroxy-4-(trifluoromethyl)phenyl]-6-methyl-phthalazin-1-yl]amino]propane-1,2-diol;
(2R)-3-[[4-[2-hydroxy-4-(trifluoromethyl)phenyl]-6-methyl-phthalazin-1-yl]amino]propane-1,2-diol;
2-[4-[[(1R,3R)-3-hydroxycyclopentyl]amino]phthalazin-1-yl]-5-(trifluoromethyl)phenol;
2-[4-[[(1S,3S)-3-hydroxycyclopentyl]amino]phthalazin-1-yl]-5-(trifluoromethyl)phenol;
2-[4-[[(1R,3S)-3-hydroxycyclopentyl]amino]phthalazin-1-yl]-5-(trifluoromethyl)phenol;
2-[4-[[(1S,3R)-3-hydroxycyclopentyl]amino]phthalazin-1-yl]-5-(trifluoromethyl)phenol;
2-[4-[[(1R,3R)-3-hydroxycyclopentyl]amino]phthalazin-1-yl]-5-methylsulfonyl-phenol;
2-[4-[[(1S,3S)-3-hydroxycyclopentyl]amino]phthalazin-1-yl]-5-methylsulfonyl-phenol;
2-[4-[[(1R,3S)-3-hydroxycyclopentyl]amino]phthalazin-1-yl]-5-methylsulfonyl-phenol;
2-[4-[[(1S,3R)-3-hydroxycyclopentyl]amino]phthalazin-1-yl]-5-methylsulfonyl-phenol;
2-[4-[[(1R,2S)-2-hydroxycyclopentyl]amino]phthalazin-1-yl]-5-(trifluoromethyl)phenol;
2-[4-[[(1R,2R)-2-hydroxycyclopentyl]amino]phthalazin-1-yl]-5-(trifluoromethyl)phenol;
2-[4-[[(1S,2R)-2-hydroxycyclopentyl]amino]phthalazin-1-yl]-5-(trifluoromethyl)phenol;
2-[4-[[(1S,2S)-2-hydroxycyclopentyl]amino]phthalazin-1-yl]-5-(trifluoromethyl)phenol;
2-[4-[[(1R,2S)-2-hydroxycyclohexyl]amino]phthalazin-1-yl]-5-(trifluoromethyl)phenol;
2-[4-[[(1R,2R)-2-hydroxycyclohexyl]amino]phthalazin-1-yl]-5-(trifluoromethyl)phenol;
2-[4-[[(1S,2R)-2-hydroxycyclohexyl]amino]phthalazin-1-yl]-5-(trifluoromethyl)phenol;
2-[4-[[(1S,2S)-2-hydroxycyclohexyl]amino]phthalazin-1-yl]-5-(trifluoromethyl)phenol;
(1R,2R)-2-[[4-[2-hydroxy-4-(trifluoromethyl)phenyl]phthalazin-1-yl]amino]cycloheptanol;
(1S,2S)-2-[[4-[2-hydroxy-4-(trifluoromethyl)phenyl]phthalazin-1-yl]amino]cycloheptanol;
(1R,2S)-2-[[4-[2-hydroxy-4-(trifluoromethyl)phenyl]phthalazin-1-yl]amino]cycloheptanol;
(1S,2R)-2-[[4-[2-hydroxy-4-(trifluoromethyl)phenyl]phthalazin-1-yl]amino]cycloheptanol;
2-(4-(((1R,3R)-3-hydroxycyclohexyl)amino)phthalazin-1-yl)-5-(trifluoromethyl)phenol;
2-(4-(((1S,3S)-3-hydroxycyclohexyl)amino)phthalazin-1-yl)-5-(trifluoromethyl)phenol;
2-[4-[[(1S,3R)-3-hydroxycyclohexyl]amino]phthalazin-1-yl]-5-(trifluoromethyl)phenol;
2-[4-[[(1R,3S)-3-hydroxycyclohexyl]amino]phthalazin-1-yl]-5-(trifluoromethyl)phenol;
2-(4-(((1r,3r)-3-hydroxycyclobutyl)amino)phthalazin-1-yl)-5-(trifluoromethyl)phenol;
2-[4-[[(1s,3s)-3-hydroxycyclobutyl]amino]phthalazin-1-yl]-5-(trifluoromethyl)phenol;
3-fluoro-2-(4-(((1s,3s)-3-hydroxy-3-methylcyclobutyl) amino)phthalazin-1-yl)phenol;
3-fluoro-2-(4-(((1r,3r)-3-hydroxy-3-methylcyclobutyl) amino)phthalazin-1-yl)phenol;
2-(4-(((1s,3s)-3-hydroxy-3-methylcyclobutyl)amino)phthalazin-1-yl)-5-(trifluoromethyl)phenol;
2-(4-(((1r,3r)-3-hydroxy-3-methylcyclobutyl)amino)phthalazin-1-yl)-5-(trifluoromethyl)phenol;
2-[4-[[(1R,3R)-3-hydroxy-3-methyl-cyclopentyl]amino] pyrido[3,4-d]pyridazin-1-yl]-5-(trifluoromethyl)phenol;
2-[4-[[(1R,3S)-3-hydroxy-3-methyl-cyclopentyl]amino] pyrido[3,4-d]pyridazin-1-yl]-5-(trifluoromethyl)phenol;
2-[4-[[(1S,3S)-3-hydroxy-3-methyl-cyclopentyl]amino] pyrido[3,4-d]pyridazin-1-yl]-5-(trifluoromethyl)phenol;
2-[4-[[(1S,3R)-3-hydroxy-3-methyl-cyclopentyl]amino] pyrido[3,4-d]pyridazin-1-yl]-5-(trifluoromethyl)phenol;
2-[4-[[(1S,3R)-3-hydroxycyclohexyl]amino]pyrido[3,4-d] pyridazin-1-yl]-5-(trifluoromethyl)phenol;
2-[4-[[(1S,3R)-3-hydroxycyclohexyl]amino]pyrido[3,4-d] pyridazin-1-yl]-5-(trifluoromethyl)phenol;
2-[4-[[(1R,3R)-3-hydroxycyclohexyl]amino]pyrido[3,4-d] pyridazin-1-yl]-5-(trifluoromethyl)phenol;
2-[4-[[(1S,3S)-3-hydroxycyclohexyl]amino]pyrido[3,4-d] pyridazin-1-yl]-5-(trifluoromethyl)phenol;
2-[1-[[(1R,3S)-3-hydroxycyclohexyl]amino]pyrido[3,4-d] pyridazin-4-yl]-5-(trifluoromethyl)phenol;
2-[1-[[(1S,3R)-3-hydroxycyclohexyl]amino]pyrido[3,4-d] pyridazin-4-yl]-5-(trifluoromethyl)phenol;
2-[1-[[(1R,3R)-3-hydroxycyclohexyl]amino]pyrido[3,4-d] pyridazin-4-yl]-5-(trifluoromethyl)phenol;
2-[1-[[(1S,3S)-3-hydroxycyclohexyl]amino]pyrido[3,4-d] pyridazin-4-yl]-5-(trifluoromethyl)phenol;
5-chloro-2-[4-[[(1R,3S)-3-hydroxycyclohexyl]amino] pyrido[3,4-d]pyridazin-1-yl]phenol;
5-chloro-2-[4-[[(1S,3R)-3-hydroxycyclohexyl]amino] pyrido[3,4-d]pyridazin-1-yl]phenol;
5-chloro-2-[4-[[(1R,3R)-3-hydroxycyclohexyl]amino] pyrido[3,4-d]pyridazin-1-yl]phenol;
5-chloro-2-[4-[[(1S,3S)-3-hydroxycyclohexyl]amino] pyrido[3,4-d]pyridazin-1-yl]phenol;
3-fluoro-2-[4-[[(1R,3S)-3-hydroxycyclohexyl]amino] pyrido[3,4-d]pyridazin-1-yl]-5-(trifluoromethyl)phenol;
3-fluoro-2-[4-[[(1S,3R)-3-hydroxycyclohexyl]amino] pyrido[3,4-d]pyridazin-1-yl]-5-(trifluoromethyl)phenol;
3-fluoro-2-[4-[[(1R,3R)-3-hydroxycyclohexyl]amino] pyrido[3,4-d]pyridazin-1-yl]-5-(trifluoromethyl)phenol;
3-fluoro-2-[4-[[(1S,3S)-3-hydroxycyclohexyl]amino]pyrido [3,4-d]pyridazin-1-yl]-5-(trifluoromethyl)phenol;
5-chloro-3-fluoro-2-[4-[[(1R,3S)-3-hydroxycyclohexyl] amino]pyrido[3,4-d]pyridazin-1-yl]phenol;

5-chloro-3-fluoro-2-[4-[[(1S,3R)-3-hydroxycyclohexyl]
amino]pyrido[3,4-d]pyridazin-1-yl]phenol;
5-chloro-3-fluoro-2-[4-[[(1R,3R)-3-hydroxycyclohexyl]
amino]pyrido[3,4-d]pyridazin-1-yl]phenol;
5-chloro-3-fluoro-2-[4-[[(1S,3S)-3-hydroxycyclohexyl]
amino]pyrido[3,4-d]pyridazin-1-yl]phenol;
3-fluoro-2-[4-[[(1R,3S)-3-hydroxycyclohexyl]amino]
pyrido[3,4-d]pyridazin-1-yl]phenol;
3-fluoro-2-[4-[[(1S,3R)-3-hydroxycyclohexyl]amino]
pyrido[3,4-d]pyridazin-1-yl]phenol;
3-fluoro-2-[4-[[(1R,3R)-3-hydroxycyclohexyl]amino]
pyrido[3,4-d]pyridazin-1-yl]phenol;
3-fluoro-2-[4-[[(1S,3S)-3-hydroxycyclohexyl]amino]pyrido
[3,4-d]pyridazin-1-yl]phenol;
2-[4-[[(1R,3S)-3-hydroxycyclohexyl]amino]pyrido[3,4-d]
pyridazin-1-yl]-5-(trifluoromethoxy)phenol;
2-[4-[[(1S,3R)-3-hydroxycyclohexyl]amino]pyrido[3,4-d]
pyridazin-1-yl]-5-(trifluoromethoxy)phenol;
2-[4-[[(1R,3R)-3-hydroxycyclohexyl]amino]pyrido[3,4-d]
pyridazin-1-yl]-5-(trifluoromethoxy)phenol;
2-[4-[[(1S,3S)-3-hydroxycyclohexyl]amino]pyrido[3,4-d]
pyridazin-1-yl]-5-(trifluoromethoxy)phenol;
2-[4-[[(1R,3S)-3-hydroxycyclohexyl]amino]pyrido[3,4-d]
pyridazin-1-yl]-3-(trifluoromethyl)phenol;
2-[4-[[(1S,3R)-3-hydroxycyclohexyl]amino]pyrido[3,4-d]
pyridazin-1-yl]-3-(trifluoromethyl)phenol;
2-[4-[[(1R,3R)-3-hydroxycyclohexyl]amino]pyrido[3,4-d]
pyridazin-1-yl]-3-(trifluoromethyl)phenol;
2-[4-[[(1S,3S)-3-hydroxycyclohexyl]amino]pyrido[3,4-d]
pyridazin-1-yl]-3-(trifluoromethyl)phenol;
5-ethyl-2-[4-[[(1R,3S)-3-hydroxycyclohexyl]amino]pyrido
[3,4-d]pyridazin-1-yl]phenol;
5-ethyl-2-[4-[[(1S,3R)-3-hydroxycyclohexyl]amino]pyrido
[3,4-d]pyridazin-1-yl]phenol;
5-ethyl-2-[4-[[(1R,3R)-3-hydroxycyclohexyl]amino]pyrido
[3,4-d]pyridazin-1-yl]phenol;
5-ethyl-2-[4-[[(1S,3S)-3-hydroxycyclohexyl]amino]pyrido
[3,4-d]pyridazin-1-yl]phenol;
5-cyclopropyl-2-[4-[[(1R,3S)-3-hydroxycyclohexyl]amino]
pyrido[3,4-d]pyridazin-1-yl]phenol;
5-cyclopropyl-2-[4-[[(1S,3R)-3-hydroxycyclohexyl]amino]
pyrido[3,4-d]pyridazin-1-yl]phenol;
5-cyclopropyl-2-[4-[[(1R,3R)-3-hydroxycyclohexyl]amino]
pyrido[3,4-d]pyridazin-1-yl]phenol;
5-cyclopropyl-2-[4-[[(1S,3S)-3-hydroxycyclohexyl]amino]
pyrido[3,4-d]pyridazin-1-yl]phenol;
4-fluoro-2-[4-[[(1R,3S)-3-hydroxycyclohexyl]amino]
pyrido[3,4-d]pyridazin-1-yl]-5-(trifluoromethyl)phenol;
4-fluoro-2-[4-[[(1S,3R)-3-hydroxycyclohexyl]amino]
pyrido[3,4-d]pyridazin-1-yl]-5-(trifluoromethyl)phenol;
4-fluoro-2-[4-[[(1R,3R)-3-hydroxycyclohexyl]amino]
pyrido[3,4-d]pyridazin-1-yl]-5-(trifluoromethyl)phenol;
4-fluoro-2-[4-[[(1S,3S)-3-hydroxycyclohexyl]amino]pyrido
[3,4-d]pyridazin-1-yl]-5-(trifluoromethyl)phenol;
4-fluoro-2-[4-[[(1R,2R)-2-hydroxycyclohexyl]amino]
pyrido[3,4-d]pyridazin-1-yl]-5-(trifluoromethyl)phenol;
4-fluoro-2-[4-[[(1S,2R)-2-hydroxycyclohexyl]amino]
pyrido[3,4-d]pyridazin-1-yl]-5-(trifluoromethyl)phenol;
4-fluoro-2-[4-[[(1R,2S)-2-hydroxycyclohexyl]amino]
pyrido[3,4-d]pyridazin-1-yl]-5-(trifluoromethyl)phenol;
4-fluoro-2-[4-[[(1S,2S)-2-hydroxycyclohexyl]amino]pyrido
[3,4-d]pyridazin-1-yl]-5-(trifluoromethyl)phenol;
3-fluoro-2-[4-[[(1R,2R)-2-hydroxycyclohexyl]amino]
pyrido[3,4-d]pyridazin-1-yl]-5-(trifluoromethyl)phenol;
3-fluoro-2-[4-[[(1R,2S)-2-hydroxycyclohexyl]amino]
pyrido[3,4-d]pyridazin-1-yl]-5-(trifluoromethyl)phenol;
3-fluoro-2-[4-[[(1S,2R)-2-hydroxycyclohexyl]amino]
pyrido[3,4-d]pyridazin-1-yl]-5-(trifluoromethyl)phenol;
3-fluoro-2-[4-[[(1S,2S)-2-hydroxycyclohexyl]amino]pyrido
[3,4-d]pyridazin-1-yl]-5-(trifluoromethyl)phenol;
2-[4-[[(1R,2R)-2-hydroxycyclohexyl]amino]pyrido[3,4-d]
pyridazin-1-yl]-5-(trifluoromethoxy)phenol;
2-[4-[[(1S,2S)-2-hydroxycyclohexyl]amino]pyrido[3,4-d]
pyridazin-1-yl]-5-(trifluoromethoxy)phenol;
2-[4-[[(1R,2S)-2-hydroxycyclohexyl]amino]pyrido[3,4-d]
pyridazin-1-yl]-5-(trifluoromethoxy)phenol;
2-[4-[[(1S,2R)-2-hydroxycyclohexyl]amino]pyrido[3,4-d]
pyridazin-1-yl]-5-(trifluoromethoxy)phenol;
5-chloro-3-fluoro-2-[4-[[(1R,2R)-2-hydroxycyclohexyl]
amino]pyrido[3,4-d]pyridazin-1-yl]phenol;
5-chloro-3-fluoro-2-[4-[[(1S,2S)-2-hydroxycyclohexyl]
amino]pyrido[3,4-d]pyridazin-1-yl]phenol;
5-chloro-3-fluoro-2-[4-[[(1R,2S)-2-hydroxycyclohexyl]
amino]pyrido[3,4-d]pyridazin-1-yl]phenol;
5-chloro-3-fluoro-2-[4-[[(1S,2R)-2-hydroxycyclohexyl]
amino]pyrido[3,4-d]pyridazin-1-yl]phenol;
5-chloro-2-[4-[[(1R,2R)-2-hydroxycyclohexyl]amino]
pyrido[3,4-d]pyridazin-1-yl]phenol;
5-chloro-2-[4-[[(1S,2S)-2-hydroxycyclohexyl]amino]
pyrido[3,4-d]pyridazin-1-yl]phenol;
5-chloro-2-[4-[[(1R,2S)-2-hydroxycyclohexyl]amino]
pyrido[3,4-d]pyridazin-1-yl]phenol;
5-chloro-2-[4-[[(1S,2R)-2-hydroxycyclohexyl]amino]
pyrido[3,4-d]pyridazin-1-yl]phenol;
2-(4-(((1R,3R)-3-hydroxycyclopentyl)amino)pyrido[3,4-d]
pyridazin-1-yl)-5-(trifluoromethyl)phenol;
2-(4-(((1R,3S)-3-hydroxycyclopentyl)amino)pyrido[3,4-d]
pyridazin-1-yl)-5-(trifluoromethyl)phenol;
2-(4-(((1S,3R)-3-hydroxycyclopentyl)amino)pyrido[3,4-d]
pyridazin-1-yl)-5-(trifluoromethyl)phenol;
2-(4-(((1S,3S)-3-hydroxycyclopentyl)amino)pyrido[3,4-d]
pyridazin-1-yl)-5-(trifluoromethyl)phenol;
2-[4-[[(1R,3R)-3-hydroxy-3-methyl-cyclohexyl]amino]
pyrido[3,4-d]pyridazin-1-yl]-5-(trifluoromethyl)phenol;
2-[4-[[(1R,3S)-3-hydroxy-3-methyl-cyclohexyl]amino]
pyrido[3,4-d]pyridazin-1-yl]-5-(trifluoromethyl)phenol;
2-[4-[[(1S,3R)-3-hydroxy-3-methyl-cyclohexyl]amino]
pyrido[3,4-d]pyridazin-1-yl]-5-(trifluoromethyl)phenol;
2-[4-[[(1S,3S)-3-hydroxy-3-methyl-cyclohexyl]amino]
pyrido[3,4-d]pyridazin-1-yl]-5-(trifluoromethyl)phenol;
2-(4-(((1s,3s)-3-hydroxy-3-methylcyclobutyl)amino)pyrido
[3,4-d]pyridazin-1-yl)-5-(trifluoromethoxy)phenol;
2-(4-(((1r,3r)-3-hydroxy-3-methylcyclobutyl)amino)pyrido
[3,4-d]pyridazin-1-yl)-5-(trifluoromethoxy)phenol;
3-fluoro-2-(4-(((1s,3s)-3-hydroxy-3-methylcyclobutyl)
amino)pyrido[3,4-d]pyridazin-1-yl)phenol;
3-fluoro-2-(4-(((1r,3r)-3-hydroxy-3-methylcyclobutyl)
amino)pyrido[3,4-d]pyridazin-1-yl)phenol;
3-chloro-2-fluoro-6-(4-(((1s,3s)-3-hydroxy-3-methylcy-
clobutyl)amino)pyrido[3,4-d]pyridazin-1-yl)phenol;
3-chloro-2-fluoro-6-(4-(((1r,3r)-3-hydroxy-3-methylcy-
clobutyl)amino)pyrido[3,4-d]pyridazin-1-yl)phenol;
4,5-difluoro-2-(4-(((1s,3s)-3-hydroxy-3-methylcyclobutyl)
amino)pyrido[3,4-d]pyridazin-1-yl)phenol;
4,5-difluoro-2-(4-(((1r,3r)-3-hydroxy-3-methylcyclobutyl)
amino)pyrido[3,4-d]pyridazin-1-yl)phenol;
3-fluoro-2-(4-(((1s,3s)-3-hydroxy-3-methylcyclobutyl)
amino)pyrido[3,4-d]pyridazin-1-yl)-5-(trifluoromethyl)
phenol;
3-fluoro-2-(4-(((1r,3r)-3-hydroxy-3-methylcyclobutyl)
amino)pyrido[3,4-d]pyridazin-1-yl)-5-(trifluoromethyl)
phenol;

5-chloro-2-(4-(((1s,3s)-3-hydroxy-3-methylcyclobutyl)amino)pyrido[3,4-d]pyridazin-1-yl)phenol;
5-chloro-2-(4-(((1r,3r)-3-hydroxy-3-methylcyclobutyl)amino)pyrido[3,4-d]pyridazin-1-yl)phenol;
3,5-difluoro-2-(4-(((1s,3s)-3-hydroxy-3-methylcyclobutyl)amino)pyrido[3,4-d]pyridazin-1-yl)phenol;
3,5-difluoro-2-(4-(((1r,3r)-3-hydroxy-3-methylcyclobutyl)amino)pyrido[3,4-d]pyridazin-1-yl)phenol;
2-[4-[(2-hydroxy-2-methyl-propyl)amino]pyrido[3,4-d]pyridazin-1-yl]-5-(trifluoromethyl)phenol;
5-chloro-2-[4-[(2-hydroxy-2-methyl-propyl)amino]pyrido[3,4-d]pyridazin-1-yl]phenol;
2-[4-[(2-hydroxy-2-methyl-propyl)amino]pyrido[3,4-d]pyridazin-1-yl]-5-(trifluoromethoxy)phenol;
5-chloro-3-fluoro-2-[4-[(2-hydroxy-2-methyl-propyl)amino]pyrido[3,4-d]pyridazin-1-yl]phenol;
3-fluoro-2-[4-[(2-hydroxy-2-methyl-propyl)amino]pyrido[3,4-d]pyridazin-1-yl]-5-(trifluoromethyl)phenol;
5-fluoro-2-(4-(((1R,2R)-2-hydroxycyclohexyl)amino)pyrido[3,4-d]pyridazin-1-yl)phenol;
5-fluoro-2-(4-(((1S,2S)-2-hydroxycyclohexyl)amino)pyrido[3,4-d]pyridazin-1-yl)phenol;
5-fluoro-2-(4-(((1S,2R)-2-hydroxycyclohexyl)amino)pyrido[3,4-d]pyridazin-1-yl)phenol;
5-fluoro-2-(4-(((1R,2S)-2-hydroxycyclohexyl)amino)pyrido[3,4-d]pyridazin-1-yl)phenol;
3-fluoro-2-(4-(((1R,2R)-2-hydroxycyclohexyl)amino)pyrido[3,4-d]pyridazin-1-yl)phenol;
3-fluoro-2-(4-(((1S,2S)-2-hydroxycyclohexyl)amino)pyrido[3,4-d]pyridazin-1-yl)phenol;
3-fluoro-2-(4-(((1S,2R)-2-hydroxycyclohexyl)amino)pyrido[3,4-d]pyridazin-1-yl)phenol;
3-fluoro-2-(4-(((1R,2S)-2-hydroxycyclohexyl)amino)pyrido[3,4-d]pyridazin-1-yl)phenol;
3-fluoro-2-(1-(((1R,2R)-2-hydroxycyclohexyl)amino)pyrido[3,4-d]pyridazin-4-yl)phenol;
3-fluoro-2-(1-(((1S,2S)-2-hydroxycyclohexyl)amino)pyrido[3,4-d]pyridazin-4-yl)phenol;
3-fluoro-2-(1-(((1S,2R)-2-hydroxycyclohexyl)amino)pyrido[3,4-d]pyridazin-4-yl)phenol;
3-fluoro-2-(1-(((1R,2S)-2-hydroxycyclohexyl)amino)pyrido[3,4-d]pyridazin-4-yl)phenol;
5-fluoro-2-(1-(((1R,2R)-2-hydroxycyclohexyl)amino)pyrido[3,4-d]pyridazin-4-yl)phenol;
5-fluoro-2-(1-(((1S,2S)-2-hydroxycyclohexyl)amino)pyrido[3,4-d]pyridazin-4-yl)phenol;
5-fluoro-2-(1-(((1R,2S)-2-hydroxycyclohexyl)amino)pyrido[3,4-d]pyridazin-4-yl)phenol;
5-fluoro-2-(1-(((1S,2R)-2-hydroxycyclohexyl)amino)pyrido[3,4-d]pyridazin-4-yl)phenol;
2-[4-[[(1S,2R)-2-hydroxycyclohexyl]amino]pyrido[3,4-d]pyridazin-1-yl]-5-(trifluoromethyl)phenol;
2-[4-[[(1R,2S)-2-hydroxycyclohexyl]amino]pyrido[3,4-d]pyridazin-1-yl]-5-(trifluoromethyl)phenol;
2-[4-[[(1S,2S)-2-hydroxycyclohexyl]amino]pyrido[3,4-d]pyridazin-1-yl]-5-(trifluoromethyl)phenol;
2-[4-[[(1R,2R)-2-hydroxycyclohexyl]amino]pyrido[3,4-d]pyridazin-1-yl]-5-(trifluoromethyl)phenol;
2-(4-(((1r,3r)-3-hydroxy-3-methylcyclobutyl)amino)pyrido[3,4-d]pyridazin-1-yl)-5-(trifluoromethyl)phenol;
2-(4-(((1s,3s)-3-hydroxy-3-methylcyclobutyl)amino)pyrido[3,4-d]pyridazin-1-yl)-5-(trifluoromethyl)phenol;
5-fluoro-2-(4-(((1R,3R)-3-hydroxycyclopentyl)amino)pyrido[3,4-d]pyridazin-1-yl)phenol;
5-fluoro-2-(4-(((1S,3S)-3-hydroxycyclopentyl)amino)pyrido[3,4-d]pyridazin-1-yl)phenol;
5-fluoro-2-(4-(((1R,3S)-3-hydroxycyclopentyl)amino)pyrido[3,4-d]pyridazin-1-yl)phenol;
5-fluoro-2-(4-(((1S,3R)-3-hydroxycyclopentyl)amino)pyrido[3,4-d]pyridazin-1-yl)phenol;
3-fluoro-2-(1-(((1R,3R)-3-hydroxycyclopentyl)amino)pyrido[3,4-d]pyridazin-4-yl)phenol;
3-fluoro-2-(1-(((1R,3S)-3-hydroxycyclopentyl)amino)pyrido[3,4-d]pyridazin-4-yl)phenol;
3-fluoro-2-(1-(((1S,3R)-3-hydroxycyclopentyl)amino)pyrido[3,4-d]pyridazin-4-yl)phenol;
3-fluoro-2-(1-(((1S,3S)-3-hydroxycyclopentyl)amino)pyrido[3,4-d]pyridazin-4-yl)phenol;
(2S)-3-[[1-[2-hydroxy-4-(trifluoromethyl)phenyl]pyrido[3,4-d]pyridazin-4-yl]amino]propane-1,2-diol;
(2R)-3-[[1-[2-hydroxy-4-(trifluoromethyl)phenyl]pyrido[3,4-d]pyridazin-4-yl]amino]propane-1,2-diol;
2-[8-[[(1R,3S)-3-hydroxycyclohexyl]amino]pyrido[2,3-d]pyridazin-5-yl]-5-(trifluoromethyl)phenol;
2-[8-[[(1S,3R)-3-hydroxycyclohexyl]amino]pyrido[2,3-d]pyridazin-5-yl]-5-(trifluoromethyl)phenol;
2-[8-[[(1R,3R)-3-hydroxycyclohexyl]amino]pyrido[2,3-d]pyridazin-5-yl]-5-(trifluoromethyl)phenol;
2-[8-[[(1S,3S)-3-hydroxycyclohexyl]amino]pyrido[2,3-d]pyridazin-5-yl]-5-(trifluoromethyl)phenol;
3-fluoro-2-(8-(((1s,3s)-3-hydroxy-3-methylcyclobutyl)amino)pyrido[2,3-d]pyridazin-5-yl)phenol;
3-fluoro-2-(8-(((1r,3r)-3-hydroxy-3-methylcyclobutyl)amino)pyrido[2,3-d]pyridazin-5-yl)phenol;
2-[8-[[(1R,3S)-3-hydroxycyclohexyl]amino]-2-methyl-pyrido[2,3-d]pyridazin-5-yl]-5-(trifluoromethyl)phenol;
2-[8-[[(1S,3R)-3-hydroxycyclohexyl]amino]-2-methyl-pyrido[2,3-d]pyridazin-5-yl]-5-(trifluoromethyl)phenol;
2-[8-[[(1R,3R)-3-hydroxycyclohexyl]amino]-2-methyl-pyrido[2,3-d]pyridazin-5-yl]-5-(trifluoromethyl)phenol;
2-[8-[[(1S,3S)-3-hydroxycyclohexyl]amino]-2-methyl-pyrido[2,3-d]pyridazin-5-yl]-5-(trifluoromethyl)phenol;
(S)-3-((4-(2-hydroxy-4-(trifluoromethyl)phenyl)phthalazin-1-yl)amino)-2-methylpropane-1,2-diol; and
(R)-3-((4-(2-hydroxy-4-(trifluoromethyl)phenyl)phthalazin-1-yl)amino)-2-methylpropane-1,2-diol;
or a pharmaceutically acceptable salt thereof.

In an embodiment, there is provided a compound selected from:

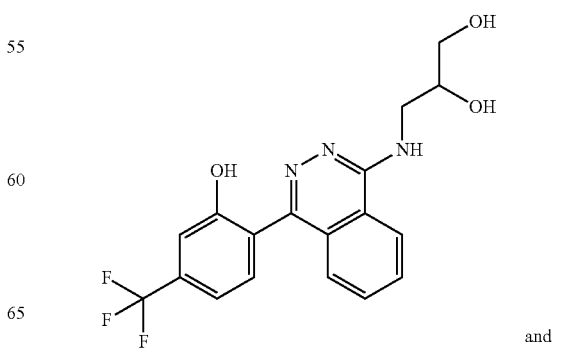

and

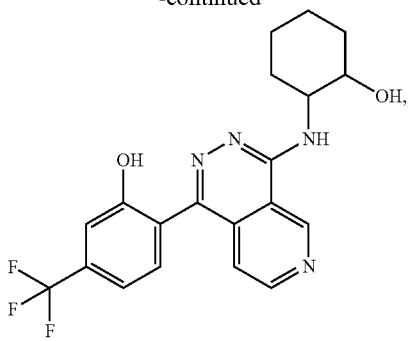

or a pharmaceutically acceptable salt thereof.

In an embodiment, there is provided a compound that is:

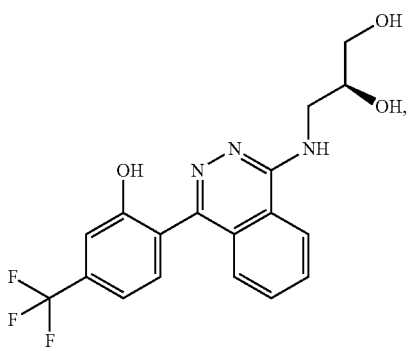 [SMILES: OC[C@@H](O)CNc1nnc(-c2ccc(C(F)(F)F)cc2O)c2ccccc12]

or a pharmaceutically acceptable salt thereof.

In an embodiment, there is provided a compound that is:

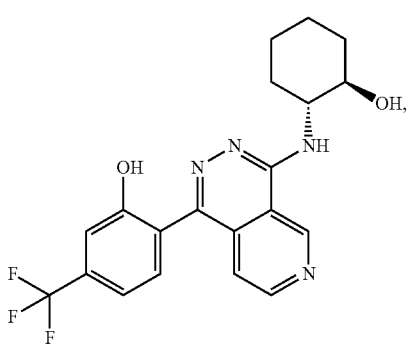 [SMILES: Oc1cc(C(F)(F)F)ccc1-c1nnc(N[C@@H]2CCCC[C@H]2O)c2cnccc12]

or a pharmaceutically acceptable salt thereof.

Terms not specifically defined herein should be understood to have the meanings that would be given to them by one of skill in the art in light of the disclosure and the context. As used in the specification, however, unless specified to the contrary, the following terms have the meaning indicated and the following conventions are adhered to. In the groups defined below, the number of carbon atoms is often specified preceding the group, for example, $C_{1-3}$ alkyl means an alkyl group or radical having 1 to 3 carbon atoms.

"Alkyl" means a saturated aliphatic branched or straight-chain hydrocarbon group having the specified number of carbon atoms. For example, $C_{1-3}$ alkyl means a group having from 1-3 carbon atoms in a linear or branched arrangement, such as —$CH_2CH_2CH_3$ or —$CH(CH_3)_2$.

"Halogen" means a fluorine (fluoro), chlorine (chloro), bromine (bromo), or iodine (iodo) radical.

The chemical names of compounds described in this specification were generated using ChemDraw® Professional version 19.0.0.22 from PerkinElmer® or Biovia Draw 2020 EE. The skilled person will understand that different chemical naming software may generate different chemical names for a particular compound. In case a compound described herein is depicted in form of a chemical name and as a formula, the formula shall prevail in case of any discrepancy.

In substituents such as —OH and —CN, "-" denotes the point of attachment of the substituent to the remainder of the molecule.

In fragments such as

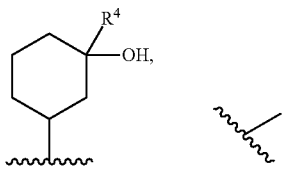

designates the point of attachment of the fragment to the remainder of the molecule.

The term "pharmaceutically acceptable" is used to specify that an object (for example a salt, dosage form or excipient) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zirich:Wiley-VCH/VHCA, 2002. A suitable pharmaceutically acceptable salt of a compound of Formula (I) is, for example, an acid-addition salt or a base-addition salt. An acid addition salt of a compound of Formula (I) may be formed by bringing the compound into contact with a suitable inorganic or organic acid under conditions known to the skilled person. An acid addition salt may for example be formed using an inorganic acid selected from the group consisting of hydrochloric acid, hydrobromic acid, sulphuric acid and phosphoric acid. An acid addition salt may also be formed using an organic acid selected from the group consisting of trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and para-toluenesulfonic acid.

Therefore, in one embodiment there is provided a compound of Formula (I) or a pharmaceutically acceptable salt thereof, where the pharmaceutically acceptable salt is a hydrochloric acid, hydrobromic acid, sulphuric acid, phosphoric acid, trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid or para-toluenesulfonic acid salt.

Compounds described in this specification may form base addition salts. A base-addition salt of a compound of Formula (I) may be formed by bringing the compound into contact with a suitable inorganic or organic base under conditions known to the skilled person. For example, it may be possible to make an alkali metal (such as sodium, potassium, or lithium) or an alkaline earth metal (such as a calcium) salt by treating a compound with an alkali metal or alkaline earth metal hydroxide or alkoxide (e.g., an ethoxide or methoxide) or a suitably basic organic amine (e.g., a choline or meglumine) in an aqueous medium. Therefore, in one embodiment there is provided a compound of Formula (I) or a pharmaceutically acceptable salt thereof, where the pharmaceutically acceptable salt is a sodium, potassium, lithium, calcium, choline or meglumine salt.

In one embodiment there is provided a compound of Formula (I), or a pharmaceutically acceptable salt thereof.

In one embodiment there is provided a compound of Formula (I).

In one embodiment there is provided a pharmaceutically acceptable salt of a compound of Formula (I).

Compounds and salts described in this specification may exist in solvated forms and unsolvated forms. For example, a solvated form may be a hydrated form, such as a hemi-hydrate, a mono-hydrate, a di-hydrate, a tri-hydrate or an alternative quantity thereof. All such solvated and unsolvated forms of compounds of Formula (I) are encompassed herein.

Atoms of the compounds and salts described in this specification may exist as their isotopes. All compounds of Formula (I) where an atom is replaced by one or more of its isotopes (for example a compound of Formula (I) where one or more carbon atoms is an $^{11}C$ or $^{13}C$ carbon isotope, or where one or more hydrogen atoms is a $^{2}H$ or $^{3}H$ isotope) are encompassed herein.

Compounds of the application may exist in one or more geometrical, optical, enantiomeric, and diastereomeric forms, including, but not limited to, cis- and trans-forms, E- and Z-forms, and R-, S- and meso-forms. Unless otherwise stated a reference to a particular compound includes all such isomeric forms, including racemic and other mixtures thereof. Where appropriate, such isomers can be separated from their mixtures by the application or adaptation of known methods (e.g. chromatographic techniques and recrystallisation techniques).

The compounds of Formula (I) may include one or more chiral centres. To the extent a structure or chemical name in this specification does not indicate chirality, the structure or name is intended to encompass any single stereoisomer corresponding to that structure or name, as well as any mixture of stereoisomers (e.g. a racemate). Where a structure in this specification includes bonds drawn as solid or hashed wedges (i.e. ▬ and ''''''''' ), it is intended that the solid and hashed wedges indicate the absolute configuration of a chiral centre, unless the "or" or "&" chiral flags are present at the chiral centre. Groups of related chiral flags are indicated with the same integer, for example "or1", "&1", "or2", "&2" etc. The skilled person will understand the meaning of chiral flags at a chiral centres. For example, the structure

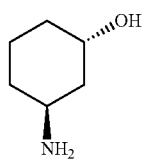

indicates that the compound is a single stereoisomer with the defined absolute configuration. As a further example, the structure

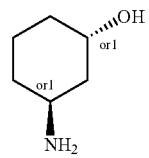

indicates that the compound is a single stereoisomer with the defined relative configuration at the flagged chiral centres, but unknown absolute configuration at the flagged chiral centres. As a further example, the structure

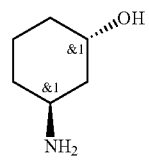

indicates that the compound is a mixture of stereoisomers having the defined relative configuration at the flagged chiral centres.

It is well-known in the art how such optically-active forms can be separated. For example, a single stereoisomer can be obtained by isolating it from a mixtures of isomers (e.g. a racemate) using, for example, chiral chromatographic separation. In other embodiments, a single stereoisomer is obtained through direct synthesis from, for example, a chiral starting material.

According to one embodiment, there is provided a compound of Formula (I), or a pharmaceutically acceptable salt thereof, which is a single enantiomer being in enantiomer excess (% ee) of ≥95%, ≥98%, or ≥99%. Conveniently a single enantiomer is present in an enantiomer excess of ≥99%.

According to one embodiment, there is provided a compound of Formula (I), or a pharmaceutically acceptable salt thereof, which is a single enantiomer being in enantiomer excess (% ee) in the range 95 to 100%.

According to one embodiment, there is provided a pharmaceutical composition, which comprises a compound of Formula (I) which is a single enantiomer being in enantiomer excess (% ee) of ≥95%, ≥98%, or ≥99% or a pharmaceutically acceptable salt thereof, in association with a pharmaceutically acceptable diluent or carrier. Conveniently, the single enantiomer is present in an enantiomer excess of ≥99%.

According to one embodiment, there is provided a pharmaceutical composition, which comprises a compound of Formula (I) which is a single enantiomer being in enantiomer excess (% ee) in the range 95 to 100%, or a pharmaceutically acceptable salt thereof, in association with a pharmaceutically acceptable diluent or carrier.

Compounds of the application may exist in one or more tautomeric forms, including, but not limited to, keto-, and enol-forms. A reference to a particular compound includes all tautomeric forms, including mixtures thereof. Accordingly, a structure depicted herein as one tautomer is intended to also include other tautomers.

The compounds of Formula (I) may be administered in the form of a prodrug, which is a compound which that is broken down in the human or animal body to release the compound of Formula (I). Such, pharmaceutically acceptable, prodrugs of compounds for Formula (I) also form an embodiment. Various forms of prodrugs are known in the art. For example, see
a) Design of Pro-drugs, edited by H. Bundgaard, (Elsevier, 1985);
b) A Textbook of Drug Design and Development, edited by Krogsgaard-Larsen and H. Bundgaard, Chapter 5 "Design and Application of Pro-drugs", by H. Bundgaard p. 113-191 (1991);
c) H. Bundgaard, *Advanced Drug Delivery Reviews*, 8, 1-38 (1992);
d) H. Bundgaard, et al., *Journal of Pharmaceutical Sciences*, 77, 285 (1988); and
e) N. Kakeya, et al., *Chem. Pharm. Bull.*, 32, 692 (1984).

In one embodiment there is provided a prodrug of a compound of Formula (I) as herein defined, or a pharmaceutically acceptable salt thereof.

In one embodiment there is provided an N-oxide of a compound of Formula (I) as herein defined, or a prodrug or pharmaceutically acceptable salt thereof.

As a result of their NLRP3 inflammasome inhibitory activity, the compounds of Formula (I), and pharmaceutically acceptable salts thereof are expected to be useful in therapy.

The term "therapy" is intended to have its normal meaning of dealing with a disease or condition in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

The term "prophylaxis" is intended to have its normal meaning and includes primary prophylaxis to prevent the development of the disease or condition and secondary prophylaxis whereby the disease or condition has already developed and the patient is temporarily or permanently protected against exacerbation or worsening of the disease or condition, or the development of new symptoms associated with the disease or condition.

The term "treatment" is used synonymously with "therapy". Similarly the term "treat" can be regarded as "applying therapy" where "therapy" is as defined herein.

Accordingly, the compounds or pharmaceutical compositions described herein may be used in therapy, for example for treating a disease or disorder. Also provided is a method of treating a disease or disorder comprising administering to a subject or patient in need thereof a therapeutically effective amount of the compounds described herein.

In one embodiment there is provided a method for treating a disease or condition in which NLRP3 inflammasome activity is implicated, in a subject in need of such treatment, which comprises administering to said subject a therapeutically effective amount of a compound of Formula (I), or a pharmaceutically acceptable salt thereof.

In one embodiment there is provided a method for treating a disease or condition selected from kidney diseases such as acute kidney injury, chronic kidney disease, and diabetic kidney disease; cardiovascular diseases such as coronary atherosclerotic heart disease, cardiomyopathy, myocardial infarction, cardiac hypertrophy, and ischaemia-reperfusion injury; liver diseases such as nonalcoholic fatty liver disease, nonalcoholic steatohepatitis, alcoholic steatohepatitis, chronic hepatitis C virus infection, and paracetamol-induced liver injury; inflammatory diseases such as autoinflammatory disorders, Cryopyrin-associated periodic syndromes, familial cold autoinflammatory syndrome (FCAS), Muckle-Wells syndrome (MWS), chronic infantile neurologic cutaneous articular (CINCA) syndrome, and neonatal onset multi-system inflammatory disease (NOMID); inflammatory skin diseases such as acne vulgaris, and hidradenitis suppurativa; inflammatory bowel diseases such as ulcerative colitis (UC), and Crohn's disease; autoimmune diseases such as gout, pseudo gout, rheumatoid arthritis (RA), multiple sclerosis (MS), Addison's disease, celiac disease, systemic lupus erythematous (SLE), and vitiligo; and respiratory diseases such as chronic pulmonary diseases, idiopathic pulmonary fibrosis (IPF), chronic obstructive pulmonary disease (COPD), and asthma, in a subject in need of such treatment, which comprises administering to said subject a therapeutically effective amount of a compound of Formula (I), or a pharmaceutically acceptable salt thereof.

In one embodiment there is provided a method for treating a disease or condition selected from acute kidney injury, chronic kidney disease, diabetic kidney disease, coronary atherosclerotic heart disease, cardiomyopathy, myocardial infarction, cardiac hypertrophy, ischaemia-reperfusion injury, nonalcoholic fatty liver disease, nonalcoholic steatohepatitis, alcoholic steatohepatitis, chronic hepatitis C virus infection, paracetamol-induced liver injury, autoinflammatory disorders, Cryopyrin-associated periodic syndromes, familial cold autoinflammatory syndrome (FCAS), Muckle-Wells syndrome (MWS), chronic infantile neurologic cutaneous articular (CINCA) syndrome, neonatal onset multi-system inflammatory disease (NOMID), acne vulgaris, hidradenitis suppurativa, ulcerative colitis (UC), Crohn's disease, gout, pseudo gout, rheumatoid arthritis (RA), multiple sclerosis (MS), Addison's disease, celiac disease, systemic lupus erythematous (SLE), vitiligo, chronic pulmonary diseases, idiopathic pulmonary fibrosis (IPF), chronic obstructive pulmonary disease (COPD), and asthma, in a subject in need of such treatment, which comprises administering to said subject a therapeutically effective amount of a compound of Formula (I), or a pharmaceutically acceptable salt thereof.

In one embodiment there is provided a compound of Formula (I), or a pharmaceutically acceptable salt thereof, for use in therapy.

In one embodiment there is provided a compound of Formula (I), or a pharmaceutically acceptable salt thereof, for use in the treatment of a subject with a disease or condition in which NLRP3 inflammasome activity is implicated.

In one embodiment there is provided a compound of Formula (I), or a pharmaceutically acceptable salt thereof, for use in the treatment of a disease or condition selected from kidney diseases such as acute kidney injury, chronic kidney disease, and diabetic kidney disease; cardiovascular diseases such as coronary atherosclerotic heart disease, cardiomyopathy, myocardial infarction, cardiac hypertrophy, and ischaemia-reperfusion injury; liver diseases such as nonalcoholic fatty liver disease, nonalcoholic steatohepatitis, alcoholic steatohepatitis, chronic hepatitis C virus infection, and paracetamol-induced liver injury; inflammatory diseases such as autoinflammatory disorders, Cryopyrin-associated periodic syndromes, familial cold autoinflammatory syndrome (FCAS), Muckle-Wells syndrome (MWS), chronic infantile neurologic cutaneous articular (CINCA) syndrome, and neonatal onset multi-system inflammatory disease (NOMID); inflammatory skin diseases such as acne vulgaris, and hidradenitis suppurativa; inflammatory bowel diseases such as ulcerative colitis (UC), and Crohn's disease; autoimmune diseases such as gout, pseudo gout, rheumatoid arthritis (RA), multiple sclerosis (MS), Addison's disease, celiac disease, systemic lupus erythematous (SLE), and vitiligo; and respiratory diseases such as chronic pulmonary diseases, idiopathic pulmonary fibrosis (IPF), chronic obstructive pulmonary disease (COPD), and asthma.

In one embodiment there is provided a compound of Formula (I), or a pharmaceutically acceptable salt thereof, for use in the treatment of a disease or condition selected from acute kidney injury, chronic kidney disease, diabetic kidney disease, coronary atherosclerotic heart disease, cardiomyopathy, myocardial infarction, cardiac hypertrophy, ischaemia-reperfusion injury, nonalcoholic fatty liver disease, nonalcoholic steatohepatitis, alcoholic steatohepatitis, chronic hepatitis C virus infection, paracetamol-induced liver injury, autoinflammatory disorders, Cryopyrin-associated periodic syndromes, familial cold autoinflammatory syndrome (FCAS), Muckle-Wells syndrome (MWS), chronic infantile neurologic cutaneous articular (CINCA) syndrome, neonatal onset multi-system inflammatory disease (NOMID), acne vulgaris, hidradenitis suppurativa, ulcerative colitis (UC), Crohn's disease, gout, pseudo gout, rheumatoid arthritis (RA), multiple sclerosis (MS), Addison's disease, celiac disease, systemic lupus erythematous (SLE), vitiligo, chronic pulmonary diseases, idiopathic pulmonary fibrosis (IPF), chronic obstructive pulmonary disease (COPD), and asthma.

In one embodiment there is provided the use of a compound of Formula (I), or a pharmaceutically acceptable salt thereof, in the manufacture of a medicament for the treatment of a disease or condition in which NLRP3 inflammasome activity is implicated.

In one embodiment there is provided the use of a compound of Formula (I), or a pharmaceutically acceptable salt thereof, in the manufacture of a medicament for the treatment of a disease or condition selected from kidney diseases such as acute kidney injury, chronic kidney disease, and diabetic kidney disease; cardiovascular diseases such as coronary atherosclerotic heart disease, cardiomyopathy, myocardial infarction, cardiac hypertrophy, and ischaemia-reperfusion injury; liver diseases such as nonalcoholic fatty liver disease, nonalcoholic steatohepatitis, alcoholic steatohepatitis, chronic hepatitis C virus infection, and paracetamol-induced liver injury; inflammatory diseases such as autoinflammatory disorders, Cryopyrin-associated periodic syndromes, familial cold autoinflammatory syndrome (FCAS), Muckle-Wells syndrome (MWS), chronic infantile neurologic cutaneous articular (CINCA) syndrome, and neonatal onset multi-system inflammatory disease (NOMID); inflammatory skin diseases such as acne vulgaris, and hidradenitis suppurativa; inflammatory bowel diseases such as ulcerative colitis (UC), and Crohn's disease; autoimmune diseases such as gout, pseudo gout, rheumatoid arthritis (RA), multiple sclerosis (MS), Addison's disease, celiac disease, systemic lupus erythematous (SLE), and vitiligo; and respiratory diseases such as chronic pulmonary diseases, idiopathic pulmonary fibrosis (IPF), chronic obstructive pulmonary disease (COPD), and asthma.

In one embodiment there is provided the use of a compound of Formula (I), or a pharmaceutically acceptable salt thereof, in the manufacture of a medicament for the treatment of a disease or condition selected from acute kidney injury, chronic kidney disease, diabetic kidney disease, coronary atherosclerotic heart disease, cardiomyopathy, myocardial infarction, cardiac hypertrophy, ischaemia-reperfusion injury, nonalcoholic fatty liver disease, nonalcoholic steatohepatitis, alcoholic steatohepatitis, chronic hepatitis C virus infection, paracetamol-induced liver injury, autoinflammatory disorders, Cryopyrin-associated periodic syndromes, familial cold autoinflammatory syndrome (FCAS), Muckle-Wells syndrome (MWS), chronic infantile neurologic cutaneous articular (CINCA) syndrome, neonatal onset multi-system inflammatory disease (NOMID), acne vulgaris, hidradenitis suppurativa, ulcerative colitis (UC), Crohn's disease, gout, pseudo gout, rheumatoid arthritis (RA), multiple sclerosis (MS), Addison's disease, celiac disease, systemic lupus erythematous (SLE), vitiligo, chronic pulmonary diseases, idiopathic pulmonary fibrosis (IPF), chronic obstructive pulmonary disease (COPD), and asthma.

The term "therapeutically effective amount" refers to an amount of a compound of Formula (I) as described in any of the embodiments herein which is effective to provide "therapy" in a subject, or to "treat" a disease or condition in a subject. The therapeutically effective amount may cause any of the changes observable or measurable in a subject as described in the definition of "therapy", "treatment" and "prophylaxis" above. As recognized by those skilled in the art, effective amounts may vary depending on route of administration, excipient usage, and co-usage with other agents. For example, where a combination therapy is used, the amount of the compound of Formula (I) or pharmaceutically acceptable salt described in this specification and the amount of the other pharmaceutically active agent(s) are, when combined, jointly effective to treat a targeted disorder or condition in the subject. In this context, the combined amounts are in a "therapeutically effective amount" if they are, when combined, sufficient to decrease the symptoms of a disease or condition responsive to inhibition of the NLRP3 inflammasome as described above. Typically, such amounts may be determined by one skilled in the art by, for example, starting with the dosage range described in this specification for the compound of Formula (I) or pharmaceutically acceptable salt thereof and an approved or otherwise published dosage range(s) of the other pharmaceutically active compound(s).

"Subjects" include, for example, mammals, for example, humans.

The compounds of Formula (I), and pharmaceutically acceptable salts thereof, may be administered as pharmaceutical compositions, comprising one or more pharmaceutically acceptable excipients.

Therefore, in one embodiment there is provided a pharmaceutical composition comprising a compound of Formula (I), or a pharmaceutically acceptable salt thereof, and at least one pharmaceutically acceptable excipient.

The excipient(s) selected for inclusion in a particular composition will depend on factors such as the mode of administration and the form of the composition provided. Suitable pharmaceutically acceptable excipients are well known to persons skilled in the art and are described, for example, in the *Handbook of Pharmaceutical Excipients*, Sixth edition, Pharmaceutical Press, edited by Rowe, Ray C; Sheskey, Paul J; Quinn, Marian. Pharmaceutically acceptable excipients may function as, for example, adjuvants, diluents, carriers, stabilisers, flavourings, colorants, fillers, binders, disintegrants, lubricants, glidants, thickening agents and coating agents. As persons skilled in the art will appreciate, certain pharmaceutically acceptable excipients may serve more than one function and may serve alternative functions depending on how much of the excipient is present in the composition and what other excipients are present in the composition.

In one embodiment there is provided a pharmaceutical composition comprising a compound of Formula (I), or a pharmaceutically acceptable salt thereof, and at least one pharmaceutically acceptable excipient, wherein the amount of pharmaceutically acceptable excipient in the composition is greater than or equal to 1 mg. In a further embodiment, the amount of pharmaceutically acceptable excipient in the composition is greater than or equal to 10 mg. In a further embodiment, the amount of pharmaceutically acceptable excipient in the composition is greater than or equal to 100 mg.

The pharmaceutical compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing), or as a suppository for rectal dosing. The compositions may be obtained by conventional procedures well known in the art. Compositions intended for oral use may contain additional components, for example, one or more colouring, sweetening, flavouring and/or preservative agents.

The compound of Formula (I) will normally be administered to a subject at a unit dose within the range 2.5-5000 mg/m$^2$ body area of the subject, or approximately 0.05-100 mg/kg, and this normally provides a therapeutically-effective dose. A unit dose form such as a tablet or capsule may contain, for example 0.1-400 mg of active ingredient. The daily dose will necessarily be varied depending upon the host treated, the particular route of administration, any therapies being co-administered, and the severity of the disease or condition being treated.

The pharmaceutical compositions described herein comprise compounds of Formula (I), or a pharmaceutically acceptable salt thereof, and are therefore expected to be useful in therapy.

As such, in one embodiment there is provided a pharmaceutical composition as disclosed herein for use in therapy.

In one embodiment there is provided a pharmaceutical composition as disclosed herein for use in the treatment of a subject with a disease or condition in which NLRP3 inflammasome activity is implicated.

In one embodiment there is provided a pharmaceutical composition as disclosed herein for use in the treatment of a disease or condition selected from kidney diseases such as acute kidney injury, chronic kidney disease, and diabetic kidney disease; cardiovascular diseases such as coronary atherosclerotic heart disease, cardiomyopathy, myocardial infarction, cardiac hypertrophy, and ischaemia-reperfusion injury; liver diseases such as nonalcoholic fatty liver disease, nonalcoholic steatohepatitis, alcoholic steatohepatitis, chronic hepatitis C virus infection, and paracetamol-induced liver injury; inflammatory diseases such as autoinflammatory disorders, Cryopyrin-associated periodic syndromes, familial cold autoinflammatory syndrome (FCAS), Muckle-Wells syndrome (MWS), chronic infantile neurologic cutaneous articular (CINCA) syndrome, and neonatal onset multi-system inflammatory disease (NOMID); inflammatory skin diseases such as acne vulgaris, and hidradenitis suppurativa; inflammatory bowel diseases such as ulcerative colitis (UC), and Crohn's disease; autoimmune diseases such as gout, pseudo gout, rheumatoid arthritis (RA), multiple sclerosis (MS), Addison's disease, celiac disease, systemic lupus erythematous (SLE), and vitiligo; and respiratory diseases such as chronic pulmonary diseases, idiopathic pulmonary fibrosis (IPF), chronic obstructive pulmonary disease (COPD), and asthma.

In one embodiment there is provided a pharmaceutical composition as disclosed herein for use in the treatment of a disease or condition selected from acute kidney injury, chronic kidney disease, diabetic kidney disease, coronary atherosclerotic heart disease, cardiomyopathy, myocardial infarction, cardiac hypertrophy, ischaemia-reperfusion injury, nonalcoholic fatty liver disease, nonalcoholic steatohepatitis, alcoholic steatohepatitis, chronic hepatitis C virus infection, paracetamol-induced liver injury, autoinflammatory disorders, Cryopyrin-associated periodic syndromes, familial cold autoinflammatory syndrome (FCAS), Muckle-Wells syndrome (MWS), chronic infantile neurologic cutaneous articular (CINCA) syndrome, neonatal onset multi-system inflammatory disease (NOMID), acne vulgaris, hidradenitis suppurativa, ulcerative colitis (UC), Crohn's disease, gout, pseudo gout, rheumatoid arthritis (RA), multiple sclerosis (MS), Addison's disease, celiac disease, systemic lupus erythematous (SLE), vitiligo, chronic pulmonary diseases, idiopathic pulmonary fibrosis (IPF), chronic obstructive pulmonary disease (COPD), and asthma.

Synthetic Methods

The compounds of Formula (I) may be prepared according to the procedures of the following schemes, using appropriate materials, and are further exemplified by the specific examples provided herein. Moreover, by utilising the procedures described herein, one of ordinary skill in the art can readily prepare additional compounds that fall within the scope of the present claims. The examples further illustrate details for the preparation of the compounds disclosed herein. Those skilled in the art will readily understand that known variations of the conditions and processes of the following preparative procedures can be used to prepare these compounds.

The compounds exemplified herein may also be isolated in the form of their pharmaceutically acceptable salts, such as those described previously herein.

It may be necessary to protect reactive functional groups (e.g. hydroxy) in intermediates used in the preparation of compounds of Formula (I) to avoid their unwanted participation in a reaction leading to the formation of the compounds. Conventional protecting groups, for example those described by P. G. M. Wuts in "Greene's Protective Groups in Organic Synthesis", Fifth Edition., John Wiley & Sons Inc., 2014, may be used. For example, where a phenolic hydroxy group is protected as a methyl ether, the protecting group may be removed by using BBr$_3$ in dichloromethane. Benzyl protecting groups may be removed by hydrogenation over a palladium catalyst, and paramethoxybenzyl groups may be removed using HCl in an alcohol. Acetal protecting groups of diols may be removed by treatment with an acid (for example AcOH/H$_2$O, or HCl in 1,4-dioxane).

Scheme 1

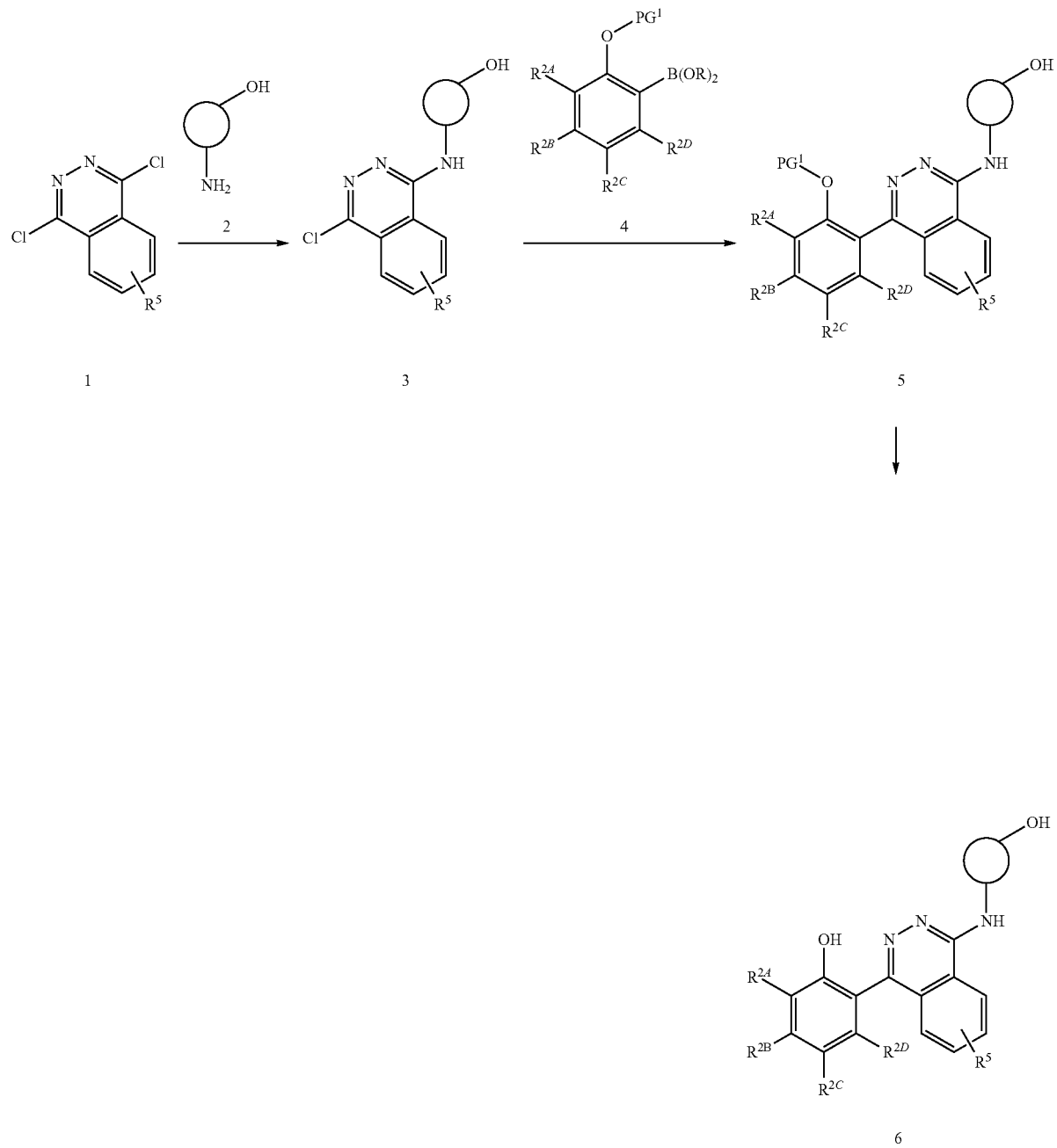

Compound 6 can be prepared by the process illustrated in Scheme 1. Compound 1 can react with an aminoalcohol (2) in the presence of a base (such as DIPEA) in a polar solvent (such as NMP) to afford compound 3. When $R^5$ is not —H, the resulting regioisomers may be separated using appropriate separation techniques such as chromatography. Compound 3 can react with an optionally protected aryl boronic acid/boronate ester (4) in a Suzuki cross-coupling reaction in the presence of a suitable transition metal catalyst to afford compound 5. $PG^1$ is an appropriate phenolic hydroxy protecting group such as methyl, benzyl or 4-methoxybenzyl. Compound 6 is afforded by removal of the $PG^1$ protecting group (when present) using appropriate conditions.

Scheme 2

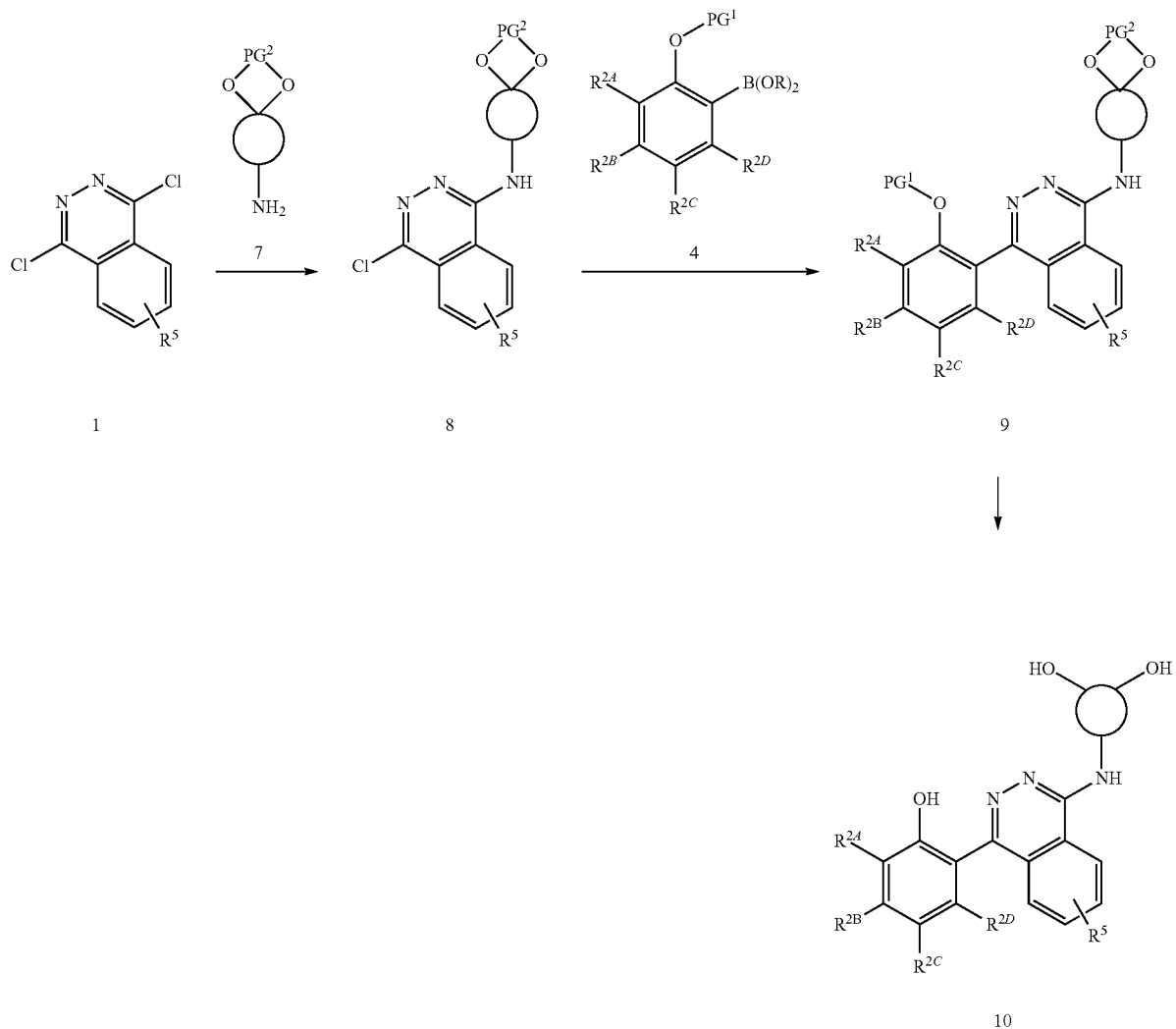

Compound 10 can be prepared by the process illustrated in Scheme 2. Compound 1 can react with an optionally protected aminodiol (7) in the presence of a base (such as DIPEA) in a polar solvent (such as NMP) to afford compound 8. $PG^2$ is an appropriate protecting group for a diol, such as an acetal. When $R^5$ is not —H, the resulting regioisomers may be separated using appropriate separation techniques such as chromatography. Compound 8 can react with an optionally protected aryl boronic acid/boronate ester (4) in a Suzuki cross-coupling reaction in the presence of a suitable transition metal catalyst to afford compound 9. $PG^1$ is an appropriate phenolic hydroxy protecting group such as methyl, benzyl or 4-methoxybenzyl. Compound 10 is afforded by removal of the $PG^1$ and $PG^2$ protecting groups (when present) using appropriate conditions. Alternatively, an unprotected aminodiol may be used in the first step, and protecting group $PG^2$ introduced before the Suzuki cross-coupling reaction.

Aza derivatives of compounds 6 and 10 can be prepared using the processes illustrated in Scheme 1 and Scheme 2 using compounds 11 and 12 instead of compound 1, and separating the resulting regioisomers using appropriate separation techniques such as chromatography.

11

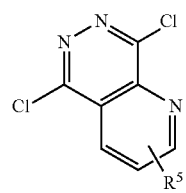

12

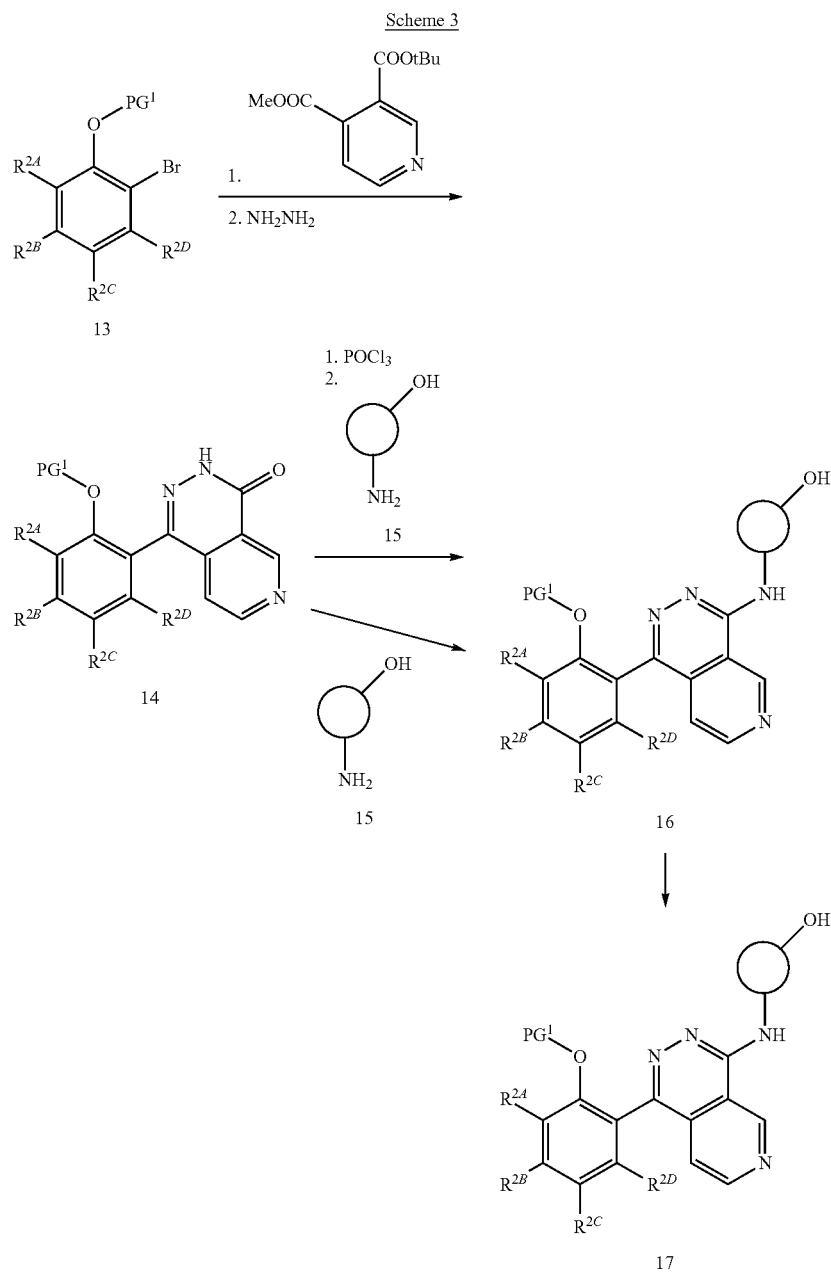

Compound 17 can be prepared by the process illustrated in Scheme 3. Compound 14 is afforded by lithium-halogen exchange of compound 13 with an alkyllithium (such as n-BuLi) in a solvent such as THF, followed by addition to 3-(tert-butyl) 4-methyl pyridine-3,4-dicarboxylate, and reaction with hydrazine to afford compound 14. $PG^1$ is an appropriate phenolic hydroxy protecting group such as methyl, benzyl or 4-methoxybenzyl. Compound 16 may be chlorinated with a chlorinating agent such as phosphoryl trichloride in the presence of a base (such as pyridine) and a solvent (such as 1,4-dioxane), followed by reaction with aminoalcohol 15 in the presence of a base (such as triethylamine) and a polar solvent (such as MeCN). Alternatively, compound 16 may be afforded by coupling with aminoalcohol 15 in the presence of a coupling reagent (such as BOP) and a base (such as DBU) in the presence of a polar solvent (such as DMF). Compound 17 is afforded by removal of the $PG^1$ protecting group from compound 16 using appropriate conditions.

In Schemes 1-3 above,

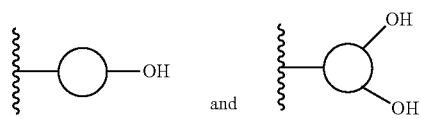

represent $R^1$ as described herein.

EXAMPLES

The compounds described in this specification are further illustrated in the following Examples. These Examples are given by way of illustration only and are non-limiting.

In the examples, high resolution mass spectra were recorded on a Micromass LCT mass spectrometer equipped with an electrospray interface (LC-HRMS).

$^1$H NMR measurements were performed on Bruker Avance III 300, 400, 500 and 600 spectrometers, operating at $^1$H frequencies of 300, 400, 500 and 600 MHz, respectively. The experiments were typically recorded at 25° C. Chemical shifts are given in ppm with the solvent as internal standard. Protons on heteroatoms such as NH and OH protons are only reported when detected in NMR and can therefore be missing. The following abbreviations have been used (and derivatives thereof, e.g. dd, doublet of doublets, etc.): s, singlet; d, doublet; t, triplet; q, quartet; m, multiplet; br, broad; qn, quintet; p, pentet.

Flash chromatography was performed using either normal phase silica FLASH+® (40M, 25M or 12M), Biotage® SNAP Cartridges KP-Sil (340, 100, 50 or 10), Biotage® SNAP Cartridges KP-NH (340, 100, 50 or 10), or Agela® Flash Column Silica-CS Cartridges (330, 180, 120, 80) unless otherwise stated.

Reversed phase flash chromatography was performed using Agela® C-18 spherical 20-35 μm 100 A cartridges unless otherwise stated.

Purifications were performed by preparative HPLC, preparative SFC or reversed phase flash chromatography on a standard equipment, using MS or UV triggered fraction collection, and using stated conditions.

In general, all solvents used were commercially available and of analytical grade. Anhydrous solvents were routinely used for reactions.

Microwave reactions were performed on a Biotage® Initator+ using the adequate glass reactor.

The Intermediates and Examples named below were named using ChemDraw Professional version 19.0.0.22 from PerkinElmer or Biovia Draw 2020 EE. The skilled person will understand that different chemical naming software may generate different chemical names for a particular compound.

List of Abbreviations

AcOH=acetic acid
aq.=aqueous
BOP=(Benzotriazol-1-yloxy)tris(dimethylamino)phosphonium hexafluorophosphate
d=days
DBU=1,8-Diazabicyclo[5.4.0]undec-7-ene
DCM=Dichloromethane
DIPEA=N,N-Diisopropylethylamine
DMAP=Dimethylaminopyridine
DME=Dimethoxyethane
DMF=Dimethylformamide
DMSO=Dimethylsulfoxide
DMSO-d6=Hexadeuterodimethyl sulfoxide
Et$_2$O=Diethyl ether
EtOAc=Ethyl acetate
EtOH=Ethanol
h=hours
HPLC=High Performance Liquid Chromatography
IPA=2-propanol
IPE=isopropyl ether
iPrOAc=Isopropyl acetate
KOAc=potassium acetate
LCMS=Liquid Chromatography Mass Spectrometry
MeCN=acetonitrile
MeLi=Methyl lithium
MeOH=Methanol
min=minutes
MS (ESI)/HRMS (ESI)=Mass spectrometry (electrospray ionisation)/High resolution mass spectrometry
MTBE=tert-Butyl methylether
NaOAc=Sodium acetate
n-BuLi=1-Butyl lithium
n-BuNH$_2$=1-Butylamine
NMP=N-Methyl-2-pyrrolidone
Pd/C=Palladium on carbon
PdCl$_2$(Amphos)$_2$=Bis(di-tert-butyl(4-dimethylaminophenyl)phosphine)dichloropalladium(II)
Pd(dppf)Cl$_2$=[1,1'-Bis(diphenylphosphino)ferrocene]dichloropalladium(II)
Pd(dppf)Cl$_2$·CH$_2$Cl$_2$=[1,1'-Bis(diphenylphosphino)ferrocene]dichloropalladium(II), complex with dichloromethane
Pd(PPh$_3$)$_4$=Tetrakis(triphenylphosphine)palladium(0)
PMBCl=4-methoxybenzyl chloride
rt=room temperature
RT=retention time
sat.=saturated
SFC=Supercritical Fluid Chromatography
SPhos Pd G3=(2-Dicyclohexylphosphino-2',6'-dimethoxybiphenyl) [2-(2'-amino-1,1'-biphenyl)]palladium(II) methanesulfonate
TEA=triethylamine
TFA=trifluoroacetic acid
THF=tetrahydrofuran
TLC=Thin Layer chromatography
Xphos Pd G3=(2-dicyclohexylphosphino-2',4',6'-triisopropyl-1,1'-biphenyl)[2-(2'-amino-1,1'-biphenyl)]palladium(II) methanesulfonate

Intermediates

Intermediate 1

Step 1: Intermediate 2: tert-butyl 4-[2-methoxy-4-(trifluoromethyl)benzoyl]pyridine-3-carboxylate

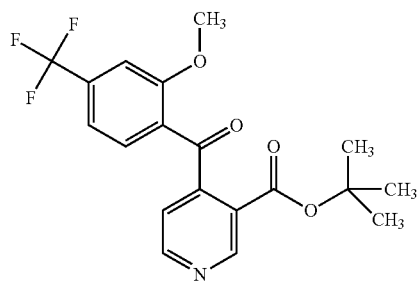 [SMILES: COc1cc(C(F)(F)F)ccc1C(=O)c1ccncc1C(=O)OC(C)(C)C]

To a solution of 1-bromo-2-methoxy-4-(trifluoromethyl)benzene (37.7 g, 148.0 mmol, 1.0 eq) in THF (100 mL) was added n-BuLi (100 mL, 158.0 mmol, 1.1 eq) (1.6 M in hexanes) at −78° C. and the solution was stirred at −78° C. After 10 min, 03-tert-butyl 04-methyl pyridine-3,4-dicarboxylate (35.1 g, 148.0 mmol, 1.0 eq) in THF (20 mL) was added dropwise by syringe during 20 min and the reaction mixture was stirred at −78° C. for 2 h. To the mixture was added AcOH (9.1 mL) in 350 mL H₂O at −78° C., and the reaction mixture was allowed to reach rt. To the mixture was added EtOAc and the two phases were separated, and aqueous phase was extracted with EtOAc. The organic phase was dried over Na₂SO₄ and evaporated to give the title compound (57.5 g, 62%) as a brown oil. MS (ESI): m/z [M+H]⁺: 382.2.

Step 2: Intermediate 3: 1-[2-methoxy-4-(trifluoromethyl)phenyl]-3H-pyrido[3,4-d]pyridazin-4-one

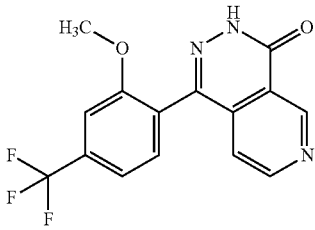 [SMILES: COc1cc(C(F)(F)F)ccc1-c1n[nH]c(=O)c2cnccc12]

Intermediate 2 (57.4 g, 91.8 mmol, 61 wt % purity) was dissolved in EtOH (306 mL) and hydrazine monohydrate (26.8 mL, 551.1 mmol, 6.0 eq) was added and the mixture was stirred for 10 min, then 4.0 M NaOH aq. (92.0 mL, 367.4 mmol, 6.0 eq) was added. The reaction mixture was stirred at rt for 2 h. The mixture was added AcOH (31.5 mL, 551.1 mmol, 6.0 eq) and product started to precipitate. The reaction mixture was filtered, and the solid was washed with EtOH/H₂O (1:1, 400 mL) and dried to give the title compound (21.7 g, 68%) as a pale-yellow solid. MS (ESI): m/z [M+H]⁺: 322.1. ¹H NMR (400 MHz, DMSO-d6) δ 3.81 (s, 3H), 7.21 (dd, 1H), 7.47-7.54 (m, 2H), 7.63 (d, 1H), 8.94 (d, 1H), 9.51 (d, 1H), 13.24 (br s, 1H).

Step 3: Intermediate 1: 4-chloro-1-[2-methoxy-4-(trifluoromethyl)phenyl]pyrido[3,4-d]pyridazine

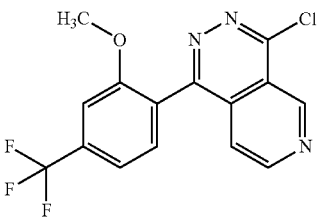 [SMILES: COc1cc(C(F)(F)F)ccc1-c1nnc(Cl)c2cnccc12]

To a suspension of Intermediate 3 (32 g, 100 mmol) in 1,4-dioxane (100 mL) and phosphoryl trichloride (200 g, 1304 mmol) was added pyridine (12 mL, 149.6 mmol) at rt. The mixture was heated to 110° C. and stirred for 1 h. The mixture was concentrated in vacuo and then the residue was azeotropic with toluene. The residue was dissolved in CHCl₃ (amylene added) and brine, and the layer was separated. The aqueous layer was extracted with EtOAc, combined organic layer was dried over Na₂SO₄ and concentrated in vacuo. The residue was azeotropic with toluene, and then the crude mixture was triturated with hexane/EtOAc (8:2) and filtered to give the Intermediate 1 (22.3 g, 66%) as a brown solid. MS (ESI): m/z [M+H]⁺: 340.1/342.1. ¹H NMR (400 MHz, CDCl₃) δ 3.78 (s, 3H), 7.31 (s, 1H), 7.43 (dd, 1H), 7.45-7.49 (m, 1H), 7.63 (dd, 1H), 9.04 (d, 1H), 9.82 (d, 1H).

Intermediates 4 and 5

Step 1: Intermediate 6: tert-butyl N-[(1R,3S)-3-hydroxycyclopentyl]carbamate

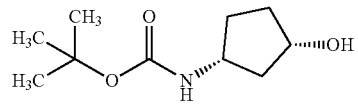

To a solution of (1S,3R)-3-aminocyclopentanol hydrochloride (3.0 g, 21.8 mmol) and TEA (6.1 mL, 43.6 mmol) in THF (50 mL) was added di-tert-butyl dicarbonate (5.7 g, 26.2 mmol) at rt. The mixture was heated to 60° C. and stirred for 16 h. The reaction mixture was cooled to rt, and filtrated. The filtrate was concentrated in vacuo. The residue was purified by silica gel column chromatography using a gradient of 40-100% EtOAc in hexane as mobile phase to give the title compound (4.3 g, 97%) as a colorless syrup. MS (ESI): m/z [M+H]⁺: 202.0. ¹H NMR (400 MHz, CDCl₃) δ 1.44 (s, 9H), 1.57-1.67 (m, 1H), 1.70-1.83 (m, 2H), 1.87-2.12 (m, 2H), 2.31-2.52 (m, 1H), 3.96-4.09 (m, 1H), 4.31-4.42 (m, 1H), 5.05-5.33 (m, 1H).

Step 2: Intermediate 7: tert-butyl N-[(1R)-3-oxocyclopentyl]carbamate

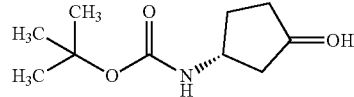

To a solution of Intermediate 6 (4.3 g, 21.1 mmol) in CH₂Cl₂ (100 mL) was added (1,1-diacetoxy-3-oxo-1λ⁵,2-benziodoxol-1-yl) acetate (13.5 g, 31.8 mmol) slowly at 0° C. The reaction mixture was stirred for 2 h at 0° C. The reaction mixture was quenched with sat. aq. NaHCO₃ and stirred for 20 min and then the mixture was added sat. aq. Na₂S₂O₃ and stirred for 20 min. The mixture was extracted with CHCl₃. The organic layer was washed with brine, dried over Na₂SO₄, and concentrated in vacuo. The residue was purified by column chromatography using a gradient of 10-60% EtOAc in hexane as mobile phase to give the title compound (3.8 g, 90%) as a colorless powder. ¹H NMR (400 MHz, CDCl₃) δ 1.45 (s, 9H), 1.78-1.91 (m, 1H), 2.07-2.16 (m, 1H), 2.17-2.29 (m, 1H), 2.30-2.43 (m, 2H), 2.62 (dd, 1H), 4.23 (br d, 1H), 4.64 (br s, 1H).

Step 3: Intermediate 4: tert-butyl N-[(1R,3S)-3-hydroxy-3-methyl-cyclopentyl]carbamate and Intermediate 5: tert-butyl N-[(1R,3R)-3-hydroxy-3-methyl-cyclopentyl]carbamate

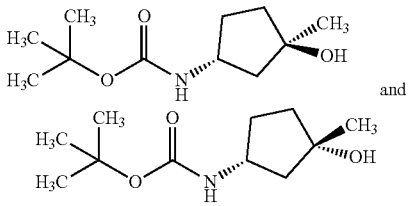

To a solution of Intermediate 7 (3.8 g, 19.0 mmol) in THF (160 mL) was added MeLi (24.5 mL, 3.1 mol/L in Et$_2$O, 76 mmol) dropwise at −78° C. and the mixture was stirred at −78° C. After 1 h, to the reaction mixture was added MeLi (24.5 mL, 3.1 mol/L in Et$_2$O, 76 mmol) dropwise at −78° C. and the mixture was stirred at −78° C. for 1 h. To the mixture was added sat NH$_4$Cl aq. and the mixture was warmed to rt. The mixture was extracted with EtOAc, washed by brine, dried over Na$_2$SO$_4$ and concentrated in vacuo. The residue was purified by silica gel column chromatography using a gradient of 20-70% EtOAc in hexane as mobile phase to give Intermediate 4 (926 mg, 23%) as a colorless liquid and Intermediate 5 (779 mg, 19%) as a colorless liquid.

Intermediate 4: $^1$H NMR (400 MHz, CDCl$_3$) δ 1.36 (s, 3H), 1.43 (s, 9H), 1.54-1.62 (m, 1H), 1.63-1.70 (m, 1H), 1.73-1.86 (m, 2H), 1.87-1.97 (m, 1H), 2.06-2.16 (m, 1H), 2.44 (br s, 1H), 3.96-4.16 (m, 1H), 5.30 (br s, 1H).

Intermediate 5: $^1$H NMR (400 MHz, CDCl$_3$) δ 1.37 (s, 3H), 1.44 (s, 11H), 1.66-1.84 (m, 2H), 1.95-2.04 (m, 1H), 2.11-2.20 (m, 1H), 2.21-2.33 (m, 1H), 4.11-4.30 (m, 1H), 4.55 (br s, 1H).

Intermediate 8: 3-(tert-butyl) 4-methyl pyridine-3,4-dicarboxylate

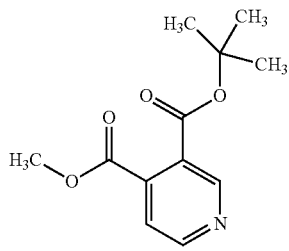 [SMILES: COC(=O)c1ccncc1C(=O)OC(C)(C)C]

Tert-butanol (200 mL) was added to 4-(methoxycarbonyl) nicotinic acid (25.0 g, 138 mmol) followed by the addition of di-tert-butyl dicarbonate (60.2 g, 276 mmol) and pyridine (25 mL). DMAP (100 mg, cat.) was added and the reaction stirred at 35° C. overnight. Water and iPrOAc were added and the two phases separated. The organic extract was washed with two portions of water, evaporated and the residue was evaporated two times with toluene. The residue was filtered through a column of silica using 40% MTBE in heptane as mobile phase to afford the title compound (27.7 g, 84%) as a pale yellow oil. $^1$H NMR (500 MHz, DMSO-d6) δ 1.52 (s, 9H), 3.88 (s, 3H), 7.65 (dd, 1H), 8.87 (d, 1H), 8.96 (d, 1H).

Intermediate 9: 2-[2-fluoro-6-methoxy-4-(trifluoromethyl)phenyl]-4,4,5,5-tetramethyl-1,3,2-dioxaborolane

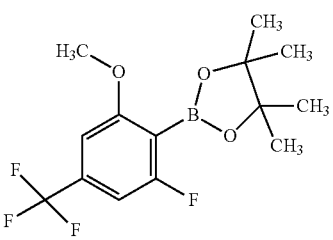 [SMILES: COc1cc(C(F)(F)F)cc(F)c1B1OC(C)(C)C(C)(C)O1]

To a solution of 1-fluoro-3-methoxy-5-(trifluoromethyl) benzene (2.00 g, 10.3 mmol) in THF (20 mL) was added n-BuLi (6.5 mL, 10.3 mmol) at −78° C. and the mixture was stirred at −78° C. After 1 h, to the reaction mixture was added 2-isopropoxy-4,4,5,5-tetramethyl-1,3,2-dioxaborolane (2.3 mL, 11.0 mmol) at −78° C. and the mixture was stirred at −78° C. for 2 h. To the mixture were added 10% citric acid aq. and EtOAc, and the mixture was warmed to rt, extracted with EtOAc, washed by brine, dried over Na$_2$SO$_4$ and filtered. The solvent was evaporated under reduced pressure. The crude mixture was triturated with IPE and filtered to give the title compound (1055 mg, 32%) as a colorless powder. The solvent was evaporated under reduced pressure and the crude mixture was purified by silica gel column chromatography using a gradient of 20-50% EtOAc in hexane as mobile phase to give the title compound (1814 mg, 55%) as a colorless powder. MS (ESI): m/z [M−C$_6$H$_{11}$]$^-$ 237.0. $^1$H NMR (400 MHz, CDCl$_3$) δ 1.39 (s, 12H), 3.85 (s, 3H), 6.83 (s, 1H), 6.91 (dd, 1H).

Intermediate 10: [2-fluoro-6-hydroxy-4-(trifluoromethyl)phenyl]boronic acid

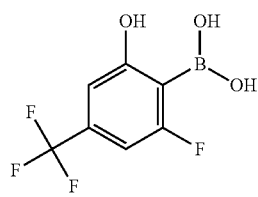 [SMILES: OB(O)c1c(O)cc(C(F)(F)F)cc1F]

To a solution of Intermediate 9 (614.6 mg, 1.9 mmol) in CH$_2$Cl$_2$ (4 mL) at 0° C. was added BBr$_3$ (6.0 mL, 6.0 mmol, 1 M in CH$_2$Cl$_2$) and stirred at 0° C. for 1 h. The reaction mixture was poured into ice water and extracted with CHCl$_3$. The organic layer was separated and concentrated in vacuo. The residue was triturated with hexane and filtered to give the tittle compound (285 mg, 50%) as a pink powder. MS (ESI): m/z [M−H]$^-$ 222.9. $^1$H NMR (400 MHz, CDCl$_3$) δ 5.87 (br d, 2H), 6.83 (dd, 1H), 7.00 (s, 1H), 9.07 (s, 1H).

Intermediate 11: (4-chloro-2-fluoro-6-hydroxy-phenyl)boronic acid

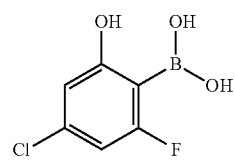 [SMILES: OB(O)c1c(O)cc(Cl)cc1F]

The title compound (2.2 g, 77%) as a white powder was prepared analogous to Intermediate 10 using (4-chloro-2-fluoro-6-methoxy-phenyl)boronic acid (3.0 g, 14.7 mmol). MS (ESI): m/z [M−H]$^-$ 188.9/190.9. $^1$H NMR (400 MHz, CD$_3$OD) δ 3.37 (s, 1H), 6.59-6.66 (m, 2H).

Intermediate 12: 1-bromo-4-cyclopropyl-2-methoxy-benzene

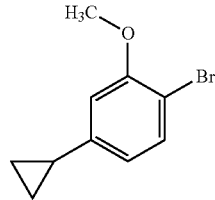

To a suspension of 1-bromo-4-iodo-2-methoxy-benzene (2.0 g, 6.4 mmol) and potassium; cyclopropyl(trifluoro)boranuide (1.4 g, 9.7 mmol) in toluene (12 mL) and $H_2O$ (6 mL) was added $Cs_2CO_3$ (6.3 g, 19.3 mmol), butyldi-1-adamantylphosphine (230 mg, 0.64 mmol) and diacetoxypalladium (74 mg, 0.33 mmol) at rt. The mixture was heated at 100° C. and stirred for 6 h. The reaction mixture was cooled to rt and added $H_2O$, and the mixture was extracted with EtOAc. The organic layer was washed with brine, dried over $Na_2SO_4$ and concentrated in vacuo. The residue was purified by silica gel column chromatography using a gradient of 0-10% EtOAc in hexane as mobile phase to give the title compound (992.7 mg, 48%) as a brown liquid. MS (ESI): m/z [M–H]$^-$ no detected. $^1$H NMR (400 MHz, CDCl$_3$) δ 0.65-0.71 (m, 2H), 0.95-1.01 (m, 2H), 1.82-1.92 (m, 1H), 3.88 (s, 3H), 6.53 (dd, 1H), 6.65 (d, 1H), 7.38 (d, 1H).

Intermediate 13: 2-(4-cyclopropyl-2-methoxy-phenyl)-4,4,5,5-tetramethyl-1,3,2-dioxaborolane

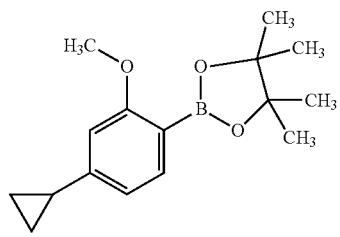 [SMILES: COc1cc(C2CC2)ccc1B1OC(C)(C)C(C)(C)O1]

The title compound (371 mg, 43%) as a brown solid was prepared analogous to Intermediate 9 using Intermediate 12 (987.2 mg, 3.1 mmol). MS (ESI): m/z [M+H]$^+$ 275.1. $^1$H NMR (400 MHz, CDCl$_3$) δ 0.70-0.75 (m, 2H), 0.93-1.00 (m, 2H), 1.33 (s, 12H), 1.88 (tt, 1H), 3.82 (s, 3H), 6.59 (d, 1H), 6.62 (dd, 1H), 7.57 (d, 1H).

Intermediate 14: 2-[5-fluoro-2-methoxy-4-(trifluoromethyl)phenyl]-4,4,5,5-tetramethyl-1,3,2-dioxaborolane

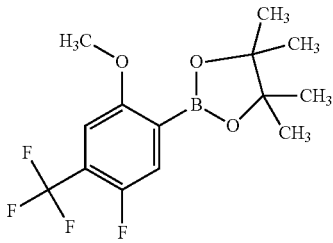 [SMILES: COc1cc(C(F)(F)F)c(F)cc1B1OC(C)(C)C(C)(C)O1]

To a solution of 1-fluoro-5-iodo-4-methoxy-2-(trifluoromethyl)benzene (2.8 g, 8.8 mmol) in 1,4-dioxane (30 mL) were added 4,4,5,5-tetramethyl-2-(4,4,5,5-tetramethyl-1,3,2-dioxaborolan-2-yl)-1,3,2-dioxaborolane (2.8 g, 11.0 mmol), KOAc (2.5 g, 25.4 mmol) and Pd(dppf)Cl$_2$·CH$_2$Cl$_2$ (689 mg, 0.84 mmol) at rt. The mixture was heated at 100° C. and stirred for 4 h. The reaction mixture was cooled to rt and added $H_2O$, and the mixture was filtered. The filtrate was extracted with EtOAc (2 times). The organic layer was washed with brine, dried over $Na_2SO_4$ and concentrated in vacuo. The residue was purified by silica gel column chromatography using a gradient of 10-40% EtOAc in hexane as mobile phase to give a brown gum. The resulted was triturated with EtOAc and filtered. The filtrate was concentrated in vacuo to give title compound (459.7 mg, 16%) as a black gum. MS (ESI): m/z [M–H]$^-$ no detected. $^1$H NMR (400 MHz, CDCl$_3$) δ 1.36 (s, 12H), 3.85 (s, 3H), 6.99 (d, 1H), 7.46 (d, 1H).

Intermediate 15

Step 1: Intermediate 16: 2-benzyloxy-1-bromo-4-methylsulfonyl-benzene

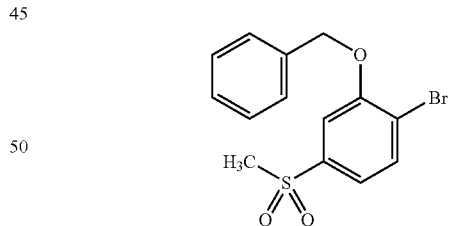

To a suspension of sodium hydride (60% in mineral oil, 1.9 g, 48.0 mmol, 1.1 eq) in DMF (80 mL, 0.5 M), benzyl alcohol (5.0 mL, 48.0 mmol, 1.1 eq) was added at 0° C., and the solution was stirred for 5 min. Then, 2-bromo-5-methylsulfonylphenol (11.1 g, 43.9 mmol, 1.0 eq) was added to the mixture at 0° C. The mixture was warmed to rt and stirred for 2 h. The reaction mixture was cooled to 0° C., and then added $H_2O$ (100 mL) slowly. The precipitate was collected by filtration and washed with $H_2O$ (100 mL). The precipitate was washed with hexane/EtOAc=48/2 (300 mL) to give the title compound (16.3 g, 47.7 mmol, quant.) as a white solid. MS (ESI): m/z [M+H]$^+$ 338.7/340.9.

Step 2: Intermediate 15: 2-(2-Benzyloxy-4-methyl-sulfonyl-phenyl)-4,4,5,5-tetramethyl-1,3,2-dioxaborolane

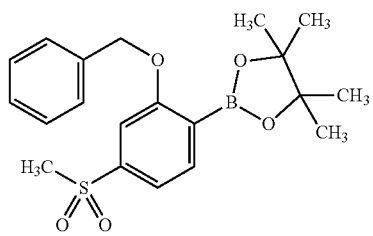 [SMILES: CC1(C)OB(c2ccc(S(C)(=O)=O)cc2OCc2ccccc2)OC1(C)C]

To a solution of Intermediate 16 (13.9 g, 40.6 mmol, 1.0 eq) in 1,4-dioxane (135 mL), bis(pinacolato)diboron (15.5 g, 60.9 mmol, 1.5 eq), KOAc (10.0 g, 102.0 mmol, 2.5 eq) and Pd(dppf)Cl$_2$·CH$_2$Cl$_2$ (1.7 g, 2.0 mmol, 0.05 eq) was added at rt. The mixture was heated to 110° C. and stirred for 26 h. The reaction mixture was cooled to rt and filtered through Celite®. The insolubles were washed with EtOAc (300 mL). The filtrate was washed with H$_2$O (100 mL) and brine (30 mL). The organic layer was dried over Na$_2$SO$_4$ and concentrated in vacuo. The residue was purified by silica gel column chromatography using a gradient of 20-40% EtOAc in hexane as mobile phase to give a pale-yellow syrup. Then, the resulted syrup was crystallized with hexane to give the title compound (11.0 g, 69%) as a white powder; MS (ESI): m/z [M+H]$^+$ 389.3.

EXAMPLES

Example 1

Step 1: Intermediate 17: 4-chloro-N-[[(4S)-2,2-dimethyl-1,3-dioxolan-4-yl]methyl]phthalazin-1-amine

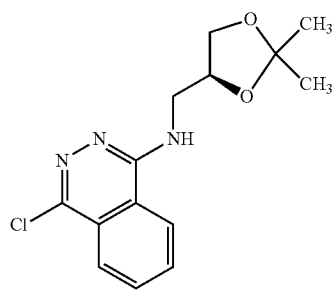 [SMILES: CC1(C)OC[C@H](CNc2nnc(Cl)c3ccccc23)O1]

To a solution of 1,4-dichlorophthalazine (177 g, 889 mmol, 1.0 eq) in anhydrous NMP (450 mL) were added DIPEA (310 mL, 1.78 mmol, 2.0 eq) and (S)-(2,2-dimethyl-1,3-dioxolan-4-yl)methanamine (123 g, 938 mmol, 1.05 eq) at rt and the mixture was stirred at 110° C. for 5 h. The reaction mixture was cooled to rt and poured into H$_2$O. The mixture was extracted with EtOAc/hexane=1:1 and washed by H$_2$O. The organic layer was evaporated under reduced pressure. The residue was triturated with IPE and filtered to give the title compound (212 g, 81%) as a pale yellow powder. MS(ESI): m/z 294.1/296.1 [M+H]$^+$. $^1$H NMR (400 MHz, DMSO-d6) δ 1.28 (s, 3H), 1.38 (s, 3H), 3.50-3.77 (m, 3H), 4.00-4.20 (m, 1H), 4.40-4.48 (m, 1H), 7.83-7.91 (m, 1H), 7.97-8.04 (m, 2H), 8.05-8.11 (m, 1H), 8.35-8.41 (m, 1H).

Step 2: Intermediate 18: 2-[4-[[(4S)-2,2-dimethyl-1,3-dioxolan-4-yl]methylamino]phthalazin-1-yl]-5-(trifluoromethyl)phenol

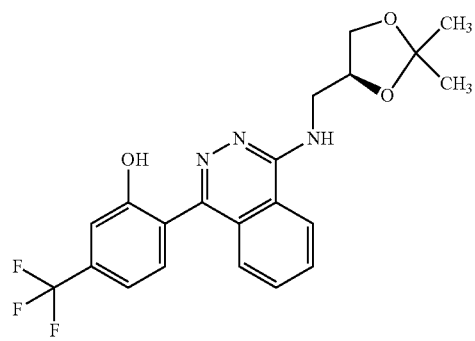 [SMILES: CC1(C)OC[C@H](CNc2nnc(-c3ccc(C(F)(F)F)cc3O)c3ccccc23)O1]

To a suspension of the Intermediate 17 (203 g, 691 mmol, 1.0 eq) and (2-hydroxy-4-(trifluoromethyl)phenyl)boronic acid (213 g, 1.03 mol 1.5 eq) in 1,4-dioxane (1.7 L) and 2.0 M aq. Na$_2$CO$_3$ (1.04 L, 2.08 mol, 3.0 eq) was added Pd(dppf)Cl$_2$·CH$_2$Cl$_2$ (11.3 g, 13.8 mmol, 0.02 eq) and the mixture was stirred and refluxed under argon atmosphere for 6 h. To the reaction mixture were added (2-hydroxy-4-(trifluoromethyl)phenyl)boronic acid (28.5 g, 138 mmol) and Pd(dppf)Cl$_2$·CH$_2$Cl$_2$ (11.3 g, 13.8 mmol, 0.02 eq). After 3 h, the mixture was cooled to rt and poured into H$_2$O and EtOAc. To the solvent was added activated carbon and the mixture was stirred and filtered through Celite®. The filtrate was extracted with EtOAc and the organic layer was evaporated under reduced pressure. The crude mixture was purified by flash chromatography (silica; CHCl$_3$/MeOH=100/0-19/1-8/2). The collected fractions were further purified by flash chromatography (NH-silica; CHCl$_3$/MeOH=100/0-39/1-8/2) to give the title compound (112 g, 39%) as a brown solid. MS(ESI) m/z 420.2 [M+H]$^+$. $^1$H NMR (400 MHz, DMSO-d6) δ 1.29 (s, 3H), 1.40 (s, 3H), 3.60-3.73 (m, 1H), 3.76-3.87 (m, 2H), 4.01-4.10 (m, 1H), 4.46-4.55 (m, 1H), 7.25-7.33 (m, 2H), 7.41-7.57 (m, 2H), 7.69-7.91 (m, 3H) 8.32-8.38 (m, 1H), 10.3 (br s, 1H).

Step 3: Example 1: (2S)-3-[[4-[2-hydroxy-4-(trifluoromethyl)phenyl]phthalazin-1-yl]amino]propane-1,2-diol

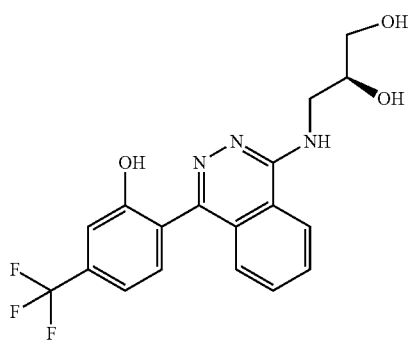 [SMILES: OC[C@@H](O)CNc1nnc(-c2ccc(C(F)(F)F)cc2O)c2ccccc12]

To a suspension of the Intermediate 18 (112 g, 267 mmol) in AcOH (240 mL) was added H$_2$O (80 mL) and the mixture was stirred at 80° C. for 5 h. The mixture was cooled to rt and evaporated under reduced pressure. The crude mixture was purified by flash chromatography (silica; CHCl$_3$/MeOH=100/0-90/10-80/20) to give the title compound (65.3 g, 57%) as a colorless solid. The residue (65.3 g+7.51 g (the residue of a previous batch)) was triturated with MeOH and filtered. To the obtained solid was added EtOH, and the solvent was evaporated under reduced pressure to give the title compound (62.7 g, 86%) as a colorless solid. MS(ESI): m/z 380.1 [M+H]$^+$. $^1$H NMR (400 MHz, DMSO-d6) δ 3.39-3.49 (m, 2H), 3.51-3.61 (m, 1H), 3.70-3.80 (m, 1H), 3.82-3.91 (m, 1H), 4.80-4.90 (m, 1H), 5.21-5.29 (m, 1H), 7.26-7.32 (m, 2H), 7.43-7.48 (m, 1H), 7.49-7.54 (m, 1H), 7.71 (br s, 1H), 7.77-7.83 (m, 1H), 7.85-7.92 (m, 1H), 8.32-8.41 (m, 1H), 10.37 (br s, 1H).

Examples 2-11 in Table 1 below were synthesized from Intermediate 17, using the below specified boronic acids in analogy with the procedure of Example 1. Example 12 was synthesized using the R-enantiomer of Intermediate 17 in analogy with preparation of Example 1.

TABLE 1

| Ex No. | Name | Boronic acid | Product |
|---|---|---|---|
| 2 | (2S)-3-[[4-(4-chloro-3-fluoro-2-hydroxyphenyl)phthalazin-1-yl]amino]propane-1,2-diol | | |
| 3 | (2S)-3-[[4-(4,5-difluoro-2-hydroxyphenyl)phthalazin-1-yl]amino]propane-1,2-diol | | |
| 4 | (2S)-3-[[4-(2-fluoro-6-hydroxyphenyl)phthalazin-1-yl]amino]propane-1,2-diol | | |
| 5 | (2S)-3-[[4-(4-chloro-2-hydroxyphenyl)phthalazin-1-yl]amino]propane-1,2-diol | | |

TABLE 1-continued

| Ex No. | Name | Boronic acid | Product |
|---|---|---|---|
| 6 | (2S)-3-[[4-[2-hydroxy-4-(trifluoromethoxy)phenyl]phthalazin-1-yl]amino]propane-1,2-diol | | |
| 7 | (2S)-3-[[4-[2-fluoro-6-hydroxy-4-(trifluoromethyl)phenyl]phthalazin-1-yl]amino]propane-1,2-diol | Intermediate 10 | |
| 8 | (2S)-3-[[4-(2,4-difluoro-6-hydroxy-phenyl)phthalazin-1-yl]amino]propane-1,2-diol | | |
| 9 | (2S)-3-[[4-(4-chloro-2-fluoro-6-hydroxy-phenyl)phthalazin-1-yl]amino]propane-1,2-diol | Intermediate 11 | |
| 10 | (2S)-3-[[4-(2-chloro-6-hydroxy-phenyl)phthalazin-1-yl]amino]propane-1,2-diol | | |

TABLE 1-continued

| Ex No. | Name | Boronic acid | Product |
|---|---|---|---|
| 11 | (2S)-3-[[4-(2-hydroxy-4-methyl-phenyl)phthalazin-1-yl]amino]propane-1,2-diol | | |
| 12 | (2R)-3-[[4-[2-hydroxy-4-(trifluoromethyl)phenyl]phthalazin-1-yl]amino]propane-1,2-diol | | |

Example 13

Step 1: Intermediate 19: 2-bromo-1-[(4-methoxyphenyl)methoxy]-4-methyl-benzene

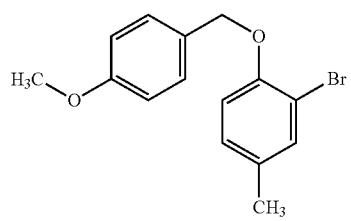 [SMILES: COc1ccc(COc2ccc(C)cc2Br)cc1]

To a suspension of 2-bromo-4-methyl-phenol (1.0 g, 5.3 mmol) and $K_2CO_3$ (2.2 g, 16 mmol) in DMF (9 mL) was added PMBCl (1.0 g, 6.4 mmol) at rt and the mixture was stirred at rt for 4 d. The reaction mixture was poured into $H_2O$ and extracted with EtOAc. The organic layer was washed by $H_2O$ and evaporated under reduced pressure. The crude mixture was purified by flash chromatography (Normal silica; hexane/EtOAc=95/5-80/20) to give the title compound (1.7 g, quant) as a colorless oil. MS(ESI): not detected.

Step 2: Intermediate 20: 2-[2-[(4-methoxyphenyl)methoxy]-5-methyl-phenyl]-4,4,5,5-tetramethyl-1,3,2-dioxaborolane

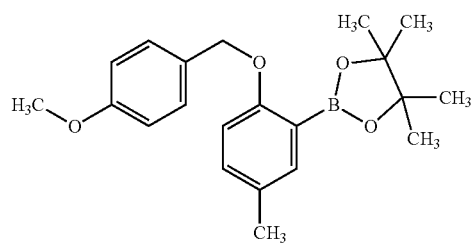

To a suspension of Intermediate 19 (1.7 g, 5.5 mmol), NaOAc (1.1 g, 11 mmol) and bis(pinacolate)diboron (1.7 g, 6.7 mmol) in 1,4-dioxane (14 mL) was added $PdCl_2$(dppf) $CH_2Cl_2$ (0.45 g, 0.55 mmol) and the mixture was heated to 100° C. and stirred for 4 h. The mixture was cooled to rt, poured into $H_2O$ and filtrated through Celite®. The solvent was extracted with EtOAc and evaporated under reduced pressure. The crude mixture was purified by flash chromatography (silica; hexane/EtOAc=100/0-80/20) to give the title compound (1.73 g, 88%) as a yellow oil. MS(ESI): m/z 355.0 [M+H]$^+$.

Step 3: Intermediate 21: N-[[(4S)-2,2-dimethyl-1,3-dioxolan-4-yl]methyl]-4-[2-[(4-methoxyphenyl)methoxy]-5-methyl-phenyl]phthalazin-1-amine

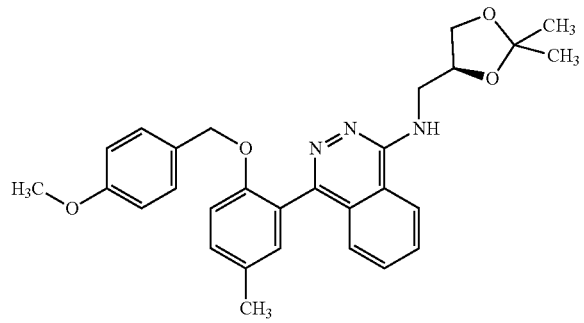

To a suspension of the Intermediate 20 (271 mg, 0.766 mmol), Intermediate 17 (150 mg, 0.511 mmol) and Na$_2$CO$_3$ (162 mg, 1.53 mmol) in 1,4-dioxane (2.6 mL) and H$_2$O (0.5 mL) was added SPhos Pd G3 (40 mg, 0.051 mmol). The vial was sealed and the reaction was run at 120° C. for 1 h in a microwave reactor. The reaction mixture was poured into brine and extracted with CHCl$_3$. The organic layer was evaporated under reduced pressure. The crude mixture was purified by flash chromatography (silica; CHCl$_3$/MeOH=100/0-93/7). The collected fractions were further purified by flash chromatography (NH-silica; CHCl$_3$/MeOH=100/0-90/10) to give the title compound (182 mg, 73%) as a yellow amorphous. MS(ESI): m/z 484.4 [M−H]$^−$ Step 4: Example 13: (2S)-3-[[4-(2-hydroxy-5-methyl-phenyl)phthalazin-1-yl]amino]propane-1,2-diol

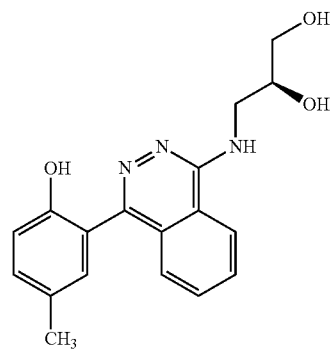 [SMILES: Cc1ccc(O)c(-c2nnc(NC[C@H](O)CO)c3ccccc23)c1]

To a suspension of Intermediate 21 (180 mg) in MeOH (1 mL) was added 2 M HCl in 1,4-dioxane (1 mL) and the reaction mixture was stirred at rt for 2 h. The solvent was evaporated under reduced pressure. The crude mixture was purified by flash chromatography (silica; 100/0 to 85/15) and reversed phase flash chromatography on a C18 column using a gradient of 20-50% MeCN in (NH$_4$)$_2$CO$_3$ (10 mM, aq) as mobile phase to give the title compound (55 mg, 46%) as a pale yellow amorphous. MS(ESI): m/z 326.1 [M+H]$^+$. $^1$H NMR (400 MHz, DMSO-d6) δ 2.27 (s, 3H), 3.39-3.47 (m, 2H), 3.50-3.60 (m, 1H), 3.68-3.77 (m, 1H), 3.80-3.89 (m, 1H), 4.84-4.91 (m, 1H), 5.30-5.38 (m, 1H), 6.85-6.90 (m, 1H), 6.95-7.16 (m, 2H), 7.48-7.59 (m, 2H), 7.75-7.90 (m, 2H), 8.30-8.35 (m, 1H), 9.30-9.45 (m, 1H).

Example 14 and Example 15

Step 1: Intermediate 22: 6-methyl-2,3-dihydrophthalazine-1,4-dione

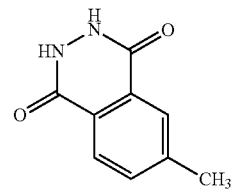

To a solution of 5-methylisobenzofuran-1,3-dione (5.0 g, 31 mmol) in AcOH (15 mL) was added hydrazine monohydrate (4.9 mL, 0.10 mol) at rt and the mixture was stirred at rt for 16 h and heated to 110° C. After 1 h, the mixture was cooled to rt and to the mixture were added IPE and EtOH. The precipitate was filtrated and poured into H$_2$O. The precipitate was filtrated and dried to give the title compound (4.97 g, 91%) as a colorless powder. MS(ESI): m/z 177.1 [M+H]$^+$.

Step 2: Intermediate 23: 1,4-dichloro-6-methyl-phthalazine

To a solution of the Intermediate 22 (4.97 g, 28.2 mmol) in toluene (1.0 mL) and pyridine (4.5 mL) was added phosphoryl trichloride (13.2 mL) at rt and the mixture was stirred at 100° C. for 2 h. The mixture was cooled to rt and evaporated under reduced pressure. The crude mixture was poured into H$_2$O at 0° C. and stirred at rt. The precipitate was filtrated and dried to give the title compound (5.10 g, 83%) as a pale yellow powder. MS(ESI): m/z 213.1/215.1 [M+H]$^+$.

Step 3: Intermediate 24: 4-chloro-N-[[(4S)-2,2-dimethyl-1,3-dioxolan-4-yl]methyl]-7-methyl-phthalazin-1-amine Step 4: Intermediate 26: 2-[4-[[(4S)-2,2-dimethyl-1,3-dioxolan-4-yl]methylamino]-6-methyl-phthalazin-1-yl]-5-(trifluoromethyl)phenol

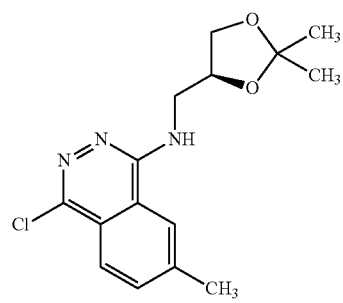 [SMILES: Cc1ccc2c(Cl)nnc(NC[C@H]3COC(C)(C)O3)c2c1]

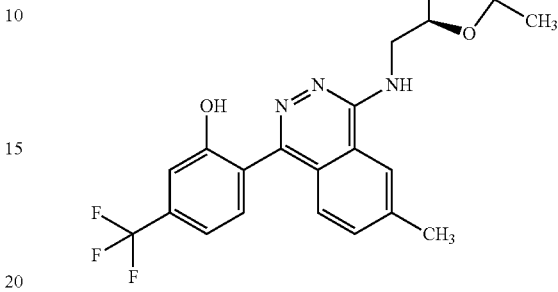

and Intermediate 25: 4-chloro-N-[[(4S)-2,2-dimethyl-1,3-dioxolan-4-yl]methyl]-6-methyl-phthalazin-1-amine and Intermediate 27: 2-[4-[[(4S)-2,2-dimethyl-1,3-dioxolan-4-yl]methylamino]-7-methyl-phthalazin-1-yl]-5-(trifluoromethyl)phenol

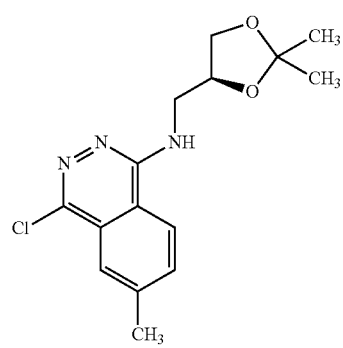 [SMILES: Cc1ccc2c(NC[C@H]3COC(C)(C)O3)nnc(Cl)c2c1]

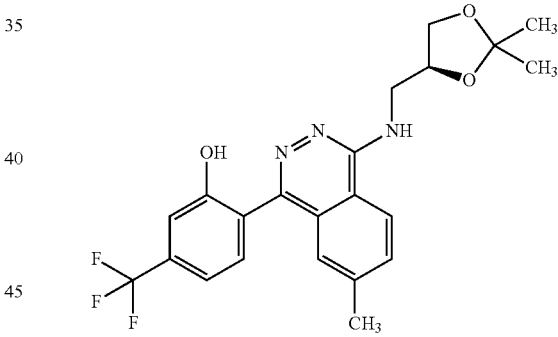

To a solution of Intermediate 23 (2.10 g, 9.86 mmol) in anhydrous NMP (10 mL) were added DIPEA (4.11 mL, 29.6 mmol) and (S)-(2,2-dimethyl-1,3-dioxolan-4-yl)methanamine (1.40 g, 10.7 mmol) at rt and the mixture was stirred at 100° C. for 4 h. The reaction mixture was cooled to rt and poured into H$_2$O. The mixture was extracted with EtOAc and the organic layer was evaporated under reduced pressure. The crude mixture was purified by flash chromatography (silica, hexane/EtOAc=100/0-20/80) to give a 1:1 mixture intermediates 22 and 23 (0.898 g, 30%) as a pale yellow amorphous. MS(ESI): m/z 308.1/310.1 [M+H]$^+$ To a suspension of a 1:1 mixture of Intermediate 24 and Intermediate 25 (400 mg, 1.30 mmol), (2-hydroxy-4-(trifluoromethyl)phenyl)boronic acid (401 mg, 1.95 mmol) and Na$_2$CO$_3$ (413 mg, 3.90 mmol) in 1,4-dioxane (3.2 mL) and H$_2$O (1 mL) was added SPhos Pd G3 (101 mg, 0.130 mmol). The vial was sealed and the reaction was run at 120° C. for 30 min in a microwave reactor. The reaction mixture was poured into H$_2$O and extracted with CHCl$_3$. The organic layer was evaporated under reduced pressure. The crude mixture was purified by column chromatography (silica, CHCl$_3$/MeOH=100/0-95/5). The collected fractions were further purified by column chromatography (NiI-silica, CHCl$_3$/MeOH=100/0-95/5) to give the title compound (180 mg, 32%) as a yellow amorphous. The isolated material had a 1:1 6-methyl/7-methyl ratio. MS(ESI): m/z 434.2 [M+H]$^+$ Step 5: Example 14: (2S)-3-[[4-[2-hydroxy-4-(trifluoromethyl)phenyl]-7-methyl-phthalazin-1-yl]amino]propane-1,2-diol

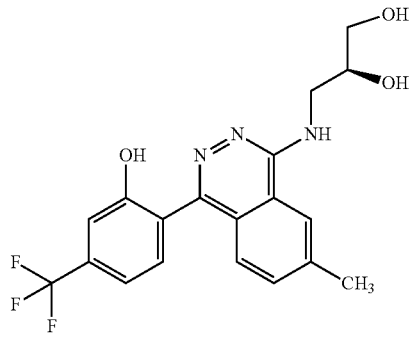 [SMILES: Cc1ccc2c(-c3ccc(C(F)(F)F)cc3O)nnc(NC[C@H](O)CO)c2c1]

and Example 15: (2S)-3-[[4-[2-hydroxy-4-(trifluoromethyl)phenyl]-6-methyl-phthalazin-1-yl]amino]propane-1,2-diol

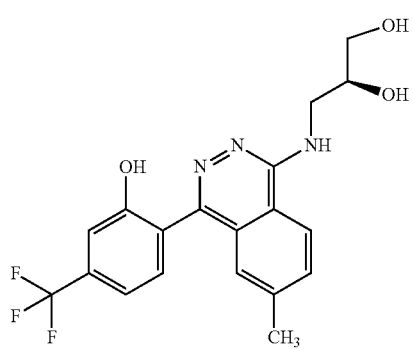 [SMILES: Cc1ccc2c(NC[C@H](O)CO)nnc(-c3ccc(C(F)(F)F)cc3O)c2c1]

To a suspension of a 1:1 mixture of Intermediate 26 and Intermediate 27 (179 mg, 0.41 mmol) in MeOH (1 mL) was added 2 M HCl in 1,4-dioxane (4 mL) and the reaction mixture was stirred at rt for 1 h. The solvent was evaporated under reduced pressure. The crude mixture was purified by flash chromatography (Normal silica; CHCl$_3$/MeOH=100/0-80/20) to give Example 14 (24 mg, 15%) as a pale yellow amorphous and Example 15 (64 mg, 39%) as a pale yellow amorphous.

Example 14: $^1$H NMR (400 MHz, DMSO-d6) δ 2.47 (s, 3H), 3.38-3.78 (m, 4H), 3.85-3.93 (m, 1H), 7.29-7.37 (m, 3H), 7.52-7.57 (m, 1H), 7.80-7.91 (m, 1H), 8.45-8.60 (m, 1H). MS(ESI): m/z 394.1 [M+H]$^+$.

Example 15: $^1$H NMR (400 MHz, DMSO-d6) δ 2.47 (s, 3H), 3.41-3.52 (m, 2H), 3.57-3.68 (m, 1H), 3.72-3.81 (m, 1H), 3.87-3.93 (m, 1H), 7.30-7.36 (m, 2H), 7.37-7.42 (m, 1H), 7.52-7.56 (m, 1H), 7.82-7.88 (m, 1H), 8.60-8.67 (m, 1H). MS(ESI): m/z 394.1 [M+H]$^+$.

Example 16

Step 1: Intermediate 28: (1R,3R)-3-[(4-chlorophthalazin-1-yl)amino]cyclopentanol

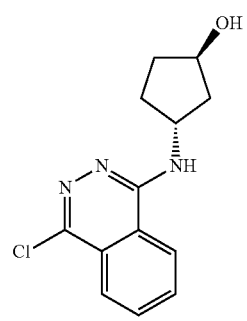 [SMILES: O[C@@H]1CC[C@@H](Nc2nnc(Cl)c3ccccc23)C1]

To a solution of 1,4-dichlorophthalazine (1.40 g, 7.0 mmol) in NMP (9 mL), (1R,3R)-3-aminocyclopentanol; hydrochloride (0.97 g, 7.0 mmol, 1.0 eq) and DIPEA (6.1 mL, 35 mmol, 5.0 eq) were added at rt and the reaction mixture was heated at 110° C. for 22 h. The reaction mixture was cooled to rt, quenched with saturated aqueous NaHCO$_3$ solution and extracted with CHCl$_3$. The combined organic layer was washed with brine, dried over Na$_2$SO$_4$ and concentrated under reduced pressure to give a crude material. The crude compound was purified by column chromatography (silica, CHCl$_3$/MeOH=100:0-90:10) to give the title compound (1.37 g, 74%) as a brown powder. MS(ESI): m/z 264.1/266.1 [M+H]$^+$. $^1$H NMR (400 MHz, CDCl$_3$) δ 1.52-1.54 (m, 1H), 1.57-1.67 (m, 1H), 1.70-1.80 (m, 1H), 1.81-1.91 (m, 1H), 2.10-2.20 (m, 1H), 2.34-2.42 (m, 1H), 2.48-2.58 (m, 1H), 4.48-4.55 (m, 1H), 4.83-4.92 (m, 1H), 5.00-5.07 (m, 1H), 7.72-7.75 (m, 1H), 7.82-7.89 (m, 2H), 8.17-8.20 (m, 1H).

Step 2: Example 16: 2-[4-[[(1R,3R)-3-hydroxycyclopentyl]amino]phthalazin-1-yl]-5-(trifluoromethyl)phenol

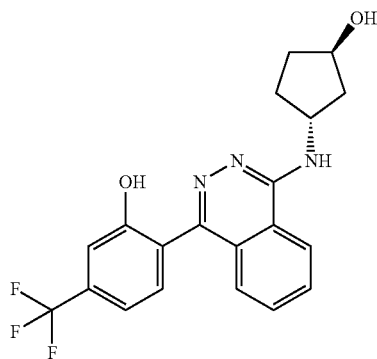 [SMILES: Oc1cc(C(F)(F)F)ccc1-c1nnc(N[C@@H]2CC[C@@H](O)C2)c2ccccc12]

To a solution of Intermediate 28 (400 mg, 27.0 mmol, 1.1 eq) and [2-hydroxy-4-(trifluoromethyl)phenyl]boronic acid (310 mg, 1.5 mmol, 1.0 eq) in DME (5.0 mL) were added Pd(dppf)Cl$_2$·CH$_2$Cl$_2$ (124 mg, 0.15 mmol, 0.1 eq) and 2 M aq. Na$_2$CO$_3$ (2.3 mL, 3.0 eq) at rt. The mixture was heated at 85° C. and stirred for 5 h. The reaction mixture was cooled to rt and added H$_2$O, then the mixture was extracted with CHCl₃ (3 times). The organic layer was dried over Na₂SO₄ and concentrated in vacuo. The residue was purified by column chromatography (NH-silica, CHCl₃/MeOH=100:0-80:20). The collected fractions were further purified by column chromatography (silica gel, CHCl₃/MeOH=100:0-90:10) to give the title compound (217 mg, 37%) as a yellow powder. MS(ESI): m/z 390.2 [M+H]⁺. ¹H NMR (400 MHz, DMSO-d6) δ 1.51-1.68 (m, 2H), 1.80-1.88 (m, 1H), 1.96-2.10 (m, 2H), 2.21-2.31 (m, 1H), 4.27-4.35 (m, 1H), 4.53 (d, 1H), 4.77-4.88 (m, 1H), 7.22-7.30 (m, 3H), 7.44 (d, 1H), 7.52 (d, 1H), 7.76 (td, 1H), 7.84 (td, 1H), 8.39 (d, 1H), 10.0-10.6 (m, 1H).

Example 17

Step 1: Intermediate 29: (1S,3S)-3-[(4-chlorophthalazin-1-yl)amino]cyclopentanol

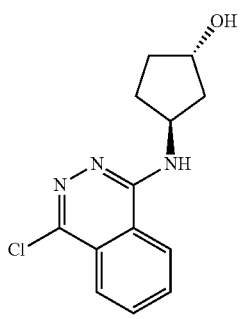 [SMILES: O[C@H]1CC[C@H](Nc2nnc(Cl)c3ccccc23)C1]

The title compound was prepared using the same procedure as Intermediate 28 using the starting material (1S,3S)-3-aminocyclopentanol hydrochloride. The compound was isolated as a brown solid. MS(ESI): m/z 264.1/266.1 [M+H]⁺. ¹H NMR (400 MHz, CDCl₃) δ 1.50-1.54 (m, 1H), 1.57-1.66 (m, 1H), 1.70-1.80 (m, 1H), 1.81-1.91 (m, 1H), 2.10-2.20 (m, 1H), 2.34-2.42 (m, 1H), 2.48-2.58 (m, 1H), 4.48-4.55 (m, 1H), 4.83-4.92 (m, 1H), 5.00-5.07 (m, 1H), 7.72-7.75 (m, 1H), 7.82-7.89 (m, 2H), 8.17-8.20 (m, 1H).

Step 2: Example 17: 2-[4-[[(1S,3S)-3-hydroxycyclopentyl]amino]phthalazin-1-yl]-5-(trifluoromethyl)phenol

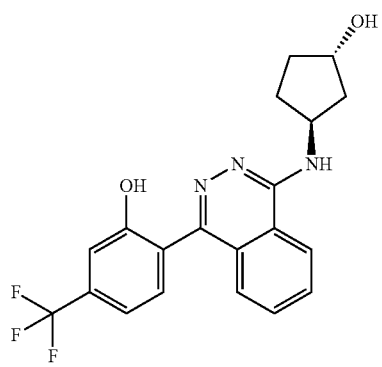 [SMILES: Oc1cc(C(F)(F)F)ccc1-c1nnc(N[C@H]2CC[C@H](O)C2)c2ccccc12]

The title compound was prepared using the same procedure as Example 16 using Intermediate 29 as starting material. The compound was isolated as a brown solid. MS(ESI): m/z 390.2 [M+H]⁺. ¹H NMR (400 MHz, DMSO-d6) δ 1.50-1.69 (m, 2H), 1.80-1.89 (m, 1H), 1.94-2.12 (m, 2H), 2.21-2.31 (m, 1H), 4.26-4.36 (m, 1H), 4.52 (d, 1H), 4.77-4.88 (m, 1H), 7.23-7.33 (m, 3H), 7.44 (d, 1H), 7.52 (d, 1H), 7.76 (td, 1H), 7.84 (td, 1H), 8.39 (d, 1H), 10.0-10.6 (m, 1H).

Example 18

Step 1: Intermediate 30: (1R,3R)-3-[[4-(2-benzyloxy-4-methylsulfonyl-phenyl)phthalazin-1-yl]amino]cyclopentanol

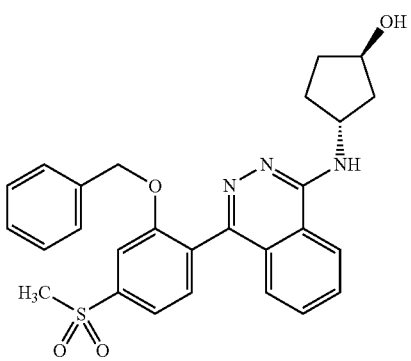 [SMILES: CS(=O)(=O)c1ccc(-c2nnc(N[C@@H]3CC[C@@H](O)C3)c3ccccc23)c(OCc2ccccc2)c1]

To a solution of Intermediate 28 (70 mg, 0.265 mmol, 1.0 eq) and Intermediate 15 (104 mg, 0.268 mmol, 1.0 eq) in DME (0.5 mL) were added Pd(dppf)Cl₂·CH₂Cl₂ (22 mg, 0.0265 mmol, 0.1 eq) and 2 M aq. Na₂CO₃ (0.8 mL, 3.0 eq) at rt. The mixture was heated at 90° C. and stirred for 3 h. The reaction mixture was cooled to rt and added H₂O, then the mixture was extracted with EtOAc (3 times). The organic layer was dried over Na₂SO₄ and concentrated in vacuo. The residue was purified by column chromatography (silica, EtOAc/MeOH=100:0-93:7) to give the title compound (34.3 mg, 26%) as an orange solid. MS(ESI): m/z 490.3 [M+H]⁺. ¹H NMR (400 MHz, CDCl₃) δ 1.50-1.70 (m, 2H), 1.70-1.83 (m, 1H), 1.85-1.98 (m, 1H), 2.12-2.15 (m, 1H), 2.53-2.63 (m, 1H), 3.09 (s, 3H), 4.51-4.58 (m, 1H), 4.95-5.05 (m, 1H), 5.05-5.18 (m, 3H), 6.97-7.03 (m, 2H), 7.13-7.20 (m, 3H), 7.53 (d, 1H), 7.63 (d, 1H), 7.65-7.72 (m, 2H), 7.75 (s, 1H), 7.76-7.79 (m, 2H).

Step 2: Example 18: 2-[4-[[(1R,3R)-3-hydroxycyclopentyl]amino]phthalazin-1-yl]-5-methylsulfonyl-phenol

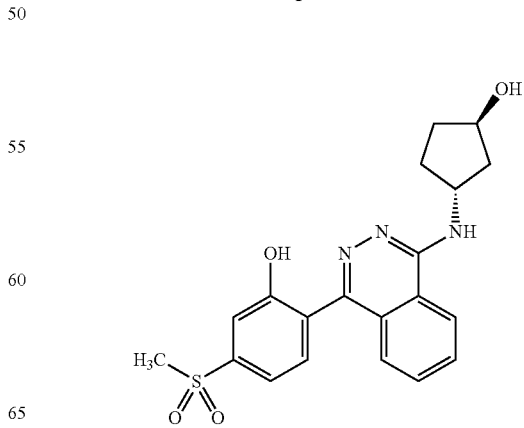

To a solution of Intermediate 30 (34.3 mg, 0.070 mmol, 1.0 eq) in EtOH (2 mL) was added Pd/C (26.0 mg, 5% wet) in nitrogen atmosphere. Then nitrogen was replaced by 1 atm of hydrogen and the reaction mixture was stirred for 7 h at rt. The mixture was filtered through a Celite® pad. The filtrate was concentrated in vacuo. The residue was purified by flash column chromatography using a gradient of 5-10% MeOH in EtOAc as mobile phase, to give the title compound (24.7 mg, 88%) as a yellowish powder. MS(ESI): m/z 400.2 [M+H]+. 1H NMR (400 MHz, DMSO-d6) δ 1.50-1.69 (m, 2H), 1.80-1.89 (m, 1H), 1.95-2.10 (m, 2H), 2.21-2.31 (m, 1H), 3.26 (s, 3H), 4.27-4.33 (m, 1H), 4.52 (d, 1H), 4.78-4.90 (m, 1H), 7.25 (d, 1H), 7.44 (d, 1H), 7.47-7.52 (m, 2H), 7.56 (d, 1H), 7.77 (td, 1H), 7.85 (td, 1H), 8.39 (d, 1H), 10.2-10.7 (m, 1H).

Examples 19 to 37 in Table 2 were all prepared analogously to the procedure for Example 17 using the appropriate aminoalcohol.

TABLE 2

| Ex No. | Name | Product |
|---|---|---|
| 19 | 2-[4-[[(1R,2S)-2-hydroxycyclopentyl]amino]phthalazin-1-yl]-5-(trifluoromethyl)phenol | |
| 20 | 2-[4-[[(1R,2R)-2-hydroxycyclopentyl]amino]phthalazin-1-yl]-5-(trifluoromethyl)phenol | |
| 21 | 2-[4-[[(1S,2R)-2-hydroxycyclopentyl]amino]phthalazin-1-yl]-5-(trifluoromethyl)phenol | |
| 22 | 2-[4-[[(1S,2S)-2-hydroxycyclopentyl]amino]phthalazin-1-yl]-5-(trifluoromethyl)phenol | |

TABLE 2-continued

| Ex No. | Name | Product |
|---|---|---|
| 23 | 2-[4-[[(1R,2S)-2-hydroxycyclohexyl]amino]phthalazin-1-yl]-5-(trifluoromethyl)phenol | |
| 24 | 2-[4-[[(1R,2R)-2-hydroxycyclohexyl]amino]phthalazin-1-yl]-5-(trifluoromethyl)phenol | |
| 25 | 2-[4-[[(1S,2R)-2-hydroxycyclohexyl]amino]phthalazin-1-yl]-5-(trifluoromethyl)phenol | |
| 26 | 2-[4-[[(1S,2S)-2-hydroxycyclohexyl]amino]phthalazin-1-yl]-5-(trifluoromethyl)phenol | |

TABLE 2-continued

| Ex No. | Name | Product |
|---|---|---|
| 27 | rac-(1R,2R)-2-[[4-[2-hydroxy-4-(trifluoromethyl)phenyl]phthalazin-1-yl]amino]cycloheptanol | |
| 28 | rel-2-(4-(((1R,3R)-3-hydroxycyclohexyl)amino)phthalazin-1-yl)-5-(trifluoromethyl)phenol (Opposite enantiomer to Example 29, unknown absolute configuration) | |
| 29 | rel-2-(4-(((1R,3R)-3-hydroxycyclohexyl)amino)phthalazin-1-yl)-5-(trifluoromethyl)phenol (Opposite enantiomer to Example 28, unknown absolute configuration) | |
| 30 | 2-[4-[[(1S,3R)-3-hydroxycyclohexyl]amino]phthalazin-1-yl]-5-(trifluoromethyl)phenol | |

TABLE 2-continued

| Ex No. | Name | Product |
|---|---|---|
| 31 | 2-[4-[[(1R,3S)-3-hydroxycyclohexyl]amino]phthalazin-1-yl]-5-(trifluoromethyl)phenol | |
| 32 | 2-(4-(((1r,3r)-3-hydroxycyclobutyl)amino)phthalazin-1-yl)-5-(trifluoromethyl)phenol | |
| 33 | 2-(4-(((1s,3s)-3-hydroxycyclobutyl)amino)phthalazin-1-yl)-5-(trifluoromethyl)phenol | |
| 34 | rel-2-(4-(((1R,3S)-3-hydroxycyclopentyl)amino)phthalazin-1-yl)-5-(trifluoromethyl)phenol (Opposite enantiomer to Example 35, unknown absolute configuration) | |

TABLE 2-continued

| Ex No. | Name | Product |
|---|---|---|
| 35 | rel-2-(4-(((1R,3S)-3-hydroxycyclopentyl)amino)phthalazin-1-yl)-5-(trifluoromethyl)phenol (Opposite enantiomer to Example 34, unknown absolute configuration) | |
| 36 | 3-fluoro-2-(4-(((1s,3s)-3-hydroxy-3-methylcyclobutyl)amino)phthalazin-1-yl)phenol | |
| 37 | 2-(4-(((1s,3s)-3-hydroxy-3-methylcyclobutyl)amino)phthalazin-1-yl)-5-(trifluoromethyl)phenol | |

Example 38

Step 1: Intermediate 31: (1R,3R)-3-[[1-[2-methoxy-4-(trifluoromethyl)phenyl]pyrido[3,4-d]pyridazin-4-yl]amino]-1-methyl-cyclopentanol

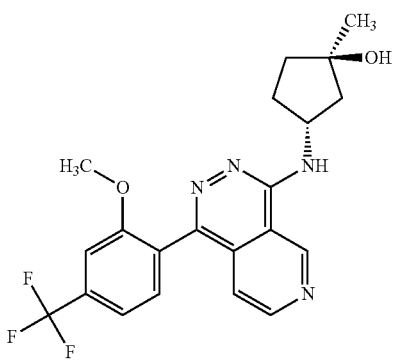 [SMILES: COc1cc(C(F)(F)F)ccc1-c1nnc(N[C@@H]2CC[C@@](C)(O)C2)c2cnccc12]

To a solution of Intermediate 5 (149.8 mg, 0.70 mmol) in CH$_2$Cl$_2$ (2 mL) was added TFA (1.0 mL, 13.1 mmol) at rt. The mixture was stirred for 40 min at rt and the reaction mixture was concentrated. The residue was azeotroped with toluene. To a solution of the residue in MeCN (1.2 mL) was added TEA (0.49 mL, 3.50 mmol) and the mixture was stirred for 10 min at rt. To the mixture was added Intermediate 1 (199.3 mg, 0.59 mmol) and the vial was sealed. The reaction was run at 130° C. for 2.5 h in a microwave reactor. The reaction mixture was concentrated and the residue was purified by NH-silica gel column chromatography using a gradient of 0-10% MeOH in EtOAc as mobile phase to give the title compound (195 mg, 74%) as a brown powder. MS (ESI): m/z [M+H]$^+$: 419.1. $^1$H NMR (400 MHz, CDCl$_3$) δ 1.47 (s, 3H), 1.67-1.80 (m, 2H), 1.83-2.02 (m, 2H), 2.52-2.72 (m, 2H), 3.76 (s, 3H), 4.99-5.15 (m, 1H), 5.50 (br d, 1H), 7.23-7.29 (m, 2H), 7.41 (dd, 1H), 7.63 (d, 1H), 8.83 (d, 1H), 9.32 (s, 1H).

Step 2: Example 38: 2-[4-[[(1R,3R)-3-hydroxy-3-methyl-cyclopentyl]amino]pyrido[3,4-d]pyridazin-1-yl]-5-(trifluoromethyl)phenol

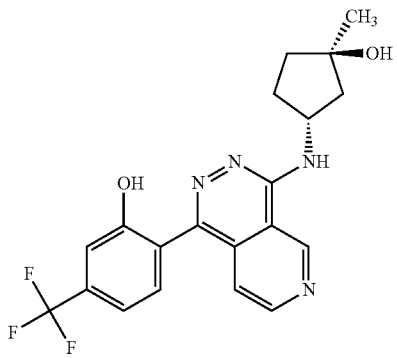 [SMILES: C[C@@]1(O)CC[C@@H](Nc2nnc(-c3ccc(C(F)(F)F)cc3O)c3ccncc23)C1]

To a solution of Intermediate 31 (195 mg, 0.44 mmol) in 2,4,6-trimethylpyridine (5 mL) was added LiI (626.9 mg, 4.68 mmol) at rt. The mixture was stirred for 4 h at 160° C. in the dark. The reaction mixture was cooled to rt, and added H₂O. The mixture was extracted with EtOAc (3 times). The combined organic layer was washed with brine, dried over Na₂SO₄, and concentrated in vacuo. The residue was purified by NH column chromatography using a gradient of 10-30% MeOH in EtOAc as mobile phase to give a red gum. The resulted was purified by flash column chromatography using a gradient of 0-20% MeOH in EtOAc as mobile phase to give the title compound (102.6 mg, 56%) as a yellow powder. MS (ESI): m/z [M+H]⁺ 405.0. ¹H NMR (400 MHz, DMSO-d6) δ 1.33 (s, 3H), 1.64-1.86 (m, 4H), 2.22 (dd, 1H), 2.28-2.41 (m, 1H), 4.41 (s, 1H), 4.86-5.01 (m, 1H), 7.24-7.30 (m, 2H), 7.32 (d, 1H), 7.56 (d, 1H), 7.80 (d, 1H), 8.84 (d, 1H), 9.78 (d, 1H), 10.44 (br s, 1H).

Example 39: 2-[4-[[(1R,3S)-3-hydroxy-3-methyl-cyclopentyl]amino]pyrido[3,4-d]pyridazin-1-yl]-5-(trifluoromethyl)phenol

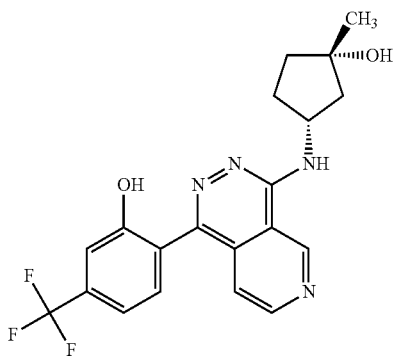 [SMILES: C[C@]1(O)CC[C@@H](Nc2nnc(-c3ccc(C(F)(F)F)cc3O)c3ccncc23)C1]

The title compound was prepared analogously to Example 38 using Intermediate 4 instead of Intermediate 5. MS (ESI): m/z [M+H]⁺ 405.2. ¹H NMR (400 MHz, DMSO-d6) δ 1.30 (s, 3H), 1.51-1.67 (m, 1H), 1.74-1.91 (m, 2H), 1.93-2.08 (m, 1H), 2.10-2.25 (m, 2H), 4.59-4.80 (m, 2H), 7.22-7.36 (m, 3H), 7.56 (d, 1H), 7.90 (br d, 1H), 8.84 (d, 1H), 9.78 (s, 1H).

Example 40

Step 1: Intermediate 32: 1-bromo-2-((4-methoxybenzyl)oxy)-4-(trifluoromethyl)benzene

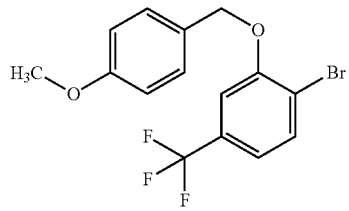 [SMILES: COc1ccc(COc2cc(C(F)(F)F)ccc2Br)cc1]

2-bromo-5-(trifluoromethyl)phenol (3.0 g, 12.45 mmol) and 1-(bromomethyl)-4-methoxybenzene (2.53 g, 12.57 mmol) was dissolved in MeCN (30 mL) and potassium carbonate (1.892 g, 13.69 mmol) was added in one portion (no or very weak exotherm). The reaction mixture turns yellow. The reaction mixture was stirred at rt overnight. The reaction was complete after 16 h according to NMR. Water and EtOAc were added and the phases were separated. The aqueous phase was extracted with EtOAc and the combined organic extract was washed with brine and evaporated. This gave a pale orange oil that did not crystallize from IPA (approximately 15 mL). The oil was instead purified by column chromatography (silica gel, heptane/EtOAc:20/1 as eluent) to yield 3.58 g (80%) of the title compound as a colorless oil that crystallized upon standing. ¹H NMR (500 MHz, DMSO-d6) δ 3.76 (s, 3H), 5.23 (s, 2H), 6.95-7.00 (m, 2H), 7.22-7.28 (m, 1H), 7.42 (d, 2H), 7.51 (d, 1H), 7.80-7.86 (m, 1H).

Step 2: Intermediate 33: tert-butyl 4-[2-[(4-methoxyphenyl)methoxy]-4-(trifluoromethyl)benzoyl]pyridine-3-carboxylate

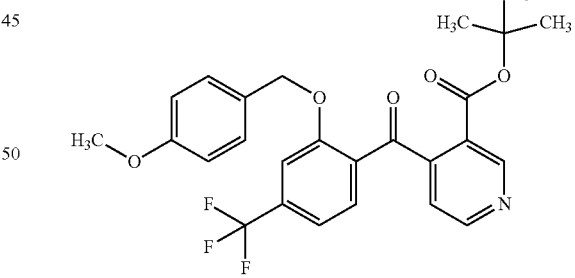

Intermediate 8 (7.0 g, 29.6 mmol) was dissolved in THF (50 mL) and cooled to −78° C. In another flask, Intermediate 32 (10.7 g, 29.6 mmol) was dissolved in THF (50 mL) and n-BuLi (19.4 mL, 31.1 mmol, 1.6 M in hexanes) was added at −78° C. The light yellow solution was stirred at −78° C. for 15 seconds before added dropwise via cannula to the first solution. The reaction mixture was stirred at −78° C. for 10 min, then AcOH (1.9 mL in 100 mL water) was added followed by the addition of EtOAc. The reaction mixture was allowed to reach rt and the two phases were separated. The organic extract was washed with water and evaporated to afford the title compound (14.4 g, quant.) as an orange oil. Used in the next step without further purification. MS (ESI): m/z [M+H]+ 488.3.

Step 3: Intermediate 34: 1-[2-[(4-methoxyphenyl)methoxy]-4-(trifluoromethyl)phenyl]-3H-pyrido[3,4-d]pyridazin-4-one

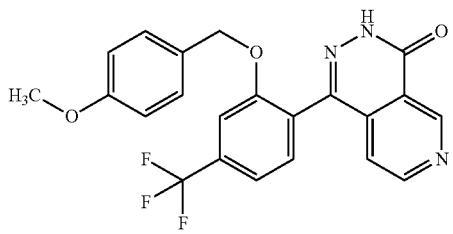 [SMILES: COc1ccc(COc2cc(C(F)(F)F)ccc2-c2n[nH]c(=O)c3cnccc23)cc1]

Intermediate 33 (41.4 g, 84.9 mmol) was dissolved in THF (300 mL), hydrazine monohydrate (21.1 mL, 340 mmol, 50% in water) was added and the reaction mixture was stirred at 60° C. for 16 h. Water (100 mL) was added and the mixture was stirred at rt before being poured into water (600 mL). The solid was filtered off and washed with water and MTBE. The product was slurried in refluxing EtOAc (1 L), cooled to rt and filtered to afford the title compound (17.3 g, 48%) as an off-white solid. MS (ESI): m/z [M+H]+ 428.2. 1H NMR (500 MHz, DMSO-d6) δ 3.68 (s, 3H), 5.15 (s, 2H), 6.75 (d, 2H), 7.02 (d, 2H), 7.27 (d, 1H), 7.51 (d, 1H), 7.65 (d, 2H), 8.93 (d, 1H), 9.48 (s, 1H), 13.23 (s, 1H).

Step 4: Intermediate 35: 4-chloro-1-[2-[(4-methoxyphenyl)methoxy]-4-(trifluoromethyl)phenyl]pyrido[3,4-d]pyridazine

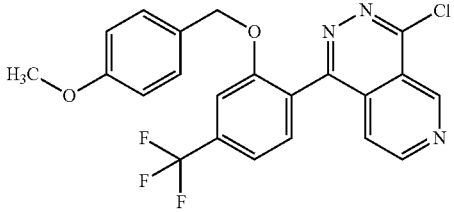 [SMILES: COc1ccc(COc2cc(C(F)(F)F)ccc2-c2nnc(Cl)c3cnccc23)cc1]

Intermediate 34 (6.0 g, 14.0 mmol) was slurried in 1,4-dioxane (55 mL). Pyridine (9.9 mL, 122 mmol) and phosphoryl trichloride (4.6 mL, 48.9 mmol) were added and the reaction stirred at 60° C. for 19 h. The mixture was cooled to rt and then added to tri-sodium citrate (180 mL, aq., 1 M). The precipitated product was filtered off, washed with water (2×50 mL) and dried under vacuum give a tan solid. The crude was slurried in MeCN (80 mL) and heated to 80° C. until dissolved. The mixture was cooled to rt and the formed precipitate was filtered off, washed with MeCN (2×15 mL) and dried to afford the title compound (2.57 g, 41%) as a tan solid. MS (ESI): m/z [M+H]+ 446.3. 1H NMR (500 MHz, DMSO-d6) δ 3.66 (s, 3H), 5.15 (s, 2H), 6.73 (d, 2H), 6.99 (d, 2H), 7.58 (d, 1H), 7.65 (dd, 1H), 7.72 (d, 2H), 9.10 (d, 1H), 9.69-9.82 (m, 1H).

Step 5: Intermediate 36: (1R,2R)-2-[[1-[2-[(4-methoxyphenyl)methoxy]-4-(trifluoromethyl)phenyl]pyrido[3,4-d]pyridazin-4-yl]amino]cyclohexanol

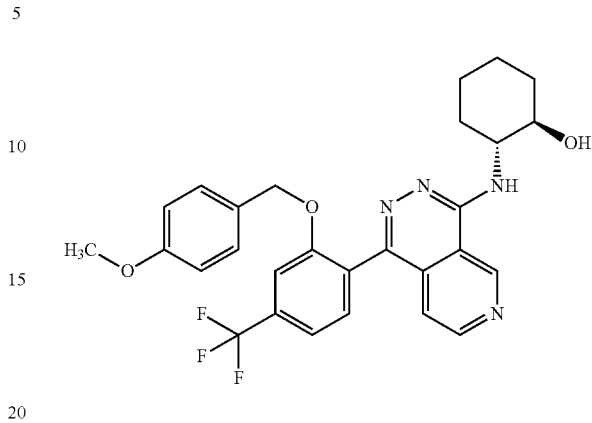

Intermediate 35 (2.6 g, 5.7 mmol), (1R,2R)-2-aminocyclohexan-1-ol (1.1 g, 9.2 mmol) and NaHCO3 (2.4 g, 28.7 mmol) were mixed in IPA (22 mL) and stirred at 80° C. for 3 d. The reaction mixture was poured into water (100 mL) and stirred to rt for 2 h. The solid was filtered off, washed with water and dried under vacuum at 40° C. to afford the title compound (2.9 g, 96%) as a tan solid. MS (ESI): m/z [M+H]+ 535.6. 1H NMR (500 MHz, DMSO-d6) δ 1.30 (s, 4H), 1.69 (d, 2H), 1.97 (d, 1H), 2.12 (s, 1H), 3.61 (d, 1H), 3.66 (s, 3H), 4.19 (s, 1H), 4.83 (s, 1H), 5.11 (s, 2H), 6.74 (d, 2H), 7.03 (d, 2H), 7.26 (d, 1H), 7.48 (d, 1H), 7.60 (s, 2H), 7.67 (d, 1H), 8.81 (d, 1H), 9.76 (s, 1H).

Step 6: Example 40: 2-(4-(((1R,2R)-2-hydroxycyclohexyl)amino)pyrido[3,4-d]pyridazin-1-yl)-5-(trifluoromethyl)phenol

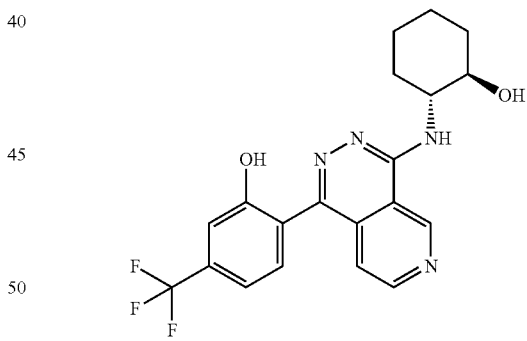

Intermediate 36 (2.9 g, 5.5 mmol) was slurried in absolute EtOH (99.5%, 7 mL), HCl (4 M in 1,4-dioxane, 20.7 mL, 82.9 mmol) was added and the reaction stirred at rt for 2 h. The mixture was added dropwise to Et2O (150 mL) under stirring to give a precipitate which was filtered off, washed with Et2O and dried to give a light yellow solid (HCl-salt). The solid was slurried in water (50 mL), made basic (pH=9) with sat. aq. NaHCO3 and extracted with DCM:MeOH=9:1 (multiple times). The combined organic extracts were filtered through a phase separator and evaporated to give 1.85 g orange semi-solid. This crude was dissolved in MeCN (20 mL) and IPA (0.5 mL) at 70° C., cooled to rt, filtered, washed with MeCN and dried under vacuum at 40° C. to afford the title compound (1.25 g, 56%) as an yellow solid. MS (ESI):

m/z [M+H]⁺405.3. HRMS (ESI): m/z [M+H]⁺ calcd for C₂₀H₁₉F₃N₄O₂: 405.1538, found: 405.1538. ¹H NMR (500 MHz, DMSO-d6) δ 1.25-1.41 (m, 4H), 1.72 (d, 2H), 1.99 (d, 1H), 2.13 (s, 1H), 3.56-3.69 (m, 1H), 4.17-4.28 (m, 1H), 7.24-7.36 (m, 3H), 7.55 (d, 1H), 7.71 (d, 1H), 8.84 (d, 1H), 9.80 (s, 1H), 10.46 (s, 1H).

Example 41

Step 1: Intermediate 37: (1S,3R)-3-[(1-chloropyrido[3,4-d]pyridazin-4-yl)amino]cyclohexanol

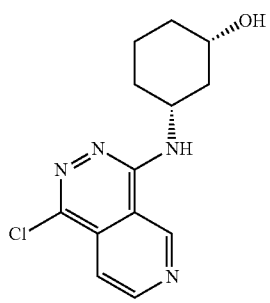 [SMILES: O[C@H]1CCC[C@@H](Nc2nnc(Cl)c3ccncc23)C1]

and Intermediate 38: (1S,3R)-3-[(4-chloropyrido[3,4-d]pyridazin-1-yl)amino]cyclohexanol

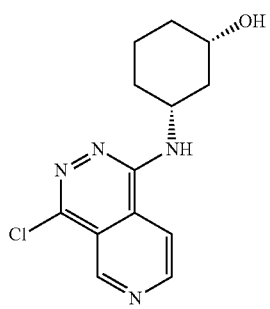 [SMILES: O[C@H]1CCC[C@@H](Nc2nnc(Cl)c3cnccc23)C1]

To a suspension of (1S,3R)-3-aminocyclohexanol hydrochloride (0.93 g, 6.1 mmol, 1.1 eq) in NMP (12 mL, 0.5 M), 1,4-dichloropyrido[3,4-d]pyridazine (1.1 g, 5.7 mmol, 1.0 eq) and DIPEA (4.0 mL, 23 mmol, 4.1 eq) were added at rt. The mixture was heated to 90° C. and stirred for 20 h. The reaction mixture was cooled to rt and concentrated in vacuo. The residue was purified by column chromatography (silica, hexane/EtOAc=50:50) to give the title compound mixture (Intermediate 37/Intermediate 38=7:3, 2.1 g, 89%) as a yellow caramel. MS(ESI): m/z 279.1/281.1 [M+H]⁺. ¹H NMR (400 MHz, CDCl₃) δ 1.4-1.5 (m, 1H), 1.6-1.7 (m, 1H), 2.1-1.8 (m, 6H), 2.18 (br s, 2H), 4.19 (br s, 1H), 4.5-4.6 (m, 0.3H), 4.6-4.7 (m, 0.7H), 6.5-6.7 (m, 0.3H), 6.9-7.1 (m, 0.7H), 7.55 (dd, 0.3H), 7.87 (dd, 0.7H), 8.99 (d, 0.3H), 9.00 (d, 0.7H), 9.28 (d, 0.7H), 9.52 (d, 0.3H).

Step 2: Intermediate 39: N-[(1R,3S)-3-[tert-butyl(dimethyl)silyl]oxycyclohexyl]-1-chloro-pyrido[3,4-d]pyridazin-4-amine

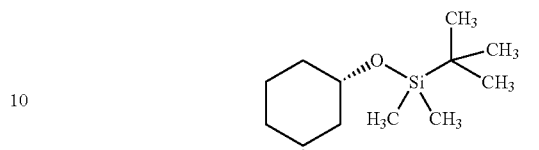

and Intermediate 40: N-[(1R,3S)-3-[tert-butyl(dimethyl)silyl]oxycyclohexyl]-4-chloro-pyrido[3,4-d]pyridazin-1-amine

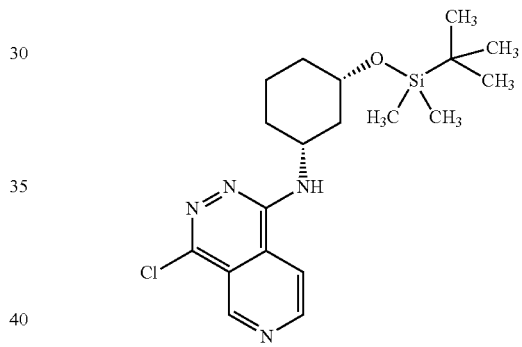

To a solution of the mixture of Intermediate 37 and Intermediate 38 from the previous step (1.7 g, 4.1 mmol, 1.0 eq) in DMF (25 mL) were added imidazole (0.34 g, 5.0 mmol, 1.2 eq), tert-butyldimethylsilyl chloride (0.68 mg, 4.5 mmol, 1.1 eq), and DMAP (0.16 mg, 1.3 mmol, 0.3 eq) at 0° C., and the mixture was stirred for 22 h at rt. The reaction mixture was poured into iced water, and extracted with EtOAc (50 mL, 2 times). The organic layer was washed with H₂O (20 mL, 3 times) and brine, dried over Na₂SO₄, and concentrated in vacuo. The residue was purified by column chromatography (silica, hexane/EtOAc=70:30) to give Intermediate 39 (798 mg, 50%) as a pale yellow amorphous and Intermediate 40 (176 mg, 11%) as a pale yellow powder.

Intermediate 39: ¹H NMR (400 MHz, CDCl₃) δ 0.18 (s, 3H), 0.21 (s, 3H), 0.96 (s, 9H), 1.4-1.5 (m, 1H), 1.6-1.8 (m, 3H), 1.8-2.0 (m, 3H), 2.0-2.1 (m, 1H), 4.1-4.2 (m, 1H), 4.6-4.7 (m, 1H), 7.00 (br s, 1H), 7.86 (dd, 1H), 9.01 (d, 1H), 9.24 (s, 1H). MS(ESI): m/z 393.2/395.2 [M+H]+.

Intermediate 40: ¹H NMR (400 MHz, CDCl₃) δ 0.16 (s, 3H), 0.19 (s, 3H), 0.96 (s, 9H), 1.39-1.50 (m, 1H), 1.51-1.96 (m, 6H), 1.99-2.09 (m, 1H), 4.11-4.20 (m, 1H), 4.61-4.70 (m, 1H), 6.65 (br s, 1H), 7.53 (d, 1H), 8.98 (d, 1H) 9.53 (s, 1H). MS(ESI): m/z 393.2/395.2 [M+H]⁺.

Step 3: Intermediate 41: 2-[4-[[(1R,3S)-3-[tert-butyl(dimethyl)silyl]oxycyclohexyl]amino]pyrido[3,4-d]pyridazin-1-yl]-5-(trifluoromethyl)phenol

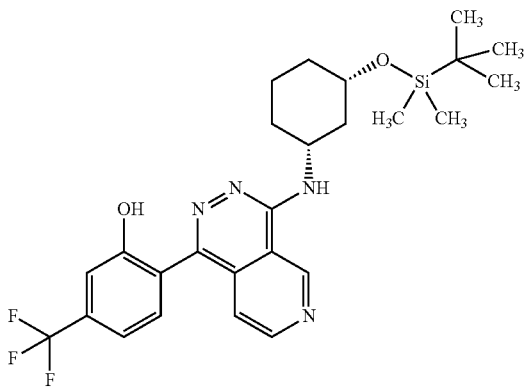 [SMILES: CC(C)(C)[Si](C)(C)O[C@H]1CCC[C@@H](Nc2nnc(-c3ccc(C(F)(F)F)cc3O)c3ccncc23)C1]

A solution of Intermediate 39 from the previous step (201 mg, 0.51 mmol, 1.0 eq), [2-hydroxy-4-(trifluoromethyl)phenyl]boronic acid (131 mg, 0.63 mmol, 1.2 eq), and Pd(dppf)Cl$_2$·CH$_2$Cl$_2$ (45 mg, 0.06 mmol, 0.1 eq) in 1,4-dioxane (4 mL, 0.1 M) was added 2 M Na$_2$CO$_3$ aq. (0.80 mL, 1.6 mmol, 3.1 eq). The mixture was heated at 100° C. and stirred for 4 h under argon atmosphere. The reaction mixture was cooled to rt and diluted with H$_2$O and EtOAc. The organic layer was extracted with EtOAc (10 mL, 2 times), washed with brine, dried over Na$_2$SO$_4$, and concentrated in vacuo. The residue was purified by column chromatography (silica, hexane/EtOAc=60:40) and then (NH-silica, EtOAc/MeOH=95:5) to give the title compound (145 mg, 52%) as a yellow amorphous. MS(ESI): m/z 519.2 [M+H]$^+$. $^1$H NMR (400 MHz, CDCl$_3$) δ 0.21 (s, 3H), 0.25 (s, 3H), 0.99 (s, 9H), 1.4-1.6 (m, 2H), 1.6-1.8 (m, 3H), 1.9-2.1 (m, 3H), 4.27 (d, 1H), 4.80 (td, 1H), 4.80 (td, 1H), 7.2-7.3 (m, 1H), 7.43 (d, 1H), 7.6-7.4 (br s, 1H), 7.68 (d, 1H), 7.98 (dd, 1H), 8.98 (d, 1H), 9.36 (s, 1H), 11.63 (br s, 1H).

Step 4: Example 41: 2-[4-[[(1R,3S)-3-hydroxycyclohexyl]amino]pyrido[3,4-d]pyridazin-1-yl]-5-(trifluoromethyl)phenol

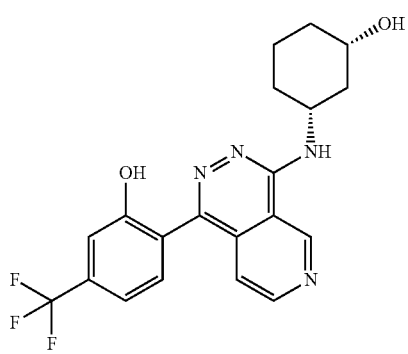 [SMILES: Oc1cc(C(F)(F)F)ccc1-c1nnc(N[C@@H]2CCC[C@H](O)C2)c2cnccc12]

To a solution of the Intermediate 41 (140 mg, 0.26 mmol, 1.0 eq) in THF (3 mL) was added 1 M tetrabutylammonium fluoride in THF solution (0.4 mL, 0.40 mmol, 1.6 eq) at rt. The mixture was stirred at rt for 22 h. To the resulting mixture was added sat. aq. NaHCO$_3$ and extracted with EtOAc (15 mL, 2 times). The organic layer was washed with brine, dried over Na$_2$SO$_4$, and concentrated in vacuo. The residue was purified by column chromatography (silica, EtOAc/MeOH=95:5) to give the title compound (96 mg, 89%) as a yellow amorphous.

MS(ESI): m/z 405.1 [M+H]$^+$. $^1$H NMR (400 MHz, CDCl$_3$) δ 1.5-1.6 (m, 1H), 1.7-2.1 (m, 6H), 2.1-2.2 (m, 1H), 3.7-3.8 (m, 1H), 4.2-4.3 (m, 1H), 4.7-4.8 (m, 1H), 7.25 (m, 1H), 7.2-7.3 (m, 1H), 7.43 (d, 1H), 7.68 (d, 1H), 7.98 (d, 1H), 8.98 (d, 1H), 9.37 (s, 1H), 11.4-11.7 (m, 1H).

Example 42

Step 1: Intermediate 42: (1S,3R)-3-[[1-[2-[(4-methoxyphenyl)methoxy]-4-(trifluoromethyl)phenyl]pyrido[3,4-d]pyridazin-4-yl]amino]cyclohexanol

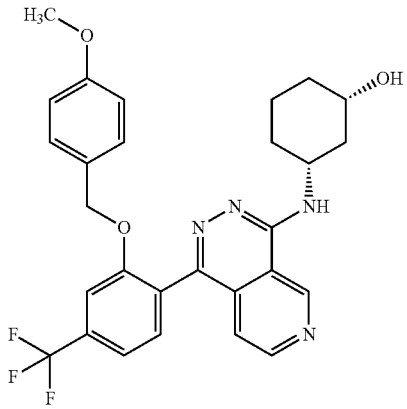 [SMILES: COc1ccc(COc2cc(C(F)(F)F)ccc2-c2nnc(N[C@@H]3CCC[C@H](O)C3)c3cnccc23)cc1]

Intermediate 35 (1.45 g, 3.3 mmol), (1S,3R)-3-aminocyclohexan-1-ol, HCl (0.54 g, 3.6 mmol) and Na$_2$CO$_3$ (0.72 g, 6.8 mmol) were mixed in sulfolane (14 mL) and the reaction was stirred at 120° C. for 3 h. The reaction mixture was cooled to rt before water and iPrOAc were added and the phases separated. The aqueous phase was extracted with iPrOAc and the combined organic extract was washed twice with water and evaporated. The residue was purified by flash chromatography using EtOAc as mobile phase to afford the title compound (1.47 g, 86%) as a pale yellow solid. MS (ESI): m/z [M+H]$^+$525.5.

Step 2: Example 42: 2-(4-(((1R,3S)-3-hydroxycyclohexyl)amino)pyrido[3,4-d]pyridazin-1-yl)-5-(trifluoromethyl)phenol dihydrochloride

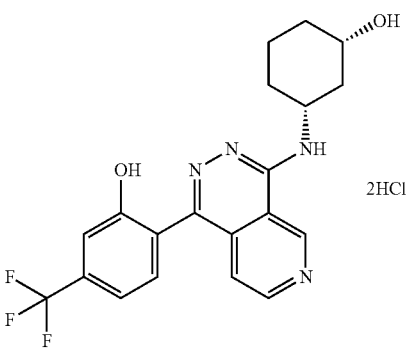 [SMILES: Oc1cc(C(F)(F)F)ccc1-c1nnc(N[C@@H]2CCC[C@H](O)C2)c2cnccc12]

HCl (15 mL, 60 mmol, 4 M in 1,4-dioxane) was added to Intermediate 42 (1.75 g, 3.34 mmol) in absolute EtOH (3 mL) to give a clear solution. The reaction was stirred at 40° C. for 15 min, then to rt. The reaction mixture was added dropwise to Et$_2$O (100 mL) and the solid was filtered off and washed with Et$_2$O. The solid was re-dissolved in EtOH and EtOAc was added to precipitate the product. The solid was filtered, washed with two portions of EtOAc and dried to give a yellow solid. The solid was further dissolved in MeCN/water and freeze-dried to afford the title compound (1.45 g, 91%). MS (ESI): m/z [M+H]$^+$405.3. HRMS (ESI): m/z [M+H]$^+$ calcd for C$_{20}$H$_{19}$F$_3$N$_4$O$_2$: 405.1536, found: 405.1534. $^1$H NMR (500 MHz, DMSO-d6) δ 1.09-1.21 (m, 1H), 1.38 (q, 1H), 1.46-1.63 (m, 2H), 1.80 (dt, 1H), 1.87 (m, 1H), 1.98 (d, 1H), 2.24 (d, 1H), 3.57 (ddd, 1H), 4.15 (dt, 1H), 7.39 (d, 1H), 7.43 (s, 1H), 7.51 (d, 1H), 7.58 (d, 1H), 9.11 (d, 1H), 10.24 (s, 1H), 11.02 (s, 1H).

Example 43: 2-[1-[[(1R,3S)-3-hydroxycyclohexyl]amino]pyrido[3,4-d]pyridazin-4-yl]-5-(trifluoromethyl)phenol

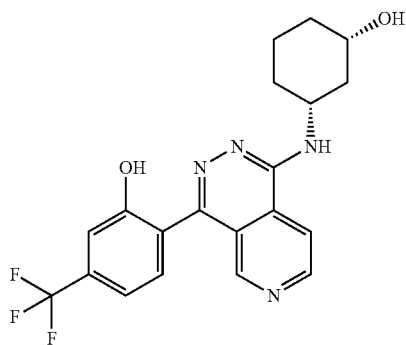

The title compound was prepared analogously to Example 41 using Intermediate 40 instead of Intermediate 39. MS(ESI): m/z 405.2 [M+H]$^+$. $^1$H NMR (400 MHz, DMSO-d6) δ 1.10-1.20 (m, 1H), 1.20-1.45 (m, 3H), 1.72-1.82 (m, 1H), 1.82-1.93 (m, 1H), 1.98-2.08 (m, 1H), 2.23-2.33 (m, 1H), 3.50-3.63 (m, 1H), 4.22-4.35 (m, 1H), 4.65-4.75 (m, 1H), 7.15-7.30 (m, 2H), 7.45-7.60 (m, 2H), 8.25 (d, 1H), 8.85 (s, 1H), 8.90 (d, 1H).

Example 44

Step 1: Intermediate 43: 2-[4-[[(1R,3S)-3-[tert-butyl(dimethyl)silyl]oxycyclohexyl]amino]pyrido[3,4-d]pyridazin-1-yl]-5-chloro-phenol

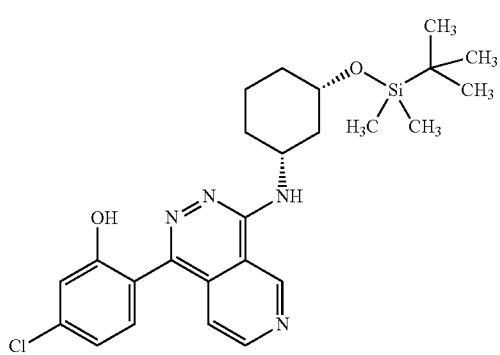 [SMILES: CC(C)(C)[Si](C)(C)O[C@H]1CCC[C@@H](Nc2nnc(-c3ccc(Cl)cc3O)c3ccncc23)C1]

A solution of Intermediate 39 in (1.1 g, 2.8 mmol), 5-chloro-2-(4,4,5,5-tetramethyl-1,3,2-dioxaborolan-2-yl)phenol (1.0 g, 3.9 mmol), and Pd(dppf)Cl$_2$·CH$_2$Cl$_2$ (231 mg, 0.283 mmol, 0.1 eq) in 1,4-dioxane (4 mL) was added 2 M Na$_2$CO$_3$ aq. (4.2 mL, 8.4 mmol, 3.0 eq). The mixture was heated at 100° C. and stirred for 2.5 h under argon atmosphere. The reaction mixture was cooled to rt and diluted with H$_2$O. The mixture was extracted with EtOAc and the organic layer was washed with brine, dried over Na$_2$SO$_4$, and concentrated in vacuo. The residue was purified by silica gel column chromatography using a gradient of 20-50% EtOAc in hexane as mobile phase. The collected fractions were further purified by NH-silica gel column chromatography using a gradient of 50-100% EtOAc in hexane as mobile phase to give the title compound (774.7 mg, 55%) as a yellow amorphous. MS (ESI): m/z [M+H]$^+$ 485.2/487.1. $^1$H NMR (400 MHz, CDCl$_3$) δ 0.20 (s, 3H), 0.24 (s, 3H), 0.99 (s, 9H), 1.45-1.62 (m, 1H), 1.63-1.83 (m, 3H), 1.87-2.10 (m, 4H), 4.20-4.30 (m, 1H), 4.72-4.83 (m, 1H), 6.99 (dd, 1H), 7.18 (d, 1H), 7.32 (br s, 1H), 7.50 (d, 1H), 7.97 (dd, 1H), 8.96 (d, 1H), 9.33-9.35 (m, 1H), 11.63 (br s, 1H).

Step 2: Example 44: 5-chloro-2-[4-[[(1R,3S)-3-hydroxycyclohexyl]amino]pyrido[3,4-d]pyridazin-1-yl]phenol

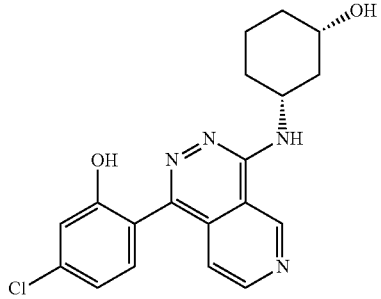 [SMILES: Oc1cc(Cl)ccc1-c1nnc(N[C@@H]2CCC[C@H](O)C2)c2cnccc12]

To a solution of the Intermediate 43 (174.6 mg, 0.35 mmol, 1.0 eq) in THF (3 mL) was added 1 M tetrabutylammonium fluoride in THF solution (0.52 mL, 0.52 mmol, 1.5 eq) at rt. The mixture was stirred for 21 h at rt. The resulting mixture was added sat. NaHCO$_3$ aq. and extracted with EtOAc. The organic layer was washed with brine, dried over Na$_2$SO$_4$, and concentrated in vacuo. The residue was purified by flash column chromatography using a gradient of 0-5% MeOH in EtOAc as mobile phase to give the title compound (114.5 mg, 81%) as a yellow amorphous. MS (ESI): m/z [M+H]$^+$ 371.1/373.1. $^1$H NMR (400 MHz, DMSO-d6) δ 1.08-1.21 (m, 1H), 1.22-1.44 (m, 3H), 1.71-1.82 (m, 1H), 1.82-1.93 (m, 1H), 1.98-2.08 (m, 1H), 2.24-2.36 (m, 1H), 3.50-3.63 (m, 1H), 4.25-4.40 (m, 1H), 6.91 (dd, 1H), 6.96 (d, 1H), 7.28 (d, 1H), 7.30 (dd, 1H), 7.67 (d, 1H), 8.82 (d, 1H), 9.74 (d, 1H).

The examples included in Table 3 below were synthesized analogously to the two step procedure of Example 44 using the specified boronic acids and borolanes.

TABLE 3

| Ex No. | Name | Boronic acid starting material | Product |
|---|---|---|---|
| 45 | 3-fluoro-2-[4-[[(1R,3S)-3-hydroxycyclohexyl]amino]pyrido[3,4-d]pyridazin-1-yl]-5-(trifluoromethyl)phenol | | |
| 46 | 5-chloro-3-fluoro-2-[4-[[(1R,3S)-3-hydroxycyclohexyl]amino]pyrido[3,4-d]pyridazin-1-yl]phenol | | |
| 47 | 3-fluoro-2-[4-[[(1R,3S)-3-hydroxycyclohexyl]amino]pyrido[3,4-d]pyridazin-1-yl]phenol | | |
| 48 | 2-[4-[[(1R,3S)-3-hydroxycyclohexyl]amino]pyrido[3,4-d]pyridazin-1-yl]-5-(trifluoromethoxy)phenol | | |

Example 49 and Example 50: (R) and (S) atropisomers of 2-[4-[[(1R,3S)-3-hydroxycyclohexyl]amino]pyrido[3,4-d]pyridazin-1-yl]-3-(trifluoromethyl)phenol

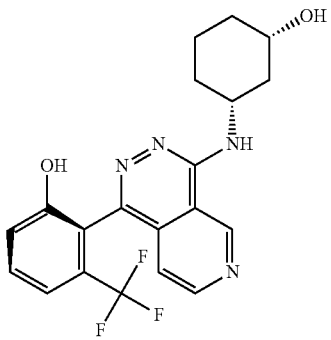

A solution of Intermediate 39 in (200 mg, 0.51 mmol, 1.0 eq), [2-hydroxy-6-(trifluoromethyl)phenyl]boronic acid (125.8 mg, 0.61 mmol), and SPhos Pd G3 (39.8 mg, 0.05 mmol, 0.1 eq) in 1,4-dioxane (0.77 mL) was added 2 M Na$_2$CO$_3$ aq. (0.77 mL, 1.5 mmol, 3.0 eq) and the vial was sealed. The reaction was run at 150° C. for 1 h in a microwave reactor. The reaction mixture was cooled to rt and diluted with H$_2$O and EtOAc. The organic layer was extracted with EtOAc (3 times), washed with brine, dried over Na$_2$SO$_4$, and concentrated in vacuo. The residue was purified by column chromatography using a gradient of 0-10% MeOH in EtOAc and then NH column chromatography using a gradient of 5-20% MeOH in EtOAc as mobile phase to give a product mixture as a pale yellow powder. The residue was dissolved in THF (3 mL), and to the mixture was added 1 M tetrabutylammonium fluoride in THF solution (0.6 mL, 0.60 mmol) at rt. The mixture was stirred for 6 h at rt. To the resulting mixture was added sat. NaHCO$_3$ aq. and extracted with EtOAc (2 times). The organic layer was washed with brine, dried over Na$_2$SO$_4$, and concentrated in vacuo. The residue was purified by reversed phase flash chromatography on a C18 column using a gradient of 20-50% MeCN in (NH$_4$)$_2$CO$_3$ (10 mM, aq.) as mobile phase to give the first eluting compound Isomer 1 Example 49 (33.3 mg) as a beige powder, and the second eluting compound Isomer 2 Example 50 (30.3 mg) as a beige powder.

Example 49: MS (ESI): m/z [M+H]$^+$ 405.0. $^1$H NMR (400 MHz, DMSO-d6) δ 1.09-1.21 (m, 1H), 1.21-1.47 (m, 3H), 1.72-1.82 (m, 1H), 1.83-1.93 (m, 1H), 2.01-2.13 (m, 1H), 2.21-2.37 (m, 1H), 3.51-3.63 (m, 1H), 4.24-4.39 (m, 1H), 4.74 (br d, 1H), 7.02 (dd, 1H), 7.27 (d, 1H), 7.34 (d, 1H), 7.56 (dd, 1H), 7.71 (d, 1H), 8.81 (d, 1H), 9.77 (s, 1H), 10.16 (br s, 1H).

Example 50: MS (ESI): m/z [M+H]$^+$ 405.0. $^1$H NMR (400 MHz, DMSO-d6) δ 1.09-1.21 (m, 1H), 1.27-1.45 (m, 3H), 1.74-1.83 (m, 1H), 1.83-1.93 (m, 1H), 1.96-2.06 (m, 1H), 2.28-2.39 (m, 1H), 3.49-3.62 (m, 1H), 4.25-4.41 (m, 1H), 4.72 (br d, 1H), 7.02 (dd, 1H), 7.28 (d, 1H), 7.34 (d, 1H), 7.56 (dd, 1H), 7.71 (d, 1H), 8.81 (d, 1H), 9.77 (s, 1H), 10.15 (br s, 1H).

Example 51

Step 1: Intermediate 44: 2-[4-[[(1R,3S)-3-[tert-butyl(dimethyl)silyl]oxycyclohexyl]amino]pyrido[3,4-d]pyridazin-1-yl]-5-vinyl-phenol

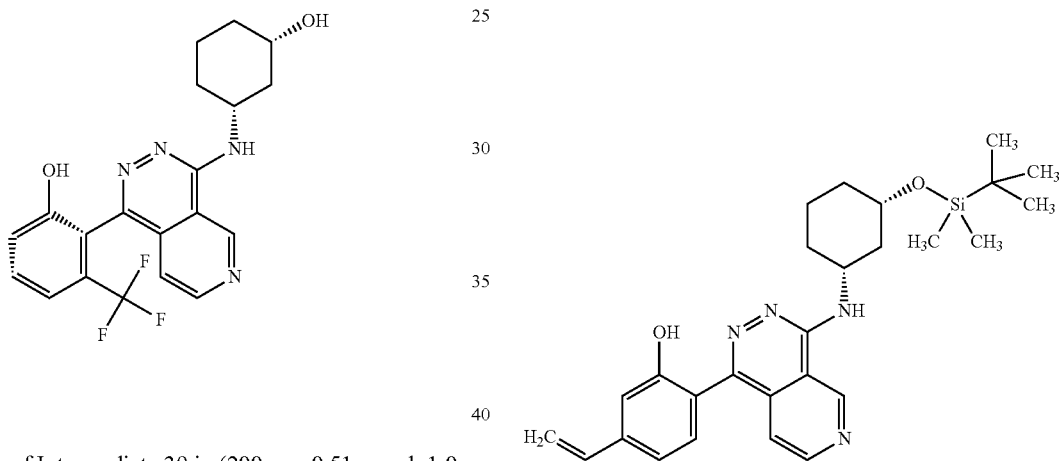

To a solution of Intermediate 43 (185.2 mg, 0.37 mmol) in 1,4-dioxane (1.2 mL) and water (0.8 mL) was added K$_3$PO$_4$ (477.2 mg, 2.2 mmol), potassium; trifluoro(vinyl)boranuide (149.6 mg, 1.1 mmol) and Xphos Pd G3 (30.0 mg, 0.035 mmol). The vial was sealed and the reaction was run at 120° C. for 30 min in a microwave reactor. The reaction was then diluted with EtOAc and H$_2$O. The layers were separated, the aqueous layer was extracted with EtOAc and the combined organic layers were washed with sat aq. NaHCO$_3$ and brine. The organic layer was dried over Na$_2$SO$_4$, filtered and evaporated. The crude product was purified by flash column chromatography using a gradient of 15-70% EtOAc in hexane as mobile phase to give the title compound (54.3 mg, 30%) as a brown powder. MS (ESI): m/z [M+H]$^+$ 477.2. $^1$H NMR (400 MHz, CDCl$_3$) δ 0.20 (s, 3H), 0.24 (s, 3H), 0.99 (s, 9H), 1.44-1.53 (m, 1H), 1.64-1.84 (m, 3H), 1.87-2.11 (m, 4H), 4.20-4.27 (m, 1H), 4.72-4.83 (m, 1H), 5.34 (d, 1H), 5.85 (d, 1H), 6.73 (dd, 1H), 7.06 (dd, 1H), 7.23 (d, 1H), 7.53 (d, 1H), 8.03 (d, 1H), 8.95 (d, 1H), 9.33 (s, 1H).

85

Step 2: Intermediate 45: 2-[4-[[(1R,3S)-3-[tert-butyl(dimethyl)silyl]oxycyclohexyl]amino]pyrido[3,4-d]pyridazin-1-yl]-5-ethyl-phenol

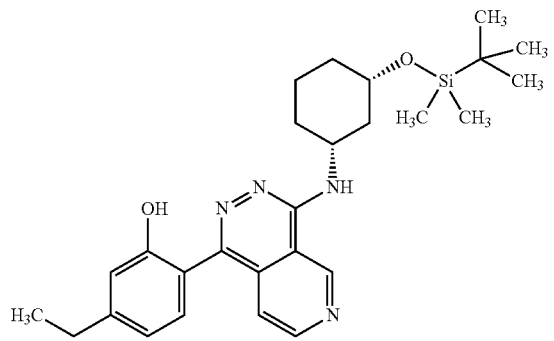 [SMILES: CCc1ccc(-c2nnc(N[C@@H]3CCC[C@H](O[Si](C)(C)C(C)(C)C)C3)c3cnccc23)c(O)c1]

To a solution of Intermediate 44 (52 mg, 0.11 mmol) in EtOAc (2 mL) was added Pd/C (22 mg, 10% wet) in nitrogen atmosphere. Then nitrogen was replaced by 1 atm of hydrogen and the reaction mixture was stirred at rt for 1 h. The mixture was filtered through a Celite® pad. The filtrate was concentrated in vacuo. The residue was purified by flash column chromatography using a gradient of 10-35% EtOAc in hexane as mobile phase, to give the title compound (33.4 mg, 66%) as a yellow powder. MS (ESI): m/z [M+H]$^+$ 479.2. $^1$H NMR (400 MHz, CDCl$_3$) δ 0.20 (s, 3H), 0.23 (s, 3H), 0.98 (s, 9H), 1.30 (t, 3H), 1.45-1.55 (m, 1H), 1.63-1.84 (m, 3H), 1.88-2.12 (m, 4H), 2.69 (q, 2H), 4.19-4.27 (m, 1H), 4.72-4.82 (m, 1H), 6.85 (dd, 1H), 7.03 (d, 1H), 7.48 (d, 1H), 8.05 (dd, 1H), 8.94 (d, 1H), 9.33 (d, 1H), 11.26 (br s, 1H).

Step 3: Example 51: 5-ethyl-2-[4-[[(1R,3S)-3-hydroxycyclohexyl]amino]pyrido[3,4-d]pyridazin-1-yl]phenol

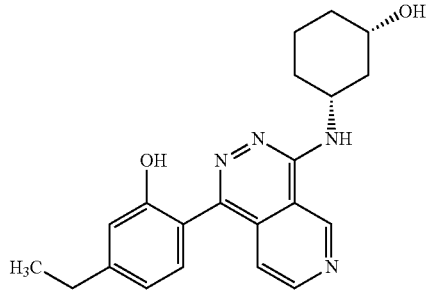 [SMILES: CCc1ccc(-c2nnc(N[C@@H]3CCC[C@H](O)C3)c3cnccc23)c(O)c1]

The title compound was obtained analogously to Example 44 using Intermediate 45. MS (ESI): m/z [M+H]$^+$ 365.2. $^1$H NMR (400 MHz, CDCl$_3$) δ 1.29 (t, 3H), 1.47-1.76 (m, 3H), 1.79-2.04 (m, 4H), 2.12-2.25 (m, 1H), 2.69 (q, 2H), 4.24 (br s, 1H), 4.61-4.79 (m, 1H), 6.86 (dd, 1H), 7.03 (d, 1H), 7.47 (d, 1H), 8.05 (dd, 1H), 8.93 (d, 1H), 9.34 (s, 1H).

86

Example 52

Step 1: Intermediate 46: (1S,3R)-3-[[1-(4-cyclopropyl-2-methoxy-phenyl)pyrido[3,4-d]pyridazin-4-yl]amino]cyclohexanol

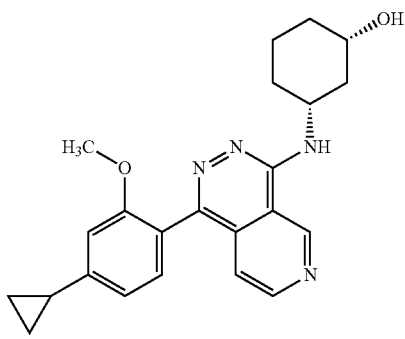 [SMILES: COc1cc(C2CC2)ccc1-c1nnc(N[C@@H]2CCC[C@H](O)C2)c2cnccc12]

The title compound was obtained analogously to Example 44 using Intermediate 13. MS (ESI): m/z [M+H]$^+$ 391.2. $^1$H NMR (400 MHz, CDCl$_3$) δ 0.76-0.83 (m, 2H), 1.00-1.08 (m, 2H), 1.42-1.81 (m, 4H), 1.82-2.03 (m, 3H), 2.17-2.33 (m, 2H), 3.69 (s, 3H), 4.06-4.17 (m, 1H), 4.62-4.77 (m, 1H), 6.42-6.63 (m, 1H), 6.76 (d, 1H), 6.80 (dd, 1H), 7.32 (dd, 1H), 7.37 (d, 1H), 8.77 (d, 1H), 9.28 (s, 1H).

Step 2: Example 52: 5-cyclopropyl-2-[4-[[(1R,3S)-3-hydroxycyclohexyl]amino]pyrido[3,4-d]pyridazin-1-yl]phenol

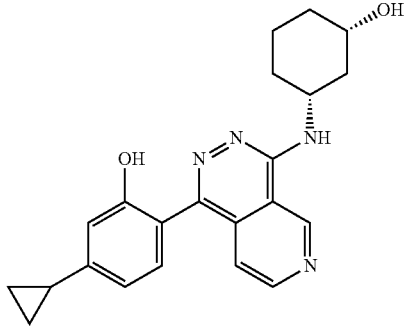 [SMILES: Oc1cc(C2CC2)ccc1-c1nnc(N[C@@H]2CCC[C@H](O)C2)c2cnccc12]

To a solution of Intermediate 46 (200 mg, 0.45 mmol) in CH$_2$Cl$_2$ (4 mL) was added BBr$_3$ (3.0 mL, 3.0 mmol, 1 M in CH$_2$Cl$_2$) at −78° C. The reaction mixture was stirred at 0° C. for 1 h. The reaction was quenched with NaHCO$_3$ aq. and extracted with CHCl$_3$-MeOH (3 times). The organic layer was dried over Na$_2$SO$_4$ and concentrated in vacuo. The residue was purified by flash column chromatography using a gradient of 0-10% MeOH in CHCl$_3$ as mobile phase to give a brown gum. The resulted was purified by reversed phase flash chromatography on a C18 column using a gradient of 30-60% MeCN in (NH$_4$)$_2$CO$_3$ (10 mM, aq) as mobile phase to afford the title compound (98.7 mg, 50%) as an orange powder. MS (ESI): m/z [M+H]$^+$377.1. $^1$H NMR (400 MHz, DMSO-d6) δ 0.65-0.74 (m, 2H), 0.95-1.03 (m, 2H), 1.08-1.21 (m, 1H), 1.23-1.45 (m, 3H), 1.72-1.82 (m, 1H), 1.83-1.97 (m, 2H), 2.03 (br d, 1H), 2.21-2.36 (m, 1H), 3.48-3.63 (m, 1H), 4.21-4.42 (m, 1H), 4.72 (br d, 1H), 6.64-6.73 (m, 2H), 7.19 (d, 1H), 7.32 (dd, 1H), 7.64 (d, 1H), 8.83 (d, 1H), 9.66 (br s, 1H), 9.73 (d, 1H).

Example 53: 4-fluoro-2-[4-[[(1R,3S)-3-hydroxycyclohexyl]amino]pyrido[3,4-d]pyridazin-1-yl]-5-(trifluoromethyl)phenol

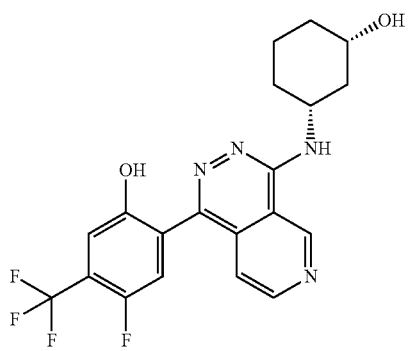 [SMILES: Oc1cc(C(F)(F)F)c(F)cc1-c1nnc(N[C@@H]2CCC[C@H](O)C2)c2cnccc12]

Using Intermediate 14 following the two step procedure described for Example 52, the title compound was obtained. MS (ESI): m/z [M+H]$^+$ 423.0. $^1$H NMR (400 MHz, DMSO-d6) δ 1.09-1.21 (m, 1H), 1.23-1.45 (m, 3H), 1.73-1.82 (m, 1H), 1.83-1.93 (m, 1H), 1.97-2.09 (m, 1H), 2.24-2.36 (m, 1H), 3.50-3.65 (m, 1H), 4.27-4.40 (m, 1H), 4.73 (br s, 1H), 7.25 (d, 1H), 7.32 (dd, 1H), 7.48 (d, 1H), 7.82 (d, 1H), 8.84 (d, 1H), 9.77 (s, 1H).

Example 54

Step 1: Intermediate 47: (1R,2R)-2-[(1-chloropyrido[3,4-d]pyridazin-4-yl)amino]cyclohexanol

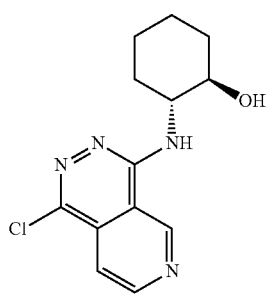 [SMILES: O[C@@H]1CCCC[C@H]1Nc1nnc(Cl)c2ccncc12]

and Intermediate 48: (1R,2R)-2-[(4-chloropyrido[3,4-d]pyridazin-1-yl)amino]cyclohexanol

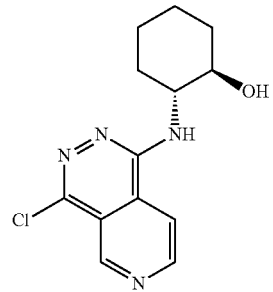 [SMILES: O[C@@H]1CCCC[C@H]1Nc1nnc(Cl)c2cnccc12]

To a suspension of (1R,2R)-2-aminocyclohexanol hydrochloride (3.18 g, 21 mmol, 1.1 eq) in MeCN (20 mL, 1 M), 1,4-dichloropyrido[3,4-d]pyridazine (4.0 g, 20 mmol, 1.0 eq) and DIPEA (10.4 mL, 60 mmol, 3 eq) were added at rt. The mixture was heated to 100° C. and stirred for 4 h. The reaction mixture was cooled to rt and concentrated in vacuo. The residue was purified by column chromatography using a gradient of 0-3% MeOH in EtOAc as mobile phase to give a 3:1 mixture of Intermediate 47 and Intermediate 48 (4.2 g, 56%) as a pale yellow solid. MS (ESI): m/z [M+H]$^+$ 279.1/281.1.

Step 2: Intermediate 49: 1-chloro-N-[(1R,2R)-2-triisopropylsilyloxycyclohexyl]pyrido[3,4-d]pyridazin-4-amine

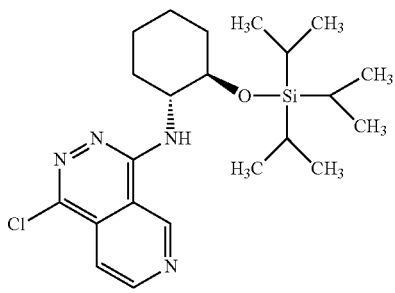 [SMILES: CC(C)[Si](O[C@@H]1CCCC[C@H]1Nc1nnc(Cl)c2ccncc12)(C(C)C)C(C)C]

To a solution of the mixture of Intermediate 47 and Intermediate 48 from the previous step (3.2 g, 11.5 mmol, 1.0 eq) in CH$_2$Cl$_2$ (35 mL) was added 2,6-dimethylpyridine (2.7 mL, 23 mmol, 2 eq), triisopropylsilyl trifluoromethanesulfonate (4.63 mL, 17.2 mmol, 1.5 eq) at 0° C., and the mixture was stirred for 30 min at same temperature. The reaction mixture was diluted with H₂O and the mixture was stirred. The organic layer was separated and concentrated in vacuo. The residue was purified by NH column chromatography using a gradient of 10-30% EtOAc in hexane as mobile phase to give the title compound (3.1 g, 61%) as a pale yellow amorphous. MS (ESI): m/z [M−H]⁻ 433.3/435.3. ¹H NMR (400 MHz, CDCl₃) δ 1.00-1.14 (m, 21H), 1.17-1.44 (m, 2H), 1.45-1.73 (m, 3H), 1.78-1.89 (m, 1H), 1.99-2.12 (m, 1H), 2.57-2.71 (m, 1H), 3.87-3.99 (m, 1H), 4.09-4.20 (m, 1H), 5.65 (br d, 1H), 7.89 (dd, 1H), 9.02 (d, 1H), 9.21-9.24 (m, 1H).

Step 3: Intermediate 50: 1-[5-fluoro-2-methoxy-4-(trifluoromethyl)phenyl]-N-[(1R,2R)-2-triisopropylsilyloxycyclohexyl]pyrido[3,4-d]pyridazin-4-amine

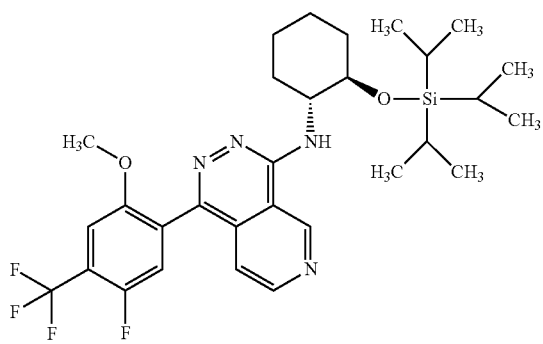 [SMILES: COc1cc(C(F)(F)F)c(F)cc1-c1nnc(N[C@@H]2CCCC[C@H]2O[Si](C(C)C)(C(C)C)C(C)C)c2cnccc12]

To a solution of Intermediate 49 (150 mg, 0.34 mmol), Intermediate 14 (206.9 mg, 0.52 mmol), and PdCl₂(Amphos)₂ (12.2 mg, 0.02 mmol, 0.05 eq) in 1,4-dioxane (2 mL) and H₂O (0.5 mL) was added Cs₂CO₃ (337 mg, 1.03 mmol, 3.0 eq) and the vial was sealed. The reaction was run at 120° C. for 1 h in a microwave reactor. The reaction mixture was cooled to rt and diluted with H₂O. The mixture was added CHCl₃ and stirred. The organic layer was separated and concentrated in vacuo. The residue was purified by column chromatography using a gradient of 5-35% EtOAc in hexane as mobile phase to give the title compound (126.3 mg, 62%) as a pale yellow amorphous. MS (ESI): m/z [M−H]⁻ 591.3. ¹H NMR (400 MHz, CDCl₃) δ 0.99-1.16 (m, 21H), 1.23-1.46 (m, 2H), 1.47-1.75 (m, 3H), 1.78-1.90 (m, 1H), 2.02-2.15 (m, 1H), 2.65-2.79 (m, 1H), 3.74 (s, 3H), 3.90-4.01 (m, 1H), 4.20-4.31 (m, 1H), 5.76 (d, 1H), 7.20 (d, 1H), 7.24-7.27 (m, 1H), 7.41 (d, 1H), 8.84 (d, 1H), 9.28 (d, 1H).

Step 4: Intermediate 51: (1R,2R)-2-[[1-[5-fluoro-2-methoxy-4-(trifluoromethyl)phenyl]pyrido[3,4-d]pyridazin-4-yl]amino]cyclohexanol

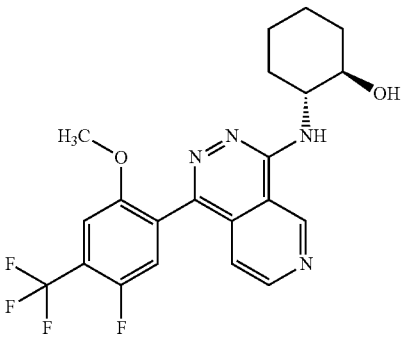 [SMILES: COc1cc(C(F)(F)F)c(F)cc1-c1nnc(N[C@@H]2CCCC[C@H]2O)c2cnccc12]

Starting with Intermediate 50, the title compound was prepared analogously to Example 44. MS (ESI): m/z [M+H]⁺ 437.0. ¹H NMR (400 MHz, CDCl₃) δ 1.46-1.72 (m, 3H), 1.76-2.03 (m, 4H), 2.17-2.28 (m, 1H), 3.74 (s, 3H), 4.15-4.25 (m, 1H), 4.69-4.81 (m, 1H), 6.76-6.96 (m, 1H), 7.19 (d, 1H), 7.23 (dd, 1H), 7.40 (d, 1H), 8.83 (d, 1H), 9.30-9.33 (m, 1H).

Step 5: Example 54: 4-fluoro-2-[4-[[(1R,2R)-2-hydroxycyclohexyl]amino]pyrido[3,4-d]pyridazin-1-yl]-5-(trifluoromethyl)phenol

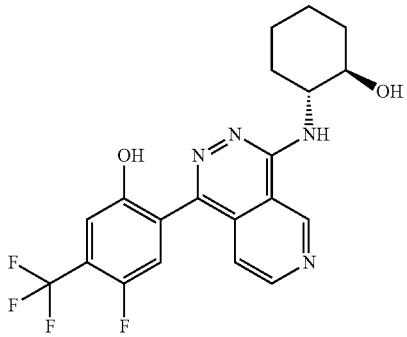 [SMILES: Oc1cc(C(F)(F)F)c(F)cc1-c1nnc(N[C@@H]2CCCC[C@H]2O)c2cnccc12]

Starting with Intermediate 51, the title compound was prepared analogously to Step 2 of Example 52. MS (ESI): m/z [M+H]⁺ 422.9. ¹H NMR (400 MHz, DMSO-d6) δ ppm 1.22-1.43 (m, 4H), 1.63-1.78 (m, 2H), 1.92-2.06 (m, 1H), 2.06-2.19 (m, 1H), 3.57-3.68 (m, 1H), 4.18-4.30 (m, 1H), 4.81 (br d, 1H), 7.26 (d, 1H), 7.31 (dd, 1H), 7.48 (d, 1H), 7.73 (d, 1H), 8.84 (d, 1H), 9.80 (s, 1H).

The examples included in Table 4 below were synthesized in analogy with the procedure of Example 54 steps 3 and 4 starting from Intermediate 49 and the specified boronic acids as starting material.

TABLE 4

| Ex No. | Name | Boronic acid starting material | Product |
|---|---|---|---|
| 55 | 3-fluoro-2-[4-[[(1R,2R)-2-hydroxycyclohexyl]amino]pyrido[3,4-d]pyridazin-1-yl]-5-(trifluoromethyl)phenol | | |
| 56 | 2-[4-[[(1R,2R)-2-hydroxycyclohexyl]amino]pyrido[3,4-d]pyridazin-1-yl]-5-(trifluoromethoxy)phenol | | |
| 57 | 5-chloro-3-fluoro-2-[4-[[(1R,2R)-2-hydroxycyclohexyl]amino]pyrido[3,4-d]pyridazin-1-yl]phenol | | |
| 58 | 5-chloro-2-[4-[[(1R,2R)-2-hydroxycyclohexyl]amino]pyrido[3,4-d]pyridazin-1-yl]phenol | | |

Example 59

Step 1: Intermediate 52: (1R,3R)-3-[[1-[2-[(4-methoxyphenyl)methoxy]-4-(trifluoromethyl)phenyl]pyrido[3,4-d]pyridazin-4-yl]amino]cyclopentanol

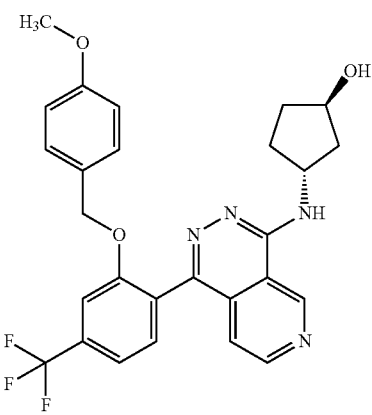 [SMILES: COc1ccc(COc2cc(C(F)(F)F)ccc2-c2nnc(N[C@@H]3CC[C@@H](O)C3)c3cnccc23)cc1]

Intermediate 35 (2.6 g, 5.8 mmol), (1R,3R)-3-aminocyclopentan-1-ol hydrochloride (0.96 g, 7.0 mmol) and NaHCO$_3$ (2.94 g, 35 mmol) were mixed in IPA (25 mL) and stirred at 80° C. for 20 h. The mixture was poured out on water (100 mL), the mixture cooled to rt, the solid product filtered off, washed with water and dried to afford the title compound (2.82 g, 95%) as a beige solid. MS (ESI): m/z [M+H]$^+$ 511.5. $^1$H NMR (500 MHz, DMSO) δ 1.61 (ddd, 2H), 1.84 (dt, 1H), 1.94-2.15 (m, 2H), 2.25 (dd, 1H), 3.67 (s, 3H), 4.20-4.39 (m, 1H), 4.57 (d, 1H), 4.84 (h, 1H), 5.11 (s, 2H), 6.73 (d, 2H), 7.02 (d, 2H), 7.28 (d, 1H), 7.50 (d, 1H), 7.56-7.69 (m, 2H), 7.76 (d, 1H), 8.83 (d, 1H), 9.75 (s, 1H).

Step 2: Example 59: 2-(4-(((1R,3R)-3-hydroxycyclopentyl)amino)pyrido[3,4-d]pyridazin-1-yl)-5-(trifluoromethyl)phenol

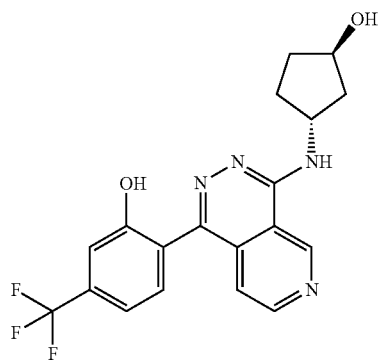

Intermediate 52 (2.7 g, 5.29 mmol) was slurried in absolute EtOH (7 mL) and HCl (4 M in 1,4-dioxane, 19.8 mL, 79 mmol) was added and the reaction stirred at rt for 2 h, before being added dropwise to Et$_2$O (150 mL) under stirring. The precipitate was filtered off and washed with Et$_2$O. The crude solid was dissolved in water (100 mL) and washed with DCM (2×50 mL). The aqueous phase was then made basic with NaHCO$_3$ (sat., 50 mL, pH=9), the formed slurry stirred at rt for 1 h, solid filtered off, washed with water and dried under vacuum to give the title compound (1.8 g, 87%) as a tan solid. MS (ESI): m/z [M+H]$^+$ 391.3. HRMS (ESI): m/z [M+H]$^+$ calcd for C$_{19}$H$_{17}$F$_3$N$_4$O$_2$: 391.1382, found: 391.1392. $^1$H NMR (500 MHz, DMSO-d6) δ 1.51-1.70 (m, 2H), 1.85 (dt, 1H), 1.95-2.12 (m, 2H), 2.27 (dq, 1H), 4.26-4.34 (m, 1H), 4.57 (d, 1H), 4.86 (h, 1H), 7.23-7.34 (m, 3H), 7.55 (d, 1H), 7.78 (d, 1H), 8.82 (d, 1H), 9.77 (s, 1H), 10.42 (s, 1H).

Example 60

Step 1: Intermediate 53: (1S,3R)-3-[[1-[2-[(4-methoxyphenyl)methoxy]-4-(trifluoromethyl)phenyl]pyrido[3,4-d]pyridazin-4-yl]amino]cyclopentanol

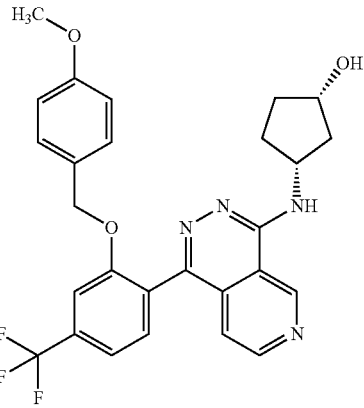

Intermediate 35 (2.6 g, 5.8 mmol), (1S,3R)-3-aminocyclopentan-1-ol hydrochloride (0.95 g, 6.9 mmol) and NaHCO$_3$ (2.94 g, 35.0 mmol) were mixed in IPA (25 mL) and stirred at 80° C. for 20 h. The mixture was poured out on water (100 mL), the mixture cooled to rt, the solid product filtered off, washed with water and dried to afford the title compound (2.87 g, 96%) as a beige solid. MS (ESI): m/z [M+H]$^+$ 511.5. $^1$H NMR (500 MHz, DMSO-d6) δ 1.58-1.95 (m, 4H), 2.07 (d, 1H), 2.32-2.45 (m, 1H), 3.67 (s, 3H), 4.18 (s, 1H), 4.58 (h, 1H), 4.74 (d, 1H), 5.11 (s, 2H), 6.74 (d, 2H), 7.01 (d, 2H), 7.28 (d, 1H), 7.49 (d, 1H), 7.58-7.66 (m, 2H), 7.86 (d, 1H), 8.83 (d, 1H), 9.76 (s, 1H).

Step 2: Example 60: 2-(4-(((1R,3S)-3-hydroxycyclopentyl)amino)pyrido[3,4-d]pyridazin-1-yl)-5-(trifluoromethyl)phenol

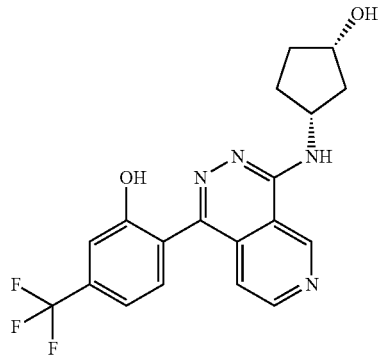 [SMILES: Oc1cc(C(F)(F)F)ccc1-c1nnc(N[C@@H]2CC[C@H](O)C2)c2cnccc12]

Intermediate 53 (2.8 g, 5.4 mmol) was slurried in absolute EtOH (7 mL) and HCl (4 M in 1,4-dioxane, 20.2 mL, 80.8 mmol) was added and the reaction stirred at rt for 2 h, before being added dropwise to Et$_2$O (150 mL) under stirring. The precipitate was filtered off and washed with Et$_2$O. The crude solid was slurried in water (130 mL) and washed with DCM (3×50 mL). The aqueous phase was then made basic with NaHCO$_3$ (sat., 50 mL, pH=9) and extracted with DCM:MeOH 9:1 several times. The combined organic extracts were evaporated down to give an aqueous slurry and after stirring for 2 h, the slurry was filtered, the solid washed with water and dried under vacuum at 40° C. to afford the title compound (1.45 g, 69%) as a tan solid. MS (ESI): m/z [M+H]$^+$391.3. HRMS (ESI): m/z [M+H]$^+$ calcd for C$_{19}$H$_{17}$F$_3$N$_4$O$_2$: 391.1382, found: 391.1382.

1H NMR (500 MHz, DMSO-d6) δ 1.67 (ddt, 2H), 1.78 (dq, 1H), 1.87 (dt, 1H), 2.08 (dq, 1H), 2.39 (dt, 1H), 4.18 (p, 1H), 4.59 (h, 1H), 7.19-7.31 (m, 3H), 7.53 (d, 1H), 7.86 (d, 1H), 8.82 (d, 1H), 9.78 (s, 1H).

Example 61

Step 1 Intermediate 54: tert-butyl N-[(1R)-3-hydroxy-3-methyl-cyclohexyl]carbamate

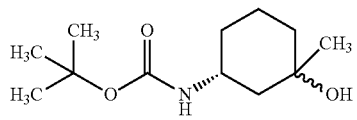 [SMILES: CC1(O)CCC[C@@H](NC(=O)OC(C)(C)C)C1]

To a stirred solution of tert-butyl N-[(1R)-3-oxocyclohexyl]carbamate (920 mg, 4.31 mmol) in THF (40 mL) was added methyllithium in Et$_2$O (1.06 mol/L, 16.3 mL, 17.3 mmol) at −78° C., and the solution was stirred at −78° C. for 1 h. To this solution was added methyllithium in Et$_2$O (1.06 mol/L, 16.3 mL, 17.3 mmol) at −78° C. again, and the solution was stirred at −78° C. for 1 h, quenched with saturated aqueous NH$_4$Cl solution (50 mL), and extracted with EtOAc. The organic layer was washed with saturated brine, dried over sodium sulfate, filtrated, and evaporated under reduced pressure. To the residue was added hexane, and resulting precipitate was collected by filtration to give the title compound (1:4 mixture, 584 mg, 59%) as a colorless amorphous. MS (ESI): m/z [M+H]$^+$230.2.

Step 2: Intermediate 55: (3R)-3-amino-1-methyl-cyclohexanol

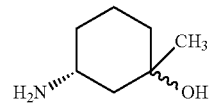

To a solution of Intermediate 54 (580 mg, 2.53 mmol) from the previous step in CH$_2$Cl$_2$ (6 mL) was added TFA (3 mL), and the solution was stirred at rt for 2 h. The reaction solution was evaporated under reduced pressure to give the title compound (1176 mg, 27.7% purity, quant.) as a colorless oil. The material was used in the next step without further purification.

Step 3: Intermediate 56: (1R,3R)-3-[[1-[2-[(4-methoxyphenyl)methoxy]-4-(trifluoromethyl)phenyl]pyrido[3,4-d]pyridazin-4-yl]amino]-1-methyl-cyclohexanol

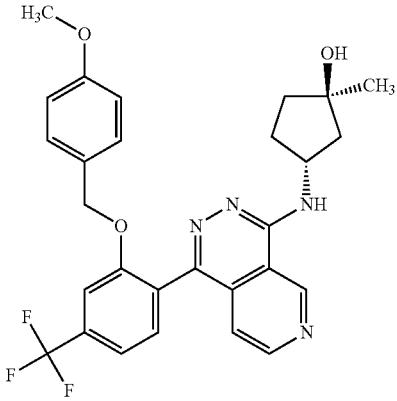 [SMILES: COc1ccc(COc2cc(C(F)(F)F)ccc2-c2nnc(N[C@@H]3CC[C@@](C)(O)C3)c3cnccc23)cc1]

and Intermediate 57: (1S,3R)-3-[[1-[2-[(4-methoxyphenyl)methoxy]-4-(trifluoromethyl)phenyl]pyrido[3,4-d]pyridazin-4-yl]amino]-1-methyl-cyclohexanol

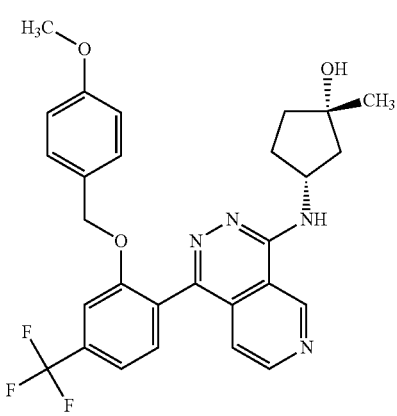 [SMILES: COc1ccc(COc2cc(C(F)(F)F)ccc2-c2nnc(N[C@@H]3CC[C@](C)(O)C3)c3cnccc23)cc1]

To a solution of Intermediate 55 (540 mg, 27.7% purity, 1.17 mmol) in the previous step and Intermediate 34 (500 mg, 1.17 mmol) in DMF (2 mL) were added DBU (1.31 mL, 8.78 mmol) and BOP (1280 mg, 2.63 mmol), and the solution was stirred at rt for 17 h. The reaction solution was poured into saturated aqueous NaHCO₃ solution, and the mixture was extracted with CHCl₃. The organic layer was washed with brine, dried over Na₂SO₄, filtered, and evaporated under reduced pressure. The residue was purified by flash chromatography eluting with a gradient of CHCl₃ to CHCl₃/MeOH (90/10), followed by chiral HPLC (column: CHIRALPAK IE Φ30 mm*250 mm, solvent: hexane/EtOH/nBuNH₂ (35/65/0.1), flow rate: 20 mL/min) to give Intermediate 56 (40 mg, 6%, MS (ESI): m/z 539.3 [M+H]⁺) as a colorless powder, and Intermediate 57 (49 mg, 8%, MS (ESI): m/z 539.3 [M+H]⁺) as a colorless powder.

Step 4: Example 61: 2-[4-[[(1R,3R)-3-hydroxy-3-methyl-cyclohexyl]amino]pyrido[3,4-d]pyridazin-1-yl]-5-(trifluoromethyl)phenol

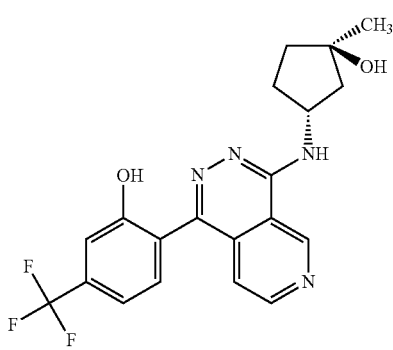 [SMILES: C[C@@]1(O)CC[C@@H](Nc2nnc(-c3ccc(C(F)(F)F)cc3O)c3ccncc23)C1]

To a flask containing Intermediate 56 (35 mg, 0.065 mmol) from the previous step was added hydrogen chloride in 1,4-dioxane (4 M, 2 mL, 8.0 mmol), and the solution was stirred at rt for 2 h. The reaction solution was poured into sat. aq. NaHCO₃ solution, and the mixture was extracted with CHCl₃. The organic layer was washed with brine, dried over Na₂SO₄, filtered, and evaporated under reduced pressure. The residue was recrystallized from EtOAc and hexane to give the title compound (22 mg, 81%) as a yellow powder. MS (ESI): m/z 419.2 [M+H]⁺. ¹H NMR (400 MHz, DMSO-d6) δ 1.19 (s, 3H), 1.21-1.33 (m, 2H), 1.47 (t, 1H), 1.54-1.59 (m, 2H), 1.72-1.85 (m, 1H), 1.94-2.00 (m, 1H), 2.08-2.15 (m, 1H), 4.21 (s, 1H), 4.64-4.75 (m, 1H), 7.26-7.28 (m, 1H), 7.29 (br s, 1H), 7.32 (d, 1H), 7.55 (d, 1H), 7.61 (d, 1H), 8.83 (d, 1H), 9.77 (s, 1H), 10.44 (br s, 1H).

Example 62: 2-[4-[[(1R,3S)-3-hydroxy-3-methyl-cyclohexyl]amino]pyrido[3,4-d]pyridazin-1-yl]-5-(trifluoromethyl)phenol

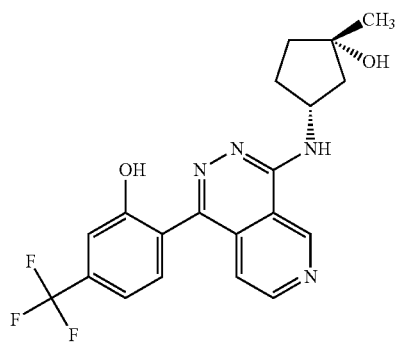 [SMILES: C[C@]1(O)CC[C@@H](Nc2nnc(-c3ccc(C(F)(F)F)cc3O)c3ccncc23)C1]

The title compound (24 mg, 70%) as a yellow powder was prepared analogously to Example 61 from Intermediate 57 (44 mg, 0.082 mmol). MS (ESI): m/z 419.2 [M+H]⁺. ¹H NMR (400 MHz, DMSO-d6) δ 1.23 (s, 3H) 1.36-1.53 (m, 3H) 1.53-1.61 (m, 1H) 1.62-1.68 (m, 1H) 1.69-1.81 (m, 1H) 1.88-2.00 (m, 1H) 4.39-4.54 (m, 1H) 4.69 (s, 1H) 7.27-7.29 (m, 1H) 7.29 (s, 1H) 7.30-7.35 (m, 1H) 7.55 (d, 1H) 7.87 (d, 1H) 8.84 (d, 1H) 9.66 (s, 1H) 10.23-10.61 (br, 1H).

Example 63

Step 1: Intermediate 58: (1s,3s)-3-((1-chloropyrido[3,4-d]pyridazin-4-yl)amino)-1-methylcyclobutan-1-ol

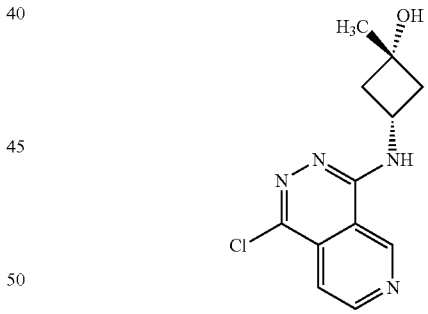

To a suspension of 3-amino-1-methyl-cyclobutanol hydrochloride (1.5 g, 11.0 mmol, 1.1 eq) in MeCN (10 mL), 1,4-dichloropyrido[3,4-d]pyridazine (2.0 g, 10.0 mmol, 1.0 eq) and DIPEA (5.2 mL, 30.0 mmol, 3.0 eq) were added at rt. The mixture was run at 130° C. for 0.5 h in a microwave reactor. The reaction mixture was cooled to rt, and was added H₂O (50 mL), and the mixture was extracted with EtOAc (30 mL, 3 times). The organic layer was dried over Na₂SO₄, and concentrated in vacuo. The residue was purified by silica gel column chromatography using a gradient of 0-5% MeOH in CHCl₃ as mobile phase and reversed phase flash chromatography on a C18 column using a gradient of 12-17% MeCN in (NH₄)₂CO₃ (10 mM, aq.) as mobile phase to give the title compound (1.1 g, 43%).

Step 2: Example 63: 2-(4-(((1s,3s)-3-hydroxy-3-methylcyclobutyl)amino)pyrido[3,4-d]pyridazin-1-yl)-5-(trifluoromethoxy)phenol

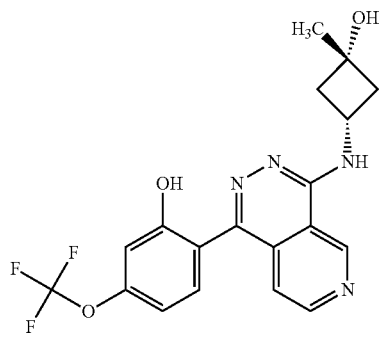 [SMILES: C[C@]1(O)C[C@@H](Nc2nnc(-c3ccc(OC(F)(F)F)cc3O)c3ccncc23)C1]

To a solution of Intermediate 58 (80.9 mg, 0.28 mmol, 1.0 eq) and [2-hydroxy-4-(trifluoromethoxy)phenyl]boronic acid (91.6 mg, 0.41 mmol, 1.5 eq) in 1,4-dioxane (1.8 mL) was added Pd(dppf)Cl$_2$·CH$_2$Cl$_2$ (22.5 mg, 2.5 mmol, 0.1 eq) and Na$_2$CO$_3$ (0.41 mL, 0.83 mmol, 2.0 M in H$_2$O) at rt. The mixture was run at 100° C. for 0.5 h in a microwave reactor. The reaction mixture was cooled to rt, and added H$_2$O (10 mL) and CHCl$_3$ (10 mL). The mixture was filtered by Phase-separator*, and the filtrate was concentrated in vacuo. The residue was purified by reversed phase flash chromatography on a C18 column using a gradient of 30-60% MeCN in (NH$_4$)$_2$CO$_3$ (10 mM, aq) as mobile phase to give the title compound (10.4 mg, 9%); MS (ESI): m/z [M+H]$^+$ 407.1. $^1$H NMR (400 MHz, DMSO-d6) δ 1.35 (s, 3H), 2.13-2.27 (m, 2H), 2.50-2.57 (m, 2H), 4.23-4.35 (m, 1H), 5.04 (s, 1H), 6.89-6.97 (m, 2H), 7.28 (dd, 1H), 7.39-7.47 (m, 1H), 8.06 (d, 1H), 8.84 (d, 1H), 9.78 (s, 1H).

Example 64: 3-fluoro-2-(4-(((1s,3s)-3-hydroxy-3-methylcyclobutyl)amino)pyrido[3,4-d]pyridazin-1-yl)phenol

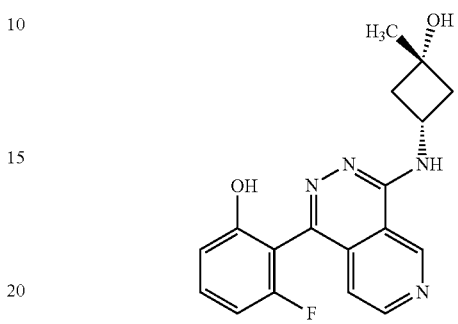

Using Intermediate 58, (2-fluoro-6-hydroxy-phenyl)boronic acid and Sphos Pd G3 according to a method analogous to Example 63, the title compound was obtained (79.9 mg, 60%). MS (ESI): m/z [M+H]$^-$ 341.1. $^1$H NMR (400 MHz, DMSO-d6) δ 1.35 (s, 3H), 2.13-2.28 (m, 2H), 2.47-2.50 (m, 2H), 4.19-4.33 (m, 1H), 5.06 (s, 1H), 6.81 (t, 1H), 6.85 (d, 1H), 7.16 (d, 1H), 7.36 (ddd, 1H), 8.11 (d, 1H), 8.85 (d, 1H), 9.81 (d, 1H), 10.03 (brs, 1H).

The examples included in Table 5 below were synthesized analogous to the procedure of Example 63 using the indicated boronic acids. The boronic acids are commercially available, unless otherwise stated.

TABLE 5

| Ex No. | Name | Structure |
|---|---|---|
| 65 | 3-chloro-2-fluoro-6-(4-(((1s,3s)-3-hydroxy-3-methylcyclobutyl)amino)pyrido[3,4-d]pyridazin-1-yl)phenol | 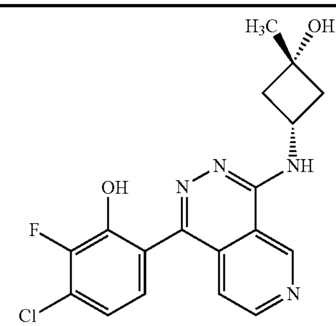 |
| 66 | 4,5-difluoro-2-(4-(((1s,3s)-3-hydroxy-3-methylcyclobutyl)amino)pyrido[3,4-d]pyridazin-1-yl)phenol | 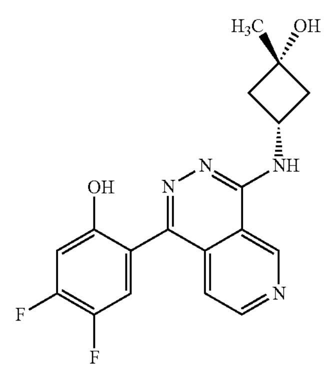 [SMILES: C[C@]1(O)C[C@@H](Nc2nnc(-c3cc(F)c(F)cc3O)c3ccncc23)C1] |

TABLE 5-continued
| Ex No. | Name | Structure |
|---|---|---|
| 67 | 3-fluoro-2-(4-(((1s,3s)-3-hydroxy-3-methylcyclobutyl)amino)pyrido[3,4-d]pyridazin-1-yl)-5-(trifluoromethyl)phenol | 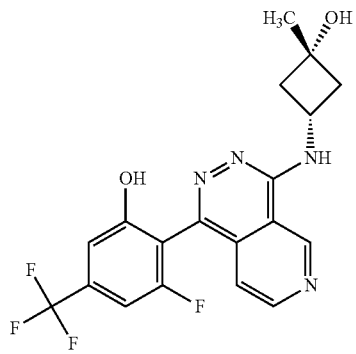 [SMILES: C[C@]1(O)C[C@@H](Nc2nnc(-c3c(O)cc(C(F)(F)F)cc3F)c3ccncc23)C1] |
| 68 | 5-chloro-2-(4-(((1s,3s)-3-hydroxy-3-methylcyclobutyl)amino)pyrido[3,4-d]pyridazin-1-yl)phenol | 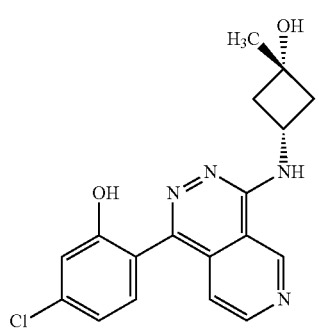 [SMILES: C[C@]1(O)C[C@@H](Nc2nnc(-c3ccc(Cl)cc3O)c3ccncc23)C1] |
| 69 | 3,5-difluoro-2-(4-(((1s,3s)-3-hydroxy-3-methylcyclobutyl)amino)pyrido[3,4-d]pyridazin-1-yl)phenol | 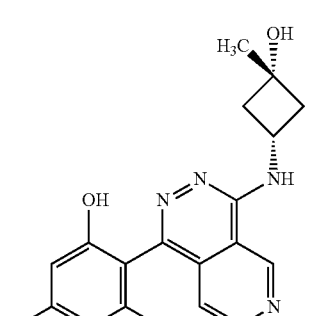 |

Example 70

Step 1: Intermediate 59: 1-[(1-chloropyrido[3,4-d]pyridazin-4-yl)amino]-2-methyl-propan-2-ol

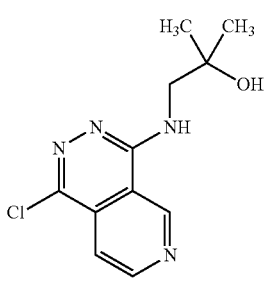 [SMILES: CC(C)(O)CNc1nnc(Cl)c2ccncc12]

To a solution of 1,4-dichloropyrido[3,4-d]pyridazine (3.0 g, 15 mmol) in MeCN (15 mL) were added TEA (6.3 mL, 45 mmol) and 1-amino-2-methyl-propan-2-ol (1.5 g, 16 mmol) at rt and the mixture was stirred at reflux temperature for 1 h. The reaction mixture was cooled to rt and evaporated under reduced pressure. To the crude mixture were added $CHCl_3$ and $H_2O$ and the two layers were separated. The organic layer was evaporated under reduced pressure. The residue was purified by flash chromatography to give the title compound (1.15 g, 30%) as a yellow amorphous solid. MS(ESI): m/z 253.1/255.1 [M+H]$^+$.

Step 2: Example 70: 2-[4-[(2-hydroxy-2-methyl-propyl)amino]pyrido[3,4-d]pyridazin-1-yl]-5-(trifluoromethyl)phenol

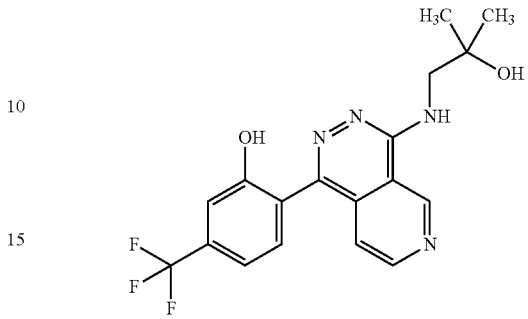

To a suspension of Intermediate 59 (200 mg, 791 mmol, 1.0 eq), (2-hydroxy-4-(trifluoromethyl)phenyl)boronic acid (261 mg, 1.273 mmol) and $Na_2CO_3$ (252 mg, 2.34 mol) in 1,4-dioxane (1 mL) and $H_2O$ (1 mL) was added SPhos Pd G3 (124 mg, 158 mmol). The vial was sealed and the reaction was run at 120° C. for 1 h in a microwave reactor. The reaction mixture was poured into $H_2O$ and extracted with $CHCl_3$. The organic layer was evaporated under reduced pressure. The crude mixture was purified by flash chromatography (silica, $CHCl_3$/MeOH=100/0-85/15) and reversed phase flash chromatography on a C18 column using a gradient of 20-30% MeCN in $(NH_4)_2CO_3$ (10 mM, aq) as mobile phase to give the title compound (77 mg, 24%) as a yellow powder. MS(ESI): m/z 379.0 [M+H]$^+$. $^1$H NMR (400 MHz, DMSO-d6) δ 1.23 (s, 6H), 3.65-3.75 (m, 2H), 5.00-5.12 (m, 1H), 7.22-7.34 (m, 3H), 7.51-7.60 (m, 2H), 7.82-7.93 (m, 1H), 8.81-8.90 (m, 1H), 9.77-9.84 (m, 1H).

The examples included in Table 6 below were synthesized analogously to the procedure of Example 70 using the specified starting material and Intermediate 59.

TABLE 6

| Ex No. | Name | Boronic acid | Product |
|---|---|---|---|
| 71 | 5-chloro-2-[4-[(2-hydroxy-2-methyl-propyl)amino]pyrido[3,4-d]pyridazin-1-yl]phenol | (structure) | (structure) |
| 72 | 2-[4-[(2-hydroxy-2-methyl-propyl)amino]pyrido[3,4-d]pyridazin-1-yl]-5-(trifluoromethoxy)phenol | (structure) | (structure) |

TABLE 6-continued

| Ex No. | Name | Boronic acid | Product |
|---|---|---|---|
| 73 | 5-chloro-3-fluoro-2-[4-[(2-hydroxy-2-methyl-propyl)amino]pyrido[3,4-d]pyridazin-1-yl]phenol | | |

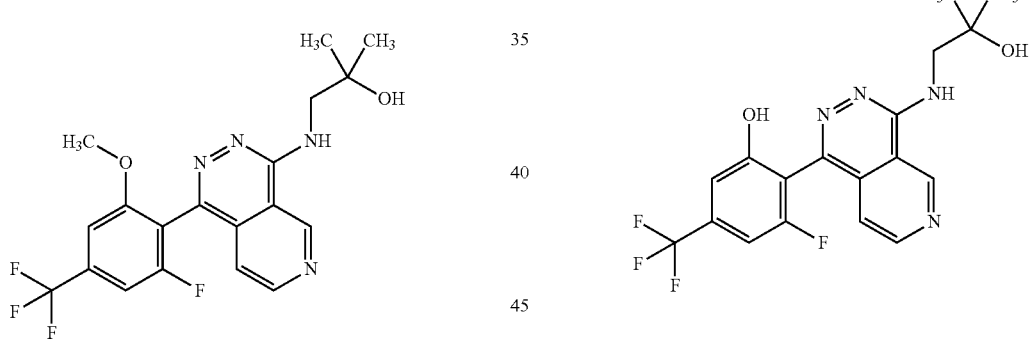

Example 74

Step 1: Intermediate 60: 1-[[1-[2-fluoro-6-methoxy-4-(trifluoromethyl)phenyl]pyrido[3,4-d]pyridazin-4-yl]amino]-2-methyl-propan-2-ol

Step 2: Example 74: 3-fluoro-2-[4-[(2-hydroxy-2-methyl-propyl)amino]pyrido[3,4-d]pyridazin-1-yl]-5-(trifluoromethyl)phenol To a suspension of Intermediate 59 (200 mg, 791 mmol), Intermediate 9 (226 mg, 950 mmol) and Na$_2$CO$_3$ (252 mg, 2.37 mol) in 1,4-dioxane (2.0 mL) and H$_2$O (1.0 mL) was added SPhos Pd G3 (62 mg, 79 mmol). The vial was sealed and the reaction was run at 120° C. for 1 h in a microwave reactor. The reaction mixture was poured into H$_2$O and extracted with CHCl$_3$. The organic layer was evaporated under reduced pressure. The crude mixture was purified by flash chromatography (silica, CHCl$_3$/MeOH=100/0-94/6) to give the title compound (342 mg, quant) as a yellow amorphous. MS(ESI): m/z 409.1 [M−H]$^-$.

To a solution of Intermediate 60 (342 mg, 833 mmol) in 2,4,6-trimethylpyridine (1.0 mL) was added LiI (1.12 g, 8.33 mol) and the mixture was heated to 160° C. and stirred. After 0.5 h, the mixture was cooled to rt and purified by flash chromatography (silica, CHCl$_3$/MeOH=100/0-80/20) and reversed phase flash chromatography on a C18 column using a gradient of 20-25% MeCN in H$_2$O as mobile phase to give the title compound (94 mg, 28%) as a yellow amorphous. MS(ESI): m/z 397.0 [M+H]$^+$. $^1$H NMR (400 MHz, DMSO-d6) δ 1.23 (s, 6H), 3.66-3.76 (m, 2H), 4.95-5.05 (m, 1H), 7.11-7.19 (m, 1H), 7.20-7.31 (m, 2H), 7.90-7.99 (m, 1H), 8.82-8.90 (m, 1H), 9.80-9.90 (m, 1H).

Example 75

Step 1: Intermediate 47: (1R,2R)-2-((1-chloropyrido[3,4-d]pyridazin-4-yl)amino)cyclohexan-1-ol

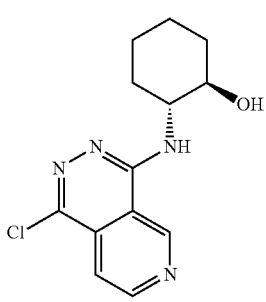 [SMILES: O[C@@H]1CCCC[C@H]1Nc1nnc(Cl)c2ccncc12]

and Intermediate 48: (1R,2R)-2-((4-chloropyrido[3,4-d]pyridazin-1-yl)amino)cyclohexan-1-ol

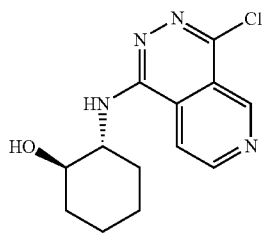 [SMILES: O[C@@H]1CCCC[C@H]1Nc1nnc(Cl)c2cnccc12]

DIPEA (6.46 g, 49.99 mmol) was added to (1R,2R)-2-aminocyclohexan-1-ol (1.267 g, 11.00 mmol), 1,4-dichloropyrido[3,4-d]pyridazine (2 g, 10.00 mmol) in NMP (25 mL) at rt. The resulting solution was stirred at 80° C. for 12 h. Solvents were removed under reduced pressure and the crude product was purified by preparative chiral-HPLC (Column: CHIRAL ART Cellulose-SB, 3*25 cm, 5 m; Mobile Phase A: CO$_2$, Mobile Phase B: IPA (0.5% 2 M NH$_3$ in MeOH); 70 mL/min with 50% B at 35° C.). Combined product fractions with a RT of 6.05 min were lyophilized to afford 0.600 g of Intermediate 47 (21.5%) as a yellow solid. Combined product fractions with a RT of 7.67 min were lyophilized to afford 0.200 g of Intermediate 48 (7.2%) as a yellow solid.

Intermediate 47: MS (ESI): m/z [M+H]$^+$279.10. $^1$H NMR (300 MHz, DMSO-d6) δ 1.10-1.42 (m, 4H), 1.67 (s, 2H), 1.83-2.11 (m, 2H), 3.50-3.65 (m, 1H), 4.10 (s, 1H), 4.75 (m, 1H), 7.70-7.85 (m, 2H), 9.02 (m, 1H), 9.78 (m, 1H).

Intermediate 48: MS (ESI): m/z [M+H]$^+$279.05. $^1$H NMR (300 MHz, DMSO-d6) δ 1.27 (m, 4H), 1.65 (m, 2H), 1.87-2.13 (m, 2H), 3.57 (m, 1H), 4.05 (m, 1H), 4.69 (m, 1H), 7.58 (m, 1H), 8.33 (m, 1H), 9.07 (m, 1H), 9.37 (m, 1H).

Step 2: Example 75: 5-fluoro-2-(4-(((1R,2R)-2-hydroxycyclohexyl)amino)pyrido[3,4-d]pyridazin-1-yl)phenol

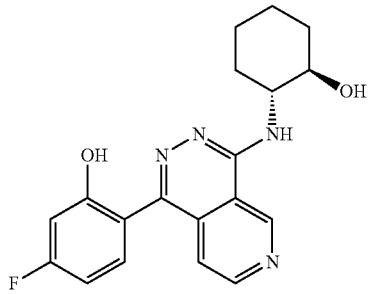 [SMILES: Oc1cc(F)ccc1-c1nnc(N[C@@H]2CCCC[C@H]2O)c2cnccc12]

Pd(PPh$_3$)$_4$ (20.73 mg, 0.02 mmol) was added to Intermediate 47 (100 mg, 0.36 mmol), (4-fluoro-2-hydroxyphenyl)boronic acid (84 mg, 0.54 mmol) and K$_3$PO$_4$ (152 mg, 0.72 mmol) in 1,4-dioxane (5 mL) and water (1 mL) under an inert atmosphere. The resulting solution was stirred at 90° C. for 12 h. The solvents were removed under reduced pressure. The crude product was purified by preparative HPLC (Column: YMC-Actus Triart C18 ExRS, 30 mm×150 mm, 5 m; Mobile Phase A: water (10 mmol/L NH$_4$HCO$_3$ and 0.1% NH$_3$), Mobile Phase B: MeCN; 60 mL/min; with a gradient from 10% to 43% B in 7 min. Combined product fractions with a RT of 6.63 min were lyophilized to afford 0.038 g of the title compound (29.9%) as a pale yellow solid. MS (ESI): m/z [M+H]$^+$ 355.05. $^1$H NMR (300 MHz, DMSO-d6) δ 1.30 (m, 4H), 1.69 (s, 2H), 2.04 (m, 2H), 3.61 (m, 1H), 4.20 (m, 1H), 4.80 (s, 1H), 6.68-6.87 (m, 2H), 7.18-7.40 (m, 2H), 7.58 (d, 1H), 8.82 (d, 1H), 9.76 (d, 1H), 10.26 (s, 1H); $^{19}$F NMR (282 MHz, DMSO-d6) δ −111.322, −111.669 (1 F).

Example 76: 3-fluoro-2-(4-(((1R,2R)-2-hydroxycyclohexyl)amino)pyrido[3,4-d]pyridazin-1-yl)phenol

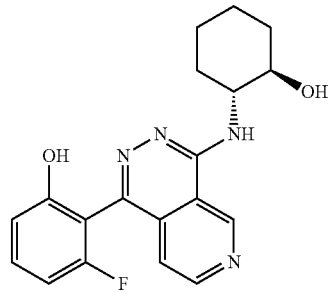 [SMILES: Oc1cccc(F)c1-c1nnc(N[C@@H]2CCCC[C@H]2O)c2cnccc12]

Pd(PPh$_3$)$_4$ (20.73 mg, 0.02 mmol) was added to Intermediate 47 (100 mg, 0.36 mmol), (2-fluoro-6-hydroxyphenyl)boronic acid (84 mg, 0.54 mmol) and K$_3$PO$_4$ (152 mg, 0.72 mmol) in 1,4-dioxane (5 mL) and water (1 mL) under an inert atmosphere. The resulting solution was stirred at 90° C. for 12 hours. The solvents were removed under reduced pressure. The crude product was purified by preparative HPLC (Column: XBridge Prep OBD C18 Column, 30×150 mm, m; Mobile Phase A: water (10 mmol/L NH$_4$HCO$_3$ and 0.1% NH$_3$), Mobile Phase B: MeCN; 60 mL/min; with a gradient from 10% to 40% B in 8 min). Combined product fractions with a RT of 7.80 min were lyophilized to afford 0.057 g of the title compound (45.1%) as a yellow solid. MS (ESI): m/z [M+H]+ 355.15. $^1$H NMR (300 MHz, DMSO-d6) δ 1.30 (m, 5H), 1.70 (m, 2H), 1.97 (s, 1H), 2.11 (s, 1H), 3.60 (s, 1H), 4.21 (s, 1H), 4.81 (m, 1H), 6.73-6.88 (m, 2H), 7.13 (m, 1H), 7.34 (m, 1H), 7.65 (m, 1H), 8.82 (m, 1H), 9.78 (m, 1H), 10.01 (s, 1H); $^{19}$F NMR (282 MHz, DMSO-d6) δ −114.433, −114.780 (1 F).

Example 77: 3-fluoro-2-(1-(((1R,2R)-2-hydroxycyclohexyl)amino)pyrido[3,4-d]pyridazin-4-yl)phenol

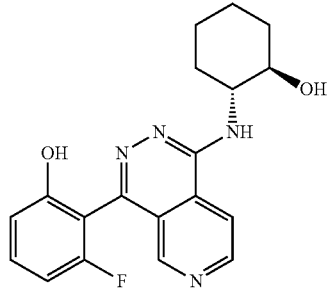 [SMILES: Oc1cccc(F)c1-c1nnc(N[C@@H]2CCCC[C@H]2O)c2ccncc12]

Pd(PPh$_3$)$_4$ (20.73 mg, 0.02 mmol) was added to Intermediate 48 (100 mg, 0.36 mmol), (2-fluoro-6-hydroxyphenyl)boronic acid (84 mg, 0.54 mmol) and K$_3$PO$_4$ (152 mg, 0.72 mmol) in 1,4-dioxane (5 mL) under an inert atmosphere. The resulting solution was stirred at 90° C. for 12 hours. The solvents were removed under reduced pressure. The crude product was purified by preparative HPLC (Column: YMC-Actus Triart C18, 30 mm×150 mm, S m; Mobile Phase A: water (10 mmol/L NH$_4$HCO$_3$ and 0.1% NH$_3$), Mobile Phase B: MeCN; 60 mL/min; with a gradient from 12% to 32% B in 10 min). Combined product fractions with a RT of 9.92 min were lyophilized to afford 0.050 g of the title compound (39.3%) as a yellow solid. MS (ESI): m/z [M+H]+ 355.00. $^1$H NMR (300 MHz, DMSO-d6) δ 1.31 (m, 4H), 1.69 (m, 2H), 1.96 (m, 1H), 2.11 (m, 1H), 3.60 (m, 1H), 4.16 (s, 1H), 4.76 (s, 1H), 6.76-6.90 (m, 2H), 7.36 (m, 1H), 7.45 (m, 1H), 8.32 (m, 1H), 8.68 (s, 1H), 8.93 (d, 1H), 10.08 (s, 1H); $^{19}$F NMR (282 MHz, DMSO-d6) δ −114.742 (1 F).

Example 78: 5-fluoro-2-(1-(((1R,2R)-2-hydroxycyclohexyl)amino)pyrido[3,4-d]pyridazin-4-yl)phenol Pd(PPh$_3$)$_4$ (20.73 mg, 0.02 mmol) was added to Intermediate 48 (100 mg, 0.36 mmol), (4-fluoro-2-hydroxyphenyl)boronic acid (84 mg, 0.54 mmol) and K$_3$PO$_4$ (152 mg, 0.72 mmol) in 1,4-dioxane (5 mL) and water (1 mL) under an inert atmosphere. The resulting solution was stirred at 90° C. for 12 hours. The solvents were removed under reduced pressure. The crude product was purified by preparative HPLC (Column: YMC-Actus Triart C18, 30 mm×150 mm, 5 m; Mobile Phase A: water (10 mmol/L NH$_4$HCO$_3$ and 0.1% NH$_3$), Mobile Phase B: MeCN; 60 mL/min; with a gradient from 16% to 36% B in 10 min). Combined product fractions with a RT of 7.80 min were lyophilized to afford 0.062 g of the title compound (48.5%) as a white solid. MS (ESI): m/z [M+H]+ 355.05. $^1$H NMR (300 MHz, DMSO-d6) δ 1.29 (m, 5H), 1.96 (m, 1H), 2.10 (m, 1H), 3.59 (s, 1H), 4.13 (s, 1H), 4.75 (s, 1H), 6.65-6.98 (m, 2H), 7.38 (m, 2H), 8.28 (m, 1H), 8.80 (s, 1H), 8.90 (m, 1H), 10.31 (s, 1H); $^{19}$F NMR (282 MHz, DMSO-d6) δ −111.459 (1 F).

The examples included in Table 7 below were synthesized analogously to Step 5 of the procedure to make Example 40 but with Intermediate 1 instead of Intermediate 35 and the specified aminoalcohol instead of (1R,2R)-2-aminocyclohexan-1-ol, followed by deprotection analogously to Step 2 of the procedure to make Example 74.

TABLE 7

| Ex No. | Name | Aminoalcohol starting material | Product |
|---|---|---|---|
| 79 | 2-[4-[[(1S,2R)-2-hydroxycyclohexyl]amino]pyrido[3,4-d]pyridazin-1-yl]-5-(trifluoromethyl)phenol | | |

TABLE 7-continued

| Ex No. | Name | Aminoalcohol starting material | Product |
|---|---|---|---|
| 80 | 2-[4-[[(1R,2S)-2-hydroxycyclohexyl]amino]pyrido[3,4-d]pyridazin-1-yl]-5-(trifluoromethyl)phenol | | |
| 81 | 2-[4-[[(1S,2S)-2-hydroxycyclohexyl]amino]pyrido[3,4-d]pyridazin-1-yl]-5-(trifluoromethyl)phenol | | |
| 82 | 2-[4-[[(1S,3R)-3-hydroxycyclohexyl]amino]pyrido[3,4-d]pyridazin-1-yl]-5-(trifluoromethyl)phenol | | |
| 83 | 2-[4-[[(1S,3R)-3-hydroxycyclopentyl]amino]pyrido[3,4-d]pyridazin-1-yl]-5-(trifluoromethyl)phenol | | |

TABLE 7-continued

| Ex No. | Name | Aminoalcohol starting material | Product |
|---|---|---|---|
| 84 | 2-(4-(((1r,3r)-3-hydroxy-3-methylcyclobutyl)amino)pyrido[3,4-d]pyridazin-1-yl)-5-(trifluoromethyl)phenol | | |

Example 85

Step 1: Intermediate 61: (1R,3R)-3-((1-chloropyrido[3,4-d]pyridazin-4-yl)amino)cyclopentan-1-ol

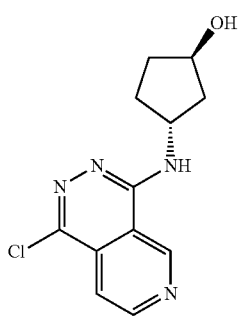 [SMILES: O[C@@H]1CC[C@@H](Nc2nnc(Cl)c3ccncc23)C1]

and Intermediate 62: (1R,3R)-3-((4-chloropyrido[3,4-d]pyridazin-1-yl)amino)cyclopentan-1-ol

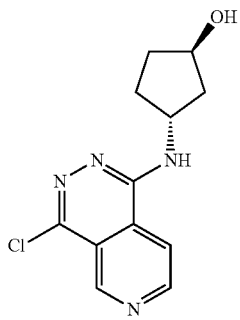 [SMILES: O[C@@H]1CC[C@@H](Nc2nnc(Cl)c3cnccc23)C1]

DIPEA (5.04 g, 39.00 mmol) was added to 1,4-dichloropyrido[3,4-d]pyridazine (1.3 g, 6.50 mmol), (1R,3R)-3-aminocyclopentan-1-ol hydrochloride (0.984 g, 7.15 mmol) in NMP (5 mL) at rt. The resulting solution was stirred at 80° C. for 12 h. The solvent was removed under reduced pressure and the crude product was purified by preparative chiral-HPLC (Column: OptiChiral-C9-5, 3*25 cm, 5 m; Mobile Phase A: CO$_2$, Mobile Phase B: MeOH (0.5% 2 M NH$_3$ in MeOH); 100 mL/min; 50% B at 35° C.). Fractions containing the desired product with a RT of 2.88 min were dried to yield 1.00 g of Intermediate 61 (58.1%) as a yellow solid. Fractions containing the desired product with a RT of 3.92 min were dried to yield 0.44 g of Intermediate 62 (25.6%) as a yellow solid.

Intermediate 61: MS (ESI): m/z [M+H]$^+$265.05. $^1$H NMR (300 MHz, DMSO-d6) δ 1.45-1.67 (m, 2H), 1.80 (m, 1H), 1.88-2.09 (m, 2H), 2.13-2.29 (m, 1H), 4.27 (m, 1H), 4.44-4.80 (m, 2H), 7.77-7.91 (m, 2H), 9.02 (m, 1H), 9.76 (m, 1H).

Intermediate 62: MS (ESI): m/z [M+H]$^+$265.05. $^1$H NMR (300 MHz, DMSO-d6) δ 1.56 (m, 2H), 1.78 (m, 1H), 1.88-2.08 (m, 2H), 2.12-2.28 (m, 1H), 4.26 (m, 1H), 4.42-4.77 (m, 2H), 7.69 (m, 1H), 8.32 (m, 1H), 9.06 (m, 1H), 9.37 (m, 1H).

Step 2: Example 85: 5-fluoro-2-(4-(((1R,3R)-3-hydroxycyclopentyl)amino)pyrido[3,4-d]pyridazin-1-yl)phenol

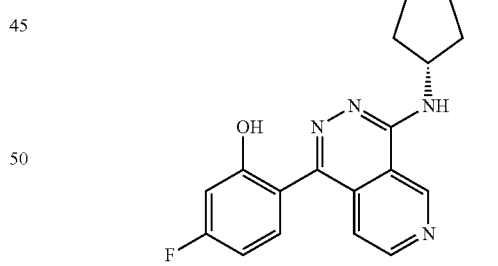

Pd(PPh$_3$)$_4$ (32.7 mg, 0.03 mmol) was added to Intermediate 61 (150 mg, 0.57 mmol), (4-fluoro-2-hydroxyphenyl)boronic acid (133 mg, 0.85 mmol) and K$_3$PO$_4$ (241 mg, 1.13 mmol) in 1,4-dioxane (5 mL) and water (0.2 mL) under an inert atmosphere. The resulting solution was stirred at 90° C. for 12 hours. The solvents were removed under reduced pressure. The crude product was purified by preparative HPLC (Column: XBridge Shield RP18 OBD Column, 30*150 mm, m; Mobile Phase A: water (10 mmol/L NH$_4$HCO$_3$ and 0.1% NH$_3$), Mobile Phase B: MeCN; 60 mL/min; with a gradient from 16% to 26% B in 8 min). Combined product fractions with a RT of 8.75 min were lyophilized to afford 0.035 g of the title compound (18.2%) as a grey solid. MS (ESI): m/z [M+H]⁻ 341.15. ¹H NMR (300 MHz, DMSO-d6) δ 1.49-1.71 (m, 2H), 1.78-1.90 (m, 1H), 2.03 (m, 2H), 2.21-2.31 (m, 1H), 4.30 (s, 1H), 4.57 (m, 1H), 4.85 (m, 1H), 6.72-6.86 (m, 2H), 7.23-7.41 (m, 2H), 7.70 (m, 1H), 8.83 (m, 1H), 9.76 (s, 1H), 10.22 (s, 1H); ¹⁹F NMR (282 MHz, DMSO-d6) δ −111.625, −111.689, −111.768 (1 F).

Example 86: 3-fluoro-2-(1-(((1R,3R)-3-hydroxycyclopentyl)amino)pyrido[3,4-d]pyridazin-4-yl)phenol

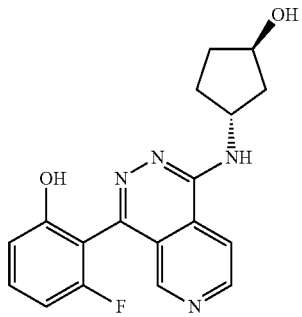 [SMILES: Oc1cccc(F)c1-c1nnc(N[C@@H]2CC[C@@H](O)C2)c2ccncc12]

Pd(PPh₃)₄ (21.8 mg, 0.02 mmol) was added to Intermediate 62 (100 mg, 0.38 mmol), (2-fluoro-6-hydroxyphenyl)boronic acid (70.7 mg, 0.45 mmol) and K₃PO₄ (241 mg, 1.13 mmol) in 1,4-dioxane (3 mL) and water (0.5 mL) under an inert atmosphere. The resulting solution was stirred at 90° C. for 16 hours. The reaction was stopped by the addition of water and extracted three times using EtOAc. The combined organic layers were dried over Na₂SO₄ and the solvents were removed under reduced pressure. The crude product was purified by preparative HPLC (Column: XSelect CSH Fluoro Phenyl, 30*150 mm, 5 m; Mobile Phase A: water (0.1% formic acid), Mobile Phase B: MeCN; 60 mL/min; with a gradient from 2% to 12% B in 7 min). Combined product fractions were lyophilized to obtain 0.072 g of the title compound (53.3%) as a yellow solid. MS (ESI): m/z [M+H]⁺ 341.00. ¹H NMR (300 MHz, DMSO-d6) δ 1.60 (m, 2H), 1.82 (m, 1H), 1.98 (m, 2H), 2.24 (m, 1H), 4.29 (s, 1H), 4.57 (s, 1H), 4.80 (m, 1H), 6.83 (m, 2H), 7.36 (m, 1H), 7.57 (m, 1H), 8.30 (m, 1H), 8.69 (s, 1H), 8.93 (m, 1H), 10.07 (s, 1H); ¹⁹F NMR (282 MHz, DMSO-d6) δ −114.705, −114.756, −135.688 (1 F).

Example 87

Step 1: Intermediate 63: (1S,3R)-3-((1-chloropyrido[3,4-d]pyridazin-4-yl)amino)cyclopentan-1-ol

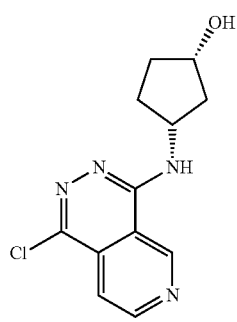

and Intermediate 64: (1S,3R)-3-((4-chloropyrido[3,4-d]pyridazin-1-yl)amino)cyclopentan-1-ol

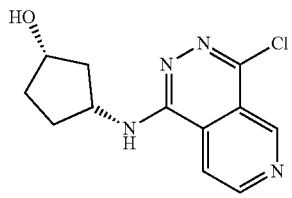

1,4-dichloropyrido[3,4-d]pyridazine (1.1 g, 5.50 mmol), (1S,3R)-3-aminocyclopentan-1-ol hydrochloride (0.795 g, 5.77 mmol), and Na₂CO₃ (1.224 g, 11.55 mmol) were diluted with sulfolane (11 mL) and heated to 80° C. for 3 h under stirring and an inert atmosphere. The formed solid was filtered off, the filtrate was washed with DCM and MeOH and the solvents were removed under reduced pressure. Prep-HPLC was used for regioisomer separation (Column: Chiralpak IB N-3, 150*4.6 mm, 3 m; Mobile Phase A: CO₂, Mobile Phase B: EtOH (20 mM DEA in EtOH); 3.5 mL/min; 25% B at 40° C.). Fractions with a RT of 2.63 min were pooled and dried to yield 1.1 g of Intermediate 63 (76.0%). Fractions with a RT of 1.96 min were pooled and dried to yield 347 mg of Intermediate 64 (23.8%).

Intermediate 63: ¹H NMR (500 MHz, DMSO-d6) δ 1.57-1.71 (m, 2H), 1.71-1.88 (m, 2H), 2.03-2.15 (m, 1H), 2.36 (m, 1H), 4.11-4.24 (m, 1H), 4.44 (m, 1H), 4.74 (m, 1H), 7.79 (s, 1H), 8.37 (s, 1H), 9.09 (s, 1H), 9.39 (s, 1H).

Intermediate 64: ¹H NMR (500 MHz, DMSO-d6) δ 1.57-1.71 (m, 2H), 1.71-1.88 (m, 2H), 2.03-2.15 (m, 1H), 2.36 (m, 1H), 4.11-4.24 (m, 1H), 4.44 (m, 1H), 4.74 (m, 1H), 7.79 (s, 1H), 8.37 (s, 1H), 9.09 (s, 1H), 9.39 (s, 1H).

Step 2: Example 87: 3-fluoro-2-(1-(((1R,3S)-3-hydroxycyclopentyl)amino)pyrido[3,4-d]pyridazin-4-yl)phenol

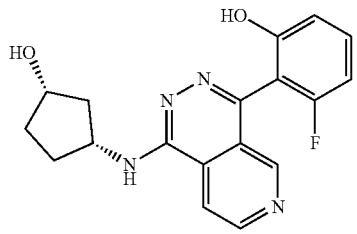 [SMILES: Oc1cccc(F)c1-c1nnc(N[C@@H]2CC[C@H](O)C2)c2ccncc12]

A mixture of Intermediate 64 (100 mg, 0.38 mmol), (2-fluoro-6-hydroxyphenyl)boronic acid (70.7 mg, 0.45 mmol), Pd(PPh₃)₄ (21.83 mg, 0.02 mmol) and K₃PO₄ (241 mg, 1.13 mmol) in water (1 mL) and 1,4-dioxane (5 mL) at rt. The resulting mixture was stirred at 90° C. for 15 hours under an inert atmosphere. The reaction was stopped by the addition of water and extracted three times with EtOAc. The combined organic layers were dried over Na₂SO₄, filtered and the solvents were removed under reduced pressure. The crude product was purified by preparative HPLC (Column: XSelect CSH Fluoro Phenyl, 30*150 mm, 5 m; Mobile Phase A: Water (0.1% formic acid), Mobile Phase B: MeCN; 60 mL/min; 2% B to 12% B in 7 min). Combined fractions with a RT of 5.72 min were pooled and lyophilized. This reaction yielded 0.089 g of the title compound (66.6%) as a pale yellow solid. MS (ESI): m/z [M+H]+ 341.00. ¹H NMR (300 MHz, DMSO-d6) δ 1.65 (m, 2H), 1.82 (m, 2H), 2.07 (m, 1H), 2.37 (m, 1H), 4.17 (m, 1H), 4.54 (m, 1H), 4.76 (s, 1H), 6.83 (m, 2H), 7.36 (m, 1H), 7.67 (m, 1H), 8.32 (m, 1H), 8.69 (s, 1H), 8.93 (m, 1H), 10.07 (s, 1H); ¹⁹F NMR (282 MHz, DMSO-d6) δ −114.714, −114.897 (1 F).

Example 88

Step 1: Intermediate 65: 2-[4-[[(4S)-2,2-dimethyl-1,3-dioxolan-4-yl]methylamino]pyrido[3,4-d]pyridazin-1-yl]-5-(trifluoromethyl)phenol

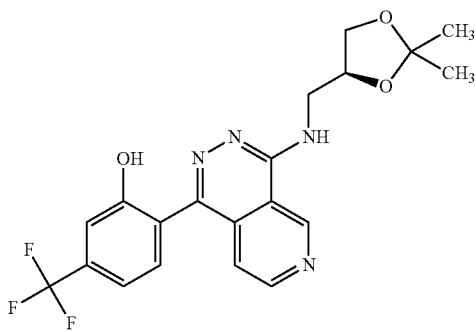 [SMILES: CC1(C)OC[C@H](CNc2nnc(-c3ccc(C(F)(F)F)cc3O)c3ccncc23)O1]

To a solution of [(4S)-2,2-dimethyl-1,3-dioxolan-4-yl]methanamine (85.0 mg, 0.65 mmol, 1.1 eq.) in MeCN (2.0 mL) were added DIPEA (0.31 mL, 1.8 mmol, 3.0 eq.) and Intermediate 1 (200.0 mg, 0.59 mmol, 1.0 eq). The mixture was stirred at 100° C. for 44 h. The reaction mixture was concentrated. To the residue were added 2,4,6-trimethylpyridine (12 mL, 89.11 mmol) and LiI (788.0 mg, 5.89 mmol, 10.0 eq.) at rt. The mixture was stirred at 160° C. for 5 h in the dark. The reaction mixture was cooled to rt. The reaction was stopped by the addition of water and extracted with CHCl₃ (3 times). The combined organic layer was dried over Na₂SO₄ and concentrated in vacuo. The residue was purified by reversed phase flash chromatography on a C18 column using a gradient of 20-50% MeCN in (NH₄)₂CO₃ (10 mM, aq) as mobile phase to give the title compound as a brown solid (129.3 mg, 50%); MS (ESI): m/z [M+H]+421.1.

Step 2: Example 88: (2S)-3-[[1-[2-hydroxy-4-(trifluoromethyl)phenyl]pyrido[3,4-d]pyridazin-4-yl]amino]propane-1,2-diol

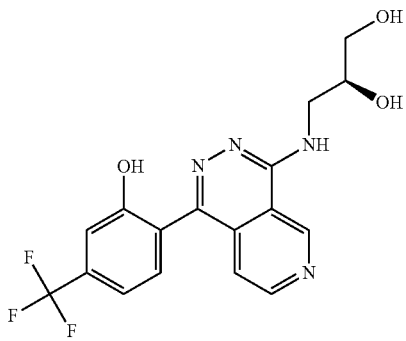 [SMILES: OC[C@@H](O)CNc1nnc(-c2ccc(C(F)(F)F)cc2O)c2ccncc12]

To a suspension of Intermediate 65 (124.6 mg, 0.30 mmol, 1.0 eq) in AcOH (2 mL) was added H₂O (0.6 mL) and the mixture was stirred at 80° C. for 1 h. The mixture was cooled to rt and concentrated. The crude mixture was purified by reversed phase flash chromatography on a C18 column using a gradient of 20-50% MeCN in (NH₄)₂CO₃ (10 mM, aq) as mobile phase to give the title compound as a white solid (47.4 mg, 39%). MS (ESI): m/z [M+H]+381.1. ¹H NMR (400 MHz, DMSO-d6) δ 3.43-3.47 (m, 2H), 3.51-3.64 (m, 1H), 3.75-3.84 (m, 1H), 3.85-3.97 (m, 1H), 4.76 (t, 1H), 5.10 (d, 1H), 7.17-7.39 (m, 3H), 7.56 (d, 1H), 8.08-8.16 (m, 1H), 8.85 (d, 1H), 9.76 (d, 1H), 10.46 (br d, 1H).

Example 89

Step 1: Intermediate 66: 6,7-dihydropyrido[2,3-d]pyridazine-5,8-dione

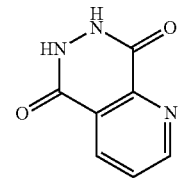 [SMILES: O=c1[nH][nH]c(=O)c2ncccc12]

To a suspension of furo[3,4-b]pyridine-5,7-dione (5.00 g, 33.5 mmol) in AcOH (25 mL) was added hydrazine monohydrate (5.3 mL, 110 mmol) at rt and the mixture was stirred at reflux for 17 h. The mixture was cooled to rt and the precipitate was filtrated and washed by H₂O to give the title compound (5.15 g, 94%) as a colorless powder. MS(ESI): m/z 164.0 [M+H]−.

Step 2: Intermediate 67: 5,8-dichloropyrido[2,3-d]pyridazine

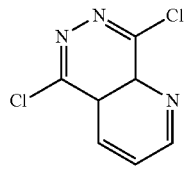

To a solution of Intermediate 66 (2.0 g, 12 mmol) in pyridine (1.9 g, 25 mmol) was added phosphoryl trichloride (10 mL) at rt and the mixture was stirred at 100° C. for 6 h. The mixture was evaporated under reduced pressure, poured into ice water, extracted with CHCl₃, dried over Na₂SO₄ and filtered. The organic solvent was evaporated under reduced pressure to give the title compound (2.4 g, 98%) as a brown solid. MS(ESI): m/z 200.0/202.0 [M+H]+.

Step 3: Intermediate 68: (1S,3R)-3-[(5-chloropyrido[2,3-d]pyridazin-8-yl)amino]cyclohexanol

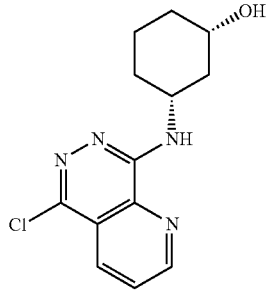 [SMILES: O[C@H]1CCC[C@@H](Nc2nnc(Cl)c3cccnc23)C1]

To a solution of Intermediate 67 (1.20 g, 6.00 mmol) and (1S,3R)-3-aminocyclohexanol hydrochloride in NMP (6.0 mL) was added DIPEA (3.5 mL) and the mixture was stirred at 80° C. for 17 h. The mixture was evaporated under reduced pressure and purified by flash chromatography (NH silica; EtOAc/MeOH=100/0-80/20) to give the title compound (236 mg, 13%) as a yellow solid. MS(ESI): m/z 279.1/281.2 [M+H]$^+$.

Step 4: Example 89: 2-[8-[[(1R,3S)-3-hydroxycyclohexyl]amino]pyrido[2,3-d]pyridazin-5-yl]-5-(trifluoromethyl)phenol

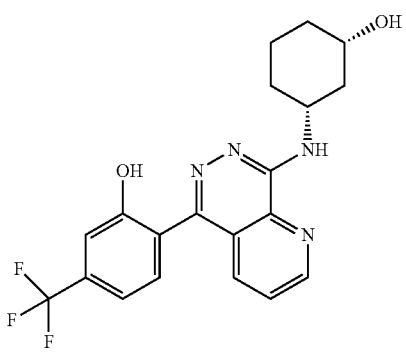 [SMILES: Oc1cc(C(F)(F)F)ccc1-c1nnc(N[C@@H]2CCC[C@H](O)C2)c2ncccc12]

To a solution of Intermediate 68 (236 mg, 0.847 mmol) and (2-fluoro-6-methoxy-phenyl)boronic acid (209 mg, 1.02 mmol) in 1,4-dioxane (5 mL) and 2.0 M Na$_2$CO$_3$ aq. (2.5 mL) was added Pd(dppf)Cl$_2$·CH$_2$Cl$_2$ (69 mg, 0.085 mmol) and the mixture was stirred at 100° C. for 5 h. The mixture was cooled to rt, poured into H$_2$O, extracted with CHCl$_3$, washed by H$_2$O, dried over Na$_2$SO$_4$, filtered and evaporated under reduced pressure. The crude mixture was purified by flash chromatography (NH silica; CHCl$_3$/MeOH=100/0-90/10). Combined product fractions were concentrated and further purified by flash chromatography (silica; CHCl$_3$/MeOH=100/0-90/10), then triturated with 10% MeOH in IPE to give the title compound (78 mg, 23%) as a pale yellow powder. MS(ESI): m/z 405.1 [M+H]$^+$. $^1$H NMR (400 MHz, CDCl$_3$) δ 1.30-1.75 (m, 5H), 1.88-2.24 (m, 3H), 2.41-2.55 (m, 1H), 3.91-4.05 (m, 1H), 4.40-4.52 (m, 1H), 7.20-7.27 (m, 1H), 7.40-7.48 (m, 1H), 7.59-7.65 (m, 1H), 7.74-7.82 (m, 1H), 8.48-8.57 (m, 1H), 9.02-9.09 (m, 1H).

Example 90: 3-fluoro-2-(8-(((1s,3s)-3-hydroxy-3-methylcyclobutyl)amino)pyrido[2,3-d]pyridazin-5-yl)phenol

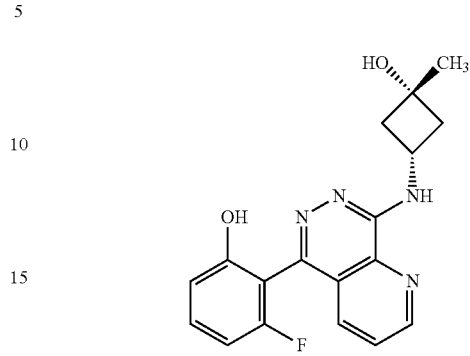

The title compound was synthesized analogously to the procedure of Example 63 starting from Intermediate 67 and (2-fluoro-6-hydroxy-phenyl)boronic acid. MS(ESI): m/z 341.1 [M+H]$^+$. $^1$H NMR (400 MHz, DMSO-d6) δ 1.33 (s, 3H), 2.16-2.27 (m, 2H), 2.45-2.55 (m, 2H), 4.31-4.42 (m, 1H), 5.01 (br s, 1H), 6.77-6.91 (m, 2H), 7.31-7.41 (m, 1H), 7.51-7.62 (m, 1H), 7.72-7.82 (m, 1H), 7.82-7.91 (m, 1H), 9.08-9.15 (m, 1H).

Example 91

Step 1: Intermediate 69: 2-methyl-6,7-dihydropyrido[2,3-d]pyridazine-5,8-dione

To a suspension of 2-methylfuro[3,4-b]pyridine-5,7-dione (5.42 g, 31.6 mmol) in AcOH (24 mL) was added hydrazine monohydrate (5.0 mL, 103 mmol) at rt and the mixture was stirred at 125° C. for 40 min. The mixture was cooled to rt and the precipitate was filtrated, washed by H$_2$O and dried to give the title compound (4.80 g, 86%) as a colorless powder. MS(ESI): m/z 178.0 [M+H]$^+$.

Step 2: Intermediate 70: 5,8-dichloro-2-methylpyrido[2,3-d]pyridazine

To a solution of Intermediate 69 (1.10 g, 6.21 mmol) in pyridine (1.0 mL) was added phosphoryl trichloride (5.0 mL) at rt and the mixture was stirred at 100° C. for 5 h under argon atmosphere. The mixture was evaporated under reduced pressure, poured into ice water, extracted with CHCl$_3$ and dried over Na$_2$SO$_4$ and filtered. The organic solvent was evaporated under reduced pressure to give the title compound (585 mg, 44%) as a red powder. MS(ESI): m/z 214.0/216.0 [M+H]$^+$.

Step 3: Example 91: 2-[8-[[(1R,3S)-3-hydroxycyclohexyl]amino]-2-methyl-pyrido[2,3-d]pyridazin-5-yl]-5-(trifluoromethyl)phenol

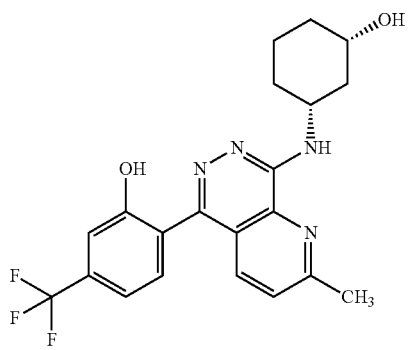 [SMILES: Cc1ccc2c(-c3ccc(C(F)(F)F)cc3O)nnc(N[C@@H]3CCC[C@H](O)C3)c2n1]

Starting from Intermediate 70, the title compound was synthesized analogously to the procedure of Example 89. MS(ESI): m/z 419.2 [M+H]$^+$. $^1$H NMR (400 MHz, DMSO-d6) δ 1.20-1.52 (m, 4H), 1.73-2.00 (m, 3H), 2.16-2.25 (m, 1H), 2.73 (s, 3H), 3.60-3.70 (m, 1H), 4.19-4.30 (m, 1H), 4.70-4.77 (m, 1H), 7.22-7.34 (m, 2H), 7.52-7.59 (m, 1H), 7.67-7.73 (m, 1H), 7.78-7.82 (m, 1H).

Example 92

Step 1: Intermediate 71: 3-[(4-chlorophthalazin-1-yl)amino]-2-methyl-propane-1,2-diol

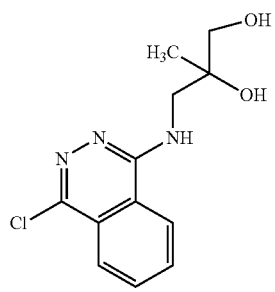 [SMILES: CC(O)(CO)CNc1nnc(Cl)c2ccccc12]

To a solution of 1,4-dichlorophthalazine (300 mg, 1.51 mmol, 1.0 eq) in MeCN (2 mL) was added DIPEA (0.78 mL, 4.52 mmol, 3.0 eq) and 3-amino-2-methyl-propane-1,2-diol (190 mg, 1.81 mmol, 1.2 eq). The vial was sealed and the reaction was run at 120° C. for 1 h in a microwave reactor. The reaction mixture was cooled to rt and the residual precipitate was triturated with CHCl$_3$ to give the title compound (290 mg, 72%) as a colorless powder. MS(ESI): m/z 268.1/270.1 [M+H]$^+$.

Step 2: Intermediate 72: 4-chloro-N-[(2,2,4-trimethyl-1,3-dioxolan-4-yl)methyl]phthalazin-1-amine

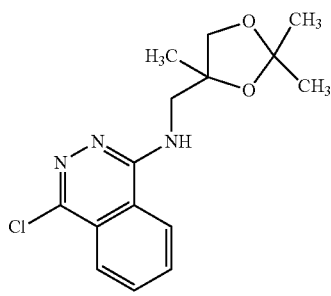 [SMILES: CC1(CNc2nnc(Cl)c3ccccc23)COC(C)(C)O1]

To a mixture of Intermediate 71 (200 mg, 0.747 mmol, 1.0 eq) in DMF (3 mL) and acetone (3 mL) were added 2,2-dimethoxypropane (3.0 mL, 24.46 mmol, 33 eq) and para-toluenesulfonic acid monohydrate (28.4 mg, 0.149 mmol, 0.2 eq), then the mixture was stirred at rt for 12 h. The reaction mixture was concentrated and saturated aqueous NaHCO$_3$ was added. The mixture was extracted with EtOAc and washed by brine, then the organic layer was evaporated under reduced pressure. The residue was purified by NH silica gel column chromatography using a gradient of 25-50% EtOAc in hexane as mobile phase to give the title compound (255 mg, 100%) as a colorless gum. MS(ESI) m/z 308.1/310.0 [M+H]$^+$. $^1$H NMR (400 MHz, DMSO-d6) δ 1.29 (s, 3H), 1.31 (s, 3H), 1.33 (s, 3H), 3.63-3.66 (m, 1H), 3.65-3.69 (m, 1H), 3.79-3.83 (m, 1H), 4.06-4.08 (m 1H), 7.61-7.63 (m, 1H), 7.97-8.02 (m, 2H), 8.06-8.09 (m, 1H), 8.41-8.45 (m, 1H).

Step 3: Intermediate 73: 5-(trifluoromethyl)-2-[4-[(2,2,4-trimethyl-1,3-dioxolan-4-yl)methylamino]phthalazin-1-yl]phenol

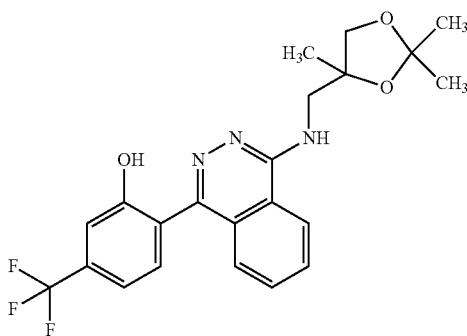 [SMILES: CC1(CNc2nnc(-c3ccc(C(F)(F)F)cc3O)c3ccccc23)COC(C)(C)O1]

To a solution of Intermediate 72 (120 mg, 0.35 mmol), [2-hydroxy-4-(trifluoromethyl)phenyl]boronic acid (108 mg, 0.53 mmol) and PdCl$_2$(Amphos)$_2$ (24.9 mg, 0.035 mmol, 0.1 eq) in DME (2 mL) and H$_2$O (0.5 mL) was added Cs$_2$CO$_3$ (343 mg, 1.05 mmol, 3.0 eq) and the vial was sealed. The reaction was run at 120° C. for 1 h in a microwave reactor. The reaction mixture was cooled to rt and diluted with H$_2$O. The mixture was added CHCl$_3$ and stirred. The organic layer was separated and concentrated in vacuo. The residue was purified by column chromatography using a gradient of 0-10% MeOH in CHCl$_3$ as mobile phase to give the title compound (135 mg, 89%) as a pale yellow powder. MS(ESI) m/z 434.2 [M+H]. $^1$H NMR (400 MHz, DMSO-d6) δ 1.34 (s, 3H), 1.35-1.36 (m, 6H), 3.68-3.71 (m, 1H), 3.73-3.76 (m, 1H), 3.89-3.94 (m, 1H), 4.13-4.15 (m, 1H), 7.27-7.30 (m, 2H), 7.44-7.47 (m, 2H), 7.51-7.54 (m, 1H), 7.77-7.81 (m, 1H), 7.86-7.88 (m, 1H), 8.38-8.40 (m, 1H), 10.36 (br s, 1H).

Step 4: Example 92: 3-[[4-[2-hydroxy-4-(trifluoromethyl)phenyl]phthalazin-1-yl]amino]-2-methylpropane-1,2-diol

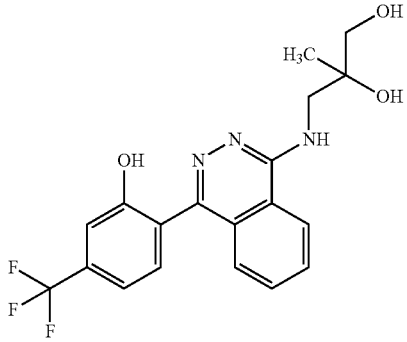 [SMILES: CC(O)(CO)CNc1nnc(-c2ccc(C(F)(F)F)cc2O)c2ccccc12]

To a solution of the Intermediate 73 (135 mg, 0.312 mmol) in trifluoroacetic acid (2 mL) was added H$_2$O (0.8 mL) and the mixture was stirred at rt for 3 h. The mixture was cooled to rt and evaporated under reduced pressure. The residue was purified by reversed phase flash chromatography on a C18 column using a gradient of 30-60% MeCN in (NH$_4$)$_2$CO$_3$ (10 mM, aq) as mobile phase to give the title compound (84 mg, 68%) as a colorless powder. MS(ESI): m/z 394.4 [M+H]$^+$. $^1$H NMR (400 MHz, DMSO-d6) δ 1.15 (s, 3H), 3.18-3.29 (m, 2H), 3.60-3.66 (m, 2H), 5.33-5.36 (m, 2H), 7.26-7.32 (m, 2H), 7.45-7.47 (m, 1H), 7.51-7.53 (m, 1H), 7.65-7.68 (m, 1H), 7.80-7.84 (m, 1H), 7.88-7.92 (m, 1H), 8.38-8.39 (m, 1H), 10.36 (br s, 1H).

TABLE 8

MS and NMR data for compounds listed in Tables

| Ex No. | MS m/z (ESI) | $^1$H NMR |
|---|---|---|
| 2 | 364.1/366.1 [M + H]$^+$ | (400 MHz, DMSO-d6) δ 3.39-3.49 (m, 2H), 3.51-3.61 (m, 1H), 3.70-3.80 (m, 1H), 3.82-3.91 (m, 1H), 4.74-4.85 (m, 1H), 5.11-5.40 (m, 1H), 7.07-7.20 (m, 2H), 7.45-7.53 (m, 1H), 7.60-7.67 (m, 1H), 7.75-7.92 (m, 2H), 8.32-8.40 (m, 1H), 10.00-10.40 (m, 1H) |
| 3 | 348.1 [M + H]$^+$ | (400 MHz, DMSO-d6) δ 3.39-3.49 (m, 2H), 3.51-3.62 (m, 1H), 3.70-3.80 (m, 1H), 3.82-3.90 (m, 1H), 4.75-4.87 (m, 1H), 5.16-5.32 (m, 1H), 6.88-6.98 (m, 1H), 7.30-7.41 (m, 1H), 7.45-7.52 (m, 1H), 7.56-7.62 (m, 1H), 7.74-7.91 (m, 2H), 8.30-8.37 (m, 1H), 9.95-10.12 (m, 1H) |
| 4 | 330.1 [M + H]$^+$ | (400 MHz, DMSO-d6) δ 3.39-3.49 (m, 2H), 3.51-3.62 (m, 1H), 3.69-3.80 (m, 1H), 3.82-3.91 (m, 1H), 4.77-4.85 (m, 1H), 5.21-5.32 (m, 1H), 6.74-6.88 (m, 2H), 7.30-7.40 (m, 2H), 7.56-7.63 (m, 1H), 7.74-7.93 (m, 2H), 8.32-8.38 (m, 1H), 9.80-10.00 (m, 1H) |
| 5 | 346.2/348.3 [M + H]$^+$ | (400 MHz, DMSO-d6) δ 3.39-3.49 (m, 2H), 3.51-3.61 (m, 1H), 3.68-3.79 (m, 1H), 3.81-3.91 (m, 1H), 4.76-4.93 (m, 1H), 5.16-5.35 (m, 1H), 6.97-7.05 (m, 2H), 7.27-7.35 (m, 1H), 7.44-7.50 (m, 1H), 7.53-7.62 (m, 1H), 7.75-7.91 (m, 2H), 8.30-8.36 (m, 1H), 9.80-10.20 (m, 1H) |
| 6 | 396.3 [M + H]$^+$ | (400 MHz, DMSO-d6) δ 3.37-3.48 (m, 2H), 3.50-3.61 (m, 1H), 3.68-3.79 (m, 1H), 3.82-3.91 (m, 1H), 4.78-4.93 (m, 1H), 5.21-5.33 (m, 1H), 6.88-6.95 (m, 2H), 7.36-7.41 (m, 1H), 7.44-7.51 (m, 1H), 7.55-7.63 (m, 1H), 7.76-7.91 (m, 2H), 8.30-8.38 (m, 1H), 10.00-10.30 (m, 1H) |
| 7 | 398.1 [M + H]$^+$ | (400 MHz, DMSO-d6) δ 3.37-3.48 (m, 2H), 3.50-3.61 (m, 1H), 3.68-3.80 (m, 1H), 3.82-3.93 (m, 1H), 4.71-4.86 (m, 1H), 5.14-.30 (m, 1H), 7.07-7.12 (m, 1H), 7.22-7.26 (m, 1H), 7.34-7.41 (m, 1H), 7.63-7.71 (m, 1H), 7.75-7.92 (m, 2H), 8.34-8.42 (m, 1H) |
| 8 | 348.1 [M + H]$^+$ | (400 MHz, DMSO-d6) δ 3.37-3.48 (m, 2H), 3.50-3.61 (m, 1H), 3.68-3.79 (m, 1H), 3.82-3.92 (m, 1H), 4.74-4.85 (m, 1H), 5.17-5.33 (m, 1H), 6.54-6.68 (m, 1H), 6.70-6.85 (m, 1H), 7.35-7.41 (m, 1H), 7.56-7.66 (m, 1H), 7.74-7.92 (m, 2H), 8.31-8.38 (m, 1H), 10.20-10.90 (m, 1H) |

TABLE 8-continued

MS and NMR data for compounds listed in Tables

| Ex No. | MS m/z (ESI) | $^1$H NMR |
|---|---|---|
| 9 | 364.1/366.1 [M + H]$^+$ | (400 MHz, DMSO-d6) δ 3.45-3.57 (m, 2H), 3.66-3.86 (m, 2H), 3.90-3.99 (m, 1H), 7.00-7.07 (m, 1H), 7.13 (dd, 1H), 7.65 (d, 1H), 8.06-8.20 (m, 2H), 8.93 (d, 1H), 10.20 (br s, 1H), 11.09 (br s, 1H) |
| 10 | 346.1/348.1 [M + H]$^+$ | (400 MHz, DMSO-d6) δ 3.39-3.57 (m, 2H), 3.65-3.87 (m, 2H), 3.91-4.02 (m, 1H), 7.05-7.17 (m, 2H), 7.41-7.53 (m, 2H), 8.07-8.20 (m, 2H), 8.91-8.99 (m, 1H), 10.02-10.52 (m, 2H) |
| 11 | 326.1 [M + H]$^+$ | (400 MHz, DMSO-d6) δ 2.35 (s, 3H), 3.45-3.85 (m, 4H), 3.91-3.98 (m, 1H), 6.82-6.93 (m, 2H), 7.17-7.28 (m, 2H), 7.58-7.75 (m, 1H), 8.04-8.20 (m, 1H), 8.95-9.00 (m, 1H), 9.78-10.36 (m, 2H) |
| 12 | 380.2 [M + H]$^+$ | (400 MHz, DMSO-d6) δ 3.40-3.46 (m, 2H), 3.53-3.62 (m, 1H), 3.70-3.79 (m, 1H), 3.82-3.90 (m, 1H), 4.75-4.84 (m, 1H), 5.17-5.26 (m, 1H), 7.25-7.31 (m, 2H), 7.43-7.53 (m, 2H), 7.57-7.62 (m, 1H), 7.75-7.82 (m, 1H), 7.83-7.90 (m, 1H), 8.32-8.37 (m, 1H) |
| 19 | 390.1 [M + H]$^+$ | (400 MHz, DMSO-d6) δ 1.60-1.75 (m, 2H), 1.75-1.95 (m, 3H), 1.95-2.10 (m, 1H), 4.28-4.38 (m, 1H), 4.38-4.52 (m, 1H), 4.70-4.82 (m, 1H), 6.95-7.08 (m, 1H), 7.25-7.38 (m, 2H), 7.44 (d, 1H), 7.51 (d, 1H), 7.78 (t, 1H), 7.86 (t, 1H), 8.42 (d, 1H), 10.37 (s, 1H) |
| 20 | 390.1 [M + H]$^+$ | (400 MHz, DMSO-d6) δ 1.45-1.88 (m, 4H), 1.88-2.10 (m, 1H), 2.15-2.35 (m, 1H), 4.05-4.20 (m, 1H), 4.20-4.35 (m, 1H), 5.30-5.65 (m, 1H), 7.15-7.65 (m, 5H), 7.65-8.00 (m, 2H), 8.35-8.55 (m, 1H), 10.36 (s, 1H) |
| 21 | 390.1 [M + H]$^+$ | (400 MHz, DMSO-d6) δ 1.50-1.65 (m, 1H), 1.66-1.78 (m, 1H), 1.82-1.95 (m, 2H), 2.05-2.10 (m, 1H), 2.10-2.25 (m, 1H), 4.20-4.35 (m, 1H), 4.38-4.45 (m, 1H), 5.00-5.15 (m, 1H), 7.35 (s, 1H), 7.38 (d, 1H), 7.60 (d, 1H), 7.65 (d, 1H), 8.09 (t, 1H), 8.15 (t, 1H), 8.96 (d, 1H), 10.81 (s, 1H) |
| 22 | 390.1 [M + H]$^+$ | (400 MHz, DMSO-d6) δ 1.50-1.62 (m, 1H), 1.65-1.82 (m, 3H), 1.95-2.10 (m, 1H), 2.18-2.30 (m, 1H), 4.10-4.18 (m, 1H), 4.25-4.38 (m, 1H), 5.38 (s, 1H), 7.25 (s, 1H), 7.30 (s, 1H), 7.40 (d, 1H), 7.49 (d, 1H), 7.79 (t, 1H), 7.85 (t, 1H), 8.37 (d, 1H) |
| 23 | 404.1 [M + H]$^+$ | (400 MHz, DMSO-d6) δ 1.30-1.50 (m, 2H), 1.55-1.88 (m, 5H), 2.05-2.10 (m, 1H), 4.05-4.15 (m, 2H), 4.38-4.45 (m, 1H), 4.95-5.20 (m, 1H), 7.34 (s, 1H), 7.38 (d, 1H), 7.60 (d, 1H), 7.64 (d, 1H), 8.07 (t, 1H), 8.14 (t, 1H), 8.97 (d, 1H), 9.05-9.25 (m, 1H), 10.78 (s, 1H) |
| 24 | 404.1 [M + H]$^+$ | (400 MHz, DMSO-d6) δ 1.20-1.40 (m, 4H), 1.65-1.70 (m, 2H), 1.95-2.05 (m, 1H), 2.10-2.20 (m, 1H), 3.55-3.68 (m, 1H), 4.10-4.20 (m, 1H), 4.80-4.90 (m, 1H), 7.14 (d, 1H), 7.27 (s, 1H), 7.29 (d, 1H), 7.43 (d, 1H), 7.51 (d, 1H), 7.78 (t, 1H), 7.86 (t, 1H), 8.41 (d, 1H), 10.37 (s, 1H) |
| 25 | 404.1 [M + H]$^+$ | (400 MHz, DMSO-d6) δ 1.35-1.48 (m, 2H), 1.50-1.95 (m, 6H), 4.08-4.15 (m, 1H), 4.28-4.38 (m, 1H), 4.73-4.85 (m, 1H), 6.83 (d, 1H), 7.27 (s, 1H), 7.30 (d, 1H), 7.44 (d, 1H), 7.50 (d, 1H), 7.78 (t, 1H), 7.86 (t, 1H), 8.42 (d, 1H), 10.36 (s, 1H) |
| 26 | 404.1 [M + H]$^+$ | (400 MHz, DMSO-d6) δ 1.23-1.43 (m, 4H), 1.65-1.75 (m, 2H), 1.95-2.05 (m, 1H), 2.10-2.15 (m, 1H), 3.55-3.68 (m, 1H), 4.05-4.20 (m, 1H), 4.75-4.95 (m, 1H), 7.13-7.21 (m, 1H), 7.27 (s, 1H), 7.29 (d, 1H), 7.43 (d, 1H), 7.51 (d, 1H), 7.78 (t, 1H), 7.86 (t, 1H), 8.41 (d, 1H), 10.38 (s, 1H) |
| 27 | 418.2 [M + H]$^+$ | (400 MHz, DMSO-d6) δ 1.43-1.95 (m, 10H), 3.83-3.95 (m, 1H), 4.20-4.30 (m, 1H), 4.85-4.95 (m, 1H), 7.22 (d, 1H), 7.27 (s, 1H), 7.29 (d, 1H), 7.43 (d, 1H), 7.51 (d, 1H), 7.77 (t, 1H), 7.86 (t, 1H), 8.44 (d, 1H), 10.35 (s, 1H) |
| 28 | 404.2 [M + H]$^+$ | (400 MHz, DMSO-d6) δ 1.35-1.52 (m, 2H), 1.52-1.63 (m, 2H), 1.68-1.83 (m, 2H), 1.92-2.07 (m, 2H), 4.03-4.10 (m, 1H), 4.44 (d, 1H), 4.63-4.75 (m, 1H), 7.02 (d, 1H), 7.25-7.31 (m, 2H), 7.44 (dd, 1H), 7.51 (d, 1H), 7.76 (td, 1H), 7.83 (td, 1H), 8.40 (d, 1H), 10.05-10.65 (m, 1H) |
| 29 | 404.3 [M + H]$^+$ | (400 MHz, DMSO-d6) δ 1.36-1.52 (m, 2H), 1.52-1.63 (m, 2H), 1.68-1.83 (m, 2H), 1.92-2.07 (m, 2H), 4.03-4.10 (m, 1H), 4.44 (d, 1H), 4.63-4.77 (m, 1H), 7.02 (d, 1H), 7.23-7.33 (m, 2H), 7.44 (dd, 1H), 7.52 (d, 1H), 7.76 (td, 1H), 7.84 (td, 1H), 8.40 (d, 1H), 10.15-10.45 (m, 1H) |
| 30 | 404.2 [M + H]$^+$ | 400 MHz, DMSO-d6) δ 1.08-1.25 (m, 1H), 1.25-1.43 (m, 3H), 1.73-1.81 (m, 1H), 1.82-1.91 (m, 1H), 1.95-2.05 (m, 1H), 2.23-2.32 (m, 1H), 3.51-3.63 (m, 1H), 4.23-4.37 (m, 1H), 4.68 (d, 1H), 7.22-7.32 (m, 3H), 7.44 (d, 1H), 7.50 (d, 1H), 7.77 (td, 1H), 7.89 (td, 1H), 8.37 (d, 1H), 10.15-10.45 (m, 1H) |
| 31 | 404.3 [M + H]$^+$ | (400 MHz, DMSO-d6) δ 1.08-1.22 (m, 1H), 1.22-1.42 (m, 3H), 1.73-1.81 (m, 1H), 1.82-1.90 (m, 1H), 1.97-2.03 (m, 1H), 2.22-2.31 (m, 1H), 3.51-3.63 (m, 1H), 4.25-4.35 (m, 1H), 4.68 (d, 1H), 7.20-7.30 (m, 3H), 7.44 (d, 1H), 7.49 (d, 1H), 7.76 (t, 1H), 7.84 (td, 1H), 8.37 (d, 1H) |
| 32 | 376.2 [M + H]$^+$ | (400 MHz, DMSO-d6) δ 2.25-2.35 (m, 2H), 2.35-2.45 (m, 2H), 4.34-4.47 (m, 1H), 4.64-4.77 (m, 1H), 4.97-5.08 (m, 1H), 7.22-7.30 (m, 2H), 7.45 (dd, 1H), 7.48-7.55 (m, 2H), 7.77 (ddd, 1H), 7.86 (ddd, 1H), 8.41 (d, 1H) |
| 33 | 376.2 [M + H]$^+$ | (400 MHz, DMSO-d6) δ 1.92-2.05 (m, 2H), 2.71-2.81 (m, 2H), 3.89-4.04 (m, 1H), 4.13-4.27 (m, 1H), 5.03-5.15 (m, 1H), 7.21-7.30 (m, 2H), 7.44 (dd, 1H), 7.49 (d, 1H), 7.55 (d, 1H), 7.76 (ddd, 1H), 7.85 (ddd, 1H), 8.41 (d, 1H) |

TABLE 8-continued

MS and NMR data for compounds listed in Tables

| Ex No. | MS m/z (ESI) | ¹H NMR |
|---|---|---|
| 34 | 390.2 [M + H]⁺ | (400 MHz, DMSO-d6) δ 1.62-1.73 (m, 2H), 1.73-1.93 (m, 2H), 2.02-2.12 (m, 1H), 2.31-2.41 (m, 1H), 4.16-4.23 (m, 1H), 4.53-4.63 (m, 1H), 4.80 (d, 1H), 7.20-7.28 (m, 2H), 7.33 (d, 1H), 7.45 (d, 1H), 7.50 (d, 1H), 7.76 (td, 1H), 7.84 (td, 1H), 8.37 (d, 1H) |
| 35 | 390.2 [M + H]⁺ | (400 MHz, DMSO-d6) δ 1.62-1.73 (m, 2H), 1.73-1.93 (m, 2H), 2.02-2.12 (m, 1H), 2.31-2.41 (m, 1H), 4.15-4.23 (m, 1H), 4.52-4.63 (m, 1H), 4.70-4.82 (m, 1H), 7.20-7.30 (m, 2H), 7.33 (d, 1H), 7.44 (d, 1H), 7.51 (d, 1H), 7.76 (td, 1H), 7.85 (td, 1H), 8.37 (d, 1H) |
| 36 | 340.1 [M + H]⁺ | (400 MHz, DMSO-d6) δ 1.34 (s, 3H), 2.15-2.25 (m, 2H), 2.45-2.55 (m, 2H), 4.19-4.32 (m, 1H), 5.00-5.08 (m, 1H), 6.75 (t, 1H), 6.85 (d, 1H), 7.28-7.36 (m, 2H), 7.61 (d, 1H), 7.71 (td, 1H), 7.85 (td, 1H), 8.44 (d, 1H) |
| 37 | 390.1 [M + H]⁺ | (600 MHz, DMSO) δ 1.35 (s, 3H), 2.17-2.22 (m, 2H), 2.48-2.52 (m, 2H), 4.22-4.30 (m, 1H), 5.00 (s, 1H), 7.26-7.32 (m, 2H), 7.42-7.47 (m, 1H), 7.50-7.54 (m, 1H), 7.60-7.66 (m, 1H), 7.76-7.81 (m, 1H), 7.84-7.89 (m, 1H), 8.42-8.46 (m, 1H), 10.35 (s, 1H) |
| 45 | 423.1 [M + H]⁺ | (400 MHz, DMSO-d6) δ 1.09-1.22 (m, 1H), 1.25-1.44 (m, 3H), 1.73-1.83 (m, 1H), 1.83-1.93 (m, 1H), 2.00-2.09 (m, 1H), 2.23-2.37 (m, 1H), 3.49-3.65 (m, 1H), 4.26-4.46 (m, 1H), 4.73 (d, 1H), 7.16 (s, 1H), 7.22 (d, 1H), 7.28 (dd, 1H), 7.85 (d, 1H), 8.85 (d, 1H), 9.80 (d, 1H), 10.81 (br s, 1H) |
| 46 | 389.1/391.1 [M + H]⁺ | (400 MHz, DMSO-d6) δ 1.09-1.23 (m, 1H), 1.25-1.55 (m, 3H), 1.72-1.84 (m, 1H), 1.84-1.93 (m, 1H), 1.96-2.07 (m, 1H), 2.21-2.31 (m, 1H), 3.50-3.63 (m, 2H), 4.05-4.21 (m, 1H), 6.96 (dd, 1H), 7.13 (dd, 1H), 7.46 (br d, 1H), 9.06 (br d, 1H), 10.01 (s, 1H), 10.91 (br s, 1H) |
| 47 | 355.1 [M + H]⁺ | (400 MHz, DMSO-d6) δ 1.11-1.20 (m, 1H), 1.26-1.44 (m, 3H), 1.73-1.82 (m, 1H), 1.85-1.92 (m, 1H), 2.00-2.07 (m, 1H), 2.24-2.37 (m, 1H), 3.49-3.62 (m, 1H), 4.25-4.40 (m, 1H), 4.74 (d, 1H), 6.76-6.87 (m, 2H), 7.16 (d, 1H), 7.31-7.40 (m, 1H), 7.76 (d, 1H), 8.84 (d, 1H), 9.78 (s, 1H) |
| 48 | 421.6 [M + H]⁺ | (400 MHz, DMSO-d6) δ 1.06-1.21 (m, 1H), 1.22-1.45 (m, 3H), 1.73-1.82 (m, 1H), 1.83-1.93 (m, 1H), 1.98-2.09 (m, 1H), 2.23-2.36 (m, 1H), 3.50-3.64 (m, 1H), 4.25-4.39 (m, 1H), 4.55-4.91 (m, 1H), 6.73-6.85 (m, 2H), 7.31 (dd, 1H), 7.33-7.39 (m, 1H), 7.65 (d, 1H), 8.80 (d, 1H), 9.73 (s, 1H) |
| 55 | 423.0 [M + H]⁺ | (400 MHz, DMSO-d6) δ 1.24-1.43 (m, 4H), 1.62-1.81 (m, 2H), 1.94-2.05 (m, 1H), 2.08-2.19 (m, 1H), 3.56-3.70 (m, 1H), 4.18-4.33 (m, 1H), 4.82 (br d, 1H), 7.16 (s, 1H), 7.20 (d, 1H), 7.28 (dd, 1H), 7.76 (d, 1H), 8.84 (d, 1H), 9.82 (s, 1H), 10.84 (br s, 1H) |
| 56 | 421.0 [M + H]⁺ | (400 MHz, DMSO-d6) δ 1.21-1.44 (m, 4H), 1.62-1.79 (m, 2H), 1.93-2.06 (m, 1H), 2.08-2.21 (m, 1H), 3.56-3.70 (m, 1H), 4.15-4.30 (m, 1H), 4.81 (d, 1H), 6.92-6.99 (m, 2H), 7.27 (dd, 1H), 7.40-7.48 (m, 1H), 7.63 (d, 1H), 8.84 (d, 1H), 9.78 (d, 1H), 10.40 (br s, 1H) |
| 57 | 389.0/391.0 [M + H]⁺ | (400 MHz, DMSO-d6) δ 1.23-1.42 (m, 4H), 1.63-1.81 (m, 2H), 1.93-2.05 (m, 1H), 2.07-2.18 (m, 1H), 3.56-3.69 (m, 1H), 4.16-4.31 (m, 1H), 4.81 (d, 1H), 6.90 (dd, 1H), 7.04 (dd, 1H), 7.19 (d, 1H), 7.71 (d, 1H), 8.84 (d, 1H), 9.80 (s, 1H), 10.56 (s, 1H) |
| 58 | 370.9/372.9 [M + H]⁺ | (400 MHz, DMSO-d6) δ 1.21-1.42 (m, 4H), 1.62-1.81 (m, 2H), 1.93-2.05 (m, 1H), 2.06-2.22 (m, 1H), 3.55-3.72 (m, 1H), 4.13-4.29 (m, 1H), 4.71-4.93 (m, 1H), 7.01-7.05 (m, 2H), 7.28 (dd, 1H), 7.31-7.36 (m, 1H), 7.62 (d, 1H), 8.83 (d, 1H), 9.78 (s, 1H), 10.25 (s, 1H) |
| 65 | 375.0/377.0 [M + H]⁺ | (400 MHz, DMSO-d6) δ 1.35 (s, 3H), 2.14-2.27 (m, 2H), 2.51-2.57 (m, 2H), 4.20-4.32 (m, 1H), 5.05 (s, 1H), 7.13-7.21 (m, 2H), 7.32 (dd, 1H), 8.14 (d, 1H), 8.85 (d, 1H), 9.80 (d, 1H), 10.38 (br s, 1H). |
| 66 | 359.0 [M + H]⁺ | (400 MHz, DMSO-d6) δ 1.35 (s, 3H), 2.10-2.27 (m, 2H), 2.51-2.55 (m, 2H), 4.13-4.36 (m, 1H), 5.05 (s, 1H), 6.96 (dd, 1H), 7.30 (dd, 1H), 7.41 (dd, 1H), 8.09 (d, 1H), 8.85 (d, 1H), 9.79 (d, 1H), 10.14 (br s, 1H). |
| 67 | 409.1 [M + H]⁺ | (400 MHz, DMSO-d6) δ 1.35 (s, 3H), 2.16-2.29 (m, 2H), 2.51-2.57 (m, 2H), 4.23-4.39 (m, 1H), 5.07 (s, 1H), 7.16 (s, 1H), 7.22 (d, 1H), 7.29 (d, 1H), 8.22 (d, 1H), 8.85 (d, 1H), 9.83 (s, 1H), 10.83 (br s, 1H) |
| 68 | 357.1/359.1 [M + H]⁺ | (400 MHz, DMSO-d6) δ 1.35 (s, 3H), 2.14-2.24 (m, 2H), 2.52-2.55 (m, 2H), 4.21-4.32 (m, 1H), 5.05 (s, 1H), 7.01-7.06 (m, 2H), 7.29 (d, 1H), 7.34 (d, 1H), 8.10 (brd, 1H), 8.85 (d, 1H), 9.79 (s, 1H), 10.23 (br s, 1H). |
| 69 | 359.1 [M + H]⁺ | (400 MHz, DMSO-d6) δ 1.35 (s, 3H), 2.14-2.26 (m, 2H), 2.51-2.56 (m, 2H), 4.23-4.35 (m, 1H), 5.02-5.09 (m, 1H), 6.63-6.69 (m, 1H), 6.83 (ddd, 1H), 7.20 (d, 1H), 8.14 (d, 1H), 8.85 (d, 1H), 9.81 (d, 1H), 10.56 (br s, 1H). |
| 71 | 345.0/347.0 [M + H]⁺ | (400 MHz, DMSO-d6) δ 1.22 (s, 6H), 3.65-3.75 (m, 2H), 5.00-5.12 (m, 1H), 6.94-7.05 (m, 2H), 7.25-7.36 (m, 2H), 7.79-7.90 (m, 1H), 8.81-8.88 (m, 1H), 9.75-9.81 (m, 1H) |
| 72 | 395.0 [M + H]⁺ | (400 MHz, DMSO-d6) δ 1.22 (s, 6H), 3.65-3.73 (m, 2H), 5.00-5.13 (m, 1H), 6.86-6.96 (m, 2H), 7.25-7.34 (m, 1H), 7.40-7.48 (m, 1H), 7.79-7.88 (m, 1H), 8.83-8.89 (m, 1H), 9.75-9.82 (m, 1H) |
| 73 | 362.9/364.9 [M + H]⁺ | (400 MHz, DMSO-d6) δ 1.23 (s, 6H), 3.70 (d, 2H), 5.03 (s, 1H), 6.87-6.94 (m, 1H), 7.04 (dd, 1H), 7.23 (d, 1H), 7.90 (t, 1H), 8.87 (d, 1H), 9.82 (s, 1H), 10.60 (br s, 1H) |
| 79 | 405.2 [M + H]⁺ | (400 MHz, DMSO-d6) δ 1.34-1.46 (m, 2H), 1.48-1.87 (m, 5H), 1.87-1.98 (m, 1H), 4.12-4.18 (m, 1H), 4.33-4.42 (m, 1H), 4.73 (d, 1H), 7.25-7.29 (m, 2H), 7.31 (d, 1H), 7.39 (d, 1H), 7.54 (d, 1H), 8.83 (d, 1H), 9.84 (s, 1H), 10.44 (br s, 1H) |

TABLE 8-continued

MS and NMR data for compounds listed in Tables

| Ex No. | MS m/z (ESI) | $^1$H NMR |
|---|---|---|
| 80 | 405.2 [M + H]$^+$ | (400 MHz, DMSO-d6) δ 1.32-1.47 (m, 2H), 1.49-1.86 (m, 5H), 1.87-1.98 (m, 1H), 4.12-4.18 (m, 1H), 4.32-4.42 (m, 1H), 4.69-4.77 (m, 1H), 7.25-7.33 (m, 3H), 7.39 (d, 1H), 7.54 (d, 1H), 8.83 (d, 1H), 9.84 (s, 1H), 10.43 (br s, 1H) |
| 81 | 405.2 [M + H]$^+$ | (400 MHz, DMSO-d6) δ 1.25-1.44 (m, 4H), 1.65-1.80 (m, 2H), 1.94-2.05 (m, 1H), 2.09-2.21 (m, 1H), 3.57-3.71 (m, 1H), 4.17-4.29 (m, 1H), 4.79 (d, 1H), 7.24-7.33 (m, 3H), 7.55 (d, 1H), 7.65 (d, 1H), 8.83 (d, 1H), 9.79 (s, 1H), 10.41 (br s, 1H) |
| 82 | 405.2 [M + H]$^+$ | (400 MHz, DMSO-d6) δ 1.08-1.22 (m, 1H), 1.24-1.45 (m, 3H), 1.71-1.83 (m, 1H), 1.84-1.94 (m, 1H), 1.96-2.13 (m, 1H), 2.23-2.37 (m, 1H), 3.49-3.63 (m, 1H), 4.26-4.42 (m, 1H), 4.60-4.88 (m, 1H), 7.24-7.36 (m, 3H), 7.55 (d, 1H), 7.76 (d, 1H), 8.84 (d, 1H), 9.77 (s, 1H), 10.45 (br s, 1H) |
| 83 | 391.2 [M + H]$^+$ | (400 MHz, DMSO-d6) δ 1.62-1.74 (m, 2H), 1.74-1.95 (m, 2H), 2.04-2.17 (m, 1H), 2.35-2.46 (m, 1H), 4.13-4.25 (m, 1H), 4.56-4.66 (m, 1H), 4.74 (d, 1H), 7.25-7.34 (m, 3H), 7.55 (d, 1H), 7.86 (d, 1H), 8.84 (d, 1H), 9.79 (s, 1H), 10.43 (s, 1H) |
| 84 | 391.1 [M + H]$^+$ | (400 MHz, DMSO-d6) δ 1.35 (s, 3H), 2.10-2.23 (m, 2H), 2.41-2.55 (m, 2H), 4.70-4.87 (m, 1H), 4.92 (s, 1H), 7.25-7.35 (m, 3H), 7.56 (d, 1H), 8.05 (d, 1H), 8.84 (d, 1H), 9.79 (d, 1H), 10.43 (br s, 1H) |

Biological and Physicochemical Data

Human NLRP3 Speck Formation Assay (Test A)

To profile compounds for NLRP3 antagonist activity with respect to inhibition of Nigericin triggered speck formation, the ASC-GFP Reporter Monocytes (InvivoGen #thp-ascgfp) was employed. The assay is based on NF-kB dependent expression of the ASC::GFP fusion protein. LPS-priming of cells increases ASC::GFP expression and Nigericin recruits ASC::GFP, pro-caspase-1 and NLRP3 to form micrometer-sized complexes, ASC-specks, that are quantified by fluorescence microscopy.

Preparation of Assay Reagents:

Assay medium: RPMI 1640 (Gibco #72400-021) supplemented with 10% heat inactivated FBS (Gibco #10270)

Cells: THP-ASC-GFP were cultured in RPMI 1640 (Gibco #72400-021) supplemented with 10% heat inactivated FBS (Gibco #10270) and 100 µg/mL Zeocin (Life Technologies #46-0072) (every other passage) to maintain ASC::GFP expression.

Step by Step Protocol for Running the Assay:

Day 1
1. Cells were counted with a CEDEX (Innovartis) and diluted with assay medium supplemented with 100 nM Phorbol 12-myristate 13 acetate (Sigma #P8139) to 375000 cells/mL.
2. 20 µl cell mix above were dispensed into black µclear TC-treated (Greiner #781091) 384 well plates with Multidrop Combi (ThermoFisher).
3. Plates were incubated at 37° C., 5% $CO_2$ for 20 h.

Day 2
1. 10 µl LPS (Sigma #L2654) were dispensed with Multidrop Combi (ThermoFisher) for 1 µg/mL.
2. Plates were incubated at 37° C., 5% $CO_2$ for 3 h.
3. 80 nl test compound in DMSO were prepared in concentration response curves and diluted with 20 µl assay medium supplemented with 68 µM ZVAD-FMK (Promega #7231) in polypropylen 384 well plates (Greiner #781280)
4. 10 µl above test compound solution were transferred to cell plate with Bravo (Agilent).
5. Plates were incubated at 37° C., 5% $CO_2$ for 30 min
6. 15 µl Nigericin (Sigma #SML1779) at 75 µM were dispensed to cell plates with Certus (Gyger)
7. Plates were incubated at 37° C., 5% $CO_2$ for 1 h
8. 15 µl 17.3% Formaldehyde (Sigma #F8775) supplemented with Hoechst nucleic acid stain (Life Technologies #H3570) diluted 1:5000 were added with Multi-drop (ThermoFisher)
9. Plates were incubated at RT for 15 min
10. Plates were washed two times with 40 µl PBS (Gibco #100100) with Bluewasher (BlueCatBio)
11. Plates were imaged using ImageXpress (Molecular Devices)

Image data was processed using Columbus software (Perkin Elmer) using nucei stain to identify cells and spot detection to identify the ASC-specks within the cells. Screener (Genedata AG) was used to further process data. Concentration response data of number of specks per cell were fitted using a four parameter logistic fit and $EC_{50}$ values reported in Table 9.

Nigericin Triggered (Human NLRP3) IL-1β Assay (Test B)

Compounds were profiled for NLRP3 antagonist activity with respect to inhibition of Nigericin triggered IL-1β release from THP-1 human monocytes. Quantification was performed using a commercially available human IL-1β HTRF detection kit (CisBio, 62HIL1BPEH). The assay uses two anti-IL-1β antibodies in a sandwich assay format. One labeled with a donor fluorophore (Eu cryptate), a second with an acceptor (XL). Immune-complexes containing the two antibodies bound to the same IL-1β molecule allows fluorescence resonance energy transfer (FRET) between the donor and acceptor after excitation of the donor with a light source, subsequently resulting in fluorescence at 665 nM from the acceptor. The fluorescence signal intensity is proportional to the IL-1β concentration in the sample.

Preparation of Assay Reagents:

Cells: THP human monocytic leukemia cell line. Cells generally passaged every 2-3 days with density kept from 0.2 to 0.4*10^6 cells/mL.

Culture and assay medium: RPMI 1640 (Gibco, 72400-021) supplemented with 10% FBS (Sigma, F2442)

IL-1β standard: reconstituted IL-1β standard provided in the CisBio kit was diluted in assay medium to a top final concentration of 2 ng/mL in the assay.

HTRF detection reagents: cAMP-d2 and anti-cAMP cryptate were reconstituted according to CisBio kit instructions. Just prior to use, reagents were combined using the following proportions: 10/24 Detection buffer (provided with the kit), 14/24 PBS (Gibco, 10010), 1/120 IL-1β Eu-cryptate Antibody and 1/120 IL-1β XL Antibody.

Step by step protocol for running the assay:
Day 1
1. 20 nL test compounds dissolved in DMSO were aquostically dispensed (Labcyte Echo) to white 384-well plates (Greiner; 784075), sealed and stored at rt until assayed.
2. 20 nL 50 μM of a control compound in DMSO (250 nM final concentration) was added to 100% inhibition control wells and 20 nL DMSO added to 0% control wells with Echo dispenser. The control compound may be selected from MCC950 (N-[[(1,2,3,5,6,7-hexahydro-s-indacen-4-yl)amino]carbonyl]-4-(1-hydroxy-1-methylethyl)-2-furansulfonamide) or any other compound that acts as a full antagonist in the assay.
3. An aliquot of cells was taken out from cells grown in continuous culture and counted with a CEDEX (Innovatis).
4. The number of cells needed for an experiment were centrifuged for 5 min at 250×g and resuspend to $1.0*10^6$ cells/mL with 37° C. assay medium.
5. LPS (Sigma; L2654) was added to a final concentration of 1 μg/mL.
6. Cell were LPS-primed in bulk in a 50 mL tube by incubating at 37° C., 5% $CO_2$ and 95% humidity for 3 h.
7. 4 μL cell solution at $1.0*10^6$ cells/mL was dispensed with Multidrop Combi (Thermo Fisher) to white 384-well small volume plates (Greiner; 784075) to give 4000 cells/well.
8. 30 min incubation at 37° C., 5% $CO_2$ and 95% humidity.
9. 4 μL of 40 μM nigericin in assay medium was added with Certus (Gyger) to a final concentration of 20 μM.
10. 1 h incubation at 37° C., 5% $CO_2$ and 95% humidity.
11. 4 μL HTRF detection reagents was added with Multidrop Combi.
12. 3 h incubation at rt protected from light.
13. Homogenous Time-Resolved Fluorescence (HTRF) signal was detected with an Envision (PerkinElmer) or Pherastar (BMG Labtech) reader (λex=340 nm, λem=665 and 615 nm).

Using an IL-1β standard curve, HTRF data was converted to amount IL-1β produced in the samples which was subsequentially used for calculation of concentration responses. Concentration response data were analyzed with Screener (Genedata) and fitted with a four parameter logistic fit. The results from the assay are reported in Table 9 as $IC_{50}$ (μM).

$IC_{50}$ is defined as the concentration at which the inhibitory activity reaches 50% of its maximum level. Where the assay was run multiple times for the same compound, the geometric mean is reported. To facilitate comparison of efficacy data, efficacy was normalized to % inhibitory effect of the test compound compared to the inhibition caused by a saturating concentration of the control compound (250 nM).

BzATP Triggered (Human NLRP3) IL-1β Assay (Test C)

In a variant of the IL-1β assay, compounds were tested for their ability to inhibit BzATP (2'(3')-O-(4-Benzoylbenzoyl) adenosine 5'-triphosphate) triggered IL-1β release from THP-1 human monocytes. Like the nigericin triggered assay, quantification was performed using a human IL-1β HTRF detection kit (CisBio, 62HIL1BPEH).

There were some differences between the nigericin triggered assay (Test B) and the BzATP triggered assay. Conditions in the BzATP triggered assay with relevant differences compared to the nigericin triggered assay include:
- Cell culture medium: RPMI 1640 (Gibco, 11875-119) supplemented with 10% FBS (Sigma, 171012) and Penicillin-streptomycin (Thermo Fisher, 15140-122).
- Assay medium: RPMI 1640 (Gibco, 22400-105) supplemented with 1% FBS (Sigma, 171012).
- Cells were primed with LPS (Sigma, L2630) at a final concentration of 2 μg/mL for 24 h (instead of 1 μg/mL for 3 h).
- IL-1β production was triggered by addition of BzATP (Sigma, B6396) (instead of nigericin) at a final concentration of 1 mM followed by 30 min incubation at 37° C., 5% $CO_2$ and 95% humidity.

The results from the assay are reported in Table 9 as $IC_{50}$ (μM).

hERG Assay (Test D)

Experiments were performed on the SyncroPatch 384PE (Nanion Technologies) high throughput patch clamp platform at rt and used medium resistance chips with 4 patch holes per site. hERG-expressing Chinese hamster ovary K1 (CHO) cell line were used in assay-ready format and kept in liquid nitrogen until use. 2 vials of cells ($10\times10^6$ cells per vial) were thawed and added to 20 mL Hepes-buffered saline solution (HBSS). HBSS comprised 140 mM NaCl, 4 mM KCl, 10 mM HEPES and 5 mM Glucose (pH 7.4). The internal patch clamp solution was KF 120 mM, KCl 20 mM, HEPES 10 mM, EGTA 10 mM, and 25 μM Escin (pH7.2). After the initial sealing process was complete, a seal enhancer solution comprising HBSS supplemented with 10 mM $CaCl_2$ and 1 mM $MgCl_2$ was applied to cells. The external solution was then exchanged (4 times) for external patch clamp solution comprising NaCl 80 mM, KCl 4 mM, HEPES 10 mM, $CaCl_2$ 2 mM, $MgCl_2$ 1 mM, glucose 5 mM, and NMDG 60 mM (pH 7.4). All solutions were stored at rt, except Escin, which was stored at 4° C. All compounds were dispensed in greiner-bio 384 well plates and tested in a 6 point cumulative assay (final DMSO concentration 0.33%). Only wells that passed acceptance criteria (30 MegaOhm seal resistance, Z prime >0.4 and current size >0.2 nA) were used in this analysis. The $IC_{50}$ (μM) results of the hERG assay are reported in Table 9.

Solubility (Test E)

The assay was conducted according to the Solubility Assay described in pages 164-167 of Wernevik, J. et al., "*A Fully Integrated Assay Panel for Early Drug Metabolism and Pharmacokinetics Profiling*", Assay and Drug Development Technologies, 2020, 18(4), 157-179. Data are reported in Table 9 as solubility (μM). Where the assay was run multiple times for the same compound, the arithmetic mean is reported.

Solubility (Test F)

After drying a 20 mM DMSO solution containing the test compound, disodium hydrogenphosphate-citric acid buffer solution (Diluted Mcolvaine buffer, pH6.5) was added to dilute 100 fold. Under these conditions, the theoretical maximum concentration of the test compound was 200 μM. The buffer was sonicated, shaken, and held at 25° C. for 24 to 72 h. The buffer sample was filtered and the filtrate was diluted with an equal volume of acetonitrile/methanol (1:1, v/v) in a 96 well plate. A 20 mM DMSO solution containing the test compound was diluted 100 fold with acetonitrile/methanol (1:1, v/v) and the same amount of McIlvaine buffer (pH 6.5) was added to use as the standard solution. The standard and test samples were transferred to a 384 well plate and analyzed by HPLC. The results of the solubility assay are reported in Table 9 in μg/mL.

TABLE 9

| | Assay data | | | | | |
|---|---|---|---|---|---|---|
| Example | Test A EC$_{50}$ (μM) | Test B IC$_{50}$ (μM) | Test C IC$_{50}$ (μM) | Test D hERG IC$_{50}$ (μM) | Test E Solubility (μM) | Test F Solubility (μg/mL) |
| 1 | 0.082 | 0.027 | 0.010 | >40 | 100 | 50.0 |
| 2 | | | 0.165 | | | 24.6 |
| 3 | | | 0.474 | | | 68.6 |
| 4 | | | >1.000 | | | 23.2 |
| 5 | 0.122 | 0.045 | 0.017 | | 6 | 7.9 |
| 6 | 0.201 | 0.099 | 0.040 | | 130 | >79.1 |
| 7 | 0.180 | 0.047 | 0.022 | >40 | 582 | 70.3 |
| 8 | | | 0.159 | | | 11.8 |
| 9 | 0.164 | | 0.011 | | | 67.3 |
| 10 | | | 0.434 | | | 62.9 |
| 11 | 0.207 | 0.082 | 0.023 | | >1,000 | >65.1 |
| 12 | 0.100 | | 0.022 | | 186 | 36.4 |
| 13 | | | >10.000 | | | >65.1 |
| 14 | 0.018 | | 0.005 | | 135 | 56.3 |
| 15 | 0.220 | | 0.026 | | 155 | 14.7 |
| 16 | 0.054 | 0.030 | 0.020 | 22 | | 23.9 |
| 17 | 0.290 | 0.169 | 0.086 | | | 27.5 |
| 18 | | | 0.738 | | | >79.9 |
| 19 | 0.026 | 0.020 | 0.005 | 23 | 171 | 10.6 |
| 20 | 0.162 | 0.046 | 0.010 | | 206 | 8.6 |
| 21 | 0.105 | 0.036 | 0.008 | 19 | 71 | 14.5 |
| 22 | 2.407 | | 0.187 | | 172 | 9.2 |
| 23 | 0.156 | 0.031 | 0.014 | 21 | 0.400 | 4.4 |
| 24 | 0.038 | 0.009 | 0.005 | 17 | 148 | 7.9 |
| 25 | 0.080 | 0.036 | 0.008 | 7.4 | 3 | 1.8 |
| 26 | 1.983 | | 0.602 | | 148 | 8.3 |
| 27 | 0.562 | | 0.034 | | 9 | 2.1 |
| 28 | 0.104 | 0.034 | 0.020 | | | 17.6 |
| 29 | | | 0.296 | | | 16.1 |
| 30 | | | 0.430 | | | 16.5 |
| 31 | 0.039 | 0.017 | 0.008 | 11 | | 18.6 |
| 32 | 0.248 | 0.141 | 0.063 | | | 1.4 |
| 33 | 0.206 | 0.122 | 0.046 | | | 2.6 |
| 34 | | | 0.018 | | | 9.3 |
| 35 | 0.212 | 0.071 | 0.069 | | | 10.9 |
| 36 | | | 0.976 | | | 43.0 |
| 37 | 0.339 | 0.032 | | 29 | | |
| 38 | 0.027 | 0.016 | 0.009 | >40 | 810 | >80.9 |
| 39 | 0.059 | 0.018 | 0.007 | | 48 | 10.2 |
| 40 | 0.006 | 0.004 | <0.003 | 34 | 413 | 26.0 |
| 41 | 0.011 | 0.006 | <0.003 | >40 | 67 | 8.6 |
| 43 | | | 0.033 | | | 37.3 |
| 44 | 0.016 | | <0.003 | >40 | 636 | 40.1 |
| 45 | 0.044 | 0.025 | 0.009 | >40 | 121 | 10.4 |
| 46 | 0.037 | | 0.003 | >40 | 941 | >77.8 |
| 47 | | | 0.068 | | | >70.9 |
| 48 | 0.029 | 0.014 | 0.004 | >40 | 326 | 80.4 |
| 49 | | | 0.405 | | | >80.9 |
| 50 | | | 0.047 | | | >80.9 |
| 51 | | | 0.004 | | | >72.9 |
| 52 | 0.052 | | 0.006 | 22 | 447 | 51.9 |
| 53 | | | 0.007 | | | 62.5 |
| 54 | | | 0.004 | | | 45.7 |
| 55 | 0.038 | | 0.006 | >40 | 529 | 8.8 |
| 56 | 0.025 | 0.008 | 0.003 | 19 | 263 | 14.5 |
| 57 | 0.017 | | 0.005 | >40 | 596 | 36.9 |
| 58 | 0.011 | | 0.002 | >40 | | 42.4 |
| 59 | 0.016 | 0.009 | 0.005 | >40 | 47 | >78.1 |
| 60 | 0.017 | 0.012 | <0.003 | >40 | 26 | 10.3 |
| 61 | 0.029 | | 0.007 | 34 | 389 | 64.0 |
| 62 | 0.060 | | 0.006 | >40 | 120 | 25.7 |
| 63 | | | 0.008 | | | 0.8 |
| 64 | | | 0.111 | | | >68.1 |
| 65 | 0.373 | 0.114 | 0.037 | | 11 | 1.1 |
| 66 | | | 0.570 | | | 3.6 |
| 67 | 0.067 | 0.024 | 0.008 | | 3 | 1.5 |
| 68 | 0.019 | | 0.002 | 44 | | |
| 69 | 0.301 | 0.149 | 0.038 | | 29 | 13.6 |
| 70 | 0.067 | 0.026 | 0.010 | >40 | 5 | 17.7 |
| 71 | | | 0.014 | | | 21.9 |
| 72 | | | 0.022 | | | 5.8 |
| 73 | 0.142 | | 0.015 | >40 | | 14.1 |
| 74 | 0.204 | | 0.018 | | 17 | 12.1 |
| 75 | 0.124 | 0.010 | | >40 | | |
| 76 | 0.128 | | | >40 | | |
| 77 | 2.929 | | | | | |
| 78 | 1.140 | | | | 958 | |
| 79 | 0.029 | 0.018 | 0.010 | >40 | 50 | 4.8 |
| 80 | 0.018 | 0.005 | 0.007 | >40 | 35 | 5.9 |
| 81 | 2.159 | | 0.289 | | 397 | 31.0 |
| 82 | 1.757 | | 0.091 | >40 | 34 | 9.4 |
| 83 | 0.129 | 0.038 | 0.020 | >40 | 47 | 4.7 |
| 84 | 0.088 | | 0.027 | | 20 | >78.1 |
| 85 | 0.481 | | | | 68 | |
| 86 | 6.146 | | | | | |
| 87 | 6.150 | | | | 25 | |
| 88 | 0.036 | 0.016 | 0.004 | >40 | 643 | >76.1 |
| 89 | 0.047 | 0.027 | 0.008 | 36 | 294 | 22.1 |
| 90 | | | 0.551 | | | >68.1 |
| 91 | | | 0.010 | | | 0.5 |
| 92 | 0.296 | | 0.020 | | 14 | 2.8 |

LPS/ATP Test

Male 7-week-old BALB/cAJcl mice were intraperitoneally administered 0.5 mL of 4 μg/mL LPS (Sigma-Aldrich Co. LLC, L2630) solution in PBS (Thermo Fisher Scientific Inc., 10010). One hour later, the test article suspension in 0.50 (w/v) CMC sodium (Nacalai tesque INC., 07326-95) aqueous solution was orally administered at a volume of 10 mL/kg. One hour after the article administration, 0.5 mL of 30 μmol/L ATP (Sigma-Aldrich Co. LLC, A7699) solution in PBS was intraperitoneally administered. Twenty minutes later, the animals were euthanized by cervical dislocation under sevoflurane anesthesia. Immediately after euthanasia, peritoneal cavity of each animal was washed with 3 mL of ice-cold PBS intraperitoneally injected. Then, the PBS was collected, and the concentrations of IL-1β were determined using ELISA kit (R&D Systems Inc., MLB00C). The results of the test are shown in Table 10.

TABLE 10

| | LPS/ATP test data | |
|---|---|---|
| | % inhibition of IL-1β production | |
| Example | 1 mg/kg | 3 mg/kg |
| 1 | 4 | 82 |
| 7 | 46 | 95 |
| 9 | | 77 |
| 14 | | 75 |
| 38 | 29 | 83 |
| 39 | | 58 |
| 40 | 87 | 98 |
| 41 | 94 | 99 |
| 45 | | 82 |
| 46 | 23 | 65 |
| 53 | | 65 |
| 54 | | 55 |
| 55 | | 91 |
| 56 | | 98 |
| 57 | 42 | 87 |
| 59 | 44 | 70 |
| 60 | 60 | 97 |
| 61 | | 97 |

TABLE 10-continued

LPS/ATP test data

| | % inhibition of IL-1β production | |
|---|---|---|
| Example | 1 mg/kg | 3 mg/kg |
| 62 | | 71 |
| 70 | | 98 |
| 74 | | 68 |
| 80 | | 73 |
| 89 | | 71 |

Those skilled in the art will appreciate that the biological assays described above may be performed using alternative equipment and minor variations to the protocol without significantly affecting the results.

The above description of illustrative embodiments is intended only to acquaint others skilled in the art with Applicant's invention, its principles, and its practical application so that others skilled in the art may readily adapt and apply the invention in its numerous forms, as they may be best suited to the requirements of a particular use. This description and its specific examples, while indicating embodiments of this invention, are intended for purposes of illustration only. This invention, therefore, is not limited to the illustrative embodiments described in this specification, and may be variously modified. In addition, it is to be appreciated that various features of the invention that are, for clarity reasons, described in the context of separate embodiments, also may be combined to form a single embodiment. Conversely, various features of the invention that are, for brevity reasons, described in the context of a single embodiment, also may be combined to form sub-combinations thereof.

Any publications disclosed within the specification are hereby incorporated by reference.

The invention claimed is:

1. A compound of Formula (I):

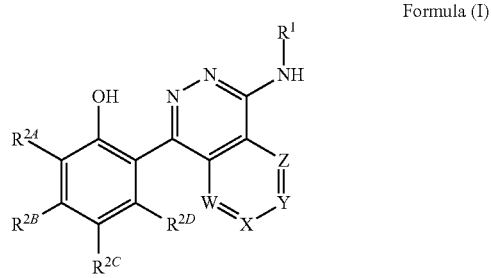

Formula (I)

or a pharmaceutically acceptable salt thereof, wherein $R^1$ is selected from

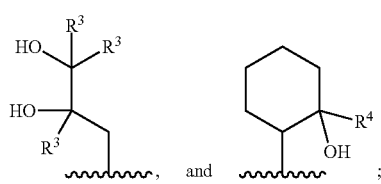

each $R^3$ is independently selected from —H and —$C_{1-3}$ alkyl;

$R^4$ is selected from —H and —$C_{1-3}$ alkyl;

$R^{2A}$, $R^{2B}$, $R^{2C}$, and $R^{2D}$ are each independently selected from —H, —F, —Cl, —$C_{1-3}$ alkyl substituted with 0-3-F substituents, cyclopropyl, —$OCF_3$, and —$SO_2Me$;

W, X, Y and Z are each independently selected from $CR^5$ and N; zero or one of W, X, Y and Z are N, and the remainder of W, X, Y and Z are $CR^5$;

each $R^5$ is independently selected from —H, -Me and —F.

2. The compound of claim 1, wherein each $R^3$ is —H.

3. The compound of claim 1, wherein $R^4$ is —H.

4. The compound of claim 1, wherein $R^1$ is

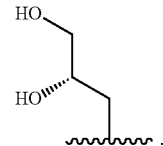

5. The compound of claim 1, wherein $R^1$ is

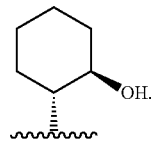 [SMILES: *[C@@H]1CCCC[C@H]1O]

6. The compound of claim 1, wherein two or three of $R^{2A}$, $R^{2B}$, $R^{2C}$, and $R^{2D}$ are —H, and the remainder of $R^{2A}$, $R^{2B}$, $R^{2C}$, and $R^{2D}$ are not —H.

7. The compound of claim 1, wherein $R^{2A}$ and $R^{2C}$ are —H.

8. The compound of claim 1, wherein $R^{2B}$ is selected from —H, —F, —$CF_3$, and —$SO_2Me$.

9. The compound of claim 1, wherein $R^{2D}$ is selected from —H and —F.

10. The compound of claim 1, wherein $R^{2B}$ is selected from —H or —Cl, and $R^{2D}$ is —F.

11. The compound of claim 1, wherein $R^{2B}$ is not —H.

12. The compound of claim 1, wherein $R^{2A}$ is —H, $R^{2B}$ is —$CF_3$, $R^{2C}$ is —H, and $R^{2D}$ is —H.

13. The compound of claim 1, wherein W, X, and Z are each CH, and Y is CH or N.

14. The compound of claim 1, wherein the compound is selected from:
3-[[4-[2-hydroxy-4-(trifluoromethyl)phenyl]phthalazin-1-yl]amino]propane-1,2-diol;
3-[[4-(4-chloro-3-fluoro-2-hydroxy-phenyl)phthalazin-1-yl]amino]propane-1,2-diol;
3-[[4-(4,5-difluoro-2-hydroxy-phenyl)phthalazin-1-yl]amino]propane-1,2-diol;
3-[[4-(2-fluoro-6-hydroxy-phenyl)phthalazin-1-yl]amino]propane-1,2-diol;
3-[[4-(4-chloro-2-hydroxy-phenyl)phthalazin-1-yl]amino]propane-1,2-diol;
3-[[4-[2-hydroxy-4-(trifluoromethoxy)phenyl]phthalazin-1-yl]amino]propane-1,2-diol;
3-[[4-[2-fluoro-6-hydroxy-4-(trifluoromethyl)phenyl]phthalazin-1-yl]amino]propane-1,2-diol;
3-[[4-(2,4-difluoro-6-hydroxy-phenyl)phthalazin-1-yl]amino]propane-1,2-diol;

3-[[4-(4-chloro-2-fluoro-6-hydroxy-phenyl)phthalazin-1-yl]amino]propane-1,2-diol;
3-[[4-(2-chloro-6-hydroxy-phenyl)phthalazin-1-yl]amino]propane-1,2-diol;
3-[[4-(2-hydroxy-4-methyl-phenyl)phthalazin-1-yl]amino]propane-1,2-diol;
3-[[4-(2-hydroxy-5-methyl-phenyl)phthalazin-1-yl]amino]propane-1,2-diol;
3-[[4-[2-hydroxy-4-(trifluoromethyl)phenyl]-7-methyl-phthalazin-1-yl]amino]propane-1,2-diol;
3-[[4-[2-hydroxy-4-(trifluoromethyl)phenyl]-6-methyl-phthalazin-1-yl]amino]propane-1,2-diol;
2-[4-[[2-hydroxycyclohexyl]amino]phthalazin-1-yl]-5-(trifluoromethyl)phenol;
4-fluoro-2-[4-[[2-hydroxycyclohexyl]amino]pyrido[3,4-d]pyridazin-1-yl]-5-(trifluoromethyl)phenol;
3-fluoro-2-[4-[[2-hydroxycyclohexyl]amino]pyrido[3,4-d]pyridazin-1-yl]-5-(trifluoromethyl)phenol;
2-[4-[[2-hydroxycyclohexyl]amino]pyrido[3,4-d]pyridazin-1-yl]-5-(trifluoromethoxy)phenol;
5-chloro-3-fluoro-2-[4-[[2-hydroxycyclohexyl]amino]pyrido[3,4-d]pyridazin-1-yl]phenol;
5-chloro-2-[4-[[2-hydroxycyclohexyl]amino]pyrido[3,4-d]pyridazin-1-yl]phenol;
5-fluoro-2-(4-((2-hydroxycyclohexyl)amino)pyrido[3,4-d]pyridazin-1-yl)phenol;
3-fluoro-2-(4-((2-hydroxycyclohexyl)amino)pyrido[3,4-d]pyridazin-1-yl)phenol;
3-fluoro-2-(1-((2-hydroxycyclohexyl)amino)pyrido[3,4-d]pyridazin-4-yl)phenol;
5-fluoro-2-(1-((2-hydroxycyclohexyl)amino)pyrido[3,4-d]pyridazin-4-yl)phenol;
2-[4-[[2-hydroxycyclohexyl]amino]pyrido[3,4-d]pyridazin-1-yl]-5-(trifluoromethyl)phenol;
3-[[1-[2-hydroxy-4-(trifluoromethyl)phenyl]pyrido[3,4-d]pyridazin-4-yl]amino]propane-1,2-diol; and
3-[[4-[2-hydroxy-4-(trifluoromethyl)phenyl]phthalazin-1-yl]amino]-2-methyl-propane-1,2-diol;
or a pharmaceutically acceptable salt thereof.

15. The compound of claim 1, wherein the compound is selected from:
(2S)-3-[[4-[2-hydroxy-4-(trifluoromethyl)phenyl]phthalazin-1-yl]amino]propane-1,2-diol;
(2R)-3-[[4-[2-hydroxy-4-(trifluoromethyl)phenyl]phthalazin-1-yl]amino]propane-1,2-diol;
(2S)-3-[[4-(4-chloro-3-fluoro-2-hydroxy-phenyl)phthalazin-1-yl]amino]propane-1,2-diol;
(2R)-3-[[4-(4-chloro-3-fluoro-2-hydroxy-phenyl)phthalazin-1-yl]amino]propane-1,2-diol;
(2S)-3-[[4-(4,5-difluoro-2-hydroxy-phenyl)phthalazin-1-yl]amino]propane-1,2-diol;
(2R)-3-[[4-(4,5-difluoro-2-hydroxy-phenyl)phthalazin-1-yl]amino]propane-1,2-diol;
(2S)-3-[[4-(2-fluoro-6-hydroxy-phenyl)phthalazin-1-yl]amino]propane-1,2-diol;
(2R)-3-[[4-(2-fluoro-6-hydroxy-phenyl)phthalazin-1-yl]amino]propane-1,2-diol;
(2S)-3-[[4-(4-chloro-2-hydroxy-phenyl)phthalazin-1-yl]amino]propane-1,2-diol;
(2R)-3-[[4-(4-chloro-2-hydroxy-phenyl)phthalazin-1-yl]amino]propane-1,2-diol;
(2S)-3-[[4-[2-hydroxy-4-(trifluoromethoxy)phenyl]phthalazin-1-yl]amino]propane-1,2-diol;
(2R)-3-[[4-[2-hydroxy-4-(trifluoromethoxy)phenyl]phthalazin-1-yl]amino]propane-1,2-diol;
(2S)-3-[[4-[2-fluoro-6-hydroxy-4-(trifluoromethyl)phenyl]phthalazin-1-yl]amino]propane-1,2-diol;
(2R)-3-[[4-[2-fluoro-6-hydroxy-4-(trifluoromethyl)phenyl]phthalazin-1-yl]amino]propane-1,2-diol;
(2S)-3-[[4-(2,4-difluoro-6-hydroxy-phenyl)phthalazin-1-yl]amino]propane-1,2-diol;
(2R)-3-[[4-(2,4-difluoro-6-hydroxy-phenyl)phthalazin-1-yl]amino]propane-1,2-diol;
(2S)-3-[[4-(4-chloro-2-fluoro-6-hydroxy-phenyl)phthalazin-1-yl]amino]propane-1,2-diol;
(2R)-3-[[4-(4-chloro-2-fluoro-6-hydroxy-phenyl)phthalazin-1-yl]amino]propane-1,2-diol;
(2S)-3-[[4-(2-chloro-6-hydroxy-phenyl)phthalazin-1-yl]amino]propane-1,2-diol;
(2R)-3-[[4-(2-chloro-6-hydroxy-phenyl)phthalazin-1-yl]amino]propane-1,2-diol;
(2S)-3-[[4-(2-hydroxy-4-methyl-phenyl)phthalazin-1-yl]amino]propane-1,2-diol;
(2R)-3-[[4-(2-hydroxy-4-methyl-phenyl)phthalazin-1-yl]amino]propane-1,2-diol;
(2S)-3-[[4-(2-hydroxy-5-methyl-phenyl)phthalazin-1-yl]amino]propane-1,2-diol;
(2R)-3-[[4-(2-hydroxy-5-methyl-phenyl)phthalazin-1-yl]amino]propane-1,2-diol;
(2S)-3-[[4-[2-hydroxy-4-(trifluoromethyl)phenyl]-7-methyl-phthalazin-1-yl]amino]propane-1,2-diol;
(2R)-3-[[4-[2-hydroxy-4-(trifluoromethyl)phenyl]-7-methyl-phthalazin-1-yl]amino]propane-1,2-diol;
(2S)-3-[[4-[2-hydroxy-4-(trifluoromethyl)phenyl]-6-methyl-phthalazin-1-yl]amino]propane-1,2-diol;
(2R)-3-[[4-[2-hydroxy-4-(trifluoromethyl)phenyl]-6-methyl-phthalazin-1-yl]amino]propane-1,2-diol;
2-[4-[[(1R,2S)-2-hydroxycyclohexyl]amino]phthalazin-1-yl]-5-(trifluoromethyl)phenol;
2-[4-[[(1R,2R)-2-hydroxycyclohexyl]amino]phthalazin-1-yl]-5-(trifluoromethyl)phenol;
2-[4-[[(1S,2R)-2-hydroxycyclohexyl]amino]phthalazin-1-yl]-5-(trifluoromethyl)phenol;
2-[4-[[(1S,2S)-2-hydroxycyclohexyl]amino]phthalazin-1-yl]-5-(trifluoromethyl)phenol;
4-fluoro-2-[4-[[(1R,2R)-2-hydroxycyclohexyl]amino]pyrido[3,4-d]pyridazin-1-yl]-5-(trifluoromethyl)phenol;
4-fluoro-2-[4-[[(1S,2R)-2-hydroxycyclohexyl]amino]pyrido[3,4-d]pyridazin-1-yl]-5-(trifluoromethyl)phenol;
4-fluoro-2-[4-[[(1R,2S)-2-hydroxycyclohexyl]amino]pyrido[3,4-d]pyridazin-1-yl]-5-(trifluoromethyl)phenol;
4-fluoro-2-[4-[[(1S,2S)-2-hydroxycyclohexyl]amino]pyrido[3,4-d]pyridazin-1-yl]-5-(trifluoromethyl)phenol;
3-fluoro-2-[4-[[(1R,2R)-2-hydroxycyclohexyl]amino]pyrido[3,4-d]pyridazin-1-yl]-5-(trifluoromethyl)phenol;
3-fluoro-2-[4-[[(1R,2S)-2-hydroxycyclohexyl]amino]pyrido[3,4-d]pyridazin-1-yl]-5-(trifluoromethyl)phenol;
3-fluoro-2-[4-[[(1S,2R)-2-hydroxycyclohexyl]amino]pyrido[3,4-d]pyridazin-1-yl]-5-(trifluoromethyl)phenol;
3-fluoro-2-[4-[[(1S,2S)-2-hydroxycyclohexyl]amino]pyrido[3,4-d]pyridazin-1-yl]-5-(trifluoromethyl)phenol;
2-[4-[[(1R,2R)-2-hydroxycyclohexyl]amino]pyrido[3,4-d]pyridazin-1-yl]-5-(trifluoromethoxy)phenol;
2-[4-[[(1S,2S)-2-hydroxycyclohexyl]amino]pyrido[3,4-d]pyridazin-1-yl]-5-(trifluoromethoxy)phenol;

2-[4-[[(1R,2S)-2-hydroxycyclohexyl]amino]pyrido[3,4-d]pyridazin-1-yl]-5-(trifluoromethoxy)phenol;
2-[4-[[(1S,2R)-2-hydroxycyclohexyl]amino]pyrido[3,4-d]pyridazin-1-yl]-5-(trifluoromethoxy)phenol;
5-chloro-3-fluoro-2-[4-[[(1R,2R)-2-hydroxycyclohexyl]amino]pyrido[3,4-d]pyridazin-1-yl]phenol;
5-chloro-3-fluoro-2-[4-[[(1S,2S)-2-hydroxycyclohexyl]amino]pyrido[3,4-d]pyridazin-1-yl]phenol;
5-chloro-3-fluoro-2-[4-[[(1R,2S)-2-hydroxycyclohexyl]amino]pyrido[3,4-d]pyridazin-1-yl]phenol;
5-chloro-3-fluoro-2-[4-[[(1S,2R)-2-hydroxycyclohexyl]amino]pyrido[3,4-d]pyridazin-1-yl]phenol;
5-chloro-2-[4-[[(1R,2R)-2-hydroxycyclohexyl]amino]pyrido[3,4-d]pyridazin-1-yl]phenol;
5-chloro-2-[4-[[(1S,2S)-2-hydroxycyclohexyl]amino]pyrido[3,4-d]pyridazin-1-yl]phenol;
5-chloro-2-[4-[[(1R,2S)-2-hydroxycyclohexyl]amino]pyrido[3,4-d]pyridazin-1-yl]phenol;
5-chloro-2-[4-[[(1S,2R)-2-hydroxycyclohexyl]amino]pyrido[3,4-d]pyridazin-1-yl]phenol;
5-fluoro-2-(4-(((1R,2R)-2-hydroxycyclohexyl)amino)pyrido[3,4-d]pyridazin-1-yl)phenol;
5-fluoro-2-(4-(((1S,2S)-2-hydroxycyclohexyl)amino)pyrido[3,4-d]pyridazin-1-yl)phenol;
5-fluoro-2-(4-(((1S,2R)-2-hydroxycyclohexyl)amino)pyrido[3,4-d]pyridazin-1-yl)phenol;
5-fluoro-2-(4-(((1R,2S)-2-hydroxycyclohexyl)amino)pyrido[3,4-d]pyridazin-1-yl)phenol;
3-fluoro-2-(4-(((1R,2R)-2-hydroxycyclohexyl)amino)pyrido[3,4-d]pyridazin-1-yl)phenol;
3-fluoro-2-(4-(((1S,2S)-2-hydroxycyclohexyl)amino)pyrido[3,4-d]pyridazin-1-yl)phenol;
3-fluoro-2-(4-(((1S,2R)-2-hydroxycyclohexyl)amino)pyrido[3,4-d]pyridazin-1-yl)phenol;
3-fluoro-2-(4-(((1R,2S)-2-hydroxycyclohexyl)amino)pyrido[3,4-d]pyridazin-1-yl)phenol;
3-fluoro-2-(1-(((1R,2R)-2-hydroxycyclohexyl)amino)pyrido[3,4-d]pyridazin-4-yl)phenol;
3-fluoro-2-(1-(((1S,2S)-2-hydroxycyclohexyl)amino)pyrido[3,4-d]pyridazin-4-yl)phenol;
3-fluoro-2-(1-(((1S,2R)-2-hydroxycyclohexyl)amino)pyrido[3,4-d]pyridazin-4-yl)phenol;
3-fluoro-2-(1-(((1R,2S)-2-hydroxycyclohexyl)amino)pyrido[3,4-d]pyridazin-4-yl)phenol;
5-fluoro-2-(1-(((1R,2R)-2-hydroxycyclohexyl)amino)pyrido[3,4-d]pyridazin-4-yl)phenol;
5-fluoro-2-(1-(((1S,2S)-2-hydroxycyclohexyl)amino)pyrido[3,4-d]pyridazin-4-yl)phenol;
5-fluoro-2-(1-(((1R,2S)-2-hydroxycyclohexyl)amino)pyrido[3,4-d]pyridazin-4-yl)phenol;
5-fluoro-2-(1-(((1S,2R)-2-hydroxycyclohexyl)amino)pyrido[3,4-d]pyridazin-4-yl)phenol;
2-[4-[[(1S,2R)-2-hydroxycyclohexyl]amino]pyrido[3,4-d]pyridazin-1-yl]-5-(trifluoromethyl)phenol;
2-[4-[[(1R,2S)-2-hydroxycyclohexyl]amino]pyrido[3,4-d]pyridazin-1-yl]-5-(trifluoromethyl)phenol;
2-[4-[[(1S,2S)-2-hydroxycyclohexyl]amino]pyrido[3,4-d]pyridazin-1-yl]-5-(trifluoromethyl)phenol;
2-[4-[[(1R,2R)-2-hydroxycyclohexyl]amino]pyrido[3,4-d]pyridazin-1-yl]-5-(trifluoromethyl)phenol;
(2S)-3-[[1-[2-hydroxy-4-(trifluoromethyl)phenyl]pyrido[3,4-d]pyridazin-4-yl]amino]propane-1,2-diol;
(2R)-3-[[1-[2-hydroxy-4-(trifluoromethyl)phenyl]pyrido[3,4-d]pyridazin-4-yl]amino]propane-1,2-diol;
(S)-3-((4-(2-hydroxy-4-(trifluoromethyl)phenyl)phthalazin-1-yl)amino)-2-methylpropane-1,2-diol; and
(R)-3-((4-(2-hydroxy-4-(trifluoromethyl)phenyl)phthalazin-1-yl)amino)-2-methylpropane-1,2-diol;
or a pharmaceutically acceptable salt thereof.

16. The compound of claim 1, wherein the compound is:

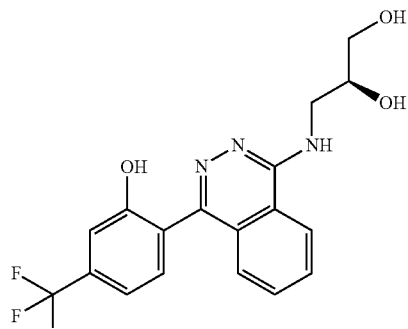

or a pharmaceutically acceptable salt thereof.

17. The compound of claim 1, wherein the compound is:

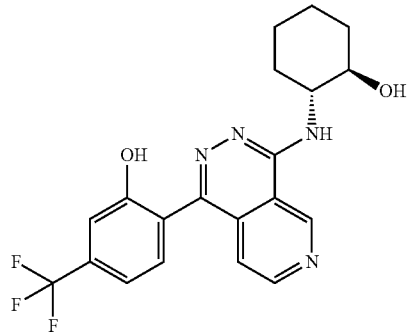 [SMILES: Oc1cc(C(F)(F)F)ccc1-c1nnc(N[C@@H]2CCCC[C@H]2O)c2cnccc12]

or a pharmaceutically acceptable salt thereof.

18. A pharmaceutical composition comprising the compound of claim 1 and a pharmaceutically acceptable excipient.

19. The compound of claim 1, wherein the compound is:

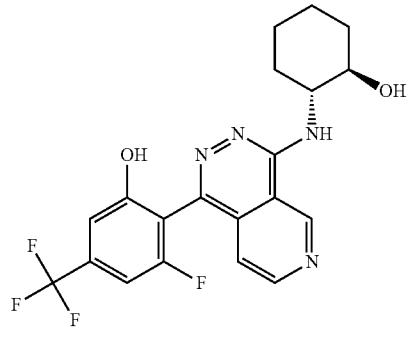 [SMILES: Oc1cc(C(F)(F)F)cc(F)c1-c1nnc(N[C@@H]2CCCC[C@H]2O)c2cnccc12]

or a pharmaceutically acceptable salt thereof.

20. The compound of claim 1, wherein the compound is:

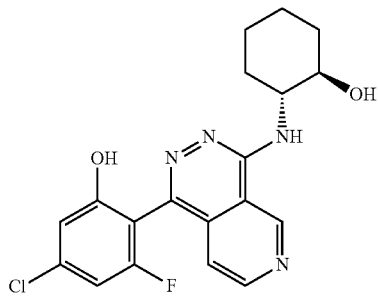 [SMILES: Oc1cc(Cl)cc(F)c1-c1nnc(N[C@@H]2CCCC[C@H]2O)c2cnccc12]

or a pharmaceutically acceptable salt thereof.

21. The compound of claim 1, wherein the compound is:

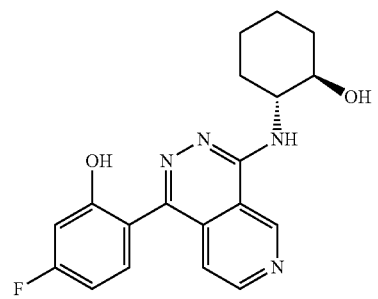 [SMILES: Oc1cc(F)ccc1-c1nnc(N[C@@H]2CCCC[C@H]2O)c2cnccc12]

or a pharmaceutically acceptable salt thereof.

22. The compound of claim 1, wherein the compound is:

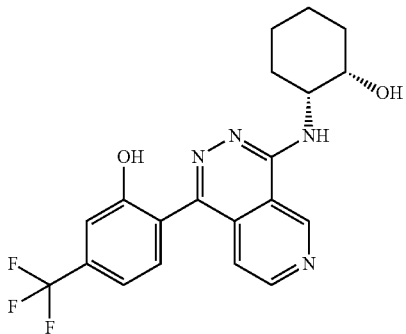 [SMILES: Oc1cc(C(F)(F)F)ccc1-c1nnc(N[C@@H]2CCCC[C@@H]2O)c2cnccc12]

or a pharmaceutically acceptable salt thereof.

23. The compound of claim 1, wherein the compound is:

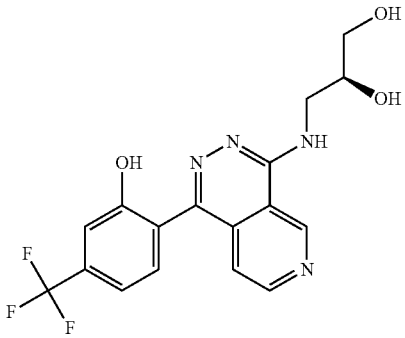 [SMILES: OC[C@@H](O)CNc1nnc(-c2ccc(C(F)(F)F)cc2O)c2ccncc12]

or a pharmaceutically acceptable salt thereof.

24. The compound of claim 1, wherein the compound is:

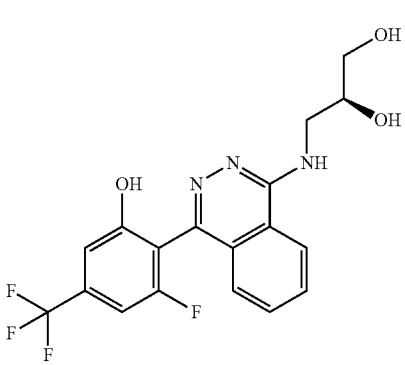

or a pharmaceutically acceptable salt thereof.

25. The compound of claim 1, wherein the compound is:

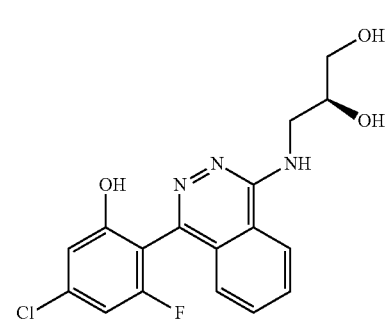 [SMILES: OC[C@@H](O)CNc1nnc(-c2c(O)cc(Cl)cc2F)c2ccccc12]

or a pharmaceutically acceptable salt thereof.

26. The compound of claim 1, wherein the compound is:

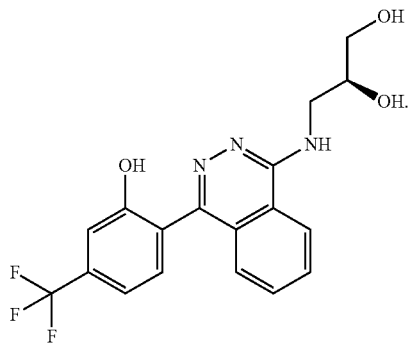

27. The compound of claim 1, wherein the compound is:

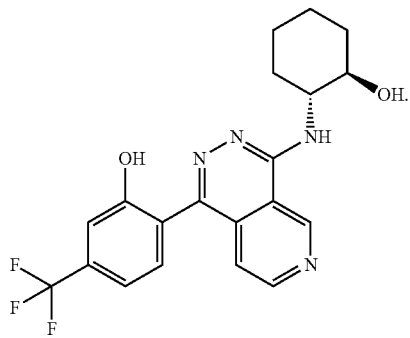 [SMILES: Oc1cc(C(F)(F)F)ccc1-c1nnc(N[C@@H]2CCCC[C@H]2O)c2cnccc12]

28. The compound of claim 1, wherein the compound is:

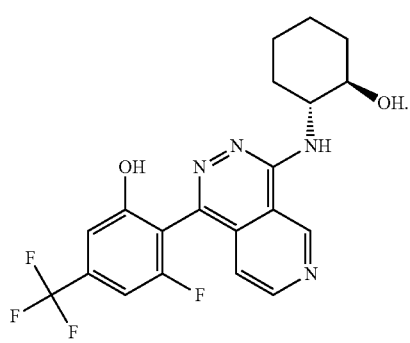 [SMILES: Oc1cc(C(F)(F)F)cc(F)c1-c1nnc(N[C@@H]2CCCC[C@H]2O)c2cnccc12]

29. The compound of claim 1, wherein the compound is:

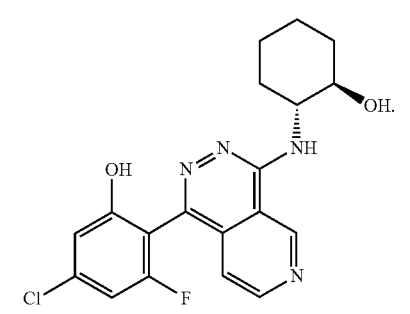 [SMILES: Oc1cc(Cl)cc(F)c1-c1nnc(N[C@@H]2CCCC[C@H]2O)c2cnccc12]

30. The compound of claim 1, wherein the compound is:

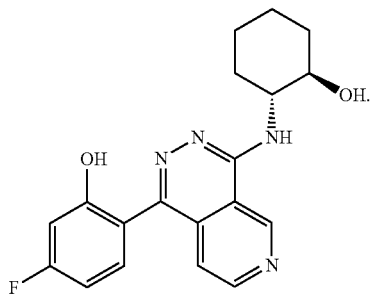 [SMILES: Oc1cc(F)ccc1-c1nnc(N[C@@H]2CCCC[C@H]2O)c2cnccc12]

31. The compound of claim 1, wherein the compound is:

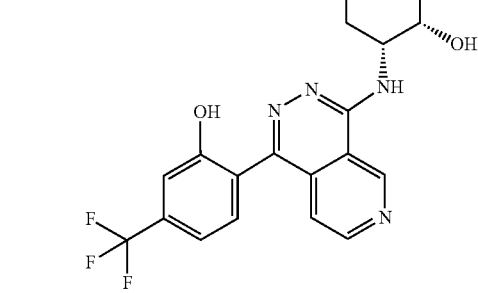

32. The compound of claim 1, wherein the compound is:

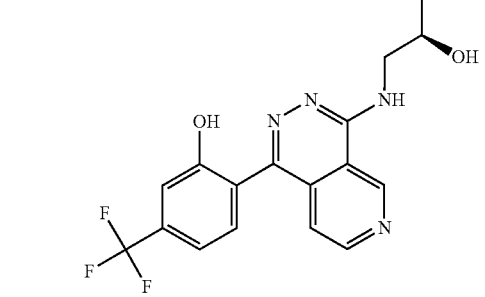

33. The compound of claim 1, wherein the compound is:

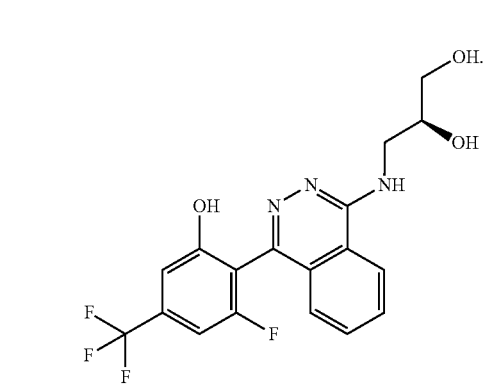 [SMILES: OC[C@@H](O)CNc1nnc(-c2c(O)cc(C(F)(F)F)cc2F)c2ccccc12]

34. The compound of claim 1, wherein the compound is:

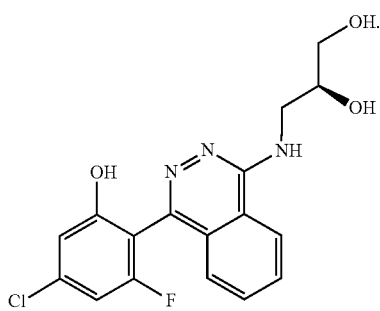 [SMILES: OC[C@@H](O)CNc1nnc(-c2c(O)cc(Cl)cc2F)c2ccccc12]

35. The compound of claim 1, wherein the compound is a pharmaceutically acceptable salt of:

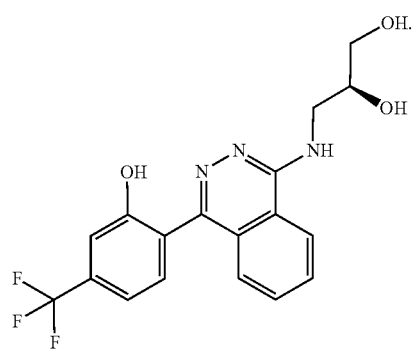

36. The compound of claim 1, wherein the compound is a pharmaceutically acceptable salt of:

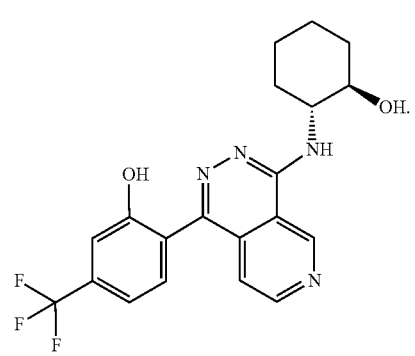

37. The compound of claim 1, wherein the compound is a pharmaceutically acceptable salt of:

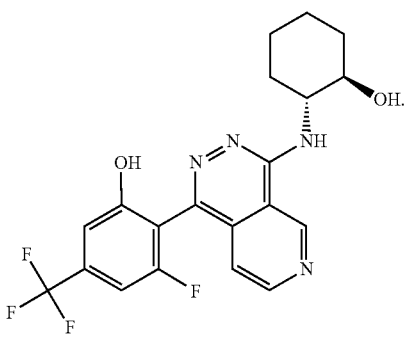 [SMILES: Oc1cc(C(F)(F)F)cc(F)c1-c1nnc(N[C@@H]2CCCC[C@H]2O)c2cnccc12]

38. The compound of claim 1, wherein the compound is a pharmaceutically acceptable salt of:

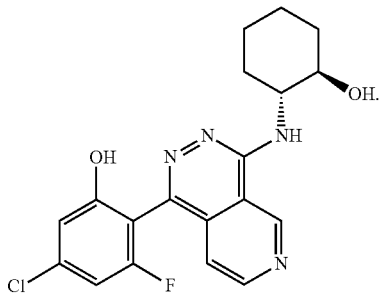 [SMILES: Oc1cc(Cl)cc(F)c1-c1nnc(N[C@@H]2CCCC[C@H]2O)c2cnccc12]

39. The compound of claim 1, wherein the compound is a pharmaceutically acceptable salt of:

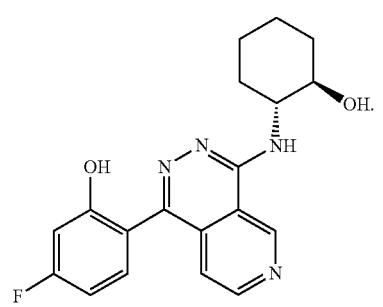

40. The compound of claim 1, wherein the compound is a pharmaceutically acceptable salt of:
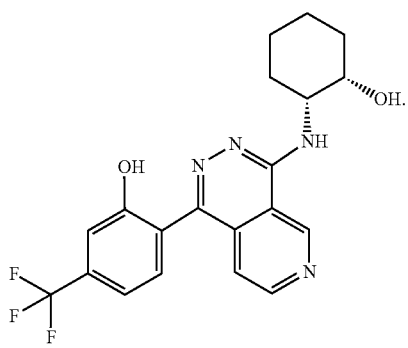
41. The compound of claim 1, wherein the compound is a pharmaceutically acceptable salt of:
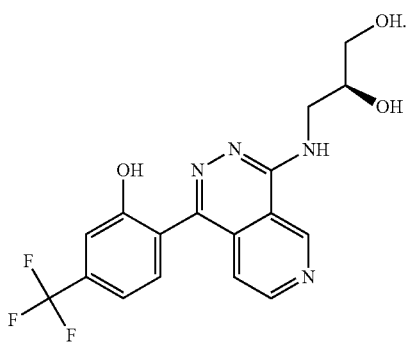 [SMILES: OC[C@@H](O)CNc1nnc(-c2ccc(C(F)(F)F)cc2O)c2ccncc12]
42. The compound of claim 1, wherein the compound is a pharmaceutically acceptable salt of:
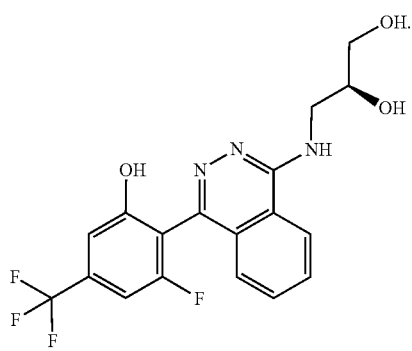 [SMILES: OC[C@@H](O)CNc1nnc(-c2c(O)cc(C(F)(F)F)cc2F)c2ccccc12]
43. The compound of claim 1, wherein the compound is a pharmaceutically acceptable salt of:
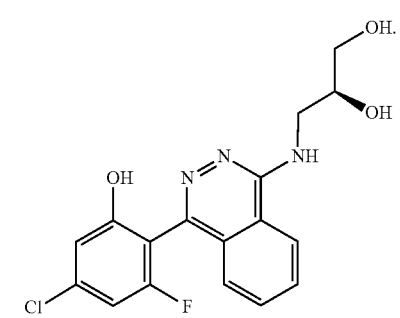 [SMILES: OC[C@@H](O)CNc1nnc(-c2c(O)cc(Cl)cc2F)c2ccccc12]
* * * * *